US012297505B2

(12) United States Patent
Whitney et al.

(10) Patent No.: US 12,297,505 B2
(45) Date of Patent: May 13, 2025

(54) ALGORITHMS FOR DISEASE DIAGNOSTICS

(71) Applicant: Veracyte, Inc., South San Francisco, CA (US)

(72) Inventors: Duncan H. Whitney, Boston, MA (US); Michael Elashoff, Redwood City, CA (US)

(73) Assignee: Veracyte, Inc., South San Francisco, CA (US)

( * ) Notice: Subject to any disclaimer, the term of this patent is extended or adjusted under 35 U.S.C. 154(b) by 0 days.

(21) Appl. No.: 17/218,127

(22) Filed: Mar. 30, 2021

(65) Prior Publication Data

US 2021/0262040 A1  Aug. 26, 2021

Related U.S. Application Data

(63) Continuation-in-part of application No. 16/875,673, filed on May 15, 2020, now abandoned, which is a continuation of application No. 16/593,918, filed on Oct. 4, 2019, now abandoned, which is a continuation of application No. 14/799,472, filed on Jul. 14, 2015, now abandoned.

(60) Provisional application No. 62/160,403, filed on May 12, 2015, provisional application No. 62/024,456, filed on Jul. 14, 2014.

(51) Int. Cl.
*C12Q 1/6886* (2018.01)
*G01N 33/574* (2006.01)
*G06N 20/00* (2019.01)
*G16B 25/00* (2019.01)
*G16B 40/00* (2019.01)
*G16H 50/20* (2018.01)

(52) U.S. Cl.
CPC ..... *C12Q 1/6886* (2013.01); *G01N 33/57407* (2013.01); *G06N 20/00* (2019.01); *G16B 40/00* (2019.02); *G16H 50/20* (2018.01); *C12Q 2600/112* (2013.01); *C12Q 2600/158* (2013.01); *G16B 25/00* (2019.02)

(58) Field of Classification Search
None
See application file for complete search history.

(56) References Cited

U.S. PATENT DOCUMENTS

| | | |
|---|---|---|
| 3,640,268 A | 2/1972 | Davis |
| 3,645,691 A | 2/1972 | Knapp et al. |
| 3,687,808 A | 8/1972 | Merigan, Jr. et al. |
| 4,641,662 A | 2/1987 | Jaicks |
| 4,800,896 A | 1/1989 | Jalowayski |
| 5,130,238 A | 7/1992 | Malek et al. |
| 5,143,854 A | 9/1992 | Pirrung et al. |
| 5,288,514 A | 2/1994 | Ellman |
| 5,384,261 A | 1/1995 | Winkler et al. |
| 5,399,491 A | 3/1995 | Kacian et al. |
| 5,422,273 A | 6/1995 | Garrison et al. |
| 5,440,942 A | 8/1995 | Hubbard |
| 5,455,166 A | 10/1995 | Walker |
| 5,477,863 A | 12/1995 | Grant |
| 5,494,810 A | 2/1996 | Barany et al. |
| 5,538,848 A | 7/1996 | Livak et al. |
| 5,677,195 A | 10/1997 | Winkler et al. |
| 5,705,365 A | 1/1998 | Ryder et al. |
| 5,710,029 A | 1/1998 | Ryder et al. |
| 5,726,060 A | 3/1998 | Bridges |
| 5,795,782 A | 8/1998 | Church et al. |
| 5,830,711 A | 11/1998 | Barany et al. |
| 5,846,717 A | 12/1998 | Brow et al. |
| 5,854,033 A | 12/1998 | Lizardi |
| 5,876,978 A | 3/1999 | Willey et al. |
| 5,888,779 A | 3/1999 | Kacian et al. |
| 5,965,360 A | 10/1999 | Zain et al. |
| 5,985,557 A | 11/1999 | Prudent et al. |
| 5,989,815 A | 11/1999 | Skolnick et al. |
| 5,994,069 A | 11/1999 | Hall et al. |
| 6,001,567 A | 12/1999 | Brow et al. |
| 6,013,431 A | 1/2000 | Soederlund et al. |
| 6,015,714 A | 1/2000 | Baldarelli et al. |
| 6,022,692 A | 2/2000 | Coulie et al. |
| 6,027,887 A | 2/2000 | Zavada et al. |
| 6,085,907 A | 7/2000 | Hochmeister et al. |

(Continued)

FOREIGN PATENT DOCUMENTS

| | | |
|---|---|---|
| CA | 2712773 A1 | 7/2009 |
| CN | 1620309 A | 5/2005 |

(Continued)

OTHER PUBLICATIONS

Hassanein et al., "The State of Molecular Biomarkers for the Early Detection of Lung Cancer" 5(8) Cancer Prevention Research 992-1006 (Year: 2012).*
Zhang et al., "Similarities and differences between smoking-related gene expression in nasal and bronchial epithelium" 41 Physiological Genomics 1-8 (Year: 2010).*
Zhang et al., "Comparison of Nasal Epithelial Smoking-Induced Gene Expression on Affymetrix Exon 1.0 and Gene 1.0 ST Arrays" 2013 The Scientific World Journal 951416 1-7 (Year: 2013).*
Abrahamson et al. Cystatins. Biochem. Soc. Symp. 70: 179-199 (2003).
Abratani, Hiroyuki. Characteristic Diagnosis of Cancer by Gene Expression Profiling. Personalized Diagnosis of Cancer by Gene Expression Profiling. English Translation. Journal of Clinical and Experimental Medicine (Igaku No Ayumi), Jun. 1, 2002, vol. 201, No. 9, p. 687-692.

(Continued)

*Primary Examiner* — Nancy J Leith
(74) *Attorney, Agent, or Firm* — WILSON SONSINI GOODRICH & ROSATI

(57) ABSTRACT

The present invention relates to compositions and methods for molecular profiling and diagnostics for genetic disorders and cancer, including but not limited to gene expression product markers associated with cancer or genetic disorders. In particular, the present invention provides algorithms and methods of classifying cancer, for example, thyroid cancer, methods of determining molecular profiles, and methods of analyzing results to provide a diagnosis.

25 Claims, 12 Drawing Sheets

Specification includes a Sequence Listing.

(56) References Cited

U.S. PATENT DOCUMENTS

| | | |
|---|---|---|
| 6,090,543 A | 7/2000 | Prudent et al. |
| 6,136,182 A | 10/2000 | Dolan et al. |
| 6,225,051 B1 | 5/2001 | Sugiyama et al. |
| 6,251,639 B1 | 6/2001 | Kurn |
| 6,268,142 B1 | 7/2001 | Duff et al. |
| 6,410,278 B1 | 6/2002 | Notomi et al. |
| 6,436,642 B1 | 8/2002 | Gould-Rothberg et al. |
| 6,627,067 B1 | 9/2003 | Branton et al. |
| 6,667,154 B1 | 12/2003 | Wang et al. |
| 6,676,609 B1 | 1/2004 | Rutenberg et al. |
| 6,723,506 B2 | 4/2004 | Fletcher et al. |
| 6,746,846 B1 | 6/2004 | Wang et al. |
| 7,186,514 B2 | 3/2007 | Zavada et al. |
| 7,211,390 B2 | 5/2007 | Rothberg et al. |
| 7,238,485 B2 | 7/2007 | Akeson et al. |
| 7,244,559 B2 | 7/2007 | Rothberg et al. |
| 7,258,838 B2 | 8/2007 | Li et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordano et al. |
| 7,662,553 B2 | 2/2010 | Lenz |
| 7,767,391 B2 | 8/2010 | Scott et al. |
| 7,901,881 B2 | 3/2011 | Libutti et al. |
| 7,901,888 B2 | 3/2011 | Kebebew |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,293,880 B2 | 10/2012 | Cote et al. |
| 8,354,228 B2 | 1/2013 | Ron |
| 8,465,914 B2 | 6/2013 | Brown et al. |
| 8,568,971 B2 | 10/2013 | Brown et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,234,244 B2 | 1/2016 | Zeiger et al. |
| 9,495,515 B1 | 11/2016 | Kennedy et al. |
| 9,587,279 B2 | 3/2017 | Fahey, III et al. |
| 9,708,667 B2 | 7/2017 | Barnett-Itzhaki et al. |
| 9,856,537 B2 | 1/2018 | Kennedy et al. |
| 9,920,374 B2 | 3/2018 | Brody et al. |
| 10,114,924 B2 | 10/2018 | Kennedy et al. |
| 10,236,078 B2 | 3/2019 | Kennedy et al. |
| 10,526,655 B2 | 1/2020 | Whitney et al. |
| 10,570,454 B2 | 2/2020 | Brody et al. |
| 10,672,504 B2 | 6/2020 | Kennedy et al. |
| 10,731,223 B2 | 8/2020 | Kennedy et al. |
| 10,808,285 B2 | 10/2020 | Brody et al. |
| 10,927,417 B2 | 2/2021 | Beane-Ebel et al. |
| 2001/0051344 A1 | 12/2001 | Shalon et al. |
| 2002/0031496 A1 | 3/2002 | Firestein et al. |
| 2002/0076735 A1 | 6/2002 | Williams et al. |
| 2002/0081612 A1 | 6/2002 | Katz et al. |
| 2002/0094547 A1 | 7/2002 | Burstein |
| 2002/0160388 A1 | 10/2002 | Macina et al. |
| 2002/0169137 A1 | 11/2002 | Reiner et al. |
| 2003/0104499 A1 | 6/2003 | Pressman et al. |
| 2003/0116159 A1 | 6/2003 | Orr et al. |
| 2003/0186248 A1 | 10/2003 | Erlander et al. |
| 2003/0190602 A1 | 10/2003 | Pressman et al. |
| 2003/0194734 A1 | 10/2003 | Jatkoe |
| 2004/0005294 A1 | 1/2004 | Lee |
| 2004/0009489 A1 | 1/2004 | Golub et al. |
| 2004/0019466 A1 | 1/2004 | Minor et al. |
| 2004/0058378 A1 | 3/2004 | Kong et al. |
| 2004/0063120 A1 | 4/2004 | Beer et al. |
| 2004/0197785 A1 | 10/2004 | Willey et al. |
| 2004/0241725 A1 | 12/2004 | Xiao et al. |
| 2004/0241728 A1 | 12/2004 | Liew |
| 2005/0042222 A1 | 2/2005 | Yamamoto et al. |
| 2005/0048533 A1 | 3/2005 | Sidransky et al. |
| 2005/0065447 A1 | 3/2005 | Lee et al. |
| 2005/0137805 A1 | 6/2005 | Lewin et al. |
| 2005/0240357 A1 | 10/2005 | Minor |
| 2005/0250125 A1 | 11/2005 | Novakoff |
| 2005/0260586 A1 | 11/2005 | Demuth et al. |
| 2005/0266409 A1 | 12/2005 | Brown et al. |
| 2005/0266443 A1 | 12/2005 | Croce et al. |
| 2006/0003171 A1 | 1/2006 | Igawa et al. |
| 2006/0019256 A1 | 1/2006 | Clarke et al. |
| 2006/0019272 A1 | 1/2006 | Geraci et al. |
| 2006/0019615 A1 | 1/2006 | Ditmer |
| 2006/0035244 A1 | 2/2006 | Riggins et al. |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2006/0127928 A1 | 6/2006 | Bacus et al. |
| 2006/0140960 A1 | 6/2006 | Wang et al. |
| 2006/0154278 A1 | 7/2006 | Brody et al. |
| 2006/0183144 A1 | 8/2006 | Willey et al. |
| 2006/0188909 A1 | 8/2006 | Willey et al. |
| 2006/0190192 A1 | 8/2006 | Willey et al. |
| 2006/0194216 A1 | 8/2006 | Willey et al. |
| 2006/0241869 A1 | 10/2006 | Schadt et al. |
| 2006/0252057 A1 | 11/2006 | Raponi et al. |
| 2007/0020657 A1 | 1/2007 | Grebe et al. |
| 2007/0031873 A1 | 2/2007 | Wang et al. |
| 2007/0037186 A1 | 2/2007 | Jiang et al. |
| 2007/0048738 A1 | 3/2007 | Donkena et al. |
| 2007/0065833 A1 | 3/2007 | Gupta |
| 2007/0092891 A1 | 4/2007 | Willey et al. |
| 2007/0092892 A1 | 4/2007 | Willey et al. |
| 2007/0092893 A1 | 4/2007 | Willey et al. |
| 2007/0099209 A1 | 5/2007 | Clarke et al. |
| 2007/0105133 A1 | 5/2007 | Clarke et al. |
| 2007/0148650 A1 | 6/2007 | Brody et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172844 A1 | 7/2007 | Lancaster et al. |
| 2007/0220621 A1 | 9/2007 | Clarke et al. |
| 2007/0238119 A1 | 10/2007 | Yu et al. |
| 2008/0028302 A1 | 1/2008 | Meschkat |
| 2008/0044824 A1 | 2/2008 | Giordano et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0254470 A1 | 10/2008 | Berlin |
| 2008/0274457 A1 | 11/2008 | Eng et al. |
| 2008/0281568 A1 | 11/2008 | Kao et al. |
| 2009/0020433 A1 | 1/2009 | Cohen et al. |
| 2009/0029477 A1 | 1/2009 | Meller et al. |
| 2009/0061454 A1 | 3/2009 | Brody et al. |
| 2009/0186951 A1 | 7/2009 | Brody et al. |
| 2009/0191535 A1 | 7/2009 | Connelly et al. |
| 2009/0204333 A1 | 8/2009 | Friend et al. |
| 2009/0246779 A1 | 10/2009 | Rabinovitch et al. |
| 2009/0280490 A1 | 11/2009 | Baker et al. |
| 2009/0291853 A1 | 11/2009 | Kim et al. |
| 2009/0311692 A1 | 12/2009 | Brody et al. |
| 2010/0035244 A1 | 2/2010 | Brody et al. |
| 2010/0055689 A1 | 3/2010 | Spira et al. |
| 2010/0055704 A1 | 3/2010 | Giordano et al. |
| 2010/0075384 A1 | 3/2010 | Kong et al. |
| 2010/0099093 A1 | 4/2010 | Weaver et al. |
| 2010/0119474 A1 | 5/2010 | Crystal et al. |
| 2010/0131286 A1 | 5/2010 | Houlgatte et al. |
| 2010/0131432 A1 | 5/2010 | Kennedy et al. |
| 2010/0143312 A1 | 6/2010 | Hariri et al. |

(56) References Cited

U.S. PATENT DOCUMENTS

| | | |
|---|---|---|
| 2010/0178653 A1 | 7/2010 | Aharonov et al. |
| 2010/0204058 A1 | 8/2010 | Chang et al. |
| 2010/0255486 A1 | 10/2010 | Showe et al. |
| 2010/0285979 A1 | 11/2010 | Zeiger et al. |
| 2010/0303813 A1 | 12/2010 | Carulli et al. |
| 2011/0053158 A1 | 3/2011 | Mambo et al. |
| 2011/0092375 A1 | 4/2011 | Zamore et al. |
| 2011/0152110 A1 | 6/2011 | Vierlinger et al. |
| 2011/0190150 A1 | 8/2011 | Brody et al. |
| 2011/0190156 A1 | 8/2011 | Whitfield et al. |
| 2011/0212855 A1 | 9/2011 | Rafnar et al. |
| 2011/0217315 A1 | 9/2011 | Schwartz et al. |
| 2011/0217717 A1 | 9/2011 | Brody et al. |
| 2011/0224313 A1 | 9/2011 | Tsao et al. |
| 2011/0229894 A1 | 9/2011 | Levy et al. |
| 2011/0230372 A1 | 9/2011 | Willman et al. |
| 2011/0269142 A1 | 11/2011 | Zavras |
| 2011/0287946 A1 | 11/2011 | Gudmundsson et al. |
| 2011/0294684 A1 | 12/2011 | Baty et al. |
| 2011/0312520 A1 | 12/2011 | Kennedy et al. |
| 2012/0015839 A1 | 1/2012 | Chinnaiyan |
| 2012/0015843 A1 | 1/2012 | Von et al. |
| 2012/0041686 A1 | 2/2012 | Brody et al. |
| 2012/0115743 A1 | 5/2012 | Davicioni et al. |
| 2012/0122698 A1 | 5/2012 | Stacey et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0190567 A1 | 7/2012 | Brody et al. |
| 2012/0208706 A1 | 8/2012 | Downing et al. |
| 2012/0214165 A1 | 8/2012 | Walfish et al. |
| 2012/0220474 A1 | 8/2012 | Kennedy et al. |
| 2012/0264626 A1 | 10/2012 | Nana-Sinkam et al. |
| 2012/0288860 A1 | 11/2012 | Van Hoek et al. |
| 2012/0322673 A1 | 12/2012 | Brody et al. |
| 2012/0329666 A1 | 12/2012 | Steele et al. |
| 2013/0023434 A1 | 1/2013 | Van |
| 2013/0023437 A1 | 1/2013 | Brody et al. |
| 2013/0029873 A1 | 1/2013 | De et al. |
| 2013/0142728 A1 | 6/2013 | Beaudenon-Huibregtse et al. |
| 2013/0172203 A1 | 7/2013 | Yeatman et al. |
| 2013/0184999 A1 | 7/2013 | Ding |
| 2013/0196868 A1 | 8/2013 | Lebowitz et al. |
| 2013/0273543 A1 | 10/2013 | Gudmundsson et al. |
| 2013/0302810 A1 | 11/2013 | Latham et al. |
| 2013/0303826 A1 | 11/2013 | Jurisica et al. |
| 2014/0030714 A1 | 1/2014 | Paschke et al. |
| 2014/0087961 A1 | 3/2014 | Sulem et al. |
| 2014/0121126 A1 | 5/2014 | Bivona et al. |
| 2014/0143188 A1 | 5/2014 | Mackey et al. |
| 2014/0179771 A1 | 6/2014 | Bancel et al. |
| 2014/0220006 A1 | 8/2014 | Aghvanyan et al. |
| 2014/0243240 A1 | 8/2014 | Soldin et al. |
| 2014/0302042 A1 | 10/2014 | Chin et al. |
| 2014/0315199 A1 | 10/2014 | Rhodes et al. |
| 2014/0315739 A1 | 10/2014 | Aharonov et al. |
| 2014/0329251 A1 | 11/2014 | Moerman et al. |
| 2014/0349856 A1 | 11/2014 | Schnabel et al. |
| 2014/0371096 A1 | 12/2014 | Umbricht et al. |
| 2014/0378425 A1 | 12/2014 | Wilde et al. |
| 2015/0038376 A1 | 2/2015 | Tian et al. |
| 2015/0080243 A1 | 3/2015 | Whitney et al. |
| 2015/0088430 A1 | 3/2015 | Whitney et al. |
| 2015/0099665 A1 | 4/2015 | Rosenfeld et al. |
| 2015/0141470 A1 | 5/2015 | Garraway et al. |
| 2015/0152474 A1 | 6/2015 | Pawlowski et al. |
| 2015/0275306 A1 | 10/2015 | Bernards et al. |
| 2015/0299808 A1 | 10/2015 | Gonzalez et al. |
| 2015/0307947 A1 | 10/2015 | Basu et al. |
| 2015/0337385 A1 | 11/2015 | Harris et al. |
| 2015/0354008 A1 | 12/2015 | Brody et al. |
| 2015/0368724 A1 | 12/2015 | Aharonov et al. |
| 2016/0024583 A1 | 1/2016 | Whitney et al. |
| 2016/0024586 A1 | 1/2016 | Delfour et al. |
| 2016/0032400 A1 | 2/2016 | Gomis et al. |
| 2016/0068915 A1 | 3/2016 | Kennedy et al. |
| 2016/0115546 A1 | 4/2016 | Rosenfeld et al. |
| 2016/0120832 A1 | 5/2016 | Rabinowitz et al. |
| 2016/0130656 A1* | 5/2016 | Whitney .............. C12Q 1/6886 506/9 |
| 2017/0127976 A1 | 5/2017 | Phillips et al. |
| 2017/0166980 A1 | 6/2017 | Fahey, III et al. |
| 2017/0226591 A1 | 8/2017 | Brody et al. |
| 2017/0247759 A1 | 8/2017 | Wilde et al. |
| 2017/0328908 A1 | 11/2017 | Brody et al. |
| 2017/0335396 A1 | 11/2017 | Kennedy et al. |
| 2018/0112275 A1 | 4/2018 | Davicioni et al. |
| 2018/0122508 A1 | 5/2018 | Wilde et al. |
| 2018/0127832 A1 | 5/2018 | Kennedy et al. |
| 2019/0080047 A1 | 3/2019 | Kennedy et al. |
| 2019/0100809 A1 | 4/2019 | Kennedy et al. |
| 2019/0172551 A1 | 6/2019 | Kennedy et al. |
| 2019/0292600 A1 | 9/2019 | Spira et al. |
| 2019/0330680 A1 | 10/2019 | Kennedy et al. |
| 2019/0376148 A1 | 12/2019 | Brody et al. |
| 2020/0096513 A1 | 3/2020 | Brody et al. |
| 2020/0115763 A1 | 4/2020 | Brody et al. |
| 2020/0176078 A1 | 6/2020 | Kennedy et al. |
| 2020/0202974 A1 | 6/2020 | Kennedy et al. |
| 2020/0232045 A1 | 7/2020 | Brody et al. |
| 2020/0248274 A1 | 8/2020 | Brody et al. |
| 2020/0405225 A1 | 12/2020 | Kennedy et al. |
| 2021/0040559 A1 | 2/2021 | Wilde et al. |
| 2021/0040562 A1 | 2/2021 | Whitney et al. |
| 2021/0079471 A1 | 3/2021 | Kennedy et al. |
| 2021/0332431 A1 | 10/2021 | Wilde et al. |
| 2021/0355524 A1 | 11/2021 | Kennedy et al. |

FOREIGN PATENT DOCUMENTS

| | | |
|---|---|---|
| CN | 1688582 A | 10/2005 |
| CN | 101501214 A | 8/2009 |
| CN | 102640001 A | 8/2012 |
| CN | 102858991 A | 1/2013 |
| CN | 104334744 A | 2/2015 |
| CN | 105247075 A | 1/2016 |
| CN | 105378104 A | 3/2016 |
| DE | 10219117 C1 | 10/2003 |
| EP | 0684315 A1 | 11/1995 |
| EP | 1403638 A1 | 3/2004 |
| EP | 1975245 A1 | 10/2008 |
| EP | 1975252 A1 | 10/2008 |
| EP | 2231874 A2 | 9/2010 |
| EP | 2295599 A1 | 3/2011 |
| EP | 2366800 A1 | 9/2011 |
| EP | 3215170 A1 | 9/2017 |
| EP | 3360978 A2 | 8/2018 |
| JP | 2004526154 A | 8/2004 |
| JP | 2005168432 A | 6/2005 |
| JP | 2005304497 A | 11/2005 |
| JP | 2007513635 A | 5/2007 |
| JP | 2008545400 A | 12/2008 |
| JP | 2008545431 A | 12/2008 |
| JP | 2013532295 A | 8/2013 |
| JP | 2015519966 A | 7/2015 |
| KR | 20130017525 | 2/2013 |
| WO | WO-9015070 A1 | 12/1990 |
| WO | WO-9210092 A1 | 6/1992 |
| WO | WO-9309668 A1 | 5/1993 |
| WO | WO-9322684 A1 | 11/1993 |
| WO | WO-9515331 A1 | 6/1995 |
| WO | WO-9960160 A1 | 11/1999 |
| WO | WO-0006780 A1 | 2/2000 |
| WO | WO-0120035 A2 | 3/2001 |
| WO | WO-0128428 A1 | 4/2001 |
| WO | WO-0206791 A2 | 1/2002 |
| WO | WO-0244331 A2 | 6/2002 |
| WO | WO-02072866 A2 | 9/2002 |
| WO | WO-02086443 A2 | 10/2002 |
| WO | WO-03015613 A2 | 2/2003 |
| WO | WO-03029273 A2 | 4/2003 |
| WO | WO-03040325 A2 | 5/2003 |
| WO | WO-03062389 A2 | 7/2003 |
| WO | WO-03097666 A2 | 11/2003 |

(56) References Cited

FOREIGN PATENT DOCUMENTS

| | | |
|---|---|---|
| WO | WO-2004005891 A2 | 1/2004 |
| WO | WO-2004029055 A1 | 4/2004 |
| WO | WO-2004091511 A2 | 10/2004 |
| WO | WO-2004111197 A2 | 12/2004 |
| WO | WO-2005000098 A2 | 1/2005 |
| WO | WO-2005005601 A2 | 1/2005 |
| WO | WO-2005047451 A2 | 5/2005 |
| WO | WO-2005085471 A2 | 9/2005 |
| WO | WO-2005100608 A2 | 10/2005 |
| WO | WO-2005005601 A3 | 4/2006 |
| WO | WO-2006047484 A2 | 5/2006 |
| WO | WO-2006062118 A1 | 6/2006 |
| WO | WO-2006105252 A2 | 10/2006 |
| WO | WO-2006113467 A2 | 10/2006 |
| WO | WO-2006127537 A2 | 11/2006 |
| WO | WO-2006113467 A3 | 4/2007 |
| WO | WO-2007038792 A2 | 4/2007 |
| WO | WO-2007103541 A2 | 9/2007 |
| WO | WO-2007038792 A3 | 11/2007 |
| WO | WO-2007126882 A2 | 11/2007 |
| WO | WO-2008104380 A2 | 9/2008 |
| WO | WO-2008119776 A1 | 10/2008 |
| WO | WO-2008104380 A3 | 11/2008 |
| WO | WO-2008140774 A2 | 11/2008 |
| WO | WO-2009006323 A2 | 1/2009 |
| WO | WO-2009020905 A2 | 2/2009 |
| WO | WO-2009026605 A2 | 3/2009 |
| WO | WO-2009029266 A2 | 3/2009 |
| WO | WO-2009037337 A1 | 3/2009 |
| WO | WO-2009039457 A1 | 3/2009 |
| WO | WO-2006127537 A3 | 4/2009 |
| WO | WO-2009042728 A1 | 4/2009 |
| WO | WO-2009068591 A2 | 6/2009 |
| WO | WO-2009079450 A2 | 6/2009 |
| WO | WO-2009121070 A1 | 10/2009 |
| WO | WO-2009126271 A1 | 10/2009 |
| WO | WO-2009143603 A1 | 12/2009 |
| WO | WO-2010018601 A2 | 2/2010 |
| WO | WO-2010028274 A1 | 3/2010 |
| WO | WO-2010054233 A1 | 5/2010 |
| WO | WO-2010056374 A2 | 5/2010 |
| WO | WO-2010073248 A2 | 7/2010 |
| WO | WO-2010056374 A3 | 9/2010 |
| WO | WO-2010073248 A3 | 9/2010 |
| WO | WO-2010099598 A1 | 9/2010 |
| WO | WO-2010123626 A1 | 10/2010 |
| WO | WO-2010124372 A1 | 11/2010 |
| WO | WO-2010127322 A1 | 11/2010 |
| WO | WO-2010129934 A2 | 11/2010 |
| WO | WO-2011079846 A2 | 7/2011 |
| WO | WO-2011086174 A2 | 7/2011 |
| WO | WO-2011094345 A1 | 8/2011 |
| WO | WO-2011143361 A2 | 11/2011 |
| WO | WO-2012006632 A2 | 1/2012 |
| WO | WO-2012129237 A2 | 9/2012 |
| WO | WO-2012149550 A1 | 11/2012 |
| WO | WO-2013033640 A1 | 3/2013 |
| WO | WO-2013049152 A2 | 4/2013 |
| WO | WO-2013063544 A1 | 5/2013 |
| WO | WO-2013086429 A2 | 6/2013 |
| WO | WO-2013086522 A1 | 6/2013 |
| WO | WO-2013088457 A1 | 6/2013 |
| WO | WO-2013148232 A1 | 10/2013 |
| WO | WO-2013163568 A2 | 10/2013 |
| WO | WO-2013177060 A2 | 11/2013 |
| WO | WO-2013190092 A1 | 12/2013 |
| WO | WO-2014043803 A1 | 3/2014 |
| WO | WO-2014144564 A2 | 9/2014 |
| WO | WO-2014144821 A1 | 9/2014 |
| WO | WO-2014151764 A2 | 9/2014 |
| WO | WO-2014186036 A1 | 11/2014 |
| WO | WO-2015068157 A1 | 5/2015 |
| WO | WO-2015071876 A2 | 5/2015 |
| WO | WO-2016011068 A1 | 1/2016 |
| WO | WO-2016073768 A1 | 5/2016 |
| WO | WO-2016094330 A2 | 6/2016 |
| WO | WO-2016141127 A1 | 9/2016 |
| WO | WO-2017197335 A1 | 11/2017 |
| WO | WO-2018009915 A1 | 1/2018 |
| WO | WO-2018048960 A1 | 3/2018 |
| WO | WO-2018223066 A1 | 12/2018 |
| WO | WO-2019023517 A2 | 1/2019 |

OTHER PUBLICATIONS

Abrosimov et al. The cytoplasmic expression of MUC1 in papillary thyroid carcinoma of different histological variants and its correlation with cyclin D1 overexpression. Endocr Pathol. 2007;18(2):68-75.

Abubaker et al. Clinicopathological analysis of papillary thyroid cancer with PIK3CA alterations in a Middle Eastern population. J Clin Endocrinol Metab. 2008;93(2):611-8.

Adams, J.U., The Human Genome project set out to sequence all of the 3 billion nucleotides in the human genome. Exactly how was this daunting task done with such incredible speed and accuracy? DNA sequencing technologies. Nature Education, 2008; 1(1):193, pp. 1-6.

Adapt, The Peterson Institute for Cancer Research, probesets for ARSG, printed Jan. 10, 2013.

Adapt, The Peterson Institute for Cancer Research, probesets for FREM2, printed Jan. 10, 2013.

Adapt, The Peterson Institute for Cancer Research, probesets for GIMAP2, printed Jan. 10, 2013.

Adapt, The Peterson Institute for Cancer Research, probesets for HRASLS3, printed Jan. 10, 2013.

Adapt, The Peterson Institute for Cancer Research, probesets for PIGN, printed Jan. 10, 2013.

Adapt website. Paterson Institute for Cancer Research. Probesets for AUTS2. Printed Jul. 1, 2014. 2 pages.

Adapt website. Paterson Institute for Cancer Research. Probesets for FXYD6. Printed Jul. 1, 2014. 1 page.

Affymetrix CDKL2 (https://www.affymetriix.com/analysis/netaffx/showresults.affx, Mar. 21, 2019).

Affymetrix: "Data Sheet Affymetrix(R) Genome-Wide Human SNP Array 6.0", 2007, pp. 1-4, XP002525407. Retrieved from the Internet: URL:http://www.affymetrix.com/support/technical/datasheets/genomewide_snp6_datasheet.pdf.

Affymetrix HG-U 133 Plus 2.0 Annotation File (filtered excerpt, obtained from http://www.affymetrix.com/Auth/analysis/downloads/na26/ivt/HG-U133_Pius_2.na26.annot.csv.zip on Mar. 18, 2013, 1 page) (Year: 2013).

Affymetrix HG-U 133A Annotation File (filtered excerpt, obtained from http://www.affymetrix.com/Auth/analysis/downloads/na35/ivt/HG-U 133A.na35.annot.csv.zip on Apr. 29, 2016, 1 page) (Year: 2016).

Affymetrix HLA-F (https://www.affymetrix.com/analysis/netaffx/showresults.affz, Mar. 21, 2019).

Affymetrix Technical Note: GeneChip® Gene 1.0 ST Array Design (created Sep. 5, 2007; downloaded from http://media.affymetrix.com/support/technical/technotes/gene_1_0_st_technote.pdf).

Affymetrix website for HG-U133A probe set list version 2004, Archived NetAffx Annotation Files (http://www.affymetrix.com/estore/catalog/131537/AFFY/Human+Genome+U133A+2.0+Array#1_3) printed Mar. 2015.

Afink, et al. Molecular characterization of iodotyrosine dehalogenase deficiency in patients with hypothyroidism. J Clin Endocrinol Metab. Dec. 2008;93(12):4894-901.

Aggarwal et al. Thyroid carcinoma-associated genetic mutations also occur in thyroid lymphomas. Mod Pathol. vol. 25 No. 9. May 11, 2012. pp. 1203-1211.

Agrawal, et al. Cancer Genome Atlas Research Network. Integrated genomic characterization of papillary thyroid carcinoma. Cell. Oct. 23, 2014;159(3):676-90. doi: 10.1016/j.cell.2014.09.050.

Akashi et al. Histopathologic analysis of sixteen autopsy cases of chronic hypersensitivity pneumonitis and comparison with idiopathic pulmonary fibrosis/usual interstitial pneumonia. American Journal of Clinical Pathology (2009); 131.3: 405-415.

(56) References Cited

OTHER PUBLICATIONS

Akester et al. Cancer in the thyroid is not always thyroid cancer. Hormones-Athens-2 (2003): 250-255.
Akita, et al. Molecular Biology of Lung Cancer. The Journal of the Japanese Respiratory Society, 42(5): (2004).
Aldred et al. Caveolin-1 and caveolin-2, together with three bone morphogenetic protein-related genes, may encode novel tumor suppressors down-regulated in sporadic follicular thyroid carcinogenesis. Cancer Res. 2003;63(11):2864-71.
Aldred et al. Papillary and follicular thyroid carcinomas show distinctly different microarray expression profiles and can be distinguished by a minimum of five genes. J Clin Oncol. 2004;22(17):3531-9.
Alexander et al. Preoperative diagnosis of benign thyroid nodules with indeterminate cytology. N Engl J Med. Aug. 23, 2012;367(8):705-15.
Ali et al. Use of the Afirma® Gene Expression Classifier for Preoperative Identification of Benign Thyroid Nodules with Indeterminate Fine Needle Aspiration Cytopathology. PLoS Currents 5:pp. 1-7 (2013).
Ambion, Inc. GeneAssist Pathway Atlas for P13K Signaling. Accessed from <http://www5.appliedbiosystems.com/tools/pathway/pathway proteins.php?pathway=P13K> on May 3, 2011.
American Thoracic Society, American Thoracic Society/European Respiratory Society International Multidisciplinary Consensus Classification of the Idiopathic Interstitial Pneumonias. Am. J. Respir. Crit. Care Med. 165, 277-304, 2002.
American Thoracic Society. European Respiratory Society. Idiopathic pulmonary fibrosis: diagnosis and treatment. International consensus statement. Am J Respir Crit Care Med (2000); 161.2 pt 1: 646-664.
Anbazhagan et al. Classification of Small Cell Lung Cancer and Pulmonary Carcinoid by Gene Expression Profiles. Cancer Research, 59:5119-5122, (Oct. 15, 1999).
Anders et al. HTSeq-a Python framework to work with high-throughput sequencing data. Bioinformatics (2015); 31(2): 166-169.
Anderson et al. Deaths: Leading Causes for 2001. National Vital Statistics Report; 52(9): 1-88 (Nov. 7, 2003).
Anonymous: "Bronchogenic carcinoma / definition of bronchogenic carcinoma by Medicaldictionary," Feb. 13, 2019 (Feb. 13, 2019), retrieved from the internet: URL:https://medicaldictionary.thefreedictionary.com/bronchogenic+carcinoma [retrieved on Feb. 13, 2019].
Anonymous: "Bronchogenic carcinoma is a malignant neoplasm of the lung arising from theepithelium of the bronchus or bronchiole", Apr. 22, 2003 (Apr. 22, 2003), retrieved from theinternet:URL:http://www.meddean.luc.edu/lumen/meded/medicine/pulmonar/pathms/path19.htm[retrieved on Feb. 13, 2019].
Anthonisen et al. Effects of Smoking Intervention and the Use of an Inhaled Anticholinergic Bronchodilator on the Rate of Decline of FEV1. JAMA; 272(19):1497-1505 (Nov. 16, 1994).
Appleby et al. New technologies for ultra-high throughput genotyping in plants. Plant Genomics: Methods and Protocols (2009); 513: 19-39.
Arimura et al. Elevated Serum 6-Defensins Concentrations in Patients with Lung Cancer. Anticancer Res. Nov.-Dec. 2004;24(6):4051-7.
Arnesen et al. Expression of N-acetyl transferase human and human Arrest defective 1 proteins in thyroid neoplasms. Thyroid. 2005;15(10):1131-6.
Ashley. Towards precision medicine. Nature Reviews Genetics 17.9 (2016): 507.
Asseroshn et al. The feasibility of using fine needle aspiration from primary breast cancers for cDNA microarray analyses. Clinical Cancer Research 8.3 (2002): 794-801.
"Ausubel, et al. Current Protocols in Molecular Biology. Wiley & Sons, New York, 1995.".
Auton et al. 1000 Genomes Project Consortium. A global reference for human genetic variation. Nature 526, 7571 (2015): 68.

"Bach, et al. Benefits and harms of CT screening for lung cancer: a systematic review. Jama 307.22 (2012): 2418-2429.".
Bai et al. Mutational analysis of thyroid transcription factor-1 gene (TTF-1) in lung carcinomas. In Vitro Cell Dev Biol Anim. 2008;44(1-2):17-25.
Baker et al., Screening for bronchogenic carcinoma: The Surgical experience, J. Thorac Cardiovasc Surg, 1979; 78:876-882.
Baker, Stuart. The Central Role of Receiver Operating Characteristic (ROC) Curves in Evaluating Tests for the Early Detection of Cancer. Journal of the National Cancer Institute, 95(7): 511-515 (Apr. 2003).
Baldi; et al, "DNA microarrays and gene expression: from experiments to data analysis and modeling. Cambridge university press, 2002.".
Baloch, et al. Our approach to follicular-patterned lesions of the thyroid. J Clin Pathol. Mar. 2007;60(3):244-50. Epub Jun. 23, 2006.
Banito et al. Aneuploidy and RAS mutations are mutually exclusive events in the development of well-differentiated thyroid follicular tumours. Clin Endocrinol (Oxf). 2007;67(5):706-11.
Barden et al. Classification of follicular thyroid tumors by molecular signature: results of gene profiling. Clin Cancer Res. 2003;9(5):1792-800.
Baris et al. Transcriptional profiling reveals coordinated up-regulation of oxidative metabolism genes in thyroid oncocytic tumors. J Clin Endocrinol Metab. 2004;89(2):994-1005.
Bauer et al. A novel genomic signature with translational significance for human idiopathic pulmonary fibrosis. American Journal of Respiratory Cell and Molecular Biology (2015); 52.2: 217-231.
Beane et al. A Prediction Model for Lung Cancer Diagnosis that Integrates Genomic and Clinical Features. Cancer Prevention Research, 1:56-64 (2008).
Beane, et al., Characterizing the impact of smoking and lung cancer on the airway transcriptome using RNA-Seq. Cancer Prev Res 2011;4:803-817.
Beane et al. Reversible and permanent effects of tobacco smoke exposure on airway epithelial gene expression. Genome Biology 2007, 8:R201 (Sep. 25, 2007).
Beane-Ebel. Single-Cell RNA Sequencing of the Bronchial Epithelium in Smokers With Lung Cancer. U.S. Army Medical Research and Material Command. Jul. 2015 version. [retrieved on Sep. 19, 2017]. Retrieved from the Internet at http://www.dtic.mil/dtic/tr/fulltext/u2/a624219.pdf.
Beaudenon-Huibregtse, et al. Centralized molecular testing for oncogenic gene mutations complements the local cytopathologic diagnosis of thyroid nodules. Thyroid. Oct. 2014;24(10):1479-87. Epub Jun. 18, 2014.
Beer et al. Gene-expression profiles predict survival of patients with lung adenocarcinoma. Nature Medicine, 8: 816-824 (2002).
Belinksky et al. Aberrant promoter methylation in bronchial epithelium and sputum from current and former smokers. Cancer Res., 62(8): 2370-7 (2002).
Belperio, et al., Critical role for CXCR2 and CXCR2 ligands during the pathogenesis of ventilator-induced lung injury. J Clin Invest. 2002; 110(11): 1703-1716.
Belyavsky et al. PCR-based cDNA library construction: general cDNA libraries at the level of a few cells. Nucleic Acids Research (1989); 17.8: 2919-2932.
Benner, et al. Evolution, language and analogy in functional genomics. Trends in Genetics, 17:414-418 (2001).
Berbescu et al. Transbronchial biopsy in usual interstitial pneumonia. Chest Journal (May 2006); 129.5: 1126-1131.
Berman, Jeffrey S. Abstract Immunopathology of the nasal mucosa in sarcoidosis National Institutes of Health Grant No. 1 R21 HL077498-01 (Funding Start Date Sep. 15, 2004).
Bernard et al. Multiplex messenger assay: simultaneous, quantitative measurement of expression of many genes in the context of T cell activation. Nucleic Acids Research (1996); 24.8: 1435-1442.
Bessarabova, et al. Bimodal gene expression patterns in breast cancer. BMC Genomics. Feb. 10, 2010;11 Suppl 1:S8. doi: 10.1186/1471-2164-11-S1-S8.
Beum et al. Epidermal Growth Factor Downregulates Core 2 Enzymes in a Human Airway Adenocarcinoma Cell Line. Am. J. Respir. Cell Mol. Biol., 29:48-56 (Jan. 2003).

(56) References Cited

OTHER PUBLICATIONS

Bhattacharjee et al. Classification of human lung carcinoma by mRNA expression profiling reveals distinct adenocarcinoma subclasses. Proc Natl Acad Sci USA, 98(24): 13790-5 (Nov. 20, 2001).
Bild et al. Oncogenic Pathway Signatures in Human Cancers as a Guide to Targeted Therapies. Nature, 439: 353-357 (Jan. 2006).
Bjoraker et al. Prognostic significance of histopathologic subsets in idiopathic pulmonary fibrosis. American Journal of Respiratory and Critical Care Medicine (1998); 157.1: 199-203.
Bohula et al. The Efficacy of Small Interfering RNAs Targeted to the Type 1 Insulin-like Growth Factor Receptor (IGF1R) Is Influenced by Secondary Structure in the IGF1R Transcript. The Journal of Biological Chemistry 278(18): 15991-15997 (May 2003).
Bolstad, et al. A comparison of normalization methods for high density oligonucleotide array data based on variance and bias. Bioinformatics. Jan. 22, 2003;19(2):185-93.
Bonora et al. Novel germline variants identified in the inner mitochondrial membrane transporter TIMM44 and their role in predisposition to oncocytic thyroid carcinomas. Br J Cancer. 2006;95(11):1529-36.
Bosse et al. Molecular signature of smoking in human lung tissues. Cancer Research (2012); 72.15: 3753-3763.
Boulesteix, et al. Evaluating microarray-based classifiers: an overview. Cancer Inform. 2008;6:77-97. Epub Feb. 29, 2008.
Braakhuis et al. A Genetic Explanation of Slaughter's Concept of Field Cancerization Evidence and Clinical Implications. Cancer Research, 63: 1727-1730 (Apr. 2003).
Brambilla et al. p53 Mutant Immunophenotype and Deregulation of p53 Transcription Pathway (Bcl2, Bax and Wafl) in Precursor Bronchial Lesions of Lunch Cancer. Clinical Cancer Research (4): 1609-1618 (1998).
Brasseur et al. Papillary thyroid carcinoma in a 9-year-old girl with ataxia-telangiectasia. Pediatr Blood Cancer. 2008;50(5):1058-60.
Brenner, et al., Gene Expression analysis by massively parallel signature sequencing (MPSS) on microbead arrays. Nature Biotechnology 18.6 (Jun. 2000): 630-634, doi:10.1038/76469.
British Thoracic society bronchoscopy committee, British Thoracic Society guidelines on diagnostic flexible bronchoscopy. Thorax, 2001, 56 (suppl I): i1-i21).
Brody, Jerome S. Abstract: Airway epithelial gene expression in COPD. National Institutes of Health. Grant No. 1RO1HL071771-01 (Funding Start Date Sep. 30, 2002).
Brozek et al. Thyroid cancer in two siblings with FAP syndrome and APC mutation. Int J Colorectal Dis. 2008;23(3):331-2.
Buckanovich et al. Nova, the paraneoplastic Ri antigen, is homologous to an RNA-binding protein and is specifically expressed in the developing motor system. Neuron (1993); 11.4: 657-672.
Bugalho et al. Mutation analysis of the RET proto-oncogene and early thyroidectomy: results of a Portuguese cancer centre. Surgery. 2007;141(1):90-5.
Byron et al. Translating RNA sequencing into clinical diagnostics: opportunities and challenges. Nature Reviews Genetics 17.5 (2016): 257.
Cameselle-Teijeiro et al. Follicular thyroid carcinoma with an unusual glomeruloid pattern of growth. Hum Pathol. 2008;39(10):1540-7.
Campbell, et al., Applying gene expression microarrays to pulmonary disease. Respirology, 16; 2011:407-418.
Camus et al. Interstitial lung disease induced by drugs and radiation. Respiration. Jul.-Aug. 2004;71(4):301-26.
Carda et al. Anaplastic carcinoma of the thyroid with rhabdomyosarcomatous differentiation: a report of two cases. Virchows Arch. 2005;446(1):46-51.
Carroll et al. Promising Molecular Techniques for Discriminating Among Follicular Thyroid Neoplasms. Surgical Oncology, Blackwell Scientific Publ., Oxford, GB, vol. 15, No. 2, Aug. 1, 2006, pp. 59-64.
Castro et al. Adenomas and follicular carcinomas of the thyroid display two major patterns of chromosomal changes. J Pathol. 2005;206(3):305-11.
Castro et al.PAX8-PPARgamma rearrangement is frequently detected in the follicular variant of papillary thyroid carcinoma. J Clin Endocrinol Metab. 2006;91(1):213-20.
Centeno et al. Classification of human tumors using gene expression profiles obtained after microarray analysis of fine-needle aspiration biopsy samples. Cancer Cytopathology: Interdisciplinary International Journal of the American Cancer Society 105.2 (2005): 101-109.
Cerutti et al. A preoperative diagnostic test that distinguishes benign from malignant thyroid carcinoma based on gene expression. J Clin Invest. 2004;113(8):1234-42.
Cerutti et al. Diagnosis of suspicious thyroid nodules using four protein biomarkers. Clin Cancer Res. 2006;12(11 Pt 1):3311-8.
Chan, et al. Integrating Transcriptomics and Proteomics. Drug Discovery and Development. Apr. 1, 2006. 4 pages. Published in G&P magazine 2006 vol. 6 No. 3 pp. 20-26.
Chan et al. Integrating Transcriptomics and Proteomics. Genomics & Proteomics Magazine, 6(3), text of article reprinted and accessed from www.dddmag.com Published Oct. 4, 2007. www.dddmag.com.
Chari et al. Effect of active smoking on the human bronchial epithelium transcriptome. BMC Genomics, 8:297 (Aug. 29, 2007).
Chaudhuri et al. Low sputum MMP-9/TIMP ratio is associated with airway narrowing in smokers with asthma. European Respiratory Journal (Jul. 3, 2014); 44(4): 895-904.
Chen et al. Discordant Protein and mRNA Expression in Lung Adenocarcinomas. Molecular and Cellular Proteomics, 1: 304-313 (2001).
Chen et al. Enrichr: interactive and collaborative HTML5 gene list enrichment analysis tool. BMC Bioinformatics (2013); 14: 128.
Chen et al: "Expression of dihydrodiol dehydrogenase in theresected stage I non-small cell lung cancer", Oncologyreports, vol. 9, No. 3 May 1, 2002, pp. 515-519,.
Chen et al. Restricted kappa/lambda light chain ratio by flow cytometry in germinal center B cells in Hashimoto thyroiditis. Am J Clin Pathol. 2006;125(1):42-8.
Chen et al. Up-regulations of Tumor Interleukin-8 Expression by Infiltrating Macrophages: Its Correlation with Tumor Angiogenesis and Patient Survival in Non-Small Cell Lung Cancer. Clinical Cancer Research: p. 729, (Feb. 1, 2003).
Cheng et al. A Multi-Cancer Mesenchymal Transition Gene Expression Signature Is Associated with Prolonged Time to Recurrence in Glioblastoma. Plos One 7(4):e34705 (2012).
Cheng et al. Reduced expression levels of nucleotide excision repair genes in lung cancer: a case-control analysis. Carcinogenesis. 21(8):1527-1530 (2000).
Cheung, et al. Immunohistochemical diagnosis of papillary thyroid carcinoma. Mod Pathol. Apr. 2001;14(4):338-42.
Cheung et al. Natural variation in human gene expression assessed in lymphoblastiod cells. Nature Genetics, 33: 422-425 (Mar. 2003).
Chevillard et al. Gene expression profiling of differentiated thyroid neoplasms: diagnostic and clinical implications. Clin Cancer Res. 2004;10(19):6586-97.
Chiappetta et al. The antiapoptotic protein BAG3 is expressed in thyroid carcinomas and modulates apoptosis mediated by tumor necrosis factor-related apoptosis-inducing ligand. J Clin Endocrinol Metab. 2007;92(3):1159-63.
Chinese Search Report for Application No. 2008801147951 dated Aug. 24, 2012.
Cho et al. System biology of interstitial lung diseases: integration of mRNA and microRNA expression changes. 2011, BMC Medical Genomics, 4:8, p. 1-20.
Choi et al. Case-control association testing in the presence of unknown relationships. Genetic epidemiology 33.8 (2009): 668-678.
Chudova, et al. Molecular classification of thyroid nodules using high-dimensionality genomic data. J Clin Endocrinol Metab. Dec. 2010;95(12):5296-304. doi: 10.1210/jc.2010-1087. Epub Sep. 8, 2010.
Chung et al. Detection of BRAFV600E mutation on fine needle aspiration specimens of thyroid nodule refines cyto-pathology diagnosis, especially in BRAF600E mutation-prevalent area. Clin Endocrinol (Oxf). 2006;65(5):660-6.

(56) References Cited

OTHER PUBLICATIONS

Ciampi et al. BRAF copy number gains in thyroid tumors detected by fluorescence in situ hybridization. Endocr Pathol. 2005;16(2):99-105.
Cibas, et al. The Bethesda System for Reporting Thyroid Cytopathology. Am J Clin Pathol. Nov. 2009;132(5):658-65. doi: 10.1309/AJCPPHLWMI3JV4LA.
Cirulli Uncovering the roles of rare variants in common disease through whole-genome sequencing. Nature Reviews Genetics 11.6 (2010): 415.
Clark et al. Altered Protein Kinase C (PKC) Isoforms in Non-Small Cell Lung Cancer Cells: PKCdelta Promotes Cellular Survival and Chemotherapeutic Resistance. Cancer Research, 63(4): 780-786 (2003).
Clark et al. Discovery of tissue-specific exons using comprehensive human exon microarrays. Genome Biol. 2007;8(4):R64.
Clinical cytopathology and aspiration biopsy: Fundamental principles and practice. McGraw Hill Professional, 2001.
Cogan, et al., Rare variants in RTEL1 Are associated with familial interstitial Pneumonia. American Journal of respiratory and critical care medicine, Mar. 15, 2015; 191(6):646-655.
Cohen et al. Mutational Analysis of BRAF in Fine Needle Aspiration Biopsies of the Thyroid: A Potential Application for the Preoperative Assessment of Thyroid Nodules. Clinical Cancer Research 10:2761-2765 (Apr. 2004).
Coleman et al. Of mouse and man—what is the value of the mouse in predicting gene expression in humans? Drug Discov Today 8(6) (Mar. 2003): 233-235.
Collard et al. Changes in clinical and physiologic variables predict survival in idiopathic pulmonary fibrosis. American Journal of Respiratory and Critical Care Medicine (May 2003); 168.5: 538-542.
Combined search report and examination report dated Oct. 1, 2013 for GB Application No. 1315760.7.
Cooper, et al. Management guidelines for patients with thyroid nodules and differentiated thyroid cancer. Thyroid. Feb. 2006;16(2):109-42.
Cooper. Gene Expression Studies in Lung Cancer. The Molecular Genetics of Lung Cancer, pp. 167-186, (2005).
Co-pending U.S. Appl. No. 16/017,899, inventors Choi; Yoonha et al., filed Jun. 25, 2018.
Co-pending U.S. Appl. No. 16/551,645, inventors Kennedygiulia; C. et al., filed Aug. 26, 2019.
Co-pending U.S. Appl. No. 16/557,278, inventors Wildejonathan; I. et al., filed Aug. 30, 2019.
Co-pending U.S. Appl. No. 16/593,918, inventors Whitneyduncan; H. et al., filed Oct. 4, 2019.
Co-pending U.S. Appl. No. 16/693,194, inventors Whitneyduncan; H. et al., filed Nov. 22, 2019.
Co-pending U.S. Appl. No. 16/910,039, inventors Kennedy; Giulia C. et al., filed Jun. 23, 2020.
Co-pending U.S. Appl. No. 16/945,119, inventors Whitneyduncan; H. et al., filed Jul. 31, 2020.
Co-pending U.S. Appl. No. 17/169,082, inventors Kennedygiulia; C. et al., filed Feb. 5, 2021.
Co-pending U.S. Appl. No. 17/190,408, inventors Whitneyduncan; H. et al., filed Mar. 3, 2021.
Co-pending U.S. Appl. No. 17/476,284, inventors Kennedygiulia; C. et al., filed Sep. 15, 2021.
Co-pending U.S. Appl. No. 17/501,856, inventors Whitneyduncan; H. et al., filed Oct. 14, 2021.
Cortes et al. Support-vector networks. Machine Learning. 1995; 20:273-297.
Costa et al. New somatic mutations and WNK1-B4GALNT3 gene fusion in papillary thyroid carcinoma. Oncotarget 6:11242-11251 (2015).
Cottin et al. Neglected evidence in idiopathic pulmonary fibrosis and the importance of early diagnosis and treatment. European Respiratory Review (Mar. 1, 2014); 23.131: 106-110.
Covey et al. Factors associated with pneumothorax and pneumothorax requiring treatment after percutaneous lung biopsy in 443 consecutive patients. Journal of Vascular and Interventional Radiology (2004); 15.5: 479-483.
Crawford et al. Normal Bronchial Epithelial Cell Expression of Glutathione Transferase P1, Glutathione Transferase M3, and Glutathione Peroxidase is Low in Subjects with Bronchogenic Carcinoma. Cancer Research, 60: 1609-1618 (Mar. 15, 2000).
Crescioli et al. Methimazole inhibits CXC chemokine ligand 10 secretion in human thyrocytes. J Endocrinol. 2007;195(1):145-55.
Cross et al. The promise of molecular profiling for cancer identification and treatment. Clinical medicine & research 2.3 (2004): 147-150.
Cummings, Sr. et al. Estimating the probability of malignancy in solitary pulmonary nodules. A Bayesian approach, Am Rev Respir Dis 1986;134:449-52 (1986).
Dai et al. Evolving gene/transcript definitions significantly alter the interpretation of GeneChip data. Nucleic Acids Research 33.20 (2005): e175-e175.
Danel et al. Quantitative Assessment of the Epithelial and Inflammatory Cell Populations in Large Airways of Normals and Individuals with Cystic Fibrosis. Am. Journal of Resp. And Critical Care Medicine 153:362-368 (1996).
Dauletbaev et al. Expression of Human Beta Defensin (HBD-1 and HBD-2) mRNA in Nasal Epithelia of Adult Cystic Fibrosis Patients, Healthy Individuals, and Individuals with Acute Cold. Respiration, 69:46-51 (2002).
De Figueiredo-Pontes, Idenification and characterization of ALK kinase splicing isoforms on non-small-cell lung cancer, J Thorac Oncol, 9(2): 248-253, Feb. 2014. (Year: 2014).
De Lellis et al. The pathobiology of the human calcitonin (C)-cell: a review. Pathol Annu. 1981;16(Pt 2):25-52.
Del Senno et al. c-myc oncogene alterations in human thyroid carcinomas. Cancer Detect Prev. 1987;10(3-4):159-66.
Delellis et al. C-cell hyperplasia. An ultrastructural analysis. Lab Invest. 1977;36(3):237-48.
Delibasis, et al., "Computer-Aided Diagnosis of Thyroid Malignancy Using an Artificial Immune System Classification Algorithm," IEEE Transactions on Information Technology in Biomedicine, vol. 13, No. 5, pp. 680-686, Sep. 2009.
DeLong et al. Comparing the areas under two or more correlated receiver operating characteristic curves: a nonparametric approach. Biometrics (1988); 44(3): 837-845.
DeLuca et al. RNA-SeQC: RNA-seq metrics for quality control and process optimization. Bioinformatics (2012); 28.11: 1530-1532.
DeMeo et al. The SERPINE2 gene is associated with chronic obstructive pulmonary disease. Am J Hum Genet., 78(2): 253-264 (Feb. 2006).
Demoly et al. c-fos Proto-oncogene Expression in Bronchial Biopsies of Asthmatics. American Journal of Respiratory Cell and Molecular Biology 7:128-133 (1992).
Dempsey, et al. Lung disease and PKCs. Pharmacol Res., 55 6 : 545-59 2007.
DeMuth et al. The Gene Expression of Index c-myc X E2F-1/p21 Is Highly Predictive of Malignant Phenotype in Human Bronchial Epithelial Cells. Am. J. Cell Mol. Bio. (19): 18-24 (1998).
Deng et al. Ubiquitous Induction of Resistance to Platinum Drugs in Human Ovarian, Cervical, Germ-Cell and Lung Carcinoma Tumor Cells Overexpressing Isoforms 1 and 2 of Dihydrodiol Dehydrogenase. Cancer Chemother. PharmacoL, 54:301-307, (2004).
Denis et al. RING3 Kinase Transactivates Promoters of Cell Cycle Regulatory Genes through E2F1 Cell. Growth Differ; 11: 417-424 (Aug. 2000).
Depeursinge et al. Automated classification of usual interstitial pneumonia using regional volumetric texture analysis in high-resolution computed tomography. Invest Radiol. Apr. 2015;50(4):261-7.
DePianto et al. Heterogeneous gene expression signatures correspond to distinct lung pathologies and biomarkers of disease severity in idiopathic pulmonary fibrosis. Thorax (2015); 70.1: 48¬56.
Derringer, et al. Malignant lymphoma of the thyroid gland: a clinicopathologic study of 108 cases. Am J Surg Pathol. May 2000;24(5):623-39.

(56) References Cited

OTHER PUBLICATIONS

Details for HG-U133A:217291 _AT (CEACAMS) (https://www.affymetrix.com/analysis/netaffx/fullrecord.affx?pk=HG-U133A:217291 _AT, downloaded Apr. 22, 2016).

DetailsforHG-U112A:823_AT (http://www.affymetrix.com/analysis/netaffx/fultrecord.affx?pk=HG-U133A:823 AT, downloaded Dec. 10, 2012).

DetailsforHG-U133A:202831_AT (https://www.affymetrix.com/analysis/netaffx/fullrecord.affx?pk=HG-U133A:202831AT, downloaded Dec. 10, 2012).

DetailsforHG-U133a-207469_S_AT (https://www.affymetrix.com/analysis/netaffx/fullrecod.affx?pk=HG-U133A:207469 S AT, downloaded Dec. 10, 2012).

DetailsforHG-U133A:210519_S_AT (https://www.affvmetrix.com/analysis/netaffx/fullrecord.affx?pk=HG-U133A:210519 S AT downloaded Dec. 10, 2012).

Detterbeck et al. Screening for lung cancer: diagnosis and management of lung cancer: American College of Chest Physicians evidence-based clinical practice guidelines. Chest Journal (2013); 143.5_suppl: e78S-e92S.

Dettori et al. Aneuploidy in oncocytic lesions of the thyroid gland: diffuse accumulation of mitochondria within the cell is associated with trisomy 7 and progressive numerical chromosomal alterations. Genes Chromosomes Cancer. 2003;38(1):22-31.

Diaz-Uriarte et al. Gene selection and classification of microarray data using random forest. BMC Bioinformatics. 2006;7:3.

Ding et al. A high-throughput gene expression analysis technique using competitive PCR and matrix-assisted laser desorption ionization time-of-flight MS. Proceedings of the National Academy of Sciences USA (Mar. 2003); 100.6: 3059-3064.

Dobin, et al., Star: Ultrafast Universal RNA-Seq Aligner, Bioinformatics, Oct. 25, 2012, 29:15-21.

Doll et al. Mortality in relation to smoking: 40 years' observations on male British doctors. BMJ; 309:901-911 (Oct. 8, 1994).

Doris et al. Quantitative analysis of gene expression by ion-pair high-performance liquid chromatography. Journal of Chromatography A (1998); 806.1: 47-60.

Dougherty. The fundamental role of pattern recognition for gene-expression/microarray data in bioinformatics. Pattern recognition. 2005; 38:2226-2228.

Druckenthaner et al. Evidence for Somatostatin receptor 2 in thyroid tissue. Regul Pept. 2007;138(1):32-9.

Du Bois et al. Ascertainment of individual risk of mortality for patients with idiopathic pulmonary fibrosis. American Journal of Respiratory and Critical Care Medicine (2011); 184.4: 459-466.

Du Bois, R. M. Strategies for treating idiopathic pulmonary fibrosis. Nature reviews Drug Discovery (2010); 9.2: 129-140.

Durand et al. Evaluation of gene expression profiles in thyroid nodule biopsy material to diagnose thyroid cancer. J Clin Endocrinol Metab. 2008;93(4):1195-202.

Durante, et al. BRAF mutations in papillary thyroid carcinomas inhibit genes involved in iodine metabolism. J Clin Endocrinol Metab. Jul. 2007;92(7):2840-3. Epub May 8, 2007.

Durham et al. The Relationship Between COPD and Lung Cancer. Lung Cancer, 90:121-127, (2015).

Ebbert, et al. Lung Cancer Risk Reduction After Smoking Cessation: Observations From a Prospective Cohort of Women. J Clin Oncol; 21(5):921-926 (Mar. 1, 2003).

Elisabeth Brambilla, et al., "Advances in Brief p53 Mutant Immunophenotype and Deregulationof p53 Transcription Pathway (Bc12, Bax, and Waft) in Precursor Bronchial Lesions of LungCancer", Clinical Cancer Research 4.7 (1998): 1609-1618.

Elisei et al. RET genetic screening in patients with medullary thyroid cancer and their relatives: experience with 807 individuals at one center. J Clin Endocrinol Metab. 2007;92(12):4725-9.

Elliot, et al., Transcriptome analysis of peripheral blood mononuclear cells in human subjects following a 36 h fast provides evidence of effects on genes regulating inflammation, apoptosis and energy metabolism. Genes & Nutrition; studying the relationship between genetics and nutrition in the improvement of human health, Berlin; Heidelberg: Springer, DE. Sep. 2014; 9(6): 1-11.

Ellis, et al., Rare variants in MYD88, IRAK4 and IKBKG and susceptibility to invasive Pneumococcal disease: A population-based case-control study. PLoS ONE, Apr. 2015; 10(4): 1-9.

EMBL database (Gene: CXCL2 ENSG00000081041. https://useast.ensembl.org/Homo_sapiens/Gene/Summary?g=ENSG00000081041;r=4:740 . . . , downloaded Jul. 20, 2020.

EMBL database (Gene: ZNF671 ENSG00000083814. https://useast.ensembl.org/Homo_sapiens/Gene/Summary?g=ENSG00000083814;r=19:57719751-57727624, downloaded Jul. 20, 2020.

Enard, et al. Intra- and interspecific variation in primate gene expression patterns. Science. Apr. 12, 2002;296(5566):340-343. doi: 10.1126/science.1068996.

Endocrine website. http://www.endocrineweb.com/noduleus.html (Accessed Dec. 9, 2011) (last update Oct. 12, 2010).

Englisch, et al. Chemically Modified Oligonucleotides as Probes and Inhibitors. Angew. Chem. Int. Ed. Eng. 1991; 30:613-629.

Engstrom et al. Systematic evaluation of spliced alignment programs for RNA-seq data. Nature methods 10.12 (2013): 1185.

EP04776438.6 European Search Report dated Sep. 24, 2007.
EP12828537.6 European Search Report dated Apr. 16, 2015.
EP13782273.0 Extended Search Report dated Apr. 21, 2016.
EP14764225.0 European Search Report dated Jan. 19, 2017.
EP14764225.0 European Search Report dated Oct. 7, 2016.
EP14797859.7 Extended Search Report dated Oct. 19, 2016.
EP15822338.8 Extended Search Report dated Feb. 6, 2018.
EP16759458.9 European Search Report dated Sep. 6, 2018.
EP16759458.9 Extended European Search Report dated Sep. 6, 2018.
EP17185133.0 European Search Report dated Feb. 21, 2018.
EP17849490.2 Extended Search Report dated Apr. 20, 2020.
EP18810306.3 Extended European Search Report dated Mar. 3, 2021.
EP19190846.6 Extended European Search Report dated Feb. 3, 2020.
EP21185798.2 Extended European Search Report Dated Oct. 29, 2021.

Erdogan et al. The prevalence of RET/PTC mutations in papillary thyroid cancers in Turkish population and its relation between tumor histopathology and prognostic factors. Exp Clin Endocrinol Diabetes. 2008;116(4):225-30.

Erkkila et al. Probabilistic analysis of gene expression measurements from heterogeneous tissues. Bioinformatics 26(20):2571-2577 (2010).

Ernst et al. Interventional pulmonary procedures: guidelines from the American College of Chest Physicians. Chest Journal (May 2003); 123.5: 1693-1717.

Esperante, et al. Identification and characterization of four PAX8 rare sequence variants (p.T225M, p.L233L, p.G336S and p.A439A) in patients with congenital hypothyroidism and dysgenetic thyroid glands. Clin Endocrinol (Oxf). May 2008;68(5):828-35.

Eszlinger et al. Gene expression analysis reveals evidence for inactivation of the TGF-beta signaling cascade in autonomously functioning thyroid nodules. Oncogene. 2004;23(3):795-804.

Eszlinger et al. Meta- and reanalysis of gene expression profiles of hot and cold thyroid nodules and papillary thyroid carcinoma for gene groups. J Clin Endocrinol Metab. 2006;91(5):1934-42.

Eszlinger et al. Perspectives and limitations of microarray-based gene expression profiling of thyroid tumors. Endocr Rev. 2007;28(3):322-38.

Eszlinger, et al. Perspectives for Improved and More Accurate Classification of Thyroid Epithelial Tumors. J Clin Endocrinol Metab. Sep. 2008;93(9):3286-94. Epub Jul. 1, 2008.

European extended search report dated Mar. 28, 2018 for application No. 15857196.8.

European Search Report May 25, 2018 for EP172108505.

European search report and opinion dated Mar. 5, 2014 for EP Application No. 11781242.0.

European search report and opinion dated Apr. 28, 2016 for EP 16153243.7.

European search report and search opinion dated Jan. 28, 2013 for Application No. 10772919.6.

(56) References Cited

OTHER PUBLICATIONS

European search report and search opinion dated Nov. 27, 2012 for Application No. 09826462.5.
European Search Report for European Application No. EP 10195816, dated Oct. 13, 2011.
European Search Report in Application EP 04 81 0818, dated Oct. 28, 2010.
European Search Report in Application EP 08 83 2403, dated Oct. 22, 2010.
European Search Report in Application EP 09 72 4548, Jun. 16, 2011.
European Search Report in Application EP 10 18 4732, dated Mar. 21, 2011.
European Search Report in Application EP 10 18 4813, dated Mar. 21, 2011.
European Search Report in Application EP 10 18 4888, dated Mar. 21, 2011.
European Search Report in Application EP 10 19 5803, dated Jun. 20, 2011.
European Search Report in Application EP 10 19 5822, dated Jun. 20, 2011.
European Search Report in Application EP 12 17 0635, dated Apr. 22, 2013.
Extended European Search Report dated Apr. 22, 2016 for European Patent Application No. 13838743.6.
Extended European Search Report dated Dec. 10, 2020.
Extended European Search Report from EP 16186152.1, dated May 17, 2017.
Fahy, JV. Remodeling of the Airway Epithelium in Asthma. Am. J. Respir. Crit. Care Med. 164:S46-S51 (2001).
Ferrari, et al. An approach to estimate between- and within-group correlation coefficients in multicenter studies: plasma carotenoids as biomarkers of intake of fruits and vegetables. Am J Epidemiol. Sep. 15, 2005;162(6):591-8. Epub Aug. 10, 2005.
Fielding et al. Heterogeneous Nuclear Ribonucleoprotein A2B1 Up-Regulation in Bronchial Lavage Specimens: A Clinical Marker of Early Lung Cancer Detection. Clinical Cancer Research. 5:4048-4052 (1999).
Filicori, et al. Risk stratification of indeterminate thyroid fine-needle aspiration biopsy specimens based on mutation analysis. Surgery. Dec. 2011;150(6):1085-91.
Final Office action dated Aug. 28, 2018 for U.S. Appl. No. 13/105,756.
"Final Office action dated Sep. 7, 2018 for U.S. Appl. No. 14/775,379.".
Final Office action dated Sep. 7, 2018 for U.S. Appl. No. 15/694,157.
Final Office Action for U.S. Appl. No. 11/294,834 dated Aug. 18, 2014.
Final Office Action for U.S. Appl. No. 12/234,588, dated Nov. 4, 2011.
Final Office Action for U.S. Appl. No. 12/414,555, dated Mar. 15, 2012.
Final Office Action for U.S. Appl. No. 13/323,655 dated Jul. 17, 2014.
Final Office Action for U.S. Appl. No. 13/346,444, dated Nov. 27, 2013.
Final Office Action for U.S. Appl. No. 13/524,749, dated Apr. 3, 2014.
Final Office Action for U.S. Appl. No. 14/500,475, dated Aug. 2, 2017.
Final Office Action for U.S. Appl. No. 14/500,475, dated Feb. 28, 2017.
Final Office Action for U.S. Appl. No. 14/613,210 dated Apr. 3, 2017.
Final Office Action for U.S. Appl. No. 15/644,721, dated Jun. 20, 2018.
Final Office Action for U.S. Appl. No. 15/336,469, dated Jul. 10, 2020.
Final Office Action from U.S. Appl. No. 11/294,834, date of mailing Aug. 22, 2016.
Final Office Action issued in U.S. Appl. No. 15/336,469, dated Jun. 25, 2021.
Finley et al. Advancing the molecular diagnosis of thyroid nodules: defining benign lesions by molecular profiling. Thyroid. 2005;15(6):562-8.
Finley et al. Discrimination of benign and malignant thyroid nodules by molecular profiling. Ann Surg. 2004;240(3):425-36; discussion 436-7.
Finley et al. Molecular analysis of Hurthle cell neoplasms by gene profiling. Surgery. 2004;136(6):1160-8.
Finley et al. Molecular profiling distinguishes papillary carcinoma from benign thyroid nodules. J Clin Endocrinol Metab. 2004;89(7):3214-23.
Finn, et al. Expression microarray analysis of papillary thyroid carcinoma and benign thyroid tissue: emphasis on the follicular variant and potential markers of malignancy. Virchows Arch. Mar. 2007;450(3):249-60.
Fishel, et al. Meta-analysis of gene expression data: a predictor-based approach. Bioinformatics. Jul. 1, 2007;23(13):1599-606. Epub Apr. 26, 2007.
Flaherty et al. Clinical significance of histological classification of idiopathic interstitial pneumonia. European Respiratory Journal (2002); 19.2: 275-283.
Flaherty et al. Histopathologic variability in usual and nonspecific interstitial pneumonias. American Journal of Respiratory and Critical Care Medicine (2001); 164.9: 1722-1727.
Flaherty et al. Idiopathic interstitial pneumonia: what is the effect of a multidisciplinary approach to diagnosis?. American Journal of Respiratory and Critical Care Medicine (2004); 170.8: 904¬910.
Flaherty et al. Radiological versus histological diagnosis in UIP and NSIP: survival implications. Thorax (Feb. 2003); 58.2: 143-148.
Fontaine, et al. Increasing the number of thyroid lesions classes in microarray analysis improves the relevance of diagnostic markers. PLoS One. Oct. 29, 2009;4(10):e7632.
Fontaine et al. Microarray analysis refines classification of non-medullary thyroid tumours of uncertain malignancy. Oncogene. 2008;27(15):2228-36.
Fontaine-Delaruelle et al. Is transthoracic core needle biopsy under CT scan a good deal for benign diseases' diagnosis? European Respiratory Journal (2014); 44.Suppl 58: P679.
Foppiani et al. Uncommon association of germline mutations of RET proto-oncogene and CDKN2A gene. Eur J Endocrinol. 2008;158(3):417-22.
Fox et al. Applications of ultra-high-throughput sequencing. (ed. Belostotsky, D.A., Plant Systems Biology (2009); 5: 79-108.
Frampton, et al. Development and validation of a clinical cancer genomic profiling test based on massively parallel DNA sequencing. Nat Biotechnol. Nov. 2013;31(11):1023-31. Epub Oct. 20, 2013.
Franklin, et al. Widely Dispersed p53 Mutation in Respiratory Epithelium. The Journal of Clinical Investigation, 100(8): 2133-2137 (1997).
Frattini, et al. Alternative mutations of BRAF, RET and NTRK1 are associated with similar but distinct gene expression patterns in papillary thyroid cancer. Oncogene. Sep. 23, 2004;23(44):7436-40.
Freeman et al. DNA from Buccal Swabs Recruited by Mail: Evaluation of Storage Effects on Long-term Stability and Suitability for Multiplex Polymerase Chain Reaction Genotyping, Behavior Genetics, 33: 67 (2003).
Friedman et al. Regularization Paths for Generalized Linear Models via Coordinate Descent. J Stat Softw 33:1-22 (2010).
Fritz et al. Nasal mucosal gene expression in patients with allergic rhinitis with and without nasal polyps. Journal of Allergy Clin. Immunol, 112(6): 1057-1063 (Dec. 2003).
Frohman et al. Rapid production of full-length cDNAs from rare transcripts: amplification using a single gene-specific oligonucleotide primer. Proc Natl Acad Sci U S A. Dec. 1988;85(23):8998-9002.
Frohman On Beyond Classic RACE (Rapid Amplification of eDNA Ends) PCR Methods and Applications vol. 4, pp. S40-S58 (Year: 1994).

(56) References Cited

OTHER PUBLICATIONS

Fryknas et al. Molecular markers for discrimination of benign and malignant follicular thyroid tumors. Tumour Biol. 2006;27(4):211-20.
Fujarewicz, et al. A multi-gene approach to differentiate papillary thyroid carcinoma from benign lesions: gene selection using support vector machines with bootstrapping. Endocr Relat Cancer. Sep. 2007;14(3):809-26.
Fukumoto et al. Overexpression of the Aldo-Keto Reductase Family Protein AKR1B10 is Highly Correlated with Smokers' Non-Small Cell Lung Carcinomas. Clinical Cancer Research 11:1776-1785 (2005).
Furneaux et al. Selective expression of Purkinje-cell antigens in tumor tissue from patients with paraneoplastic cerebellar degeneration. New England Journal of Medicine (1990); 322.26: 1844-1851.
Gait. Chapter 16: Oligoribonucleotides. Antisense Research and Applications, Crookeand Lebleu Eds., CRC Press (pp. 289-302) (1993).
Garber et al. Diversity of gene expression in adenocarcinoma of the lung. PNAS, 98(24): 13784-13789 (Nov. 20, 2001).
Garcia-Alvarez et al. Tissue inhibitor of metalloproteinase-3 is up-regulated by transforming growth factor-131 in vitro and expressed in fibroblastic foci in vivo in idiopathic pulmonary fibrosis. Experimental Lung Research (Apr. 2006); 32(5): 201-214.
Garcia-Closas et al. Collection of Genomic DNA from Adults in Epidemiological Studies by Buccal Cytobrush and Mouthwash. Cancer Epidemiology, Biomarkers and Prevention, 10(6): 687-696 (2001).
Garcia-Lopez et al. Thyrocytes from autoimmune thyroid disorders produce the chemokines IP-10 and Mig and attract CXCR3+ lymphocytes. J Clin Endocrinol Metab. 2001;86(10):5008-16.
Gardina et al. Alternative splicing and differential gene expression in colon cancer detected by a whole genome exon array. BMC Genomics. 2006;7:325.
Gasparre et al. Disruptive mitochondrial DNA mutations in complex I subunits are markers of oncocytic phenotype in thyroid tumors. Proc Natl Acad Sci USA. 2007;104(21):9001-6.
Gebel, et al. Gene expression profiling in respiratory tissues from rats exposed to mainstream cigarette smoke. Carcinogenesis. Feb. 2004;25(2):169-78.
Gene Annot Website. Array Probesets for HOMER2, printed Jan. 2016.
Gene Annot website. Probesets for ALDH1B1. Printed Feb. 2018.
Gene Annot website. Probesets for AUTS2. Printed Feb. 2018.
Gene Annot website. Probesets for CFHR1. Printed Feb. 2018.
Gene Annot website. Probesets for CPE. Printed Feb. 2018.
Gene Annot website. Probesets for FN1. Printed Feb. 2018.
Gene Annot website. Probesets for GABRB2. Printed Feb. 2018.
Gene Annot website. Probesets for PLCB1. Printed Feb. 2018.
Gene Annot website. Probesets for PYGL. Printed Feb. 2018.
Gene Annot website. Probesets for ROS1. Printed Feb. 2018.
GeneAnnot Search for Affymetrix HG-U 133A microarray pro besets for TIMP1, printed Dec. 2018.
GeneAnnot Search for Affymetrix HG-U 133A microarray probesets for SLCA4, printed Dec. 2018.
GeneAnnot website. Probesets for AKT1. Printed Aug. 30, 2016. 1 page.
GeneAnnot website. Probesets for ALK. Printed Aug. 30, 2016. 1 page.
GeneAnnot website. Probesets for BRAF. Printed Aug. 30, 2016. 1 page.
GeneAnnot website. Probesets for CALCA. Printed Aug. 30, 2016. 1 page.
GeneAnnot website. Probesets for CTNNB1. Printed Aug. 30, 2016. 1 page.
GeneAnnot website. Probesets for EIF1AY. Printed Aug. 30, 2016. 1 page.
GeneAnnot website. Probesets for IGF2BP2. Printed Aug. 30, 2016. 1 page.
GeneAnnot website. Probesets for KRAS. Printed Feb. 7, 2017. 2 pages.
GeneAnnot website. Probesets for KRT7. Printed Aug. 30, 2016. 1 page.
GeneAnnot website. Probesets for MET. Printed Aug. 30, 2016. 1 page.
GeneAnnot website. Probesets for NTRK2. Printed Aug. 30, 2016. 1 page.
GeneAnnot website. Probesets for NTRK3. Printed Aug. 30, 2016. 2 pages.
GeneAnnot website. Probesets for PIK3CA. Printed Aug. 30, 2016. 1 page.
GeneAnnot website. Probesets for PPARGC1A. Printed Aug. 30, 2016. 1 page.
GeneAnnot website. Probesets for PROS1. Printed Nov. 8, 2016. 1 page.
GeneAnnot website. Probesets for PTEN. Printed Aug. 30, 2016. 2 pages.
GeneAnnot website. Probesets for PTH. Printed Aug. 30, 2016. 1 page.
GeneAnnot website. Probesets for RASA1. Printed Aug. 30, 2016. 1 page.
GeneAnnot website. Probesets for RET. Printed Aug. 30, 2016. 1 page.
GeneAnnot website. Probesets for RXRG. Printed Nov. 8, 2016. 1 page.
GeneAnnot website. Probesets for TP53. Printed Aug. 30, 2016. 1 page.
GeneAnnot website. Probesets for TSHR. Printed Aug. 30, 2016. 1 page.
GeneAnnot website. Probesets for TTF1. Printed Aug. 30, 2016. 1 page.
Geraghty et al. CT-guided transthoracic needle aspiration biopsy of pulmonary nodules: Needle size and pneumothorax rate 1. Radiology. Nov. 2003;229(2):475-81.
Gereben et al. Pretranslational regulation of type 2 deiodinase. Thyroid. 2005;15(8):855-64.
Gerstung, et al. Combining gene mutation with gene expression data improves outcome prediction in myelodysplastic syndromes. Nat Commun. Jan. 9, 2015;6:5901.
Gildea et al. Electromagnetic navigation diagnostic bronchoscopy: a prospective study. American Journal of Respiratory and Critical Care Medicine. Nov. 2006; 174(9):982-989.
Gill, et al. Nucleic acid isothermal amplification technologies: a review. Nucleosides Nucleotides Nucleic Acids. Mar. 2008;27(3):224-43.
Giordano et al. Delineation, functional validation, and bioinformatic evaluation of gene expression in thyroid follicular carcinomas with the PAX8-PPARG translocation. Clin Cancer Res. 2006;12(7 Pt 1):1983-93.
Giordano et al. Distinct transcriptional profiles of adrenocortical tumors uncovered by DNA microarray analysis. Am J Pathol. 2003;162(2):521-31.
Giordano et al. Organ-specific molecular classification of primary lung, colon, and ovarian adenocarcinomas using gene expression profiles. Am J Pathol. 2001;159(4):1231-8.
Giordano. Genome-wide studies in thyroid neoplasia. Endocrinol Metab Clin North Am. 2008;37(2):311-31, vii-viii.
Golub, et al. Molecular classification of cancer: Discovery and class prediction by gene expression monitoring. Science, 286, 531-537, 1999.
Gombos, et al. Characterization of microarray gene expression profiles of early stage thyroid tumours. Cancer Genomics Proteomics. Nov.-Dec. 2007;4(6):403-9.
Gonzalez-Campora et al. Blood group antigens in differentiated thyroid neoplasms. Arch Pathol Lab Med. 1998;122(11):957-65.
Gorringe, et al., Loss of Heterozygosity. eLS, 2016; 1-8.
Gould et al. (1987). Synaptophysin expression in neuroendocrine neoplasms as determined by immunocytochemistry. Am J Pathol. 126(2):243-57.
Gould et al. A clinical model to estimate the pretest probability of lung cancer in patients with solitary pulmonary nodules. Chest Journal (2007); 131.2: 383-388.

(56) References Cited

OTHER PUBLICATIONS

Gould et al. Evaluation of individuals with pulmonary nodules: When is it lung cancer?: Diagnosis and management of lung cancer: American College of Chest Physicians evidence-based clinical practice guidelines. Chest Journal (2013); 143.5_suppl: e93S-e120S.
Gould et al. Recent trends in the identification of incidental pulmonary nodules. Am J Respir Crit Care Med. Nov. 15, 2015;192(10):1208-14.
Gower A C et al: "Transcriptomic studies of the airway field of injury associated with smoking-related lung disease", Proceedings of the American Thoracic Society May 1, 2011 American Thoracic Society USA, val. 8, No. 2, May 1, 2011 (May 1, 2011 ), pp. 173-179.
Greenbaum, et al. Comparing protein abundance and mRNA expression levels on a genomic scale. Genome Biol. 2003;4(9):117. Epub Aug. 29, 2003.
Greenbaum, et al. Interrelating different types of genomic data, from proteome to secretome: 'oming in on function. Genome Res. Sep. 2001;11(9):1463-8.
Greenlee et al. Cancer Statistics, 2001. CA Cancer J Clin; 51(1):15-36 (2001).
Grepmeier et al. Deletions at chromosome 2q and 12p are early frequent molecular alterations in bronchial epithelium and NSCLC of long-term smokers. Int J Oncol., 27(2):481-8(2005).
Griffith, et al. Biomarker panel diagnosis of thyroid cancer: a critical review. Expert Rev Anticancer Ther. Sep. 2008;8(9):1399-413.
Griffith et al. Meta-analysis and meta-review of thyroid cancer gene expression profiling studies identifies important diagnostic biomarkers. J Clin Oncol. 2006;24(31):5043-51.
Grogan et al. Thoracic operations for pulmonary nodules are frequently not futile in patients with benign disease. Journal of Thoracic Oncology (2011); 6.10: 1720-1725.
Guajardo et al. Altered gene expression profiles in nasal respiratory epithelium reflect stable versus actue childhood asthma. J. Allergy Clin Immunol; 115(2): 243-251 (2005).
Guatelli et al. Isothermal, in vitro amplification of nucleic acids by a multienzyme reaction modeled after retroviral replication. PNAS USA 87(5):1874-1878 (1990).
Gulati, Mridu. Diagnostic assessment of patients with interstitial lung disease. Prim Care Respir J. Jun. 2011;20(2):120-7.
Gurney, JW. Determining the likelihood of malignancy in solitary pulmonary nodules with Bayesian analysis Part 1 Theory. Radiology 1993;186:405-13 (2005).
Gustafson et al. Airway PI3K Pathway Activation Is an Early and Reversible Even in Lung Cancer Development. <www.sciencetransmlationmedicine.org>. 2(26) (2010).</www.sciencetransmlationmedicine.org>.
Ha et al. Localized non-Hodgkin lymphoma involving the thyroid gland. Cancer91.4 (2001): 629-635.
Hackett, et al., The Human Airway epithelial basal cell transcriptome, Plos One, 2011; 6(5): e18378 pp. 1-22.
Hackett et al. Variability of antioxidant-related gene expression in the airway epithelium of cigarette smokers. Am J Respir Cell Mol Biol., 29: 331-43 (Apr. 2003).
Hadd, et al. Targeted, high-depth, next-generation sequencing of cancer genes in formalin-fixed, paraffin-embedded and fine-needle aspiration tumor specimens. J Mol Diagn. Mar. 2013;15(2):234-47. doi: 10.1016/j.jmoldx.2012.11.006. Epub Jan. 13, 2013.
Hamada, et al. Diagnostic usefulness of PCR profiling of the differentially expressed marker genes in thyroid papillary carcinomas. Cancer Lett. Jun. 28, 2005;224(2):289-301. Epub Nov. 18, 2004.
Hamilton et al. Diagnosis of lung cancer in primary care: a structured review. Fam Pract. Dec. 2004;21(6):605-11.
Hanley et al. The meaning and use of the area under a receiver operating characteristic (ROC) curve. Radiology. Apr. 1982;143(1):29-36.
Harach et al. Histology of familial thyroid tumours linked to a gene mapping to chromosome 19p13.2. J Pathol. 1999;189(3):387-93.
Hartigan, et al. The dip test of unimodality. Annals of Statistics. 1985; 13(1):70-84.
Haugen, et al. Development of a novel molecular classifier to accurately identify benign thyroid nodules in patients with indeterminate FNA cytology. Abstract presented at 14th International Thyroid Congress. Sep. 15, 2010.
Haugen et al. Increased expression of genes encoding mitochondrial proteins in papillary thyroid carcinomas. Thyroid. 2003;13(7):613-20.
Hawthorn, et al. TIMP1 and SERPIN-A overexpression and TFF3 and CRABP1 underexpression as biomarkers for papillary thyroid carcinoma. Head Neck. Dec. 2004;26(12):1069-83.
He, et al. A susceptibility locus for papillary thyroid carcinoma on chromosome 8q24. Cancer Res. Jan. 15, 2009;69(2):625-31.
He et al. The role of microRNA genes in papillary thyroid carcinoma. Proc Natl Acad Sci USA. 2005;102(52):19075-80.
Hecht, SS. Tobacco carcinogens, their biomarkers and tobacco-induced cancer. Nature Review Cancer; 3:733-744 (Oct. 2003).
Hellmann et al. Gene Expression Profiling of Cultured Human Bronchia Epithelial and Lung Cacinoma Cells. Toxicological Sciences, 61: 154-163 (2001).
Hellwig, et al. Comparison of scores for bimodality of gene expression distributions and genome-wide evaluation of the prognostic relevance of high-scoring genes. BMC Bioinformatics. May 25, 2010;11:276. doi: 10.1186/1471-2105-11-276.
Hemmer et al. Comparison of benign and malignant follicular thyroid tumours by comparative genomic hybridization. Br J Cancer. 1998;78(8):1012-7.
Hemmer, et al. DNA copy number changes in thyroid carcinoma. Am J Pathol. May 1999;154(5):1539-47.
Hennessy et al. Exploiting the PI3KAKT Pathway for Cancer Drug Discovery Nature vol. 4:988-1004 (2005).
Heuer et al. Different cytokine mRNA profiles in Graves' disease, Hashimoto's thyroiditis, and nonautoimmune thyroid disorders determined by quantitative reverse transcriptase polymerase chain reaction (RT-PCR). Thyroid. 1996;6(2):97-106.
Hindiyeh et al. Evaluation of a Multiplex Real-Time Reverse Transcriptase PCR Assay for Detection and Differentiation of Influenza Viruses A and B during the 2001-2002 Influenza Season in Israel. Journal of Clinical Microbiology, 2005, 43(2):589-595. doi: 10.1128/JCM.43.2.589-595.2005.
Hirsch et al. Early Detection of Lung Cancer: Clinical Perspectives of Recent Advances in Biology and Radiology. Clinical Cancer Research (7): 5-22 (2001).
Hodnett et al. Fibrosing interstitial lung disease: a practical HRCT based approach to diagnosis and management and review of the literature. Am J Respir Crit Care Med (2013); 188.2: 141-149.
Holden et al. Tyrosine kinase activating mutations in human malignancies: implications for diagnostic pathology. Exp Mol Pathol. 2008; 85(1):68-75.
Holland, et al., Detection of specific polymerase chain reaction product by utilizing the 5' to 3' exonuclease activity of Thermus aquaticus DNA polymerase. PNAS (USA) 88:7276-7280, 1991.
Hoshikawa, et al. Hypoxia induces different genes in the lungs of rats compared with mice. Physiol Genomics. Feb. 6, 2003;12(3):209-19.
Hou et al. Genetic alterations and their relationship in the phosphatidylinositol 3-kinase/Akt pathway in thyroid cancer. Clin Cancer Res. 2007;13(4):1161-70.
Howlader et al. SEER stat fact sheets: lung and bronchus cancer. Bethesda: National Cancer Institute (2011).http://seer.cancer.gov/statfacts/html/lungb.html [Downloaded Oct. 18, 2016], 9 pages.
Hsu et al. Characterization of a novel tripartite nuclear localization sequence in the EGFR family. J Biol Chem. 2007;282(14):10432-40.
Hsu et al. Overexpression of dihydrodiol dehydrogenase as a prognostic marker of non-small cell lung cancer. Cancer research, Mar. 2001; 61(6): 2727-2731.
Huang et al. A genome-wide approach to identify genetic variants that contribute to etoposide-induced cytotoxicity. Proc Natl Acad Sci USA. 2007;104(23):9758-63.
Huang et al. A tool for RNA sequencing sample identity check. Bioinformatics 29.11 (2013): 1463-1464.

(56) References Cited

OTHER PUBLICATIONS

Huang et al. Gene expression in papillary thyroid carcinoma reveals highly consistent profiles. Proc Natl Acad Sci USA. 2001;98(26):15044-9.
Huang et al. Systematic and integrative analysis of large gene lists using DAVID bioinformatics resources. Nature protocols 4:44-57 (2009).
Hummert et al. Creation and Comparison of Different Chip Definition Files for Affymetrix Microarrays. Proceedings of the International Conference on Bioinformatics and Computational Biology. BioComp'11, Jul. 18-21, 2011, Las Vegas, USA, 1(1): 16-22.
Hunt, et al. A microdissection and molecular genotyping assay to confirm the identity of tissue floaters in paraffin-embedded tissue blocks Arch Pathol Lab Med. 2003; 127(2):213-217.
Hviid et al. HLA-G polymorphisms and HLA-G expression in sarcoidosis. Sarcoidosis, vasculitis, and diffuse lung diseases: official journal of WASOG/World Association of Sarcoidosis and Other Granulomatous Disorders (Mar. 23, 2006); 23.1: 30-37.
Ikeda et al. Malignancy associated changes in bronchial epithelial cells and clinical application as a biomarker. Lung Cancer, 19(3): 161-166 (1998).
Imelfort et al. De novo sequencing of plant genomes using second-generation technologies. Briefings in Bioinformatics (2009); 10.6: 609-618.
Inaji et al. Demonstration and diagnostic significance of pro-gastrin-releasing peptide in medullary thyroid carcinoma. Oncology. 2000;59(2):122-5.
International search report and written opinion dated Jan. 19, 2012 for PCT Application No. US2011/36143.
International search report and written opinion dated Feb. 25, 2011 for PCT Application No. US2010/034140.
International search report and written opinion dated Feb. 25, 2013 for PCT Application No. US2012/068804.
International search report and written opinion dated Apr. 17, 2015 for PCT/US2014/026411.
International search report and written opinion dated May 8, 2013 for PCT Application No. US2012/068587.
International Search Report and Written Opinion dated Nov. 18, 2013 for International PCT Patent Application No. PCT/CA2013/050686.
International Search Report dated Aug. 28, 2014 for International PCT Patent Application No. PCT/US2014/025715.
International search report dated Jul. 29, 2010 for PCT Application No. US2009/06162.
International Search Report for PCT/CA2010/000266, mailed Jul. 12, 2010.
International Search Report for PCT/CA2010/000621, completed Jul. 14, 2010.
International search report with written opinion dated Apr. 4, 2017 for PCT/US2016/053578.
International search report with written opinion dated Jun. 2, 2016 for PCT/US2016/020583.
Irizarry, et al. Exploration, normalization, and summaries of high density oligonucleotide array probe level data. Biostatistics. Apr. 2003;4(2):249-64.
Irizarry et al. Summaries of Affymetrix GeneChip probe level data. Nucleic Acids Res 31(4):e15 (Feb. 2003).
Ito, et al. Distant and lymph node metastases of thyroid nodules with no pathological evidence of malignancy: a limitation of pathological examination. Endocr J. Oct. 2008; 55(5):889-94. Epub Jun. 14, 2008.
Ito et al. Simultaneous expression of keratan sulphate epitope (a sulphated poly-N-acetyllactosamine) and blood group ABH antigens in papillary carcinoma of the human thyroid gland. Histochem J. 1996;28(9):613-23.
Ivana et al. Expression of cilium-associated genes defines novel molecular subtypes of idiopathic pulmonary fibrosis. Thorax(2013): thoraxjnl-2012.

Ivana et al. Gene expression profiling of familial and sporadic interstitial pneumonia. American journal of respiratory and critical care medicine 175.1 (2007): 45-54.
Jacques et al. Two-step differential expression analysis reveals a new set of genes involved in thyroid oncocytic tumors. J Clin Endocrinol Metab. 2005;90(4):2314-20.
Jang et al. Activation of melanoma antigen tumor antigens occurs early in lung carcinogenesis. Cancer Research 61: 7959-7963 (2001).
Jarzab et al. Gene Expression Profile of Papillary Thyroid Cancer: Sources of Variability and Diagnostic Implications. Cancer Res. 2005;65(4):1587-1597.
Jazdzewski et al. Common SNP in pre-miR-146a decreases mature miR expression and predisposes to papillary thyroid carcinoma. Proc Natl Acad Sci USA. 2008;105(20):7269-74.
Ji et al., Long-term impact of initial surgical and medical therapy on young patients with papillary thyroid cancer and bilateral cervical metastases. Chinese Medical Journal, 2008; 121 (1) :63-66.
Jin et al. The Cystic fibrosis transmembrane conductance regulator as a biomarker in non-small cell lung cancer. International Journal of Oncology, 2015; 46: 2107-2115.
Jo, et al. Influence of the BRAF V600E mutation on expression of vascular endothelial growth factor in papillary thyroid cancer. J Clin Endocrinol Metab. Sep. 2006;91(9):3667-70. Epub Jun. 13, 2006.
Johansson, et al. Confirmation of a BRAF mutation-associated gene expression signature in melanoma. Pigment Cell Res. Jun. 2007;20(3):216-21.
Johnson et al. Adjusting batch effects in microarray expression data using empirical Bayes methods. Biostatistics (2007); 8.1: 118-127.
Jones et al., Value and accuracy of cytology in addition to histology in the diagnosis of lung cancer at flexible bronchoscopy. Respiratory Medicine, 2001; 95: 374-378.
Jonigk et al. Molecular profiling in lung biopsies of human pulmonary allografts to predict chronic lung allograft dysfunction. The American Journal of Pathology (2015); 185.12: 3178-3188.
Joseph et al. Lack of mutations in the thyroid hormone receptor (TR) alpha and beta genes but frequent hypermethylation of the TRbeta gene in differentiated thyroid tumors. J Clin Endocrinol Metab. 2007;92(12):4766-70.
Joshua D Campbell et al: "A gene expression signature of emphysema-related lung destruction and its reversal by the tripeptide GHK", Genome Med, Biomed Central L To, London, UK, vol. 4, No. 8, Aug. 31, 2012 (Aug. 31, 2012 ), p. 67.
Jovanovic et al. Most multifocal papillary thyroid carcinomas acquire genetic and morphotype diversity through subclonal evolution following the intra-glandular spread of the initial neoplastic clone. J Pathol. 2008;215(2):145-54.
Jun et al. Detecting and estimating contamination of human DNA samples in sequencing and array-based genotype data. The American Journal of Human Genetics 91.5 (2012): 839-848.
Jung et al., Expression of MAGE and GAGE genes in the bronchogenic cancer tissues obtained by bronchoscopy. Korean journal of medicine, 2002, 62(1): 58-68.
Kadara et al. Transcriptomic architecture of the adjacent airway field cancerization in non-small cell lung cancer. Journal of the National Cancer Institute (2014); 106.3: dju004.
Kakudo et al. Immunohistochemical study of substance P-like immunoreactivity in human thyroid and medullary carcinoma of the thyroid. J Submicrosc Cytol. 1983;15(2):563-8.
Kanehisa. Use of statistical criteria for screening potential homologies in nucleic acid sequences. Nucleic Acids Res. Jan. 11, 1984;12(1 Pt 1):203-13.
Kang et al. High prevalence of RET, RAS, and ERK expression in Hashimoto's thyroiditis and in papillary thyroid carcinoma in the Korean population. Thyroid. 2007; 17(11):1031-8.
Kannengiesser, et al. Gene expression signature associated with BRAF mutations in human primary cutaneous melanomas. Mol Oncol. Apr. 2008;1(4):425-30. doi: 10.1016/j.molonc.2008.01.002. Epub Jan. 12, 2008.
Kanner et al. Effects of randomized assignment to a smoking cessation intervention and changes in smoking habits on respiratory symptoms in smokers with early chronic obstructive pulmonary disease: the lung health study. American Journal of Medicine; 106:410-416 (1999).

(56) References Cited

OTHER PUBLICATIONS

Kao, et al. Tumor-associated Antigen L6 and the Invasion of Human Lung Cancer Cells. Clin Cancer Res. 9:2807-2816 (Jul. 2003).
Kapadia, et al. Malignant lymphoma of the thyroid gland: a clinicopathologic study. Head Neck Surg. Mar.-Apr. 1982;4(4):270-80.
Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.
Katoh et al. Thyroid transcription factor-1 in normal, hyperplastic, and neoplastic follicular thyroid cells examined by immunohistochemistry and nonradioactive in situ hybridization. Mod Pathol. 2000;13(5):570-6.
Katz et al. Automated detection of genetic abnormalities combined with cytology in sputum is a sensitive predictor of lung cancer. Modern Pathology;21:950-960 (2008).
Katzenstein, Anna-Luise A. Smoking-related interstitial fibrosis (SRIF), pathogenesis and treatment of usual interstitial pneumonia (UIP), and transbronchial biopsy in UIP. Modern Pathology (2012); 25: S68-S78.
Katzenstein et al. Diagnosis of usual interstitial pneumonia and distinction from other fibrosing interstitial lung diseases. Erratum to Diagnosis of usual interstitial pneumonia and distinction from other fibrosing interstitial lung diseases. [Hum Pathol (2008); 39: 1275-1294]. Human Pathology (2008); 39.11: 1562-1581.
Katzenstein et al. Idiopathic Pulmonary Fibrosis. Am J Respir Crit Care Med (1998); 157: 1301-1315.
Katzenstein et al. Usual interstitial pneumonia: histologic study of biopsy and explant specimens. The American Journal of Surgical Pathology (2002); 26.12: 1567-1577.
Kauffmann et al. arrayQualityMetrics—a bioconductor package for quality assessment of microarray data. Bioinformatics (2009); 25.3: 415-416.
Kawai, et al. Recent Advances of DNA chip application. Latest Situation in DNA Chip Applications. English Translation. Protein Nucleic Acid and Enzyme, Aug. 1, 2000, vol. 45, No. 11, p. 47-53.
Kazemi-Noureini et al. Differential gene expression between squamous cell carcinoma of esophageus and its normal epithelium; altered pattern of mal, akrlc2, and rab11a expression. World J Gastroenterol. Jun. 15, 2004; 10(12): 1716-1721.
Kebebew et al. Diagnostic and extent of disease multigene assay for malignant thyroid neoplasms. Cancer. 2006;106(12):2592-7.
Kebebew et al. Diagnostic and prognostic value of angiogenesis-modulating genes in malignant thyroid neoplasms. Surgery. Dec. 2005;138(6):1102-9; discussion 1109-10.
Kebebew, et al. The prevalence and prognostic value of BRAF mutation in thyroid cancer. Ann Surg. Sep. 2007;246(3):466-70; discussion 470-1.
Key, Objective cough frequency in Idiopathic Pulomnary Fibrosis, Cough, 6:4, pp. 1-7, 2010. (Year: 2010).
Khan et al. Classification and Diagnostic Prediction of Cancers Using Gene Expression Profiling and Artificial Neural Networks. Nature Medicine, 7(6):673-679, (Jun. 2001).
Kim, et al., Classification of usual interstitial pneumonia in patients with interstitial lung disease: Assessment of a machine learning approach using high-dimensional transcriptional data. The Lancet respiratory medicine, elsevier oxford, Jun. 2015; 3(6): 473-482.
Kim et al. Identification of bronchioalveolar stem cells in normal lung and lung cancer. Cell (2005); 121.6: 823-835.
King et al. Idiopathic pulmonary fibrosis. The Lancet (2011); 378.9807: 1949-1961.
King Jr. et al. A phase 3 trial of pirfenidone in patients with idiopathic pulmonary fibrosis. N Engl J Med. May 29, 2014;370(22):2083-92.
King, T.E., Clinical advances in the diagnosis and therapy of the interstitial lung diseases. Am J Resp. Crit care med. vol. 172; 2005: 268-279.

Kiss, et al. Anatomisk Atlas over Manniskokroppen, band II. Natur och Kultur Stockholm, Stockholm, Sweden ISBN: 91-27-67278-6; 1973.
Kitahara et al. Alternations of Gene Expression during Colorectal Carcinogenesis Revealed by cDNA Microarrays after Laser-Capture Microdissection of Tumor Tissues and Normal Epithelia. Cancer Research, 61: 3544-3549 (May 1, 2001).
Knudsen et al. Ri antibodies in patients with breast, ovarian or small cell lung cancer determined by a sensitive immunoprecipitation technique. Cancer Immunology Immunotherapy 55.10 (Jan. 2006): 1280-1284.
Kocarnik et al. Replication of Associations Between GWAS SNPs and Melanoma Risk in the Population Architecture Using Genomics and Epidemiology (PAGE) Study. Journal of Investigative Dermatology, 134:2049-2052, (Feb. 27, 2014).
Konishi, Gene Expression Profiles of Acute Exacerbations of Idiopathic Pulmonary Fibrosis, Am J Respir Crit Care Med, 180, 167-175, 2009. (Year: 2009).
Korn et al., Glucocorticoid receptor mRNA levels in bronchial epithelial cells of patients with COPD: influence of glucocorticoids. Respiratory Medicine, 1998; 92: 1102-1109.
Koshkin et al. LNA (locked nucleic acids): An RNA mimic forming exceedingly stable LNA: LNA duplexes. J Am Chem Soc 120:13252-13253 (1998).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kraft et al. Expression of epithelial markers in nocturnal asthma. Journal of Allergy and Clinical Immunology, 102(3): 376-381 (1998).
Krause, et al. Characterisation of DEHAL1 expression in thyroid pathologies. Eur J Endocrinol. Mar. 2007; 156(3):295-301.
Krawczak, et al. The mutational spectrum of single base-pair substitutions in mRNA splice junctions of human genes: causes and consequences. Hum Genet. Sep. 1992-Oct. 90(1-2):41-54.
Kreula, et al. Sample size in fine needle aspiration biopsy. Br J Surg. Dec. 1989;76(12):1270-2.
Kristensen, et al. Genetic variation in putative regulatory loci controlling gene expression in breast cancer. Proc Natl Acad Sci U S A. May 16, 2006;103(20):7735-40. Epub May 9, 2006.
Kroese et al. Genetic tests and their evaluation: Can we answer the key questions? Genetics in Medicine 6:475-480 (2004).
Kroschwitz. The Concise Encyclopedia Of Polymer Science And Engineering. (pp. 858-859) (1990).
Kumar, et al. The first analogues of LNA (locked nucleic acids): phosphorothioate-LNA and 2'-thio-LNA. Bioorg Med Chem Lett. Aug. 18, 1998;8(16):2219-22.
Kuriakose et al. Selection and validation of differentially expressed genes in head and neck cancer. Cellular and Molecular Life Sciences CMLS 61. (11):1372-83, Jul. 2004.
Kwan, et al. Heritability of alternative splicing in the human genome. Genome Res. Aug. 2007;17(8):1210-8.
Kwoh et al. Transcription-based amplification system and detection of amplified human immunodeficiency virus type 1 with a bead-based sandwich hybridization format. PNAS USA 86(4):1173-1177 (1989).
Lacobuzio-Donahue et al., Highly Expressed Genes in Pancreatic Ductal Adenocarcinomas: A Comprehensive Characterization and Comparison of the Transcription Profiles Obtained from Three Major Technologies. Cancer Research, Dec. 2003; 63: 8614-8622.
Lacroix, et al. PAX8 and peroxisome proliferator-activated receptor gamma 1 gene expression status in benign and malignant thyroid tissues. Eur J Endocrinol. Sep. 2004;151(3):367-74.
Lacroix et al. Sensitive Detection of Rare Cancer Cell in Sputum and Peripheral Blood Samples of Patients with Lunch Cancer by Preprogrp-Specific TR-PCR. Int. J. Cancer, vol. 92: 1-8 (2001).
Lam et al. A Phase I Study of myo-Inositol for Lung Cancer Chemoprevention. Cancer Epidemiology, Biomarkers & Prevention 15(8): 1526-1531 (Aug. 2006).
Lampe et al. Signatures of environmental exposures using peripheral leukocyte gene expression: tobacco smoke. Cancer Epidemiology Biomarkers & Prevention (2004); 13.3: 445-453.

(56) References Cited

OTHER PUBLICATIONS

Landegren, et al., A ligase-mediated gene detection technique. Science. Aug. 26, 1988;241(4869):1077-80.

Lander, et al. Initial sequencing and analysis of the human genome. Nature, 409 (Feb. 15, 2001): 860-921.

Langford et al. Is the Property of Being Positively Correlated Transitive. The American Statistician. 55(4):322-325 (2001).

Lau et al. Thyroid transcription factor-1: a review. Appl Immunohistochem Mol Morphol. 2002;10(2):97-102.

Lauter et al. Mutational analysis of CDKN1B, a candidate tumor-suppressor gene, in refractory secondary/tertiary hyperparathyroidism. Kidney Int. 2008;73(10):1137-40.

Lee, et al., Expression of mRNA of Trefoil Factor Peptides in Human Nasal Mucosa. Acta Oto-Laryngologica. 2001;121(7):849-853.

Lee et al. NGSCheckMate: software for validating sample identity in next-generation sequencing studies within and across data types. Nucleic acids research 45.11 (2017).

Lewis et al. Cotinine levels and self-reported smoking status in patients attending a bronchoscopy clinic. Biomarkers (2003); 8.3-4: 218-228.

Li et al. Gene expression profiling in human lung fibroblast following cadmium exposure. Food and Chemical Toxicology (2008); 46.3: 1131-1137.

Li, Lexin. Survival prediction of diffuse large-B-cell lymphoma based on both clinical and gene expression information. Bioinformatics 2006; 22:466-71, (Feb. 2006).

Li, X et al. American Journal of Respiratory and Critical Care Medicine 183(1 Supp.): abstract A6176 (May 1, 2011) (3 pages).

Liao et al. Expression and significance of PTEN/PI3K signal transduction-related proteins in nonsmall cell lung cancer. Ai Zheng 25: 10, p. 1238-42. Abstract (Oct. 2006).

Lima et al. Thyroid Peroxidase and Thyroglobulin Expression in Normal Human Thyroid Glands. Endocr Pathol. 1998;9(1):333-338.

Lin et al. Effects of Dexamethasone on Acute Lung Injury Rat Cells Signal Transduction Systems ERK and P13-K. Medical Journal of Chinese People's Liberation Army 6(31): 592-594 (Sep. 2006).

Lin et al. Expression of sodium iodide symporter in benign and malignant human thyroid tissues. Endocr Pathol. 2001;12(1):15-21.

Lin, et al. Thyroid ultrasonography with fine-needle aspiration cytology for the diagnosis of thyroid cancer. J Clin Ultrasound. Mar.-Apr. 1997;25(3):111-8.

Liu et al. An oligonucleotide microchip for genome-wide microRNA profiling in human and mouse tissues. Proc Natl Acad Sci USA, 2004, 101(26):9740-9744.

Liu et al. Effects of physiological versus pharmacological g-carotene supplementation on cell proliferation and histopathological changes in the lungs of cigarette smoke-exposed ferrets. Carcinogenesis, 21: 2245-2253 (2000).

Liu et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab. 2008;93(8):3106-16.

Liu, et al. Quantitative Proteome Analysis Reveals Annexin A3 as a Novel Biomarker in Lung Adenocarcinoma. Journal of Pathology, 217: 54-64 (2009).

Lockstone et al. Gene set analysis of lung samples provides insight into pathogenesis of progressive, fibrotic pulmonary sarcoidosis. American Journal of Respiratory and Critical Care Medicine (2010); 181.12: 1367-1375.

Love, et al. Moderated estimation of fold change and dispersion for RNA-seq data with DESeq2. Genome Biol. Dec. 5, 2014;15(12):550.

Lubitz et al. 2006;Microarray analysis of thyroid nodule fine-needle aspirates accurately classifies benign and malignant lesions. J Mol Diagn. 8(4):490-8; quiz 528.

Lubitz et al. Molecular analysis of minimally invasive follicular carcinomas by gene profiling. Surgery. 2005;138(6):1042-8; discussion 1048-9.

Lucentini, J. Gene Association Studies Typically Wrong. The Scientist, 18(24):20 (2004).

Lui et al. 2008;CREB3L2-PPARgamma fusion mutation identifies a thyroid signaling pathway regulated by intramembrane proteolysis. Cancer Res. 68(17):7156-64.

Machens et al. Genotype-phenotype based surgical concept of hereditary medullary thyroid carcinoma. World J Surg. 2007;31(5):957-68.

MacKay, et al. Targeting the protein kinase C family: are we there yet? Nature Reviews Cancer. 7(7):554-62 (Jul. 1, 2007).

MacMahon et al. Guidelines for management of small pulmonary nodules detected on CT scans: a statement from the Fleischner Society 1. Radiology (2005); 237.2: 395-400.

Mak (Thesis: "Expression of CFTR mRNA Epithelium and Vas Deferens", 1997, Univ of Toronto).

Manichaikul, et al. Robust relationship inference in genome-wide association studies. Bioinformatics. Nov. 15, 2010;26(22):2867-73. Epub Oct. 5, 2010.

Mannino et al. Low lung function and incident lung cancer in the United States: data From the First National Health and Nutrition Examination Survey follow-up. Arch Intern Med. 163(12):1475-80 (Jun. 23, 2003).

Margulies, et al. Genome sequencing in microfabricated high-density picolitre reactors. Nature. Sep. 15, 2005;437(7057):376-80. Epub Jul. 31, 2005.

Mariani Thomas J et al: "Molecular markers for quantitative and discrete COPD phenotypes", The Faseb Journal, Federation of American Societies for Experimental Biology, US, vol. 21, No. 5, Apr. 1, 2007 (Apr. 1, 2007 ), p. A8.

Marinov et al. Targeting mTOR signaling in lung cancer. Critical Reviews in Oncology/Hematology 63: 172-182 (Aug. 2007).

Marsh, et al. Genome-wide copy number imbalances identified in familial and sporadic medullary thyroid carcinoma. J Clin Endocrinol Metab. Apr. 2003;88(4):1866-72.

Martin. A New Access to 2'-O-Alkylated Ribonucleosides and Properties of 2'-O-Alkylated Oligoribonucleotides. Helv. Chim. Acta. 1995; 78:486-504. (in German with English abstract).

Masini-Repiso et al. Ultrastructural localization of thyroid peroxidase, hydrogen peroxide-generating sites, and monoamine oxidase in benign and malignant thyroid diseases. Hum Pathol. 2004; 35(4):436-46.

Mason, et al. Bimodal distribution of RNA expression levels in human skeletal muscle tissue. BMC Genomics. Feb. 7, 2011;12:98. doi: 10.1186/1471-2164-12-98.

Matsubayashi et al. Gastrin-releasing peptide immunoreactivity in medullary thyroid carcinoma. Cancer. 1984;53(11):2472-7.

Maximo et al. Somatic and germline mutation in GRIM-19, a dual function gene involved in mitochondrial metabolism and cell death, is linked to mitochondrion-rich (Hurthle cell) tumours of the thyroid. Br J Cancer. 2005;92(10):1892-8.

May et al., How Many Species Are There on Earth? Science, 1988; vol. 241: p. 1441.

May, Robert M. How Many Species Are There on Earth? Science, 241: 1141-1449 (1988).

Mazzanti, et al. Using gene expression profiling to differentiate benign versus malignant thyroid tumors. Cancer Res. Apr. 15, 2004;64(8):2898-903.

McCarroll, et al. Integrated detection and population-genetic analysis of SNPs and copy number variation. Nature Genetics 40, 1166-1174 (2008).

McWilliams et al. Probability of cancer in pulmonary nodules detected on first screening CT. New England Journal of Medicine (2013); 369.10: 910-919.

Medical News: Targeted, Oral Agent Enzastaurin Shows Favorable Results in Late-Stage Lung Cancer. (Jun. 11, 2007), Retrieved from the Internet URL: https://www.medicalnewstoday.com/releases/73761.php.

Memoli et al. Meta-analysis of guided bronchoscopy for the evaluation of the pulmonary nodule. Chest Journal (2012); 142.2: 385-393.

Merrium-Webster.com (http://www.merriam-webstercom/dictionary/questionnaire), downloaded Oct. 26, 2013.

Meyer et al. Support vector machines. The Interface to libsvm in package e1071. FH Technikum Wien, Austria (2015); pp. 1-8.

(56) References Cited

OTHER PUBLICATIONS

Mi, et al., The Panther database of protein families, subfamilies, functions and pathways, Neucleic acids research, 2005, 3: D284-88.
Michalczyk et al. Fresh and cultured buccal cells as a source of mRNA and protein for molecular analysis. Biotechniques. Aug. 2004;37(2):262-4, 266-9.
Miklos, et al. Microarray reality checks in the context of a complex disease. Nature Biotechnology, 22:5 (May 2005).
Mineva, et al. Differential expression of alphaB-crystallin and Hsp27-1 in anaplastic thyroid carcinomas because of tumor-specific alphaB-crystallin gene (CRYAB) silencing. Cell Stress Chaperones. 2005 Autumn;10(3):171-84.
Minhyeok; Lee et al, "Copy Number Variations of Chromosome 17p13.1 Might be Linked to High Risk of Lung Cancer in Heavy Smokers", Mol Biol Rep, 2011, 38, 5211-5217.
Mitomo et al. Downregulation of miR-138 is associated with overexpression of human telomerase reverse transcriptase protein in human anaplastic thyroid carcinoma cell lines. Cancer Sci. 2008;99(2):280-6.
Miura et al. Laser capture microdissection and microarray expression analysis of lung adenocarcinoma reveals tobacco smoking- and prognosis-related molecular profiles. Cancer Res., 62(11): 3244-50 (Jun. 1, 2002).
Miyamoto et al. Potential Marker of Oral Squamous Cell Carcinoma Aggressiveness Detected by Fluorescence in Situ Hybridization in Fine-Needle Aspiration Biopsies. Cancer American Cancer Society 95(10):2152-2159 (Jun. 6, 2002).
Mizukami, et al. Late bone metastasis from an encapsulated follicular carcinoma of the thyroid without capsular and vascular invasion. Pathol Int. Jun. 1996;46(6):457-61.
Modrek et al. Genome-wide detection of alternative splicing in expressed sequences of human genes. Nucleic Acids Research, 29(13): 2850-2859 (2001).
Moller et al. Altered Ratio of Endothelin ETA- and ETB Receptor mRNA in Bronchial Biopsies from Patients with Asthma and Chronic Airway Obstruction. (European Journal of Pharmacology, 1999, 365: R1-R3).
Mollerup et al. Sex Differences in Lung CYP1A1 Expression and DNA Adduct Levels among Lung Cancer Patients. Cancer Research, 1999, 59: 3317-3320 (1999).
Mongiat et al. Fibroblast Growth Factor-binding Protein Is a Novel Partner for Perlecan Protein Core. The Journal of Biological Chemistry; 276(13):10263-10271 (Mar. 30, 2001).
Montero-Conde et al. Molecular profiling related to poor prognosis in thyroid carcinoma. Combining gene expression data and biological information. Oncogene. 2008;27(11):1554-61.
Monti et al. Consensus Clustering: A Resampling-Based Method for Class Discovery and Visualization of Gene Expression Microarray Data. Machine Learning (Jul. 2003); 52(1): 91-118.
Morales et al. Accuracy of self-reported tobacco use in newly diagnosed cancer patients. Cancer Causes & Control (2013); 24.6: 1223-1230.
Moreno, et al. Mutations in the iodotyrosine deiodinase gene and hypothyroidism. N Engl J Med. Apr. 24, 2008;358(17):1811-8. doi: 10.1056/NEJMoa0706819.
Morin et al.: Profiling the HeLa S3 transcriptome using randomly primed cDNA and massively parallel short-read sequencing. Biotechniques. 45:81-94 (2008).
Morozova et al. Applications of next-generation sequencing technologies in functional genomics. Genomics (2008); 92.5: 255-264.
Murphy et al. Identification of immunohistochemical biomarkers for papillary thyroid carcinoma using gene expression profiling. Hum Pathol. 2008;39(3):420-6.
Nakano et al. Apoptosis-induced decrease of intrathyroidal CD4(+)CD25(+) regulatory T cells in autoimmune thyroid diseases. Thyroid. 2007;17(1):25-31.
Nakashima et al. Foci formation of P53-binding protein 1 in thyroid tumors: activation of genomic instability during thyroid carcinogenesis. Int J Cancer. 2008;122(5):1082-8.
Nakashima et al. RET oncogene amplification in thyroid cancer: correlations with radiation-associated and high-grade malignancy. Hum Pathol. 2007;38(4):621-8.
Nakayama et al. High molecular weight caldesmon positive stromal cells in the capsule of thyroid follicular tumours and tumour-like lesions. J Clin Pathol. 2002;55(12):917-20.
Nam, et al. BRAF V600E mutation analysis of thyroid nodules needle aspirates in relation to their ultrasongraphic classification: a potential guide for selection of samples for molecular analysis. Thyroid. Mar. 2010;20(3):273-9. doi: 10.1089/thy.2009.0226.
National Cancer Institute web page: "Common Cancer Types", captured by WayBack machine on Dec. 4, 2011, http://www.cancer.gov/cancertopics/types/commoncancers.
National Lung Screening Trial Research Team et al. Reduced lung-cancer mortality with low-dose computed tomographic screening. N Engl J Med 365:395-409 (2011).
NCBI gene report for LOC100131599. Printed Feb. 2018.
Neonakis et al. Expression of calcitonin and somatostatin peptide and mRNA in medullary thyroid carcinoma. World J Surg. 1994;18(4):588-93.
Neubauer et al. Cure of Helicobacter pylori Infection and Duration of Remission of Low-Grade Gastric Mucosa-Associated Lymphoid Tissue Lymphoma. J. Natl. Cancer Inst., 89(18): 1350-1355 (Sep. 17, 1997).
Newton et al. On Differential Variability of Expression Ratios: Improving Statistical Inference about Gene Expression Changes from Microarray Data. Journal of Computational Biology, 8: 37-52 (2001).
Nicholson et al. Inter-observer variation between pathologists in diffuse parenchymal lung disease. Thorax (2004); 59.6: 500-505.
Nicholson et al. The relationship between individual histologic features and disease progression in idiopathic pulmonary fibrosis. American Journal of Respiratory and Critical Care Medicine (2002); 166.2: 173-177.
Nielsen et al. Aquaporins in complex tissues. II. Subcellular distribution in respiratory and glandular tissues of rat. American Journal of Physiology—Cell Physiology (1997); 273.5: C1549-C1561.
Nielsen et al. Sequence-selective recognition of DNA by strand displacement with a thymine-substituted polyamide. Science 254:1497-1500 (1991).
Nikiforov et al. Impact of Mutational Testing on the Diagnosis and Management of Patients with Cytologically Indeterminate Thyroid Nodules: A Prospective Analysis of 1056 FNA Samples Journal of Clinical Endocrinology and Metabolism vol. 96, pp. 3390-3397 (Year: 2011).
Nikiforova, et al. Highly accurate diagnosis of cancer in thyroid nodules with follicular neoplasm/suspicious for a follicular neoplasm cytology by ThyroSeq v2 next-generation sequencing assay. Cancer. Dec. 1, 2014;120(23):3627-34. Epub Sep. 10, 2014.
Nikiforova et al. MicroRNA expression profiling of thyroid tumors: biological significance and diagnostic utility. J Clin Endocrinol Metab. 2008;93(5):1600-8.
Nikiforova, et al. Molecular diagnostics and predictors in thyroid cancer. Thyroid. Dec. 2009;19(12):1351-61.
Nikiforova, et al. Targeted Next-Generation Sequencing Panel (ThyroSeq) for Detection of Mutations in Thyroid Cancer. J Clin Endocrinol Metab. Nov. 2013; 98(11): E1852-E1860.
Nikolova et al. Genome-wide gene expression profiles of thyroid carcinoma: Identification of molecular targets for treatment of thyroid carcinoma. 2008; Oncol Rep. 20(1):105-21.
Noble et al. Pirfenidone in patients with idiopathic pulmonary fibrosis (Capacity): two randomised trials. 2011, Lancet, 377, 1760-69.
Non-Final Office Action for U.S. Appl. No. 15/644,721, dated Mar. 7, 2019.
Non-Final Office Action for U.S. Appl. No. 10/579,376, dated Jul. 9, 2008.
Non-Final Office Action for U.S. Appl. No. 11/294,834, dated Dec. 15, 2015.
Non-Final Office Action for U.S. Appl. No. 11/294,834, dated Jan. 29, 2014.
Non-Final Office Action for U.S. Appl. No. 11/294,834, dated Jun. 24, 2008.

(56) References Cited

OTHER PUBLICATIONS

Non-Final Office Action for U.S. Appl. No. 12/234,588, dated Jun. 27, 2011.
Non-Final Office Action for U.S. Appl. No. 12/414,555, dated Nov. 30, 2011.
Non-Final Office Action for U.S. Appl. No. 12/884,714, dated Sep. 23, 2011.
Non-Final Office Action for U.S. Appl. No. 13/323,655 dated Apr. 9, 2013.
Non-Final Office Action for U.S. Appl. No. 13/323,655, dated Nov. 7, 2013.
Non-Final Office Action for U.S. Appl. No. 13/346,444, dated Dec. 12, 2012.
Non-Final Office Action for U.S. Appl. No. 13/524,749, dated Sep. 9, 2013.
Non-Final Office Action for U.S. Appl. No. 14/584,960, dated Apr. 27, 2016.
Non-Final Office Action for U.S. Appl. No. 14/613,210, dated Dec. 6, 2016.
Non-Final Office Action for U.S. Appl. No. 15/439,891, dated Jun. 14, 2017.
Non-Final Office Action for U.S. Appl. No. 12/234,588 dated Mar. 28, 2014.
Notice of allowance dated Mar. 27, 2015 for U.S. Appl. No. 13/254,571.
Notice of Allowance dated Mar. 30, 2017 for U.S. Appl. No. 14/727,801.
Notice of Allowance dated Apr. 3, 2018 for U.S. Appl. No. 14/020,183.
Notice of allowance dated Jun. 13, 2013 for U.S. Appl. No. 12/592,065.
Notice of allowance dated Jul. 30, 2015 for U.S. Appl. No. 13/258,429.
Notice of Allowance dated Aug. 21, 2017 for U.S. Appl. No. 15/274,492.
Notice of allowance dated Sep. 13, 2016 for U.S. Appl. No. 12/964,666.
Notice of allowance dated Oct. 18, 2013 for U.S. Appl. No. 13/318,751.
Notice of allowance dated Oct. 24, 2018 for U.S. Appl. No. 15/661,496.
Notice of allowance dated Nov. 28, 2016 for U.S. Appl. No. 14/926,349.
Notice of allowance dated Sep. 13, 2018 for U.S. Appl. No. 15/851,377.
Notice of Allowance issued in U.S. Appl. No. 15/644,721, dated Sep. 30, 2020.
Notterman et al. Tumor Biology and Microarray Analysis of Solid Tumors: Colorectal Cancer as a Model System. Microarrays and Cancer Research, Warrington et al.(eds.), Eaton Publishing, Westborough, MA, pp. xi-xvi, (2002).
Nucera, et al. BRAF(V600E) mutation and the biology of papillary thyroid cancer. Endocr Relat Cancer. Mar. 2008;15(1):191-205. doi: 10.1677/ERC-07-0212.
Oerntoft, et al. Genome-wide study of gene copy numbers, transcripts, and protein levels in pairs of non-invasive and invasive human transitional cell carcinomas. Mol Cell Proteomics. Jan. 2002;1(1):37-45.
Office action dated Jan. 5, 2015 for U.S. Appl. No. 14/086,716.
Office Action dated Jan. 12, 2018 for U.S. Appl. No. 13/589,022.
Office action dated Jan. 16, 2013 for U.S. Appl. No. 12/592,065.
Office action dated Jan. 16, 2015 for U.S. Appl. No. 13/258,429.
Office action dated Jan. 16, 2018 for U.S. Appl. No. 13/105,756.
Office action dated Jan. 22, 2016 for U.S. Appl. No. 13/708,439.
Office Action dated Jan. 25, 2018 for U.S. Appl. No. 15/626,401.
Office action dated Feb. 4, 2014 for U.S. Appl. No. 13/708,439.
Office Action dated Feb. 13, 2017 for U.S. Appl. No. 15/164,241.
Office action dated Feb. 26, 2016 for U.S. Appl. No. 14/926,349.
Office action dated Feb. 27, 2015 for U.S. Appl. No. 13/710,134.
Office Action dated Mar. 2, 2018 for U.S. Appl. No. 13/589,022.
Office action dated Mar. 9, 2016 for U.S. Appl. No. 13/589,022.
Office Action dated Mar. 9, 2017 for U.S. Appl. No. 13/710,134.
Office action dated Mar. 11, 2014 for U.S. Appl. No. 13/254,571.
Office Action dated Mar. 21, 2017 for U.S. Appl. No. 15/164,217.
Office Action dated Mar. 21, 2017 for U.S. Appl. No. 15/164,230.
Office action dated Mar. 23, 2015 for U.S. Appl. No. 13/589,022.
Office Action dated Mar. 23, 2017 for U.S. Appl. No. 15/164,220.
Office Action dated Mar. 23, 2017 for U.S. Appl. No. 15/274,492.
Office action dated Mar. 27, 2018 for U.S. Appl. No. 114/153,219.
Office action dated Mar. 29, 2018 for U.S. Appl. No. 14/086,716.
Office action dated Apr. 6, 2012 for U.S. Appl. No. 12/964,666.
Office action dated Apr. 8, 2014 for U.S. Appl. No. 13/258,429.
Office action dated Apr. 18, 2013 for U.S. Appl. No. 13/318,751.
Office action dated Apr. 27, 2015 for U.S. Appl. No. 12/964,666.
Office Action dated May 5, 2017 for U.S. Appl. No. 14/020,183.
Office action dated May 8, 2014 for U.S. Appl. No. 13/105,756.
Office action dated May 9, 2016 for U.S. Appl. No. 12/964,666.
Office action dated May 16, 2016 for U.S. Appl. No. 14/153,219.
Office action dated May 27, 2015 for U.S. Appl. No. 13/105,756.
Office action dated Jun. 6, 2012 for U.S. Appl. No. 12/592,065.
Office action dated Jun. 10, 2014 for U.S. Appl. No. 13/708,439.
Office Action dated Jun. 12, 2017 for U.S. Appl. No. 13/105,756.
Office action dated Jun. 15, 2018 for U.S. Appl. No. 15/661,496.
Office action dated Jun. 15, 2018 for U.S. Appl. No. 15/851,377.
Office action dated Jun. 20, 2014 for U.S. Appl. No. 12/964,666.
Office Action dated Jun. 23, 2017 for U.S. Appl. No. 14/153,219.
Office action dated Jun. 29, 2018 for U.S. Appl. No. 15/702,126.
Office Action dated Jul. 5, 2017 for U.S. Appl. No. 14/086,716.
Office action dated Jul. 6, 2011 for U.S. Appl. No. 12/964,666.
Office action dated Jul. 10, 2014 for U.S. Appl. No. 13/589,022.
Office action dated Jul. 26, 2016 for U.S. Appl. No. 13/710,134.
Office action dated Jul. 30, 2014 for U.S. Appl. No. 13/710,134.
Office action dated Aug. 10, 2016 for U.S. Appl. No. 14/086,716.
Office Action dated Aug. 29, 2017 for U.S. Appl. No. 15/185,960.
Office action dated Sep. 2, 2015 for U.S. Appl. No. 14/086,716.
Office action dated Sep. 7, 2016 for U.S. Appl. No. 14/727,801.
Office action dated Sep. 8, 2016 for U.S. Appl. No. 15/164,241.
Office action dated Sep. 10, 2018 for U.S. Appl. No. 15/702,217.
Office action dated Sep. 11, 2012 for U.S. Appl. No. 13/318,751.
Office action dated Sep. 11, 2013 for U.S. Appl. No. 13/258,429.
Office action dated Sep. 19, 2016 for U.S. Appl. No. 15/164,217.
Office action dated Sep. 19, 2016 for U.S. Appl. No. 15/164,220.
Office action dated Sep. 19, 2016 for U.S. Appl. No. 15/164,230.
Office action dated Sep. 19, 2018 for U.S. Appl. No. 15/096,739.
"Office action dated Oct. 9, 2018 for U.S. Appl. No. 14/690,182.".
Office Action dated Oct. 12, 2017 for U.S. Appl. No. 13/589,022.
Office action dated Oct. 17, 2013 for U.S. Appl. No. 13/105,756.
Office action dated Nov. 7, 2016 for U.S. Appl. No. 13/105,756.
Office Action dated Nov. 9, 2018 for U.S. Appl. No. 14/851,864.
Office action dated Nov. 17, 2016 for U.S. Appl. No. 13/589,022.
Office action dated Nov. 18, 2016 for U.S. Appl. No. 14/153,219.
Office action dated Nov. 19, 2015 for U.S. Appl. No. 13/710,134.
Office Action dated Nov. 20, 2018 for U.S. Appl. No. 13/589,022.
Office action dated Nov. 29, 2013 for U.S. Appl. No. 13/710,134.
Office Action dated Nov. 29, 2018 for U.S. Appl. No. 15/626,401.
Office action dated Nov. 30, 2016 for U.S. Appl. No. 13/708,439.
Office action dated Dec. 4, 2014 for U.S. Appl. No. 13/254,571.
Office Action dated Dec. 12, 2018 for U.S. Appl. No. 14/086,716.
Office action dated Dec. 13, 2018 for U.S. Appl. No. 14/153,219.
Office Action dated Dec. 17, 2015 for U.S. Appl. No. 13/105,756.
Office Action dated Dec. 26, 2017 for U.S. Appl. No. 15/185,960.
Ohtsuka et al. ADAM28 is overexpressed in human non-small cell lung carcinomas and correlates with cell proliferation and lymph node metastasis. International Journal of Cancer, 118 2 : 263-273, Jan. 2006.
Okudela et al. K-ras Gene Mutation Enhances Motility of Immortalized Airway Cells and Lung Adenocarcinoma Cells Via Akt Activation: Possible Contribution to Non-Invasive Expansion of Lung Adenocarcinoma. Am J Pathol. Jan. 2004; 164(1): 91-100.
Oler, et al. Gene expression profiling of papillary thyroid carcinoma identifies transcripts correlated with BRAF mutational status and lymph node metastasis. Clin Cancer Res. Aug. 1, 2008;14(15):4735-42. doi: 10.1158/1078-0432.CCR-07-4372.

(56) References Cited

OTHER PUBLICATIONS

Ooi et al. Molecular Profiling of Premalignant Lesions in Lung Squamous Cell Carcinomas Identifies Mechanisms Involved in Stepwise Carcinogenesis. Cancer Prevention Research, 7(5):487-495, (Mar. 11, 2014).
Oshlack et al. FRom RNA-seq reads to differential expression results Genome Biology vol. 11, article 220 (Year: 201 0).
Ost et al. The solitary pulmonary nodule. New England Journal of Medicine (Jun. 19, 2003); 348.25: 2535-2542.
Oster et al. Identification and validation of highly frequent CpG island hypermethylation in colorectal adenomas and carcinomas. International Journal of Cancer (2011); 129.12: 2855-2866.
Otsubo et al. TSPAN2 is involved in cell invasion and motility during lung cancer progression. Cell Reports (2014); 7.2: 527-538.
Owens, et al. Metastatic breast carcinoma involving the thyroid gland diagnosed by fine-needle aspiration: a case report. Diagn Cytopathol. Aug. 2005;33(2):110-5.
Pallante et al. MicroRNA deregulation in human thyroid papillary carcinomas. Endocr Relat Cancer. 2006;13(2):497-508.
Panicker et al. A common variation in deiodinase 1 gene DIO1 is associated with the relative levels of free thyroxine and triiodothyronine. J Clin Endocrinol Metab. 2008;93(8):3075-81.
Pankratz, et al., Usual Interstitial pneumonia can be detected in transbronchial biopsies using machine learning. Annals of the American thoracic society, vol. 14, No. 11, Nov. 1, 2017, pp. 1646-1654.
Pankratz et al. Usual interstitial pneumonia can be detected in transbronchial biopsies using machine learning. Annals of the American Thoracic Society 14.11 (2017): 1646-1654.
Pardo et al. Up-regulation and profibrotic role of osteopontin in human idiopathic pulmonary fibrosis. PLoS Med (2005); 2.9: e251.
Pavelic, et al. Molecular genetic alterations of FHIT and p53 genes in benign and malignant thyroid gland lesions. Mutat Res. Jul. 25, 2006;599(1-2):45-57. Epub May 15, 2006.
Pavey, et al. Microarray expression profiling in melanoma reveals a BRAF mutation signature. Oncogene. May 20, 2004;23(23):4060-7.
PCT/US2004/018460 International Preliminary Report on Patentability dated Dec. 13, 2005.
PCT/US2004/018460 International Search Report dated Nov. 2, 2005.
PCT/US2004/018460 Written Opinion dated Nov. 2, 2005.
PCT/US2004/018492 International Search Report dated May 30, 2006.
PCT/US2004/018492 Written Opinion dated May 30, 2006.
PCT/US2006/014132 International Search Report dated Feb. 5, 2007.
PCT/US2007/006006 International Search Report dated Nov. 15, 2007.
PCT/US2008/077136 International Search Report dated Dec. 12, 2008.
PCT/US2012/053531 International Preliminary Report on Patentability dated Mar. 4, 2014.
PCT/US2012/053531 International Search Report dated Jan. 17, 2013.
PCT/US2012/053531 Written Opinion dated Jan. 17, 2013.
PCT/US2012/057263 International Search Report dated Apr. 5, 2013.
PCT/US2013/038449 International Search Report dated Dec. 16, 2013.
PCT/US2014/029029 International Preliminary Report on Patentability dated Sep. 15, 2015.
PCT/US2014/029029 International Search Report dated Oct. 2, 2014.
PCT/US2014/029029 Written Opinion dated Oct. 2, 2014.
PCT/US2015/040437 International Search Report dated Dec. 21, 2015.
PCT/US2015/059309 International Search Report and Written Opinion dated Mar. 11, 2016.
PCT/US2017/032517 International Search Report dated Oct. 2, 2017.
PCT/US2017/041267 International Search Report dated Dec. 15, 2017.
PCT/US2017/050358 International Search Report dated Dec. 18, 2017.
PCT/US2018/035702 International Search Report and Written Opinion dated Sep. 12, 2018.
PCT/US2018/043984 International Search Report and Written Opinion dated Jan. 21, 2019.
Peluso et al. Comparison of DNA adduct levels in nasal mucosa, lymphocytes and bronchial mucosa of cigarette smokers and interaction with metabolic gene polymorphisms. Carcinogenesis 25(12): 2459-2465 (2004).
Penland, et al. RNA expression analysis of formalin-fixed paraffin-embedded tumors. Lab Invest. Apr. 2007;87(4):383-91.
Penning et al. Genomics of smoking exposure and cessation: lessons for cancer prevention and treatment. Cancer Prevention Research (2008); 1.2: 80-83.
Perez et al. Incidence, prevalence, and clinical course of idiopathic pulmonary fibrosis: a population-based study. Chest Journal (2010); 137.1: 129-137.
Phenekos et al. Th1 and Th2 serum cytokine profiles characterize patients with Hashimoto's thyroiditis (Th1) and Graves' disease (Th2). Neuroimmunomodulation. 2004;11(4):209-13.
Pinto et al. mRNA expression of tachykinins and tachykinin receptors in different human tissues. Eur J Pharmacol. 2004;494(2-3):233-9.
Piotrowski et al. The selected genetic polymorphisms of metalloproteinases MMP2, 7, 9 and MMP inhibitor TIMP2 in sarcoidosis. Medical Science Monitor (2011); 17.10: CR598-CR607.
Pita et al. Gene expression profiling associated with the progression to poorly differentiated thyroid carcinomas. Br J Cancer. 2009;101(10):1782-1791.
Pittman et al. Integrated modeling of clinical and gene expression information for personalized prediction of disease outcomes. Proc Natl Acad Sci U S A. Jun. 1, 2004;101(22):8431-6.
Platform GPL6244 https://www.ncbi.nlm.nih.gov/geo/query/acc.cgi?acc=gp16244, Submission Date Dec. 5, 2007 [Downloaded Oct. 18, 2016], 3 pages.
Poletti et al. Invasive diagnostic techniques in idiopathic interstitial pneumonias. Respirology (2016); 21.1: 44-50.
Potti et al. A Genomic Strategy to Refine Prognosis in Early-Stage Non Small-Cell Lung Cancer. The New England Journal of Medicine 2006; 335(6):570-580 (Aug. 2006).
Potti et al. Genomic Signatures to Guide the Use of Chemotherapeutics. Nature Medicine, 12(11): 1294-1300 (Oct. 2006).
Powell et al. Gene expression in lung adenocarcinomas of smokers and nonsmokers. American Journal of Respiratory Cell and Molecular Biology, 29: 157-162 (Aug. 2003).
Powell et al. Patterns of allelic loss differ in lung adenocarcinomas of smokers and nonsmokers. Lung Cancer, 39 1 : 23-29 (2003).
Powell,et al., Loss of Heterozygosity in epithelial cells obtained by bronchial brushing: clinical utility in lung cancer. Clinical cancer research, Aug. 1999, 5: 2025-2034.
Prasad et al. Identification of genes differentially expressed in benign versus malignant thyroid tumors. Clin Cancer Res. 2008;14(11):3327-37.
Printout from database NCBIGEO accession No. GSE4115 [Online] NCB dated Feb. 27, 2006.
Proctor, RN. Tobacco and the global lung cancer epidemic. Nature Reviews Cancer, 1: 82-86 (Oct. 2001).
Puissegur et al. miR-210 is overexpressed in late stages of lung cancer and mediates mitochondrial alterations associated with modulation of HIF-1 activity. Cell Death Differ. 18(3):465-478 (2011).
Puskas, et al. Gene profiling identifies genes specific for well-differentiated epithelial thyroid tumors. Cell Mol Biol (Noisy-le-grand). Sep. 5, 2005;51(2):177-86.
Qian, et al. Renal cell carcinoma metastatic to Hurthle cell adenoma of thyroid. Ann Diagn Pathol. Oct. 2004;8(5):305-8.
"Quackenbush, et al. Microarray data normalization and transformation. Nature Genetics Supplement. Dec. 2002. vol. 32, p. 496-501".
Raghu et al. An official ATS/ERS/JRS/ALAT statement: idiopathic pulmonary fibrosis: evidence-based guidelines for diagnosis and

(56) References Cited

OTHER PUBLICATIONS management. American Journal of Respiratory and Critical Care Medicine (2011); 183.6: 788-824.
Ramaswamy, et al. "Multiclass cancer diagnosisusing tumor gene expression signatures" Proceedings of the National Academyof Sciences Dec. 2001, 98 (26) 15149-15154.
Reyes, et al. Identification of kallikrein 7, kallikrein 10 and secreted frizzled-related protein 2 as candidate molecular markers for papillary thyroid carcinoma using microarray analysis. Proc Amer Assoc Cancer Res. 2005, vol. 46, Abstract #38.
Reynolds et al. Pre-protachykinin-A mRNA is increased in the airway epithelium of smokers with chronic bronchitis. Respiratory, 6:187-197 (2001).
Richeldi et al. Efficacy and safety of nintedanib in idiopathic pulmonary fibrosis. N Engl J Med. May 29, 2014;370(22):2071-82.
Riise et al. Bronchial Brush Biopsies for Studies of Epithelial Inflammation in Stable Asthma and Nonobstructive Chronic Bronchitis. European Respiratory Journal, 9: 1665-1671 (1996).
Ringel et al. Expression of the sodium iodide symporter and thyroglobulin genes are reduced in papillary thyroid cancer. Mod Pathol. 2001;14(4):289-96.
Rivera et al. Establishing the diagnosis of lung cancer: Diagnosis and management of lung cancer: American College of Chest Physicians evidence-based clinical practice guidelines. Chest Journal 143.5_suppl (2013): e142S-e165S.
Robin et al. pROC: an open-source package for R and S+ to analyze and compare ROC curves. BMC Bioinformatics 12:77 (2011).
Robinson; et al, "A comparison of Affymetrix gene expression arrays. BMC bioinformatics 8.1 (2007): 449.".
Robinson et al. A dynamic programming approach for the alignment of signal peaks in multiple gas chromatography-mass spectrometry experiments. BMC bioinformatics 8.1 (2007): 419.
Rodrigues-Serpa, et al. Loss of heterozygosity in follicular and papillary thyroid carcinomas. Cancer Genet Cytogenet. Feb. 2003;141(1):26-31.
Ronaghi et al. Real-time DNA sequencing using detection of pyrophosphate release. Anal Biochem. 1996; 242(1):84-89.
Roque, et al. Chromosome imbalances in thyroid follicular neoplasms: a comparison between follicular adenomas and carcinomas. Genes Chromosomes Cancer. Mar. 2003;36(3):292-302.
Ros et al. Thyroid-specific Gene Expression in the Multi-Step Process of Thyroid Carcinogenesis, Biochimie, Masson, Paris, FR, vol. 81, No. 4, Apr. 1, 1999, pp. 389-396.
Rosai et al. Pitfalls in the diagnosis of thyroid neoplasms. Pathol Res Pract. 1987;182(2):169-79.
Rosen et al. A six-gene model for differentiating benign from malignant thyroid tumors on the basis of gene expression. Surgery. 2005;138(6):1050-6; discussion 1056-7.
Roura-Mir et al. Single-cell analysis of intrathyroidal lymphocytes shows differential cytokine expression in Hashimoto's and Graves' disease. Eur J Immunol. 1997;27(12):3290-302.
Rouskin et al. Genome-wide probing of RNA structure reveals active unfolding of mRNA structures in vivo. Nature. Jan. 30, 2014;505(7485):701-5.
Rowe et al. Utility of BRAF V600E Mutation Detection in Cytologically Indeterminate Thyroid Nodules. CytoJoural 3(10):1-10 (Apr. 2006).
Rusznak et al. Effect of Cigarette Smoke on the Permeability and IL-1B and sICAM-1 Release from Cultured Human Bronchial Epithelial Cells of Never-Smokers, Smokers, and Patients with Chronic Obstructive Pulmonary Disease. Am. J. Respir. Cell Mol. Biol., 23:530-536 (2000).
Saal et al. Poor Prognosis in Carcinoma is Associated with A Gene Expression Signature of Aberrant PTEN Tumor Suppressor Pathway Activitiy. PNAS 104(18):7564-7569 (2007).
Sabo-Attwood, et al. Gene Expression Profiles Reveal Increased mClca3 (Gob5) Expression and Mucin Production in a Murine Model of Asbestos-Induced Fibrogenesis. American Journal of Pathology. vol. 167 No. 5; Nov. 2005: pp. 1243-1256.
Saeys, et al. A review of feature selection techniques in bioinformatics. Bioinformatics. Oct. 1, 2007;23(19):2507-17. Epub Aug. 24, 2007.
Saheki et al. Pathogenesis and pathophysiology of citrin (a mitochondrial aspartate glutamate carrier) deficiency. Metabolic Brain Disease; 17(4):335-346 (Dec. 2002).
Saito-Hisaminato et al. Genome-Wide Profiling of Gene Expression in 29 Normal Human Tissues with a cNDA Microarray. DNA Research, 2002, 9:35-45.
Saiz et al. Immunohistochemical expression of cyclin D1, E2F-1, and Ki-67 in benign and malignant thyroid lesions. J Pathol. 2002;198(2):157-62.
Salemi et al. Cerebellar degeneration-related autoantigen 1 (CDR1) gene expression in prostate cancer cell lines. Int J Biol Markers (2014); 29.3: e288-290.
Salvatore et al. A cell proliferation and chromosomal instability signature in anaplastic thyroid carcinoma. Cancer Res. 2007;67(21):10148-58.
Sambrook; et al, "Molecular Cloning: A Laboratory Manual. Second edition, Cold Spring Harbor Laboratory Press, 1989.".
Sanghvi. Heterocyclic base modifications in nucleic acids and their applications in antisense oligonucleotides. in Antisense Research and Applications. Crooke, S. T. and Lebleu, B., ed., CRC Press. 1993; Ch 15 274-285.
Santarpia et al. Phosphatidylinositol 3-kinase/akt and ras/raf-mitogen-activated protein kinase pathway mutations in anaplastic thyroid cancer. J Clin Endocrinol Metab. 2008;93(1):278-84.
Santiyagu M. Savarimuthu Francis et al: "Genes and Gene Ontologies Common to Airflow Obstruction and Emphysema in the Lungs of Patients with COPD", Plos One, vol. 6, No. 3, 2011, p. e17442.
Sapio, et al., Detection of RETIPTC, TRK and BRAF mutations in preoperative diagnosis of thyroid nodules with indeterminate cytological findings, C]Jnical Endocrinology, 2007, 66: 678-683.
Satake et al. Overview of the primary structure, tissue-distribution, and functions of tachykinins and their receptors. Curr Drug Targets. 2006;7(8):963-74.
Savagner et al. Defective mitochondrial ATP synthesis in oxyphilic thyroid tumors. J Clin Endocrinol Metab. 2001;86(10):4920-5.
Savagner et al. PGC-1-related coactivator and targets are upregulated in thyroid oncocytoma. Biochem Biophys Res Commun. 2003;310(3):779-84.
Schembri et al. MicroRNAs as modulators of smoking-induced gene expression changes in human airway epithelium. Proc Natl Acad Sci U S A, 106(7),2319-24 (Feb. 2009).
Schiff, et al. Epidermal growth factor receptor (EGFR) is overexpressed in anaplastic thyroid cancer, and the EGFR inhibitor gefitinib inhibits the growth of anaplastic thyroid cancer. Clin Cancer Res. Dec. 15, 2004;10(24):8594-602.
Schraufangel. "Interstitial Lung Disease," Chapter 10, pp. 99-107, in Breathing in America: Diseases, Progress and Hope, American Thoracic Society (2010).
Schraufnagel, Dean. Breathing in America: Diseases, Progress, and Hope. The American Thoracic Society. Published 2010. 282 pages.
Schroeder, et al. The RIN: an RNA integrity number for assigning integrity values to RNA measurements. BMC Mol Biol. Jan. 31, 2006;7:3.
Schulz et al. Activation of bronchial epithelial cells in smokers without airway obstruction and patients with COPD. Chest. May 2004; 125(5):1706-13.
Schulz et al. Upregulation of MCAM in primary bronchial epithelial cells from patients with COPD. European Respiratory Journal (Sep. 2003); 22.3: 450-456.
Selman et al. Gene expression profiles distinguish idiopathic pulmonary fibrosis from hypersensitivity pneumonitis. American Journal of Respiratory and Critical Care Medicine (2006); 173.2: 188-198.
Selman et al. Idiopathic pulmonary fibrosis: aberrant recapitulation of developmental programs?. PLoS medicine 5.3 (2008): e62.
Selman et al. Revealing the pathogenic and aging-related mechanisms of the enigmatic idiopathic pulmonary fibrosis. An integral model. Am J Respir Crit Care Med. May 15, 2014;189(10):1161-72.

(56) References Cited

OTHER PUBLICATIONS

Selman, M. et al., Accelerated variant of idiopathic pulmonary fibrosis: Clinical behavior and gene expression pattern. Plos One, May 2007, Issue 5, e482, 11 Pages.
Shah et al. SIEGE: Smoking Induced Pithelial Gene Expression Database. Nucleic Acids Research, 33: D573-D579 (2005).
Shalon, D. et al. A DNA microarray system for analyzing complex DNA samples using two-color fluorescent probe hybridization. Genome research, 6(7): 639-645 (Jul. 1996).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Sheu et al. The C allele of the GNB3 C825T polymorphism of the G protein beta3-subunit is associated with an increased risk for the development of oncocytic thyroid tumours. J Pathol. 2007;211(1):60-6.
Shi, et al. Combined analysis of gene expression, DNA copy number, and mutation profiling data to display biological process anomalies in individual breast cancers. Breast Cancer Res Treat. Apr. 2014;144(3):561-8. Epub Mar. 12, 2014.
Shibru, et al. Does the 3-gene diagnostic assay accurately distinguish benign from malignant thyroid neoplasms? Cancer. Sep. 1, 2008;113(5):930-5.
Shibuya et al., Increased telomerase activity and elevated hTERT mRNA expression during multistage carcinogenesis of squamous cell carcinoma of the lung. Cancer, Aug. 2001; 92(4): 849-855.
Shields, PG. Molecular epidemiology of lung cancer. Annals of Oncology, 10(5):S7-S11 (1999).
Shih et al. A new Mel-CAM (CD146)-specific monoclonal antibody, MN-4, on paraffin-embedded tissue. Modern Pathology: an Official Journal of the United States and Canadian Academy of Pathology, Inc (1998); 11.11: 1098-1106.
Shim et al. Histopathologic findings of transbronchial biopsy in usual interstitial pneumonia. Pathology International (2010); 60.5: 373-377.
Shirasawa, S. Susceptibility genes for the development of autoimmune thyroid disease. Nippon Rinsho. Dec. 2006;64(12):2208-14. (Abstract only).
Shriver et al. Sex-Specific Expression of Gastrin-Releasing Peptide Receptor: Relationship to Smoking History and Risk of Lung Cancer. J. Natl. Cancer Inst., 92: 24-33 (2000).
Shvero et al. Immunohistochemical profile and treatment of uncommon types of thyroid carcinomas. Oncol Rep. 2003;10(6):2075-8.
Silvestri et al. A bronchial genomic classifier for the diagnostic evaluation of lung cancer. N Engl J Med. Jul. 16, 2015;373(3):243-51.
Silvestri et al. Latest advances in advanced diagnostic and therapeutic pulmonary procedures. Chest Journal (2012); 142.6: 1636-1644.
Simon et al. Up-regulation of MUC18 in airway epithelial cells by IL-13: implications in bacterial adherence. American Journal of Respiratory Cell and Molecular Biology (2011); 44.5: 606-613.
Singh et al. LNA (locked nucleic acids): synthesis and high-affinity nucleic acid recognition. Chem Commun 4:455-456 (1998).
Singh et al. Screening for genetic aberrations in papillary thyroid cancer by using comparative genomic hybridization. Surgery. 2000;128(6):888-93;discussion 893-4.
Singh et al. Synthesis of 2'-amino-LNA: A novel conformationally restricted high-affinity oligonucleotide analogues with a handle. J Bio Chem 63:10035-10039 (1998).
Singhal et al. Alterations in cell cycle genes in early stage lung adenocarcinoma identified by expression profiling. Cancer Biol Ther. May-Jun. 2003;2(3):291-8.
Singhal S et al: "Gene expression profiling of Non-small cell lung cancer", Lung Cancer, val. 60, No. 3, Jun. 1, 2008 (Jun. 1, 2008 ), pp. 313-324, XP022690999.
Siragusa et al. MUC1 oncoprotein promotes refractoriness to chemotherapy in thyroid cancer cells. Cancer Res. 2007;67(11):5522-30.

Slonim, Donna. From Patterns to Pathways: Gene Expression Data Analysis Comes of Age. Nature Genetics Supplement, 32: 502-508, 2002.
Smirnov et al. Global gene expression profiling of circulating endothelial cells in patients with metastatic carcinomas. Cancer Res. Mar. 15, 2006;66(6):2918-22.
Smith et al. Methylation status of genes in papillary thyroid carcinoma. Arch Otolaryngol Head Neck Surg. 2007;133(10):1006-11.
Smith et al. Prevalence of benign disease in patients undergoing resection for suspected lung cancer. The Annals of Thoracic Surgery (May 2006); 81.5: 1824-1829.
Smyth. Limma: Linear Models for Microarray Data. In: Bioinformatics and Computational Biology Solutions using R and Bioconductor, R. Gentleman, V. Carey, S. Dudoit, R. Irizarry, W. Huber (eds.), Springer, New York. 2005; pp. 397-420.
Smyth. Linear models and empirical bayes methods for assessing differential expression in microarray experiments. Stat Appl Genet Mol Biol. 2004;3:Article3. Epub Feb. 12, 2004.
Soni et al. Progress toward ultrafast DNA sequencing using solid-state nanopores. Clin Chem 53:1996-2001 (2007).
Sotos, et al. The Transitivity Misconception of Pearson's Correlation Coefficient. Statistics Education Research Journal. 8(2):33-55 (2009).
Soumyaroop Bhattacharya1 et al: "Molecular biomarkers for quantitative and discrete COPD phenotypes",American Journal of Respiratory Cell and Molecular Biology, American Lung Association, val. 40, No. 3, (Oct. 10, 2008), pp. 359-367.
Spargo, et al. Detection of M. tuberculosis DNA using thermophilic strand displacement amplification. Mol Cell Probes. Aug. 1996;10(4):247-56.
Spira, Avrum E. Abstract: Airway gene expression in smokers: an early diagnostic biomarker for lung cancer. National Institutes of Health Grant No. 1 RO1 CA124640-01 (Funding Start Date May 1, 2007).
Spira, Avrum E. Abstract: The airway transcriptome as a biomarker for lung cancer. National Institutes of Health Grant No. 1 R21 CA106506-01A2 (Funding Start Date Aug. 9, 2005).
Spira, et al. Airway epithelial gene expression in the diagnostic evaluation of smokers with suspect lung cancer. Nature Medicine 13: 361-366 (2007).
Spira, et al. Effects of cigarette smoke on the human airway epithelial cell transcriptome. PNAS, 101: 27, p. 10143-10148 (Jul. 6, 2004).
Spira et al. Gene Expression Profiling of Human Lung Tissue from Smokers with Severe Emphysema. Am J Respir Cell Mol Biol. Dec. 2004;31(6):601-10.
Spira, et al. Impact of cigarette smoke on the normal airway transcriptome. Chest. 125 (5 Suppl):115S (May 2004).
Spira et al. Noninvasive method for obtaining RNA from buccal mucosa epithelial cells for gene expression profiling. Biotechniques, 36(3): 484-7 (Apr. 2004).
Spivack, et al. Gene-environment interaction signatures by quantitative mRNA profiling in exfoliated buccal mucosal cells. Cancer Res. Sep. 15, 2004;64(18):6805-13.
Sridhar et al. Smoking-induced gene expression changes in the bronchial airway are reflected in nasal and buccal epithelium. BMC Genomics, 9: 259 (May 2008).
St. Croix et al. Genes Expressed in Human Tumor Endothelium. Science, 289:1197-1202, (Aug. 18, 2000).
Stanta et al. The biochemical and immunohistochemical profile of thyroid neoplasia. Pathol Annu. 1988;23 Pt 1: 129-57.
Steiling et al: "A Dynamic Bronchial AirwayGene Expression Signature of Chronic Obstructive Pulmonary Disease and LungFunction impairment", American Journal of Respiratory and Critical Caremedicine, vol. 187, No. 9, (Mar. 7, 2013), pp. 933-942.
Steiling et al. The field of tissue injury in the lung and airway. Cancer Prevention Research (2008); 1.6: 396-403.
Steiling K et al: "Airway gene expression in chronic obstructive pulmonary disease", Proceedings of the American Thoracic Society Dec. 15, 2009 American Thoracic Society USA, val. 6, No. 8, Dec. 15, 2009 (Dec. 15, 2009), pp. 697-700,ISSN: 1546-3222.

(56) References Cited

OTHER PUBLICATIONS

Stephenson et al. Integration of gene expression profiling and clinical variables to predict prostate carcinoma recurrence after radical prostatectomy, Cancer 2005; 104:290-8, 2005.
Stewart, JH. Lung Carcinoma in African Americans, A Review of the Current Literature. Cancer; 91(12): 2476-2482 (Jun. 15, 2001).
Strausberg et al. Reading the Molecular Signatures of Cancer. Microarrays and Cancer Research, Warrington et al. (eds.), Eaton Publishing, Westborough, MA, pp. 81-111, (2002).
Su et al. Molecular Classification of Human Carcinomas by Use of Gene Expression Signatures. Cancer Research, 61:7388-7393, (Oct. 15, 2001).
Subramaniam et al. Clonal characterization of sporadic cribriform-morular variant of papillary thyroid carcinoma by laser microdissection-based APC mutation analysis. Am J Clin Pathol. 2007;128(6):994-1001.
Subramanian et al. Gene set enrichment analysis: a knowledge-based approach for interpreting genome-wide expression profiles. PNAS USA 102:15545-15550 (2005).
Sugita et al. Combined Use of Oligonucleotide and Tissue Microarrays Identifies Cancer/Testis Antigens as Biomarkers in Lung Carcinoma. Cancer Research. Jul. 2002. vol. 62, Issue 14, pp. 3971-3979.
Sumikawa et al. Computed tomography findings in pathological usual interstitial pneumonia: relationship to survival. American Journal of Respiratory and Critical Care Medicine (2008); 177.4: 433-439.
Suomalainen et al. Quantitative analysis of human DNA sequences by PCR and solid-phase minisequencing. Molecular Biotechnology (2000); 15.2: 123-131.
Supplementary European search report and opinion dated Oct. 12, 2016 for EP Application No. 14770813.
Suykens et al. Least squares support vector machine classifiers. Neural Processing Letters (1999); 9.3: 293-300.
Suzanne A Eccles et al: "Metastasis: recent discoveries and novel treatment strategies", The Lancet, val. 369, No. 9574, May 1, 2007 (May 1, 2007 ), pp. 1742-1757, XP055231616.
Swensen et al. Solitary pulmonary nodules: clinical prediction model versus physicians. Mayo Clinic Proc 1999; 74:319-29 (1999).
Swensen et al. The probability of malignancy in solitary pulmonary nodules. Application to small radiologically indeterminate nodules. Arch Intern Med 1997; 157:849-55, 1997.
Symmans, et al. Total RNA Yield and Microarray Gene Expression Profiles from Fine-Needle Aspiration Biopsy and Core-Needle Biopsy Samples of Breast Carcinoma. 2003; Cancer 97(12): 2960-2971.
Takakura et al. Oncogenic role of miR-17-92 cluster in anaplastic thyroid cancer cells. Cancer Sci. 2008;99(6):1147-54.
Takano et al. Expression of oncofetal fibronectin messenger ribonucleic acid in fibroblasts in the thyroid: a possible cause of false positive results in molecular-based diagnosis of thyroid carcinomas. J Clin Endocrinol Metab. 2000;85(2):765-8.
Takano et al. Preoperative diagnosis of thyroid papillary and anaplastic carcinomas by real-time quantitative reverse transcription-polymerase chain reaction of oncofetal fibronectin messenger RNA. Cancer Res. 1999;59(18):4542-5.
Takizawa et al. Increased expression of transforming growth factor-betal in small airway epithelium from tobacco smokers and patients with chronic obstructive pulmonary disease (COPD). American Journal of Respiratory and Critical Care Medicine, 163:1476-1483 (2001).
Tamir et al. Expression and development of a functional plasmalemmal 5-hydroxytryptamine transporter by thyroid follicular cells. Endocrinology. 1996;137(10):4475-86.
Tanaka et al. Trial to establish an animal model of paraneoplastic cerebellar degeneration with anti-Yo antibody: 1. Mouse strains bearing different MHC molecules produce antibodies on immunization with recombinant Yo protein, but do not cause Purkinje cell loss. Clinical Neurology and Neurosurgery (1995); 97.1: 95-100.

Taniguchi et al. Differentiation of follicular thyroid adenoma from carcinoma by means of gene expression profiling with adapter-tagged competitive polymerase chain reaction. Oncology. 2005;69(5):428-35.
Tanque et al. Lung cancer screening. American Journal of Respiratory and Critical Care Medicine (2015); 191.1: 19-33.
Tarca et al. Analysis of microarray experiments of gene expression profiling. Am J Obstet Gynecol 195(2): 373-388 (Aug. 2006).
Team, R. Core. R: A language and environment for statistical computing. R Foundation for Statistical Computing, Vienna, Austria (2013): pp. 1-14.
Terada. Brain metastasis from thyroid adenomatous nodules or an encapsulated thyroid follicular tumor without capsular and vascular invasion: a case report. Cases J. Jul. 17, 2009;2:7180. doi: 10.4076/1757-1626-2-7180.
Tetzlaff et al. Differential expression of miRNAs in papillary thyroid carcinoma compared to multinodular goiter using formalin fixed paraffin embedded tissues. Endocr Pathol. 2007;18(3):163-73.
Theocharis et al. Metallothionein: a multifunctional protein from toxicity to cancer. Int Biol Markers, 18(3):162-169 (2003).
Thisteda. What is a P-value. Departments of Statistics and Health Studies. The University of Chicago. (May 25, 1988).
Thompson et al. Primary smooth muscle tumors of the thyroid gland. Cancer. 1997;79(3):579-87.
Thornton et al. Estimating kinship in admixed populations. The American Journal of Human Genetics 91.1 (2012): 122-138.
Thurston et al. Modeling lung cancer risk in case-control studies using a new dose metric of smoking. Cancer Epidemiol Biomarkers Prey 2005; 14(10): 2296-302 (2005).
Tian, et al. A combined oncogenic pathway signature of Braf, Kras and PI3KCA mutation improves colorectal cancer classification and cetuximab treatment prediction. Gut. Apr. 2013;62(4):540-9. doi: 10.1136/gutjnl-2012-302423. Epub Jul. 14, 2012.
Tian, et al. Effects of Gender on Gene Expression in the Blood of Ischemic Stroke Patients. Journal of Cerebral Blood Flow & Metabolism. J Cereb Blood Flow Metab. May 2012;32(5):780-91. doi: 10.1038/jcbfm.2011.179. Epub Dec. 14, 2011.
Tibshirani. Regression shrinkage and selection via the lasso. Journal of the Royal Statistical Society Series B (Methodological) 58:267-288 (1996).
Tichelaar et al. Increased staining for phospho-Akt, p65/RELA and cIAP-2 in pre-neoplastic human bronchial biopsies. BMC Cancer 5(155):1-13 (2005).
Tjarda Van Heek et al., Gene expression profiling identifies markers of ampullary adenocarcinoma. (Cancer biology & Therapy, 2004, 3(7):651-656.).
Tockman, et al., Considerations in Bringing a Cancer Biomarker to Clinical Application. Cancer Res May 1, 1992; (52): 2711s-2718s.
Todaro et al. Autocrine production of interleukin-4 and interleukin-10 is required for survival and growth of thyroid cancer cells. Cancer Res. 2006;66(3):1491-9.
Tokunaga et al., Enhanced expression of a Glyceraldehyde-3-phosphate Dehydrogenase Gene in human lung cancers. (Cancer Research, 1987, 47: 5616-5619).
Tomassetti et al. Bronchoscopic lung cryobiopsy increases diagnostic confidence in the multidisciplinary diagnosis of idiopathic pulmonary fibrosis. American Journal of Respiratory and Critical Care Medicine (2016); 193.7: 745-752.
Tomassetti et al. Transbronchial biopsy is useful in predicting UIP pattern. Respiratory Research (2012); 13.1: 96.
Trahan et al. Role of surgical lung biopsy in separating chronic hypersensitivity pneumonia from usual interstitial pneumonia/idiopathic pulmonary fibrosis: analysis of 31 biopsies from 15 patients. Chest Journal (2008); 134.1: 126-132.
Trapnell, et al. TopHat: discovering splice junctions with RNA-Seq. Bioinformatics. May 1, 2009;25(9):1105-11. doi: 10.1093/bioinformatics/btp120. Epub Mar. 16, 2009.
Travis et al. An official American Thoracic Society/European Respiratory Society statement: Update of the international multidisciplinary classification of the idiopathic interstitial pneumonias. Am J Respir Crit Care Med (2013); 188.6: 733-748.

(56) References Cited

OTHER PUBLICATIONS

Treutlein et al. Reconstructing lineage hierarchies of the distal lung epithelium using single-cell RNA-seq. Nature. May 15, 2014;509(7500):371-5. doi: 10.1038/nature13173. Epub Apr. 13, 2014.
Trovisco et al. Molecular Genetics of Papillary Thyroid Carcinoma—Great Expectations . . . Arq Bras Endocrinol Metab, Jul. 1, 2007, pp. 643-653.
Trunk et al. The management and evaluation of the solitary pulmonary nodule. Chest 1974; 66:236-9 (1974).
Tsao et al. Increased Phospho-AKT (Ser4(3) Expression in Bronchial Dysplasia: Implications for Lunch Cancer Prevention Studies. Cancer Epidemiology Biomarkers & Prevention. 12:660-664 (2003).
Tsukamoto et al. Involvement of gicerin, a cell adhesion molecule, in tracheal development and regeneration. Cell Growth and Differentiation-Publication Cell Growth & Differentiation (1996); 7.12: 1761-1768.
Tsukamoto et al. The role of gicerin, a novel cell adhesion molecule, in development, regeneration and neoplasia. Histology and Histopathology (2001); 16.2: 563-571.
Tukey et al. Population-based estimates of transbronchial lung biopsy utilization and complications. Respiratory Medicine (2012); 106.11: 1559-1565.
Tukey. Exploratory Data Analysis: Past, Present, and Future. Technical Report No. 302. Department of Statistics, Princeton University. 1971-1977. 1993.
Tzen, et al. Is atypical follicular adenoma of the thyroid a preinvasive malignancy? Hum Pathol. Jul. 2003;34(7):666-9.
Ueda, et al. Analysis of PAX8 Gene in Congenital Hypothyroidism Mass Screening Positive Subjects. Folia Endocrinologica Japonica. Mar. 30, 2007, vol. 82, No. 4, p. 859. (in Japanese with English translation).
Ullmannová, et al. The use of housekeeping genes (HKG) as an internal control for the detection of gene expression by quantitative real-time RT-PCR. Folia Biol (Praha). 2003;49(6):211-6.
Ung et al. 18Fluorodeoxyglucose positron emission tomography in the diagnosis and staging of lung cancer: a systematic review. J Nat'l Cancer Institute, 99(23): 1753-67 (2007).
Unger et al. Array CGH demonstrates characteristic aberration signatures in human papillary thyroid carcinomas governed by RET/PTC. Oncogene. 2008;27(33):4592-602.
U.S. Appl. No. 14/213,632 Office Action dated Jun. 10, 2015.
U.S. Appl. No. 14/213,632 Office Action dated Mar. 11, 2016.
U.S. Appl. No. 14/500,475 Notice of Allowance dated Oct. 15, 2019.
U.S. Appl. No. 14/500,475 Office Action dated Mar. 26, 2018.
U.S. Appl. No. 14/500,475 Office Action dated May 14, 2019.
U.S. Appl. No. 14/613,210 Notice of Allowance dated Oct. 31, 2017.
U.S. Appl. No. 14/690,182 Office Action dated Apr. 20, 2018.
U.S. Appl. No. 14/690,182 Office Action dated Mar. 22, 2019.
U.S. Appl. No. 14/775,379 Notice of Allowance dated Oct. 11, 2019.
U.S. Appl. No. 14/775,379 Office Action dated Apr. 4, 2019.
U.S. Appl. No. 14/775,379 Office Action dated Nov. 16, 2017.
U.S. Appl. No. 14/799,472 Office Action dated Jan. 18, 2019.
U.S. Appl. No. 14/799,472 Office Action dated Jul. 5, 2019.
U.S. Appl. No. 14/799,472 Office Action dated Nov. 6, 2018.
U.S. Appl. No. 14/799,472 Office Action dated Oct. 13, 2016.
U.S. Appl. No. 15/185,960 Office Action dated Dec. 21, 2018.
U.S. Appl. No. 15/261,662 Office Action dated May 1, 2019.
U.S. Appl. No. 15/336,469 Office Action dated Apr. 10, 2018.
U.S. Appl. No. 15/439,891 Office Action dated Dec. 28, 2018.
U.S. Appl. No. 15/439,891 Office Action dated Feb. 14, 2018.
U.S. Appl. No. 15/439,891 Office Action dated Jun. 18, 2019.
U.S. Appl. No. 15/440,575 Office Action dated Apr. 9, 2019.
U.S. Appl. No. 15/523,654 Office Action dated Mar. 27, 2019.
U.S. Appl. No. 15/644,721 Office Action dated Dec. 27, 2017.
U.S. Appl. No. 15/661,496 Notice of Allowance dated Feb. 11, 2019.
U.S. Appl. No. 15/694,157 Office Action dated Mar. 7, 2019.
U.S. Appl. No. 15/888,831 Office Action dated Jul. 24, 2018.
U.S. Appl. No. 15/888,831 Office Action dated Mar. 27, 2018.
U.S. Appl. No. 15/888,831 Office Action dated Mar. 27, 2019.
U.S. Appl. No. 15/888,831 Office Action dated Oct. 10, 2019.
U.S. Appl. No. 16/292,573 Office Action dated Jul. 30, 2020.
U.S. Appl. No. 16/292,573 Office Action dated Mar. 19, 2021.
U.S. Appl. No. 16/300,947 Office Action dated Oct. 22, 2020.
U.S. Appl. No. 16/353,248 Office Action dated Oct. 28, 2019.
U.S. Appl. No. 16/510,584 Office Action dated Apr. 23, 2020.
U.S. Appl. No. 16/510,584 Office Action dated Aug. 25, 2021.
U.S. Appl. No. 16/510,584 Office Action dated Feb. 11, 2021.
U.S. Appl. No. 16/510,584 Office Action dated Jan. 16, 2020.
U.S. Appl. No. 16/510,584 Office Action dated Sep. 30, 2020.
U.S. Appl. No. 16/579,798 Office Action dated Jul. 20, 2021.
U.S. Appl. No. 16/751,145 Office Action dated Aug. 18, 2021.
U.S. Appl. No. 16/810,827 Office Action dated Apr. 22, 2021.
U.S. Appl. No. 16/810,827 Office Action dated Aug. 10, 2020.
U.S. Appl. No. 16/810,827 Office Action dated Aug. 23, 2021.
U.S. Appl. No. 16/810,827 Office Action dated Nov. 23, 2020.
U.S. Appl. No. 17/218,121 Office Action dated Sep. 28, 2021.
U.S. Appl. No. 17/218,125 Office Action dated Sep. 28, 2021.
Van Allen et al. Whole-exome sequencing and clinical interpretation of formalin-fixed, paraffin-embedded tumor samples to guide precision cancer medicine. Nature medicine 20.6 (2014): 682.
Van Der Laan, et al. A new algorithm for hybrid hierarchical clustering with visualization and the bootstrap. Journal of Statistical Planning and Inference. Dec. 2003. 117(2):275-303.
Van Dyck, E. et al., Bronchial airway gene expression in smokers with lung or head and neck cancer. Cancer Medicine, Apr. 2014; 3(2): 322-336.
Vasko, et al. Gene expression and functional evidence of epithelial-to-mesenchymal transition in papillary thyroid carcinoma invasion. Proc Natl Acad Sci U S A. Feb. 20, 2007;104(8):2803-8. Epub Feb. 12, 2007.
Viale et al. Coexpression of cytokeratins and vimentin in normal and diseased thyroid glands. Lack of diagnostic utility of vimentin immunostaining. Am J Surg Pathol. 1989;13(12):1034-40.
Viney et al. Regulation of the cell-specific calcitonin/calcitonin gene-related peptide enhancer by USF and the Foxa2 forkhead protein. J Biol Chem. 2004;279(48):49948-55.
Visone et al. MicroRNAs (miR)-221 and miR-222, both overexpressed in human thyroid papillary carcinomas, regulate p27Kip1 protein levels and cell cycle. Endocr Relat Cancer. 2007;14(3):791-8.
Visone et al. Specific microRNAs are downregulated in human thyroid anaplastic carcinomas. Oncogene. 2007;26(54):7590-5.
Volm et al. Prognostic significance of the expression of c-fos, c-jun and c-erbB-1 oncogene products in human squamous cell lung carcinomas. J Cancer Res Clin Oncol, 119: 507-510 (1993).
Voynow et al. UC2, and MUC5/5AC in Nasal Epithelial Cells of Cystic Fibrosis, Allergic Rhinitis, and Normal Individuals. Lung 176: 345-354 (1998).
Wahidi, et al. Evidence for the treatment of patients with pulmonary nodules: when is it lung cancer? ACCP evidence-based clinical practice guidelines 2nd Edition. Chest 2007; 132:94-1075 (2007).
Wang et al. Association of the T1799A BRAF mutation with tumor extrathyroidal invasion, higher peripheral platelet counts, and overexpression of platelet-derived growth factor-B in papillary thyroid cancer. Endocr Relat Cancer. 2008;15(1):183-90.
Wang et al. RNA-seq: a revolutionary tool for transcriptomics. Nature Reviews Genetics 10:57-63 (2009).
Wang et al. The expression analysis of ICOS-L on activated T cells and immature dendritic cells as well as malignant B cells and Grave's-disease-derived thyroid tissues by two novel mAbs against human ICOS-L. Tissue Antigens. 2007;69(1):62-72.
Wardlaw et al. Effect of cigarette smoke on CYP1A1, CYP1A2 and CYP2B1/2 of nasal mucosae in F344 rats. Carcinogenesis 19(4): 655-662 (1998).
Watanabe et al. Decrease of intrathyroidal CD161+Valpha24+Vbeta11+ NKT cells in Graves' disease. Endocr J. 2008; 55(1):199-203.

(56) References Cited

OTHER PUBLICATIONS

Wattel, et al. Gene expression in thyroid autonomous adenomas provides insight into their physiopathology. Oncogene. Oct. 20, 2005;24(46):6902-16.
Watters et al. Developing Gene Expression Signatures of Pathway Deregulation in Tumors. Molecular Cancer Therapeutics, 5: 2444-2449, Oct. 2006.
Weber et al. A limited set of human MicroRNA is deregulated in follicular thyroid carcinoma. J Clin Endocrinol Metab. 2006;91(9):3584-91. Epub Jul. 5, 2006.
Weber et al. Genetic classification of benign and malignant thyroid follicular neoplasia based on a three-gene combination. J Clin Endocrinol Metab. 2005;90(5):2512-21.
Weber et al. Silencing of the maternally imprinted tumor suppressor ARHI contributes to follicular thyroid carcinogenesis. J Clin Endocrinol Metab. 2005;90(2):1149-55.
Wells, Athol U. Managing diagnostic procedures in idiopathic pulmonary fibrosis. European Respiratory Review (2013); 22.128: 158-162.
Wells, Athol U. The revised ATS/ERS/JRS/ALAT diagnostic criteria for idiopathic pulmonary fibrosis (IPF)-practical implications. Respiratory Research (2013); 14(Suppl 1):S2.
Weng et al., Association between the risk of lung cancer and influenza: a population-based nested case-control study. International Journal of infectious diseases, 2019, 88: 8-13.
Wessagowit, et al. Normal and abnormal mechanisms of gene splicing and relevance to inherited skin diseases. J Dermatol Sci. Nov. 2005;40(2):73-84. Epub Jul. 27, 2005.
Wessels, et al., A protocol for building and evaluating predictors of disease state based on microarray data, Bioinformatics, 2005, 21:3755-3762).
West et al. Embracing the complexity of genomic data for personalized medicine. Genome Res 2006; 16:559-66, May 2006.
West et al. Rapid Akt Activation by Nicotine and Tobacco Carcinogen Modulates the Phenotype of Normal Human Airway Epithelial Cells. The Journal of Clinical Investigation. 111(1):81-90 (Jan. 2003).
Wharam, et al. Specific detection of DNA and RNA targets using a novel isothermal nucleic acid amplification assay based on the formation of a three-way junction structure. Nucleic Acids Res. Jun. 1, 2001;29(11):E54-4.
Whitehead, et al. Variation in tissue-specific gene expression among natural populations. Genome Biol. 2005;6(2):R13. Epub Jan. 26, 2005.
Whitney et al. Derivation of a bronchial genomic classifier for lung cancer in a prospective study of patients undergoing diagnostic bronchoscopy. BMC Med Genomics. May 6, 2015;8:18.
Wiener et al. An official American Thoracic Society/American College of Chest Physicians policy statement: implementation of low-dose computed tomography lung cancer screening programs in clinical practice. Am J Respir Crit Care Med. Oct. 1, 2015;192(7):881-91.
Wiener et al. Population-based risk for complications after transthoracic needle lung biopsy of a pulmonary nodule: an analysis of discharge records. Annals of Internal Medicine (2011); 155.3: 137-144.
Wiener et al. Risks of transthoracic needle biopsy: how high? Clinical Pulmonary Medicine (2013); 20.1: 29-35.
Wilkerson et al. ConsensusClusterPlus: a class discovery tool with confidence assessments and item tracking. Bioinformatics (2010); 26.12: 1572-1573.
Willey et al. Quantitative RT-PCR Measurement of Cytochromes p450 1A1, 161, and 2B7, Microsomal Epoxide Hydrolase, and NADPH Oxidoreductase Expression in Lung Cells of Smokers and Nonsmokers. Am. J. Respir. Cell Mol. Biol., 1997, 17:114-124.
Wiseman et al. Molecular phenotyping of thyroid tumors identifies a Marker panel for differentiated thyroid cancer diagnosis. Ann Surg Oncol. 2008;15(10):2811-26.
Wistuba et al. High resolution chromosome 3p allelotyping of human lung cancer and preneoplastic/preinvasive bronchial epithelium reveals multiple, discontinuous sites of 3p allele loss and three regions of frequent breakpoints. Cancer Res., 60(7): 1949-60 (Apr. 1, 2000).
Wistuba et al. Molecular damage in the bronchial epithelium of current and former smokers. J Natl Cancer Inst., 89(18): 1366-73 (Sep. 17, 1997).
Woenckhaus et al. Expression Profiling of Non-Small Cell Lung Cancers and Bronchi of Smokers and Non Smokers. Study Group: Molecular Pathology/Pathology—Research and Practice, 200:p. 255, (2004).
Woenckhaus et al. Smoking and cancer-related gene expression in bronchial epithelium and non-small-cell lung cancers. Journal of Pathology, 210: 192-204 (Oct. 2006).
Wojnarowski et al. Cytokine Expression in Bronchial Biopsies of Cystic Fibrosis Patients With and Without Acute Exacerbation. (Eur Respir, 1999, 14: 1136-114).
Wong et al. Development of a quantitative assay for SARS coronavirus and correlation of GAPDH mRNA with SARS coronavirus in clinical specimens. J Clin Pathol, 2005, 58: 276-280, doi: 10.1136/jcp.2004016592.
Woodcock et al. The treatment of idiopathic pulmonary fibrosis. F1000Prime Rep. Mar. 3, 2014;6:16.
Wreesmann et al. Genome-wide profiling of papillary thyroid cancer identifies MUC1 as an independent prognostic marker. Cancer Res. 2004;64(11):3780-9.
Written Opinion of the International Searching Authority for PCT/CA2010/000621, mailed Aug. 11, 2010.
Wu, et al. A comparative study of 200 fine needle aspiration biopsies performed by clinicians and cytopathologists. Laryngoscope. Jul. 2006;116(7):1212-5.
Wu et al. Uncommon mutation, but common amplifications, of the PIK3CA gene in thyroid tumors. J Clin Endocrinol Metab. 2005;90(8):4688-93.
Wu, Thomas D. Analysing gene expression data from DNA microarrays to identify candidate genes. Journal of Pathology, 195:53-65 (2001).
Wuenschell et al. Embryonic mouse lung epithelial progenitor cells co-express immunohistochemical markers of diverse mature cell lineages. Journal of Histochemistry and Cytochemistry (1996); 44.2: 113-123.
Xing et al. BRAF V600E and TERT Promoter Mutations Cooperatively Identify the Most Aggressive Papillary Thyroid Cancer With Highest Recurrence Journal of Clinical Oncology vol. 32, pp. 2718-2726 (Year: 2014).
Xu et al. Differential expression of galectin-1 and galectin-3 in thyroid tumors. Potential diagnostic implications. Am J Pathol. 1995;147(3):815-22.
Yan, et al. Isothermal amplified detection of DNA and RNA. Mol Biosyst. May 2014;10(5):970-1003.
Yang et al. C-myc, N-myc, N-ras, and c-erb-B: lack of amplification or rearrangement in human medullary thyroid carcinoma and a derivative cell line. Anticancer Res. 1990;10(1):189-92.
Yang et al. Expression of cilium-associated genes defines novel molecular subtypes of idiopathic pulmonary fibrosis. Thorax (2013): 68(12):1114-11121.
Yang et al. Gene expression profiling of familial and sporadic interstitial pneumonia. American Journal of Respiratory and Critical Care Medicine (2007); 175.1: 45-54.
Yang et al. Reduction of Dihydrodiol Dehydrogenase Expression in Resected Hepatocellular Carcinoma. OncoL Rep., 10(2):271-276, (2003).
Yang, I.V., et al., Epigenetics of Idiopathic Pulmonary Fibrosis. Transl Res. Jan. 2015; 165(1): 48-60.
Yano et al. Gene expression profiling identifies platelet-derived growth factor as a diagnostic molecular marker for papillary thyroid carcinoma. Clin Cancer Res. 2004;10(6):2035-43.
Yatabe et al. Epidermal growth factor receptor gene amplification is acquired in association with tumor progression of EGFR-mutated lung cancer. Cancer Res. 2008;68(7):2106-11.
Yeh et al. Differentiated thyroid cancer cell invasion is regulated through epidermal growth factor receptor-dependent activation of matrix metalloproteinase (MMP)-2/gelatinase A. Endocr Relat Cancer. 2006;13(4):1173-83.

(56) References Cited

OTHER PUBLICATIONS

Yeh et al. Somatic mitochondrial DNA (mtDNA) mutations in papillary thyroid carcinomas and differential mtDNA sequence variants in cases with thyroid tumours. Oncogene. 2000;19(16):2060-6.
Yen-Tsung; Huang et al, "Genome-Wide Analysis of Survival in Early-Stage Non-Small-Cell Lung Cancer", Journal of Clinical Oncology, Jun. 1, 2009, 27 (16), 2660-2667.
Yoneda et al. Development of High-Density DNA Microarray Membrane for Profiling Smoke- and Hydrogen Peroxide-Induced Genes in a Human Bronchial Epithelial Cell Line. American Journal of Respiratory and Critical Care Medicine, 164:S86-S89, (2001).
Yoon et al. Identification of a novel noncoding RNA gene, NAMA, that is downregulated in papillary thyroid carcinoma with BRAF mutation and associated with growth arrest. Int J Cancer. 2007;121(4):767-75.
Yousefi et al. A SNP panel for identification of DNA and RNA specimens. BMC genomics 19.1 (2018): 90.
Yukinawa, et al. A multi-class predictor based on a probabilistic model: application to gene expression profiling-based diagnosis of thyroid tumors. BMC Genomics. Jul. 27, 2006;7:190.
Zabel et al. S-100 protein and neuron-specific enolase in parathyroid glands and C-cells of the thyroid. Histochemistry. 1987;86(4):389-92.
Zabner et al. Comparison of DNA-Lipid Complexes and DNA Alone for Gene Transfer to Cystic Fibrosis Airway Epithelia in vivo. (J Clin Invest, 1997, 100(6): 1529-1537.).
Zanna et al. Trop-1 are conserved growth stimulatory molecules that mark early stages of tumor progression. Cancer. 2007;110(2):452-64.
Zeeberg et al. GoMiner: a resource for biological interpretation of genomic and proteomic data. Genome Biology, 4(4):R28.1-R28.8 (Mar. 2003).
Zemke et al. Molecular staging of epithelial maturation using secretory cell-specific genes as markers. American Journal of Respiratory Cell and Molecular Biology (2009); 40.3: 340-348.
Zeng et al. The contributions of oestrogen receptor isoforms to the development of papillary and anaplastic thyroid carcinomas. J Pathol. 2008;214(4):425-33.
Zeskind Julie E et al: "Translating the COPD transcriptome: insights into pathogenesis and tools for clinical anagement.",Proceedings of the American Thoracic Society Dec. 1, 2008, vol. 5, No. 8, Dec. 1, 2008 (Dec. 1, 2008), pp. 834-841.
Zhang, et al. Association between single-nucleotide polymorphisms of BRAF and papillary thyroid carcinoma in a Chinese population. Thyroid. Jan. 2013;23(1):38-44. doi: 10.1089/thy.2012.0228.
Zhang, et al., Biomarkers in idiopathic pulmonary fibrosis, Current opinion in pulmonary medicine, vol. 18, No. 5, Sep. 1, 2012, 441-446.
Zhang, et al. CDC23 Regulates Cancer Cell Phenotype and is Overexpressed in Papillary Thyroid Cancer. Endocr Relat Cancer. Endocr Relat Cancer. Nov. 28, 2011;18(6):731-42. doi: 10.1530/ERC-11-0181. Print 2011.
Zhang et al. Comparison of smoking-induced gene expression on Affymetrix Exon and 3'-based expression arrays. Genome Inform. 18: 247-57 (2007).
Zhang et al. Regulation of tumor necrosis factor-related apoptosis-inducing ligand-induced apoptosis by DJ-1 in thyroid cancer cells. Endocr Relat Cancer. 2008;15(2):535-44.
Zhang et al. Similarities and differences between smoking-related gene expression in nasal and bronchial epithelium. Physiological Genomics (2010); 41(1), 1-8.
Zhou et al. RET proto-oncogene mutations are restricted to codons 634 and 918 in mainland Chinese families with MEN2A and MEN2B. Clin Endocrinol (Oxf). 2007;67(4):570-6.
Zhu et al. U1 snRNP-dependent function of TIAR in the regulation of alternative RNA processing of the human calcitonin/CGRP pre-mRNA. Mol Cell Biol. 2003;23(17):5959-71.
Zochbauer-Muller et al. 5' CpG Island Methylation of the FHIT Gene is Correlated with Loss of Gene Expression in Lung and Breast. Cancer Research, 61:3581-3585, (May 2, 2001).
Ausubel, Frederick M. Current Protocols in Molecular Biology. John Wiley & Sons:1-8 (2000).
ClinicalTrials.gov Identifier: NCT00746759. Airway Epithelium Gene Expression: AEGIS IDE (AEGIS IDE), Record created Sep. 3, 2008. pp. 1-8. [retrieved on Sep. 20, 2024] Available at URL: https://clinicaltrials.gov/study/NCT00746759?cond=NCT00746759&rank=1.
ClinicalTrials.gov Identifier: NCT01309087. Airway Epithelium Gene Expression in the Diagnosis of Lung Cancer: AEGIS CLIA (AEGIS), Record created Mar. 3, 2011. pp. 1-7. [retrieved on Sep. 20, 2024] Available at URL: https://clinicaltrials.gov/study/NCT01309087?cond=NCT01309087%20&rank=1.
OST, David E, and Michael K Gould. Decision Making in Patients With Pulmonary Nodules. American Journal of Respiratory and Critical Care Medicine 185(4):363-372 (2012). Online Published Oct. 6, 2011.
Dagliyan, Onur, et al., Optimization Based Tumor Classification from Microarray Gene Expression Data. PLoS One 6(2):1-10 (2011).
Supplementary European Search Report for European Application No. EP 17 79 6983, Issued Feb. 3, 2020.
Yu-Rong, et al. Tumor-associated antisen L6 and the invasion of human lung cancer cells. Clinical Cancer Research, Jul. 2003; vol. 9: 2807-2816.

* cited by examiner

FIGURE 10A

| Probe | Location |
|---|---|
| gacgtgaaccagaccaatgaaggc | chr19:43866831-43866855 (+) |
| tcccataggcagtccggatgctc | chr19:43866648-43866672 (+) |
| agcaggaaggcaaaccactccca | chr19:43866446-43866470 (+) |
| ccaagtgagagactccaggtcctca | chr19:43866388-43866412 (+) |
| aggaggctgcacatcacgcttctca | chr19:43866337-43866361 (+) |
| ggaggctgcacatcacgcttctcac | chr19:43866336-43866360 (+) |
| acaagaagctgaaggttgggccac | chr19:43866275-43866299 (+) |
| aatgctcatttggtggacagcca | chr19:43866241-43866265 (+) |
| ctacatctaggagcagcagcgtctc | chr19:43864533-43864557 (+) |
| agcagcgtctcctgacacacctgcc | chr19:43864519-43864543 (+) |
| tcttgagccaagttccgtgtgtca | chr19:43864450-43864474 (+) |
| tccgtgtgtcataatggtggtccc | chr19:43864436-43864460 (+) |
| gttaacgaggtgttgcagaagtcc | chr19:43858486-43858510 (+) |
| ttggagagcaccaggctcacttggg | chr19:43858362-43858386 (+) |
| tctcaatgagctcaacgtgtcctg | chr19:43858118-43858142 (+) |
| gcaggtaggacacttccacacatg | chr19:43858043-43858067 (+) |
| agggccagcagtaatacgagctca | chr19:43857868-43857892 (+) |
| gggccagcagtaatacgagctcat | chr19:43857867-43857891 (+) |
| gaccgtctgtgactggtaatctct | chr19:43857842-43857866 (+) |

FIGURE 10B

| Probe | Location |
|---|---|
| ttcctgtgtcccattgagcaggttg | chr19:43882867-43882891 (-) |
| tcccattgagcaggttgcaaactgg | chr19:43882875-43882899 (-) |
| cctgaggaggccatcataacagtgt | chr19:43883163-43883187 (-) |
| aggccatcataacagtgtgtggtcc | chr19:43883170-43883194 (-) |

ALGORITHMS FOR DISEASE DIAGNOSTICS

CROSS REFERENCE TO RELATED APPLICATIONS

The present application is a continuation-in-part application of U.S. patent application Ser. No. 16/875,673, filed May 15, 2020, which is a continuation application of U.S. patent application Ser. No. 16/593,918, filed Oct. 4, 2019, which is a continuation application of U.S. patent application Ser. No. 14/799,472, filed Jul. 14, 2015, which claims priority to U.S. Provisional Application Nos. 62/024,456, filed on Jul. 14, 2014, and 62/160,403, filed May 12, 2015, the entire contents of which are hereby incorporated by reference in their entirety for all purposes.

FIELD OF THE DISCLOSURE

The present disclosure generally relates to methods and compositions for assessing cancer using gene expression information.

BACKGROUND OF THE DISCLOSURE

A challenge in diagnosing lung cancer, particularly at an early stage where it can be most effectively treated, is gaining access to cells to diagnose disease. Early stage lung cancer is typically associated with small lesions, which may also appear in the peripheral regions of the lung airway, which are particularly difficult to reach by standard techniques such as bronchoscopy.

SUMMARY OF THE INVENTION

Provided herein is a method for determining a risk of cancer comprising (a) determining a level of gene expression products in a biological sample; (b) deriving the composition of cells in the biological sample based on the expression levels of cell-type specific markers in the sample; (c) removing technical variables prior to and during classification of the biological sample; (d) normalizing the gene product levels in step (a) based on the composition of cells determined in step (b); and (e) classifying the risk of cancer. The level of gene expression can be determined by measuring messenger ribonucleic acid expression. The messenger ribonucleic acid can be measured by one or more of the following: microarray, SAGE, blotting, RT-PCR, or quantitative PCR. The risk of cancer can be determined with a specificity of at least 70%. The risk of cancer can be determined with sensitivity of at least 70%. Provided herein are methods for establishing appropriate diagnostic intervention plans and/or treatment plans for subjects, and for aiding healthcare providers in establishing appropriate diagnostic intervention plans and/or treatment plans. In some embodiments, the methods are based on an airway field of injury concept. In some embodiments, the methods involve establishing lung cancer risk scores based on expression levels of informative-genes that are useful for assessing the likelihood that a subject has cancer. In some embodiments, methods provided herein involve making an assessment based on expression levels of informative-genes in a biological sample obtained from a subject during a routine cell or tissue sampling procedure. In some embodiments, the biological sample comprises histologically normal cells. In some embodiments, aspects of the disclosure are based, at least in part, on a determination that expression levels of certain informative-genes in apparently histologically normal cells obtained from a first airway locus can be used to evaluate the likelihood of cancer at a second locus in the airway (for example, at a locus in the airway that is remote from the locus at which the histologically normal cells were sampled). In some embodiments, sampling of histologically normal cells (e.g., cells of the bronchus) is advantageous because tissues containing such cells are generally readily available, and thus it is possible to reproducibly obtain useful samples compared with procedures that involve obtaining tissues of suspicious lesions which may be much less reproducibly sampled. In some embodiments, the methods involve making a lung cancer assessment based on expression levels of informative-genes in cytologically normal appearing cells collected from the bronchi of a subject. In some embodiments, informative-genes useful for predicting the likelihood of lung cancer are provided in Tables 1, 11, and 26.

According to some aspects of the disclosure methods are provided of determining the likelihood that a subject has lung cancer that involve subjecting a biological sample obtained from a subject to a gene expression analysis, in which the gene expression analysis comprises determining mRNA expression levels in the biological sample of one or more informative-genes that relate to lung cancer status (e. g., an informative gene selected from Table 11). In some embodiments, the methods comprise determining mRNA expression levels in the biological sample of one or more genomic correlate genes that relate to one or more self-reportable characteristics of the subject. In some embodiments, the methods further comprise transforming expression levels determined above into a lung cancer risk-score that is indicative of the likelihood that the subject has lung cancer. In some embodiments, the one or more self-reportable characteristics of the subject are selected from: smoking pack years, smoking status, age and gender. In some embodiments, a lung cancer-risk score is determined according to a model having a Negative Predictive Value (NPV) of greater than 90% for ruling out lung cancer in an intended use population. In some embodiments, a lung cancer-risk score is determined according to a model having a Negative Predictive Value (NPV) of greater than 85% for subjects diagnosed with COPD.

In some embodiments, appropriate diagnostic intervention plans are established based at least in part on the lung cancer risk scores. In some embodiments, the methods assist health care providers with making early and accurate diagnoses. In some embodiments, the methods assist health care providers with establishing appropriate therapeutic interventions early on in patient clinical evaluations. In some embodiments, the methods involve evaluating biological samples obtained during bronchoscopic procedures. In some embodiments, the methods are beneficial because they enable health care providers to make informative decisions regarding patient diagnosis and/or treatment from otherwise uninformative bronchoscopies. In some embodiments, the risk or likelihood assessment leads to appropriate surveillance for monitoring low risk lesions. In some embodiments, the risk or likelihood assessment leads to faster diagnosis, and thus, faster therapy for certain cancers.

Certain methods described herein, alone or in combination with other methods, provide useful information for health care providers to assist them in making diagnostic and therapeutic decisions for a patient. Certain methods disclosed herein are employed in instances where other methods have failed to provide useful information regarding the lung cancer status of a patient. Certain methods disclosed herein provide an alternative or complementary method for evaluating or diagnosing cell or tissue samples obtained during routine bronchoscopy procedures, and increase the likelihood that the procedures will result in useful information for managing a patient's care. The methods disclosed herein are highly sensitive, and produce information regarding the likelihood that a subject has lung cancer from cell or tissue samples (e.g., histologically normal tissue) that may be obtained from positions remote from malignant lung tissue. Certain methods described herein can be used to assess the likelihood that a subject has lung cancer by evaluating histologically normal cells or tissues obtained during a routine cell or tissue sampling procedure (e.g., ancillary bronchoscopic procedures such as brushing, such as by cytobrush; biopsy; lavage; and needle-aspiration). However, it should be appreciated that any suitable tissue or cell sample can be used. Often the cells or tissues that are assessed by the methods appear histologically normal. In some embodiments, the subject has been identified as a candidate for bronchoscopy and/or as having a suspicious lesion in the respiratory tract.

In some embodiments, the methods disclosed herein are useful because they enable health care providers to determine appropriate diagnostic intervention and/or treatment plans by balancing the risk of a subject having lung cancer with the risks associated with certain invasive diagnostic procedures aimed at confirming the presence or absence of the lung cancer in the subject. In some embodiments, an objective is to align subjects with low probability of disease with interventions that may not be able to rule out cancer but are lower risk.

According to some aspects of the disclosure, methods are provided for evaluating the lung cancer status of a subject using gene expression information that involve one or more of the following acts: (a) obtaining a biological sample from the respiratory tract of a subject, wherein the subject has been referred for bronchoscopy (e.g., has been identified as having a suspicious lesion in the respiratory tract and therefore referred for bronchoscopy to evaluate the lesion), (b) subjecting the biological sample to a gene expression analysis, in which the gene expression analysis comprises determining the expression levels of a plurality of informative-genes in the biological sample, (c) computing a lung cancer risk score based on the expression levels of the plurality of informative-genes, (d) determining that the subject is in need of a first diagnostic intervention to evaluate lung cancer status, if the level of the lung cancer risk score is beyond (e.g., above) a first threshold level, and (e) determining that the subject is in need of a second diagnostic intervention to evaluate lung cancer status, if the level of the lung cancer risk score is beyond (e.g., below) a second threshold level. In some embodiments, the methods further comprise (f) determining that the subject is in need of a third diagnostic intervention to evaluate lung cancer status, if the level of the lung cancer risk score is between the first threshold and the second threshold levels.

In particular embodiments, the approaches herein may be used when a subject was referred for bronchoscopy and the bronchoscopy procedure resulted in indeterminate or non-diagnostic information. Accordingly, disclosed herein are methods for assigning such subjects to a low-risk, including one or more of steps (a) obtaining a biological sample from the respiratory tract of the subject, wherein the subject has undergone a non-diagnostic bronchoscopy procedure, (b) subjecting the biological sample to a gene expression analysis, in which the gene expression analysis comprises determining the expression levels of a plurality of informative-genes in the biological sample, (c) computing a lung cancer risk score based on the expression levels of the plurality of informative-genes, and (d) determining that the subject is a low risk of lung cancer, if the level of the lung cancer risk score is beyond (e.g., below) a first threshold level, and optionally, (e) assigning the low-risk subjects to one or more non-invasive follow-up procedures; CT surveillance, for example. Such approaches allow a population of subjects to avoid subsequent invasive approaches. For subjects who are not below the threshold level, traditional approaches following a non-diagnostic bronchoscopy may be followed.

In some embodiments, the first diagnostic intervention comprises performing a transthoracic needle aspiration, mediastinoscopy or thoracotomy. In some embodiments, the second diagnostic intervention comprises engaging in watchful waiting (e.g., periodic monitoring). In some embodiments, watchful waiting comprises periodically imaging the respiratory tract to evaluate the suspicious lesion. In some embodiments, watchful waiting comprises periodically imaging the respiratory tract to evaluate the suspicious lesion for up to one year, two years, four years, five years or more. In some embodiments, watchful waiting comprises imaging the respiratory tract to evaluate the suspicious lesion at least once per year. In some embodiments, watchful waiting comprises imaging the respiratory tract to evaluate the suspicious lesion at least twice per year. In some embodiments, watchful waiting comprises periodic monitoring of a subject unless and until the subject is diagnosed as being free of cancer. In some embodiments, watchful waiting comprises periodic monitoring of a subject unless and until the subject is diagnosed as having cancer. In some embodiments, watchful waiting comprises periodically repeating one or more of steps (a) to (f) noted in the preceding paragraph. In some embodiments, the third diagnostic intervention comprises performing a bronchoscopy procedure. In some embodiments, the third diagnostic intervention comprises repeating steps (a) to (e) noted in the preceding paragraph. In certain embodiments, the third diagnostic intervention comprises repeating steps (a) to (e) within six months of determining that the lung cancer risk score is between the first threshold and the second threshold levels. In certain embodiments, the third diagnostic intervention comprises repeating steps (a) to (e) within three months of determining that the lung cancer risk score is between the first threshold and the second threshold levels. In some embodiments, the third diagnostic intervention comprises repeating steps (a) to (e) within one month of determining that the lung cancer risk score is between the first threshold and the second threshold levels.

In some embodiments, the plurality of informative-genes is selected from the group of genes in Table 11. In some embodiments, the expression levels of a subset of these genes are evaluated and compared to reference expression levels (e.g., for normal patients that do not have cancer). In some embodiments, the subset includes a) genes for which an increase in expression is associated with lung cancer or an increased risk for lung cancer, b) genes for which a decrease in expression is associated with lung cancer or an increased risk for lung cancer, or both. In some embodiments, at least 5%, at least 10%, at least 20%, at least 30%, at least 40%, or about 50% of the genes in a subset have an increased level of expression in association with an increased risk for lung cancer. In some embodiments, at least 5%, at least 10%, at least 20%, at least 30%, at least 40%, or about 50% of the genes in a subset have a decreased level of expression in association with an increased risk for lung cancer. In some embodiments, an expression level is evaluated (e.g., assayed or otherwise interrogated) for each of 10-80 or more genes (e.g., 5-10, 10-20, 20-30, 30-40, 40-50, 50-60, 60-70, 70-80, about 10, about 15, about 17, about 25, about 35, about 45, about 55, about 65, about 75, or more genes) selected from the genes in Table 11. In some embodiments, expression levels for one or more control genes also are evaluated (e.g., 1, 2, 3, 4, or 5 control genes). It should be appreciated that an assay can also include other genes, for example reference genes or other gene (regardless of how informative they are). However, if the expression profile for any of the informative-gene subsets described herein is indicative of an increased risk for lung cancer, then an appropriate therapeutic or diagnostic recommendation can be made as described herein.

In some embodiments, the identification of changes in expression level of one or more subsets of genes from Table 11 can be provided to a physician or other health care professional in any suitable format. In some embodiments, these gene expression profiles and/or results of a prediction model disclosed herein alone may be sufficient for making a diagnosis, providing a prognosis, or for recommending further diagnosis or a particular treatment. However, in some embodiments gene expression profiles and/or results of a prediction model disclosed herein may assist in the diagnosis, prognosis, and/or treatment of a subject along with other information (e.g., other expression information, and/or other physical or chemical information about the subject, including family history).

In some embodiments, a subject is identified as having a suspicious lesion in the respiratory tract by imaging the respiratory tract. In certain embodiments, imaging the respiratory tract comprises performing computer-aided tomography, magnetic resonance imaging, ultrasonography or a chest X-ray.

Methods are provided, in some embodiments, for obtaining biological samples from patients. Expression levels of informative-genes in these biological samples provide a basis for assessing the likelihood that the patient has lung cancer. Methods are provided for processing biological samples. In some embodiments, the processing methods ensure RNA quality and integrity to enable downstream analysis of informative-genes and ensure quality in the results obtained. Accordingly, various quality control steps (e.g., RNA size analyses) may be employed in these methods. Methods are provided for packaging and storing biological samples. Methods are provided for shipping or transporting biological samples, e.g., to an assay laboratory where the biological sample may be processed and/or where a gene expression analysis may be performed. Methods are provided for performing gene expression analyses on biological samples to determine the expression levels of informative-genes in the samples. Methods are provided for analyzing and interpreting the results of gene expression analyses of informative-genes. Methods are provided for generating reports that summarize the results of gene expression analyses, and for transmitting or sending assay results and/or assay interpretations to a health care provider (e.g., a physician). Furthermore, methods are provided for making treatment decisions based on the gene expression assay results, including making recommendations for further treatment or invasive diagnostic procedures.

In some embodiments, aspects of the disclosure relate to determining the likelihood that a subject has lung cancer, by subjecting a biological sample obtained from a subject to a gene expression analysis, wherein the gene expression analysis comprises determining expression levels in the biological sample of at least one informative-genes (e.g., at least two genes selected from Table 11), and using the expression levels to assist in determining the likelihood that the subject has lung cancer.

In some embodiments, the step of determining comprises transforming the expression levels into a lung cancer risk-score that is indicative of the likelihood that the subject has lung cancer. In some embodiments, the lung cancer risk-score is the combination of weighted expression levels. In some embodiments, the lung cancer risk-score is the sum of weighted expression levels. In some embodiments, the expression levels are weighted by their relative contribution to predicting increased likelihood of having lung cancer In some embodiments, aspects of the disclosure relate to determining a treatment course for a subject, by subjecting a biological sample obtained from the subject to a gene expression analysis, wherein the gene expression analysis comprises determining the expression levels in the biological sample of at least two informative-genes (e.g., at least two mRNAs selected from Table 11), and determining a treatment course for the subject based on the expression levels. In some embodiments, the treatment course is determined based on a lung cancer risk-score derived from the expression levels. In some embodiments, the subject is identified as a candidate for a lung cancer therapy based on a lung cancer risk-score that indicates the subject has a relatively high likelihood of having lung cancer. In some embodiments, the subject is identified as a candidate for an invasive lung procedure based on a lung cancer risk-score that indicates the subject has a relatively high likelihood of having lung cancer. In some embodiments, the invasive lung procedure is a transthoracic needle aspiration, mediastinoscopy or thoracotomy. In some embodiments, the subject is identified as not being a candidate for a lung cancer therapy or an invasive lung procedure based on a lung cancer risk-score that indicates the subject has a relatively low likelihood of having lung cancer. In some embodiments, a report summarizing the results of the gene expression analysis is created. In some embodiments, the report indicates the lung cancer risk-score.

In some embodiments, aspects of the disclosure relate to determining the likelihood that a subject has lung cancer by subjecting a biological sample obtained from a subject to a gene expression analysis, wherein the gene expression analysis comprises determining the expression levels in the biological sample of at least one informative-gene (e.g., at least one informative-mRNA selected from Table 11), and determining the likelihood that the subject has lung cancer based at least in part on the expression levels.

In some embodiments, aspects of the disclosure relate to determining the likelihood that a subject has lung cancer, by subjecting a biological sample obtained from the respiratory epithelium of a subject to a gene expression analysis, wherein the gene expression analysis comprises determining the expression level in the biological sample of at least one informative-gene (e.g., at least one informative-mRNA selected from Table 11), and determining the likelihood that the subject has lung cancer based at least in part on the expression level, wherein the biological sample comprises histologically normal tissue.

In some embodiments, aspects of the disclosure relate to a computer-implemented method for processing genomic information, by obtaining data representing expression levels in a biological sample of at least two informative-genes (e.g., at least two informative-mRNAs from Table 11), wherein the biological sample was obtained of a subject, and using the expression levels to assist in determining the likelihood that the subject has lung cancer. A computer-implemented method can include inputting data via a user interface, computing (e.g., calculating, comparing, or otherwise analyzing) using a processor, and/or outputting results via a display or other user interface.

In some embodiments, the step of determining comprises calculating a risk-score indicative of the likelihood that the subject has lung cancer. In some embodiments, computing the risk-score involves determining the combination of weighted expression levels (e.g., expression levels of one or more informative-genes alone or together with one of more genomic correlate genes), in which the expression levels are weighted by their relative contribution to predicting increased likelihood of having lung cancer. In some embodiments, genomic correlate genes are genes related to or correlated with specific clinical variables (e.g., self-reportable variables). In some embodiments, such clinical variables are correlated with cancer, e.g., lung cancer. In some embodiments, rather than using expression levels of genes, groups of related genes that vary collinearly (e.g., are correlated with one another) within a population of subjects may be combined or collapsed into a single value (e.g., the mean value of a group of related genes). In some embodiments, a computer-implemented method comprises generating a report that indicates the risk-score. In some embodiments, the report is transmitted to a health care provider of the subject.

In some embodiments, a computer-implemented method comprises obtaining data representing expression levels in a biological sample of at least 2, 3, 4, 5, 6, 7, 8, 9, or 10 genes selected from the set of genes identified in cluster 1, 2, 3, 4, 5, 6, 7, 8, 9, 10, or 11 in table 11. In some embodiments, the genes comprise MYOT.

It should be appreciated that in any embodiment or aspect described herein, a biological sample can be obtained from the respiratory epithelium of the subject. The respiratory epithelium can be of the mouth, nose, pharynx, trachea, bronchi, bronchioles, or alveoli. However, other sources of respiratory epithelium also can be used. The biological sample can comprise histologically normal tissue. The biological sample can be obtained using bronchial brushings, such as cytobrush or histobrush; broncho-alveolar lavage; bronchial biopsy; oral washings; touch preps; fine needle aspirate; or sputum collection. The subject can exhibit one or more symptoms of lung cancer and/or have a lesion that is observable by computer-aided tomography or chest X-ray. In some cases, the subject has not been diagnosed with primary lung cancer prior to being evaluating by methods disclosed herein.

In any of the embodiments or aspects described herein, the expression levels can be determined using a quantitative reverse transcription polymerase chain reaction, a bead-based nucleic acid detection assay or an oligonucleotide array assay (e.g., a microarray assay) or other technique.

In any of the embodiments or aspects described herein, the lung cancer can be a adenocarcinoma, squamous cell carcinoma, small cell cancer or non-small cell cancer.

In some embodiments, aspects of the disclosure relate to a composition consisting essentially of at least one nucleic acid probe, wherein each of the at least one nucleic acid probes specifically hybridizes with an informative-gene (e.g., at least one informative-mRNA selected from Table 11).

In some embodiments, aspects of the disclosure relate to a composition comprising up to 5, up to 10, up to 25, up to 50, up to 100, or up to 200 nucleic acid probes, wherein each of the nucleic acid probes specifically hybridizes with an informative-gene (e.g., at least one informative-mRNA selected from Table 1 or 11).

In some embodiments, a composition comprises at least 1, 2, 3, 4, 5, 6, 7, 8, 9, or 10 nucleic acid probes. In some embodiments, at least 2, 3, 4, 5, 6, 7, 8, 9, or 10 of the nucleic acid probes hybridize with an mRNA expressed from a different gene selected from clusters 1, 2, 3, 4, 5, 6, 7, 8, 9, 10, or 11 of Table 11.

In some embodiments, nucleic acid probes are conjugated directly or indirectly to a bead. In some embodiments, the bead is a magnetic bead. In some embodiments, the nucleic acid probes are immobilized to a solid support. In some embodiments, the solid support is a glass, plastic or silicon chip.

In some embodiments, aspects of the disclosure relate to a kit comprising at least one container or package housing any nucleic acid probe composition described herein.

In some embodiments, expression levels are determined using a quantitative reverse transcription polymerase chain reaction.

In some embodiments, aspects of the disclosure relate to genes for which expression levels can be used to determine the likelihood that a subject (e.g., a human subject) has lung cancer. In some embodiments, the expression levels (e.g., mRNA levels) of one or more genes described herein can be determined in airway samples (e.g., epithelial cells or other samples obtained during a bronchoscopy or from an appropriate bronchial lavage samples). In some embodiments, the patterns of increased and/or decreased mRNA expression levels for one or more subsets of informative-genes (e.g., 1-5, 5-10, 10-15, 15-20, 20-25, 25-50, 50-80, or more genes) described herein can be determined and used for diagnostic, prognostic, and/or therapeutic purposes. It should be appreciated that one or more expression patterns described herein can be used alone, or can be helpful along with one or more additional patient-specific indicia or symptoms, to provide personalized diagnostic, prognostic, and/or therapeutic predictions or recommendations for a patient. In some embodiments, sets of informative-genes that distinguish smokers (current or former) with and without lung cancer are provided that are useful for predicting the risk of lung cancer with high accuracy. In some embodiments, the informative-genes are selected from Table 1 or 11.

In some embodiments, methods provided herein for determining the likelihood that a subject has lung cancer involve subjecting a biological sample obtained from a subject to a gene expression analysis that comprises determining mRNA expression levels in the biological sample of one or more informative-genes that relate to lung cancer status (e.g., an informative gene selected from Table 1 or 11). In some embodiments, the methods comprise determining mRNA expression levels in the biological sample of one or more genomic correlate genes that relate to one or more self-reportable characteristics of the subject. In some embodiments, the methods further comprise transforming the expression levels determined above into a lung cancer risk-score that is indicative of the likelihood that the subject has lung cancer. In some embodiments, the one or more self-reportable characteristics of the subject are selected from: smoking pack years, smoking status, age and gender. In some embodiments, the lung cancer risk-score is determined according to the follow equation:

$$Score = \frac{ex^{Score1 \ or \ Score \ 2}}{(1 + ex^{Score1 \ or \ Score \ 2})}$$

wherein:

$X^{score \ 1} = W_0 + W_1 \times GG + W_2 \times GS + W_3 \times GPY + W_4 \times GA +$ $W_5 \times C1A + W_6 \times C1B + W_7 \times C2 + W_8 \times C3 + W_9 \times C4A + W_{10} \times C4B$ and $X^{score \ 2} = W_0 + W_1 \times GG + W_2 \times GS + W_3 \times GPY + W_4 \times \text{Reported Age} +$ $W_5 \times C1A + W_6 \times C1B + W_7 \times C2 + W_8 \times C3 + W_9 \times C4A + W_{10} \times C4B,$ and in which GG, GS, GPY, GA, CIA, CIB, C2, C3, C4A and C4B are determined according to the equations disclosed herein.

In some embodiments, informative-genes are selected from Table 1 or 11. In some embodiments, groups of related genes that vary collinearly (e.g., are correlated with one another) within a population of subjects may be combined or collapsed into a single value (e.g., the mean value of a group of related genes). In some embodiments, groups of related genes are correlated because they are associated with the same cellular and/or molecular pathways. In some embodiments, at least 2, at least 3, at least 4, at least 5 or more related genes (e.g., correlated genes, genes within a common cluster) are combined together in a single value. In some embodiments, groups of related genes are identified by performing a cluster analysis of expression levels obtained from multiple subjects (e.g., 2 to 100, 2 to 500, 2 to 1000 or more subjects). Any appropriate cluster analysis may be used to identify such related genes including, for example, centroid based clustering (e.g., k-means clustering), connectivity based clustering (e.g., hierarchical clustering) and other suitable approaches. Non-limiting examples of such clusters are identified in Table 11 with the values in column 2 specifying the cluster within which each gene resides such that related genes (e.g., correlated genes) are within the same cluster. In some embodiments, a value reflecting the expression status of a set of related genes is the mean expression level of the set of related genes. For example, one or more of the following values may be used: CIA, C1B, C2, C3, C4A, and C4B in a model for predicting the likelihood that a subject has cancer, in which CIA=mean of (BST1, CD177.1, CD177.2),
C1B=mean of (ATP12A, TSPAN2),
C2=mean of (GABBRI, MCAM, NOVA1, SDC2),
C3=mean of (CDR1, CGREF1, CLND22, NKX3-1),
C4A=mean of (EPHX3, LYPD2), and
C4B=mean of (MIA, RNF150).

In some embodiments genes within a cluster can be substituted for each other. Thus, in some embodiments, all genes within a cluster need to be evaluated or used in a prediction model. In some embodiments, only 1, 2, 3, 4, 5, 6, 7, 8, 9, or 10 genes within a cluster are independently selected for analysis as described herein. In some embodiments, at least 1, 2, 3, 4, 5, 6, 7, 8, 9, or 10 genes within a cluster of table 11 are identified.

In some embodiments, one or more informative-genes are selected from the set of genes identified as cluster 1 in Table 11. In some embodiments, one or more informative-genes are selected from the set of genes identified as cluster 2 in Table 11. In some embodiments, one or more informative-genes are selected from the set of genes identified as cluster 3 in Table 11. In some embodiments, one or more informative-genes are selected from the set of genes identified as cluster 4 in Table 11. In some embodiments, one or more informative-genes are selected from the set of genes identified as cluster 5 in Table 11. In some embodiments, one or more informative-genes are selected from the set of genes identified as cluster 6 in Table 11. In some embodiments, one or more informative-genes are selected from the set of genes identified as cluster 7 in Table 11. In some embodiments, one or more informative-genes are the set of genes identified as cluster 8 in Table 11. In some embodiments, one or more informative-genes are selected from the set of genes identified as cluster 9 in Table 11. In some embodiments, one or more informative-genes are selected from the set of genes identified as cluster 10 in Table 11.

In some embodiments, one or more informative-genes are selected from the set of genes identified as cluster 11 in Table 11. In some embodiments, the informative-genes comprise MYOT. In some embodiments, genes selected from a cluster are reduced to a single value, such as, for example, the mean, median, mode or other summary statistic of the expression levels of the selected genes.

In some embodiments, provided herein are methods for establishing appropriate diagnostic intervention plans and/or treatment plans for subjects and for aiding healthcare providers in establishing appropriate diagnostic intervention plans and/or treatment plans. In some embodiments, methods are provided that involve making a risk assessment based on expression levels of informative-genes in a biological sample obtained from a subject during a routine cell or tissue sampling procedure. In some embodiments, methods are provided that involve establishing lung cancer risk scores based on expression levels of informative genes. In some embodiments, appropriate diagnostic intervention plans are established based at least in part on the lung cancer risk scores. In some embodiments, methods provided herein assist health care providers with making early and accurate diagnoses. In some embodiments, methods provided herein assist health care providers with establishing appropriate therapeutic interventions early on in patients' clinical evaluations. In some embodiments, methods provided herein involve evaluating biological samples obtained during bronchoscopies procedure. In some embodiments, the methods are beneficial because they enable health care providers to make informative decisions regarding patient diagnosis and/or treatment from otherwise uninformative bronchoscopies. In some embodiments, the risk assessment leads to appropriate surveillance for monitoring low risk lesions. In some embodiments, the risk assessment leads to faster diagnosis, and thus, faster therapy for certain cancers.

Provided herein are methods for determining the likelihood that a subject has lung cancer, such as adenocarcinoma, squamous cell carcinoma, small cell cancer or non-small cell cancer. The methods alone or in combination with other methods provide useful information for health care providers to assist them in making diagnostic and therapeutic decisions for a patient. The methods disclosed herein are often employed in instances where other methods have failed to provide useful information regarding the lung cancer status of a patient. For example, approximately 50% of bronchoscopy procedures result in indeterminate or non-diagnostic information. There are multiple sources of indeterminate results, and may depend on the training and procedures available at different medical centers. However, in certain embodiments, molecular methods in combination with bronchoscopy are expected to improve cancer detection accuracy.

In some embodiments, provided herein are methods of determining the likelihood that a subject has lung cancer. In some embodiments, methods are provided that involve subjecting a biological sample obtained from a subject to a gene expression analysis, wherein the gene expression analysis comprises measuring cDNA levels of one or more informative-genes that relate to lung cancer status, and measuring cDNA levels of ore or more genomic correlate genes that relate to one or more self-reportable characteristics of the subject; and determining a lung cancer risk-score based on the cDNA levels determined in (a) and (b), that is indicative of the likelihood that the subject has lung cancer; wherein the cDNA is prepared from mRNA from the biological sample.

In some embodiments, the methods of the present disclosure include the conversion of mRNA into cDNA. In further embodiments, cDNA is amplified.

Disclosed herein is a method, comprising (a) obtaining a test sample from a subject, wherein said subject is suspected of having lung cancer based at least in part on an imaging analysis of said subject showing a suspicious lesion; (b) assaying gene expression levels in said test sample; and (c) processing said gene expression levels to determine that said suspicious lesion is associated with or is likely to be associated with said lung cancer in said subject; wherein said test sample comprises respiratory epithelial cells from a mouth, nose, pharynx, trachea, or bronchi of said subject. The imaging analysis can comprise computer-aided tomography, magnetic resonance imaging, ultrasonography, or chest X-ray. The lung cancer can be adenocarcinoma, squamous cell carcinoma, small cell lung cancer, or non-small cell lung cancer. The gene expression levels can comprise informative gene expression levels that relate to lung cancer status, and genomic correlate gene expression levels that relate to one or more self-reportable characteristics of said subject. The one or more self-reportable characteristics of the subject can comprise smoking pack years, smoking status, age, or gender. Obtaining can comprise bronchial brushing, bronchoalveolar lavage, bronchial biopsy, oral washing, or sputum collection. The method can further comprise creating a report that indicates a lung cancer risk score. The subject can be identified as a candidate for an invasive lung procedure based at least in part on said lung cancer risk score, wherein said lung cancer risk score indicates that said subject is at risk of having said lung cancer. The invasive lung procedure can be a transthoracic needle aspiration, mediatinoscopy, or thoracotomy. The lung cancer risk score can be a combination of weighted expression levels. The expression levels can be weighted by a relative contribution to predicting an increased likelihood of having said lung cancer. The lung cancer risk score can be determined using a model having a Negative Predictive Value (NPV) of greater than 90% for ruling out said lung cancer. The lung cancer risk score can be determined using a model having a Negative Predictive Value (NPV) of greater than 85% for ruling out said lung cancer in subjects diagnosed with chronic obstructive pulmonary disease (COPD). The test sample can be obtained from said nose of said subject. Assaying can comprise use of at least one nucleic acid probe that specifically hybridizes with a messenger ribonucleic acid molecule in said test sample. The least one nucleic acid probe can be conjugated to a bead. The at least one nucleic acid probe can be immobilized on a solid support. The processing can comprise comparing said gene expression levels to at least one control gene expression level. The subject can be suspected of having lung cancer based at least in part on said subject exhibiting one or more symptoms of said lung cancer. The one or more symptoms of the lung cancer can comprise a persistent cough, worsening of an existing cough, blood in sputum of said subject, persistent bronchitis, chest pain, unexplained weight loss, shortness of breath, or wheezing.

These and other aspects are described in more detail herein and are illustrated by the non-limiting figures and examples.

BRIEF DESCRIPTION OF THE DRAWINGS

FIG. 6A depicts a post-test POM related to pre-test POM based on a negative classifier call (solid line; adjusted using the negative likelihood ratio) and a positive classifier call (dotted line; adjusted using the positive likelihood ratio) calculated for the classifier in combination with bronchoscopy. The negative classifier call curve shows that for patients with a pre-test POM of <66%, the post-test POM is <10% when bronchoscopy is negative and the classifier is negative. For patients with a negative bronchoscopy and a positive classifier score, the post-test likelihood of cancer is >10% when the pre-test likelihood is greater than 5%. FIG. 6B depicts post test probability of cancer based on the pretest probability and the negative likelihood ratio of the classifier and bronchoscopy. The posttest probability of lung cancer is shown in relation to the pretest probability based on a nondiagnostic bronchoscopic examination and a negative classifier score (adjusted with the use of the negative likelihood ratio). The curve shows that for patients with a pretest probability of cancer of less than 66% (short vertical line), the posttest probability is less than 10% (broken line) when bronchoscopic findings are negative and the classifier score is negative.

FIG. 10A and FIG. 10B depicts nucleic acid probes used in hybridizing to nucleic acid sequences represented by gene classifier CD177. FIG. 10A discloses the 19 nucleic acid probes in CD177.1 (SEQ ID NOs:24-42 in order from top to bottom) and FIG. 10B discloses the 4 nucleic acid probes in CD177.2 (SEQ ID NOs:43-46 from top to bottom).

DETAILED DESCRIPTION OF THE INVENTION

Figure 1:
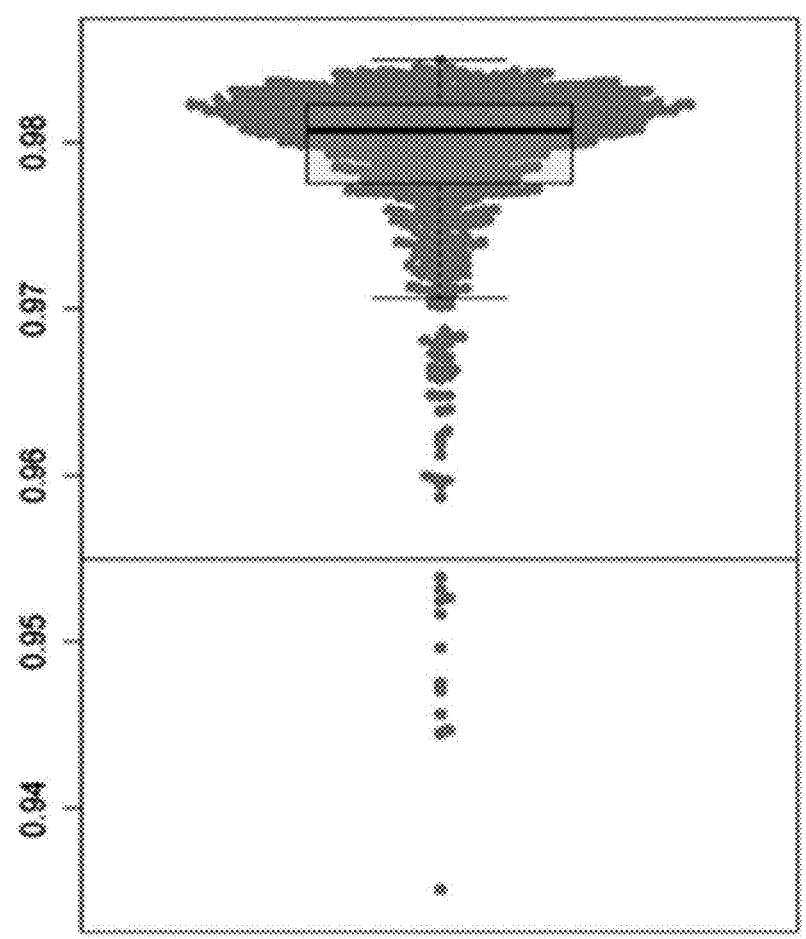
FIG. 1 is a non-limiting example of a plot of correlation coefficients from pairwise correlation of all gene expression data of all qualified AEGIS I samples; samples with a correlation coefficient <0.955 were identified as outliers and excluded from further analysis; a total of 597 samples were retained.

Methods disclosed herein provide alternative or complementary approaches for evaluating cell or tissue samples obtained by bronchoscopy procedures (or other procedures for evaluating respiratory tissue), and increase the likelihood that the procedures will result in useful information for managing the patient's care. The methods disclosed herein are highly sensitive, and produce information regarding the likelihood that a subject has lung cancer from cell or tissue samples (e.g., bronchial brushings of airway epithelial cells), which are often obtained from regions in the airway that are remote from malignant lung tissue. In general, the methods disclosed herein involve subjecting a biological sample obtained from a subject to a gene expression analysis to evaluate gene expression levels. However, in some embodiments, the likelihood that the subject has lung cancer is determined in further part based on the results of a histological examination of the biological sample or by considering other diagnostic indicia such as protein levels, mRNA levels, imaging results, chest X-ray exam results etc.

The term "subject," as used herein, generally refers to a mammal. Typically the subject is a human. However, the term embraces other species, e.g., pigs, mice, rats, dogs, cats, or other primates. In certain embodiments, the subject is an experimental subject such as a mouse or rat.

The subject may be a male or female. The subject may be an infant, a toddler, a child, a young adult, an adult or a geriatric. The subject may be a smoker, a former smoker or a non-smoker. The subject may have a personal or family history of cancer. The subject may have a cancer-free personal or family history. The subject may exhibit one or more symptoms of lung cancer or other lung disorder (e.g., emphysema, COPD). For example, the subject may have a new or persistent cough, worsening of an existing chronic cough, blood in the sputum, persistent bronchitis or repeated respiratory infections, chest pain, unexplained weight loss and/or fatigue, or breathing difficulties such as shortness of breath or wheezing. The subject may have a lesion, which may be observable by computer-aided tomography or chest X-ray. The subject may be an individual who has undergone a bronchoscopy or who has been identified as a candidate for bronchoscopy (e.g., because of the presence of a detectable lesion or suspicious imaging result). In some embodiments, a subject has or has been diagnosed with chronic obstructive pulmonary disease (COPD). In some embodiments, a subject does not have or has not been diagnosed with COPD. A subject under the care of a physician or other health care provider may be referred to as a "patient."

The term "about", as used herein, refers to plus or minus ten percent of the object that "about" modifies. Thus, the phrase "about 10, 20, or 30" encompasses 8-11, 18-22, 27-33, respectively.

Informative-Genes

The expression levels of genes of the present disclosure have been identified as providing useful information regarding the lung cancer status of a subject. These genes are referred to herein as "informative-genes." Informative-genes include protein coding genes and non-protein coding genes. It will be appreciated by the skilled artisan that the expression levels of informative-genes may be determined by evaluating the levels of appropriate gene products (e.g., mRNAs, miRNAs, proteins etc.) Accordingly, the expression levels of certain mRNAs have been identified as providing useful information regarding the lung cancer status of a subject. These mRNAs are referred to herein as "informative-mRNAs."

Table 11 provides a listing of informative-genes that are differentially expressed in cancer. In some embodiments, informative-genes that are differentially expressed in lung cancer are selected from: BST1, CD177.1, CD177.2, ATP12A, TSPAN2, GABBR1, MCAM, NOVA1, SDC2, CDR1, CGREF1, CLND22, NKX3-1, EPHX3, LYPD2, MIA, RNF150. In some embodiments, informative-genes that are differentially expressed in lung cancer are selected from: TMEM51, CR1L, PDZK1IP1, MICAL2, VWA5A, ACAD8, SAA4, GLYATL2, ETV6, CD177, CEACAM7, QPCT, CASP10, PI3, BST1, MTNR1A, STARD4, CFB, SLC26A8, VNN2, HDAC9, SLC26A4, and LCN2. In some embodiments, informative-genes that are differentially expressed in lung cancer are selected from: CCDC18, FAM72D, NUF2, FBXO28, GPR137B, STIL, DEPDC1, TSPAN2, ASPM, KIF14, KIF20B, RAD51AP1, GAS2L3, SPIC, SMAGP, ATP12A, BRCA2, BORA, SKA3, DLGAP5, CASC5, LRRC28, PYCARD, TXNL4B, EFCAB5, SPAG5, ABCA12, AURKA, SGOL1, BANK1, CENPE, CASP6, MAD2L1, CCNA2, CCNB1, KIF20A, CENPK, ERAP1, FAM54A, PHTF2, CLDN12, BPGM, PCMTD1, MELK, and MST4. In some embodiments, informative-genes that are differentially expressed in lung cancer are selected from: CR1, GOS2, CSF3R, S100A12, SELL, NCF2, LIPN, ZNF438, NAMPT, CBL, CASP5, CARD16, CARD17, CLEC4A, LRRK2, HMGN2P46, AQP9, BCL2A1, ITGAX, GPR97, CCL4, PSTPIP2, IFI30, FFAR2, EMR3, FPR1, LILRA5, PLEK, MXD1, TNFAIP6, CXCR2, IL1B, CXCR1, SIRPB1, NCF4, IRAK2, PROK2, TLR2, TREM1, SOD2, CREB5, TNFRSF10C, CSGALNACT1, and ASAP 1. In some embodiments, informative-genes that are differentially expressed in lung cancer are selected from: PLA2G2A, NFYC, RASSF10, GLB1L3, TRIM3, MCAM, MSRB3, SLITRK5, GAS6, NOVA1, GABRG3, ABCA3, LPO, FSCN2, RASD1, HILS1, SDK2, NTN5, KCNA7, ATOH8, KCNIP3, INHBB, VSTM2L, ZNRF3, PLEKHG4B, GNMT, GABBR1, ARHGEF10, SDC2, CRB2, GAS1, PNPLA7, and RAI2.

Certain methods disclosed herein involve determining expression levels in the biological sample of at least one informative-gene. However, in some embodiments, the expression analysis involves determining the expression levels in the biological sample of at least 2, at least 3, at least 4, at least 5, at least 6, at least 7, at least 8, at least 9, at least 10, at least 20, at least 30, at least 40, at least 50, at least 60, at least 70, or least 80 informative-genes. In some embodiments, the expression analysis involves determining expression levels in the biological sample of 1 to 5, 1 to 10, 5 to 10, 5 to 15, 10 to 15, 10 to 20, 15 to 20, 15 to 25, 20 to 30, 25 to 50, 25 to 75, 50 to 100, 50 to 200 or more informative-genes, such as those in table 11. In some embodiments, the expression analysis involves determining expression levels in the biological sample to at least 1 to 5, 1 to 10, 2 to 10, 5 to 10, 5 to 15, 10 to 15, 10 to 20, 15 to 20, 15 to 25, 20 to 30, 25 to 50, 25 to 75, 50 to 100, 50 to 200 or more informative-genes, such as those in table 11.

In some embodiments, the number of informative-genes for an expression analysis are sufficient to provide a level of confidence in a prediction outcome that is clinically useful. This level of confidence (e.g., strength of a prediction model) may be assessed by a variety of performance parameters including, but not limited to, the accuracy, sensitivity specificity, and area under the curve (AUC) of the receiver operator characteristic (ROC) curve. These parameters may be assessed with varying numbers of features (e.g., number of genes, mRNAs) to determine an optimum number and set of informative-genes. An accuracy, sensitivity or specificity of at least 60%, 70%, 80%, 90%, may be useful when used alone or in combination with other information.

Any appropriate system or method may be used for determining expression levels of informative-genes. Gene expression levels may be determined through the use of a hybridization-based assay. As used herein, the term, "hybridization-based assay" refers to any assay that involves nucleic acid hybridization. A hybridization-based assay may or may not involve amplification of nucleic acids. Hybridization-based assays are well known in•the art and include, but are not limited to, array-based assays (e.g., oligonucleotide arrays, microarrays), oligonucleotide conjugated bead assays (e.g., Multiplex Bead-based Luminex® Assays), molecular inversion probe assays, and quantitative RT-PCR assays. Multiplex systems, such as oligonucleotide arrays or bead-based nucleic acid assay systems are particularly useful for evaluating levels of a plurality of genes simultaneously. Other appropriate methods for determining levels of nucleic acids will be apparent to the skilled artisan.

As used herein, a "level" refers to a value indicative of the amount or occurrence of a substance, e.g., an mRNA. A level may be an absolute value, e.g., a quantity of mRNA in a sample, or a relative value, e.g., a quantity of mRNA in a sample relative to the quantity of the mRNA in a reference sample (control sample). The level may also be a binary value indicating the presence or absence of a substance. For example, a substance may be identified as being present in a sample when a measurement of the quantity of the substance in the sample, e.g., a fluorescence measurement from a PCR reaction or microarray, exceeds a background value. Similarly, a substance may be identified as being absent from a sample (or undetectable in the sample) when a measurement of the quantity of the molecule in the sample is at or below background value. It should be appreciated that the level of a substance may be determined directly or indirectly.

Further non-limiting examples of informative mRNAs are disclosed in, for example, the following patent applications, the contents of which are incorporated herein by reference in their entirety for all purposes: U.S. Patent Publication No. US2007/148650, filed on May 12, 2006, entitled ISOLATION OF NUCLEIC ACID FROM MOUTH EPITHELIAL CELLS; U.S.

Patent Publication No. US2009/311692, filed Jan. 9, 2009, entitled ISOLATION OF NUCLEIC ACID FROM MOUTH EPITHELIAL CELLS; U.S. application Ser. No. 12/884,714, filed Sep. 17, 2010, entitled ISOLATION OF NUCLEIC ACID FROM MOUTH EPITHELIAL CELLS; U.S. Patent Publication No. US2006/154278, filed Dec. 6, 2005, entitled DETECTION METHODS FOR DISORDER OF THE LUNG; U.S. Patent Publication No. US2010/035244, filed Feb. 8, 2008, entitled, DIAGNOSTIC FOR LUNG DISORDERS USING CLASS PREDICTION; U.S. application Ser. No. 12/869,525, filed Aug. 26, 2010, entitled, DIAGNOSTIC FOR LUNG DISORDERS USING CLASS PREDICTION; U.S. application Ser. No. 12/234,368, filed Sep. 19, 2008, entitled, BIOMARKERS FOR SMOKE EXPOSURE; U.S. application Ser. No. 12/905,897, filed Oct. 154, 2010, entitled BIOMARKERS FOR SMOKE EXPOSURE; U.S. Patent Application No. US2009/186951, filed Sep. 19, 2008, entitled IDENTIFICATION OF NOVEL PATHWAYS FOR DRUG DEVELOPMENT FOR LUNG DISEASE; U.S. Publication No. US2009/061454, filed Sep. 9, 2008, entitled, DIAGNOSTIC AND PROGNOSTIC METHODS FOR LUNG DISORDERS USING GENE EXPRESSION PROFILES; U.S. application Ser. No. 12/940,840, filed Nov. 5, 2010, entitled, DIAGNOSTIC AND PROGNOSTIC METHODS FOR LUNG DISORDERS USING GENE EXPRESSION PROFILES; U.S. Publication No. US2010/055689, filed Mar. 30, 2009, entitled, MULTIFACTORIAL METHODS FOR DETECTING LUNG DISORDERS; and International Patent Application No. PCT/US13/38449, filed Apr. 26, 2013, entitled METHODS FOR EVALUATING LUNG CANCER STATUS. cDNA cDNA molecules are non-naturally occurring polynucleotide sequences that are synthesized from mRNA molecules by one possessing ordinary skill in the art. In some embodiments, cDNA molecules of the present invention are obtained or acquired. The conversion of RNA to cDNA utilizing a reverse transcriptase enzyme creates cDNA, a non-naturally occurring molecule that lacks introns. Methods that rely on cDNA are necessarily relying on an artificial molecule that does not naturally occur in nature, e.g. protein expression of cDNA molecules or hybridization of cDNA molecules.

In certain aspects, mRNA in a biological sample is used to produce cDNA from a sample by reverse transcription of mRNA using at least one primer; amplifying the cDNA using polynucleotides as sense and antisense primers to amplify cDNAs therein; and detecting the presence of the amplified cDNA. In further aspects, the sequence of the amplified cDNA can be determined by any suitable method.

In one embodiment, once the mRNA is obtained from a sample, it is converted to complementary DNA (cDNA). cDNA does not exist in vivo and therefore is a non-natural molecule. In a further embodiment, the cDNA is then amplified, for example, by the polymerase chain reaction (PCR) or other amplification method known to those of ordinary skill in the art. The product of this amplification reaction, i.e., amplified cDNA is necessarily a non-natural product. As mentioned above, cDNA is a non-natural molecule. Second, in the case of PCR, the amplification process serves to create hundreds of millions of cDNA copies for every individual cDNA molecule of starting material. The number of copies generated are far removed from the number of copies of mRNA that are present in vivo.

In one embodiment, cDNA is amplified with primers that introduce an additional DNA sequence (adapter sequence) onto the fragments (with the use of adapter-specific primers). Amplification therefore serves to create non-natural double stranded molecules from the non-natural single stranded cDNA, by introducing barcode, adapter and/or reporter sequences onto the already non-natural cDNA. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature and (iv) the chemical addition of a detectable label to the cDNA molecules.

In one embodiment, the synthesized cDNA (for example, amplified cDNA) is immobilized on a solid surface via hybridization with a probe, e.g., via a microarray. In another embodiment, cDNA products are detected via real-time polymerase chain reaction (PCR) via the introduction of fluorescent probes that hybridize with the cDNA products. For example, in one embodiment, biomarker detection is assessed by quantitative fluorogenic RT-PCR (e.g., with TaqMan® probes). For PCR analysis, well known methods are available in the art for the determination of primer sequences for use in the analysis.

In one embodiment, to synthesize and amplify cDNAs, the 5'Ampli FINDER RACE kit (Manufactured by Clontech) and the 5'-RACE method using PCR (Frohman, M. A. et al., Proc. Natl. Acad. Sci. USA (1988) 85:8998-9002; Belyaysky, A. et al., Nucleic Acids Research. (1989) 17:2919-2932) can be used. In the process of such cDNA synthesis, restriction enzyme sites can be introduced into both ends of the cDNA.

Genomic Correlates

As disclosed herein, the expression levels of certain genes have been identified as being related to (correlated with) certain self-reportable characteristics of a subject. Such genes are referred to herein as "genomic correlate genes" or "genomic correlates" and are useful because they provide a surrogate marker for characteristics of a subject that could otherwise be incorrectly and/or inaccurately reported. For example, in some embodiments, a subject may incorrectly estimate information such as pack years, smoking status or age (e.g., by providing an underestimate of such information). In such embodiments, the use of a prediction model based on genomic correlate genes can reduce or eliminate variability associated with incorrect reporting because it is based on the expression of the genomic correlate genes rather than a subject's decision making about what information to report and/or a subject's recollection of circumstances. It will be appreciated by the skilled artisan that the expression levels of such genomic correlate genes may be determined by evaluating the levels of appropriate gene products (e.g., mRNAs, miRNAs, proteins etc.) Expression levels of genomic correlate genes may be determined in parallel with informative-genes of lung cancer status (e.g., an informative gene selected from Table 11) or independently of such genes.

In some embodiments, genomic correlates reflect a response of an individual to an environmental hazard (e.g., cigarette smoke). In some embodiments, genomic correlates reflect exposure to a hazard.

In some embodiment gender of a subject is determined based on one or more genomic correlate genes. In some embodiments, a genomic correlate gene related to gender is RPS4Y1. In some embodiments, if the expression of RPS4Y1 is below a threshold then the subject is identified as being a male and if the expression of RPS4Y1 is above the threshold the subject is identified as being a female. In some embodiments, a threshold is a relative expression level that accurately differentiates males and females for the gene(s) of interest.

In some embodiment smoking status (e.g., current or former) of a subject is determined based on one or more genomic correlate genes. In some embodiments, a genomic correlate gene related to smoking status is SLC7A11, CLND10 or TKT. In some embodiments, the smoking status of a subject is determined according to the following model: smoking status (also, referred to as Genomic Smoking (GS))=exp(x)/(1+exp(x)), in which $$x = \beta \frac{GS}{0} + \beta \frac{GS}{1} * SLC7A11 + \beta \frac{GS}{2} * CLND10 + \beta \frac{GS}{3} * TKT,$$

in which $$\beta \frac{GS}{n}$$

are regression weights for the regression model and gene symbols represent the relative expression intensity of each respective gene. In some embodiments, a smoker is a subject who has smoked at least 100 cigarettes in a lifetime. In some embodiments, a former smoker is a subject who quit or who has not smoked a cigarette within 1 month prior to bronchoscopy.

In some embodiment, smoking history of a subject is determined based on one or more genomic correlate genes. In some embodiments, a genomic correlate gene related to smoking history is AKR1C2 or RUNX1T1. In some embodiments, the smoking history of a subject is determined according to the following model: smoking history (also, referred to as Genomic Pack Years (GPY))=exp(x)/(1+exp(x)), in which $$x = \beta \frac{GPY}{0} + \beta \frac{GPY}{1} * RUNX1T1 + \beta \frac{GPY}{2} * AKR1C2$$

in which $$\beta \frac{GPY}{n},$$

are regression weights for the model and gene symbols represent the relative expression intensity of each respective gene.

In some embodiment, age of a subject is determined based on one or more genomic correlate genes. In some embodiments, a genomic correlate gene related to age is CD52, SYT8, TNNT3, ALX1, KLRK1, RASA3, CERS3, ASPA, GRP, APOC1, EPHX3, REEP1, FAM198B, PCDHB4, PCDHB16, FOXD1, SPARC, NKAPL, or GPR110. In some embodiments, the age of a subject is determined according to the following model: age (also referred to as genomic age $$(GA) = \beta\frac{GA}{0} + \beta\frac{GA}{1}*CD52 + \beta\frac{GA}{2}*SYT8 +$$
$$\beta\frac{GA}{3}*TNNT3 + \beta\frac{GA}{4}*ALX1 + \beta\frac{GA}{5}*KLRK1 +$$
$$\beta\frac{GA}{6}*RASA3 + \beta\frac{GA}{7}*CERS3 + \beta\frac{GA}{8}*ASPA + \beta\frac{GA}{9}*GRP +$$
$$\beta\frac{GA}{10}*APOC1 + \beta\frac{GA}{11}*EPHX3 + \beta\frac{GA}{12}*REEP1 +$$
$$\beta\frac{GA}{13}*FAM198B + \beta\frac{GA}{14}*PCDHB4 + \beta\frac{GA}{15}*PCDHB16 +$$
$$\beta\frac{GA}{16}*FOXD1 + \beta\frac{GA}{17}*SPARC\beta\frac{GA}{18}*NKAPL + \beta\frac{GA}{19}*GPR110,$$

in which $$\beta\frac{GA}{n}$$

are regression weights for the model and gene symbols represent the relative expression intensity of each respective gene.

Biological Samples

The methods generally involve obtaining a biological sample from a subject. As used herein, the phrase "obtaining a biological sample" refers to any process for directly or indirectly acquiring a biological sample from a subject. For example, a biological sample may be obtained (e.g., at a point-of-care facility, a physician's office, a hospital) by procuring a tissue or fluid sample from a subject. Alternatively, a biological sample may be obtained by receiving the sample (e.g., at a laboratory facility) from one or more persons who procured the sample directly from the subject.

The term "biological sample" refers to a sample derived from a subject, e.g., a patient. A biological sample typically comprises a tissue, cells and/or biomolecules. In some embodiments, a biological sample is obtained on the basis that it is histologically normal, e.g., as determined by endoscopy, e.g., bronchoscopy. In some embodiments, biological samples are obtained from a region, e.g., the bronchus or other area or region, that is not suspected of containing cancerous cells. In some embodiments, a histological or cytological examination is performed. However, it should be appreciated that a histological or cytological examination may be optional. In some embodiments, the biological sample is a sample of respiratory epithelium. The respiratory epithelium may be of the mouth, nose, pharynx, trachea, bronchi, bronchioles, or alveoli of the subject. The biological sample may comprise epithelium of the bronchi. In some embodiments, the biological sample is free of detectable cancer cells, e.g., as determined by standard histological or cytological methods. In some embodiments, histologically normal samples are obtained for evaluation. Often biological samples are obtained by scrapings or brushings, e.g., bronchial brushings. However, it should be appreciated that other procedures may be used, including, for example, brushings, scrapings, broncho-alveolar lavage, a bronchial biopsy or a transbronchial needle aspiration.

It is to be understood that a biological sample may be processed in any appropriate manner to facilitate determining expression levels. For example, biochemical, mechanical and/or thermal processing methods may be appropriately used to isolate a biomolecule of interest, e.g., RNA, from a biological sample. Accordingly, a RNA or other molecules may be isolated from a biological sample by processing the sample using methods well known in the art.

Tissue-Type Fingerprinting

In many cases, biological samples such as those provided by the methods of the present invention of may contain several cell types or tissues, including but not limited to blood cells (RBCs, WBCs, platelets), smooth muscle cells, ducts, duct cells, basement membrane, lumen, lobules, fatty tissue, skin cells, epithelial cells, and infiltrating macrophages and lymphocytes.

In some embodiments, the methods of the present invention provide for an upfront method of determining the cellular make-up of a particular biological sample so that the resulting molecular profiling signatures can be calibrated against the dilution effect due to the presence of other cell and/or tissue types. In one aspect, this upfront method is an algorithm that uses a combination of known cell and/or tissue specific gene expression patterns as an upfront mini-classifier for each component of the sample. This algorithm utilizes this molecular fingerprint to pre-classify the samples according to their composition and then apply a correction/normalization factor. This data may in some cases then feed in to a final classification algorithm which would incorporate that information to aid in the final diagnosis.

Lung Cancer Assessment

Methods disclosed herein may involve comparing expression levels of informative-genes with one or more appropriate references. An "appropriate reference" is an expression level (or range of expression levels) of a particular informative-gene that is indicative of a known lung cancer status. An appropriate reference can be determined experimentally by a practitioner of the methods or can be a pre-existing value or range of values. An appropriate reference represents an expression level (or range of expression levels) indicative of lung cancer. For example, an appropriate reference may be representative of the expression level of an informative-gene in a reference (control) biological sample obtained from a subject who is known to have lung cancer. When an appropriate reference is indicative of lung cancer, a lack of a detectable difference (e.g., lack of a statistically significant difference) between an expression level determined from a subject in need of characterization or diagnosis of lung cancer and the appropriate reference may be indicative of lung cancer in the subject. When an appropriate reference is indicative of lung cancer, a difference between an expression level determined from a subject in need of characterization or diagnosis of lung cancer and the appropriate reference may be indicative of the subject being free of lung cancer.

Alternatively, an appropriate reference may be an expression level (or range of expression levels) of a gene that is indicative of a subject being free of lung cancer. For example, an appropriate reference may be representative of the expression level of a particular informative-gene in a reference (control) biological sample obtained from a subject who is known to be free of lung cancer. When an appropriate reference is indicative of a subject being free of lung cancer, a difference between an expression level determined from a subject in need of diagnosis of lung cancer and the appropriate reference may be indicative of lung cancer in the subject. Alternatively, when an appropriate reference is indicative of the subject being free of lung cancer, a lack of a detectable difference (e.g., lack of a statistically significant difference) between an expression level determined from a subject in need of diagnosis of lung cancer and the appropriate reference level may be indicative of the subject being free of lung cancer.

In some embodiments, the reference standard provides a threshold level of change, such that if the expression level of a gene in a sample is within a threshold level of change (increase or decrease depending on the particular marker) then the subject is identified as free of lung cancer, but if the levels are above the threshold then the subject is identified as being at risk of having lung cancer.

In some embodiments, the methods involve comparing the expression level of an informative-gene to a reference standard that represents the expression level of the informative-gene in a control subject who is identified as not having lung cancer. This reference standard may be, for example, the average expression level of the informative-gene in a population of control subjects who are identified as not having lung cancer.

The magnitude of difference between a expression level and an appropriate reference that is statistically significant may vary. For example, a significant difference that indicates lung cancer may be detected when the expression level of an informative-gene in a biological sample is at least 1%, at least 5%, at least 10%, at least 25%, at least 50%, at least 100%, at least 250%, at least 500%, or at least 1000% higher, or lower, than an appropriate reference of that gene. Similarly, a significant difference may be detected when the expression level of informative-gene in a biological sample is at least 1.1-fold, 1.2-fold, 1.5-fold, 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more higher, or lower, than the appropriate reference of that gene. In some embodiments, at least a 20% to 50% difference in expression between an informative-gene and appropriate reference is significant. Significant differences may be identified by using an appropriate statistical test. Tests for statistical significance are well known in the art and are exemplified in Applied Statistics for Engineers and Scientists by Petruccelli, Chen and Nandram 1999 Reprint Ed.

It is to be understood that a plurality of expression levels may be compared with plurality of appropriate reference levels, e.g., on a gene-by-gene basis, in order to assess the lung cancer status of the subject. The comparison may be made as a vector difference. In such cases, Multivariate Tests, e.g., Hotelling's T2 test, may be used to evaluate the significance of observed differences. Such multivariate tests are well known in the art and are exemplified in Applied Multivariate Statistical Analysis by Richard Arnold Johnson and Dean W. Wichern Prentice Hall; 6th edition (Apr. 2, 2007).

Technical Factor Removal

Principal Component Analysis (PCA) and Variance components can be used to assess the magnitude and significance of the technical variability in the data relative to the biological signal. If it was deemed that technical sources of variability must be removed, then the regression method can be used to remove that effect.

(a) Details on the regression method: In a supervised setting, this method can be used to adjust the probe intensities for variation due to technical reasons (e.g. sample collection media) in the presence of the primary variable of interest (the disease label). Adjustments for technical factors can be made both in gene/feature selection, as well as in feature adjustment necessary for correct classification. For example:

(I) Feature Selection Linear Model:

$$E(y)=\beta 0+\beta 1 BM+\beta 2 TF1+\beta 3 BM*TF2+ \ldots +\varepsilon$$

where TF1 is technical factor 1; and BM is the variable which contains the label 'B' or 'M'. The current call to LIMMA for feature selection would be extended to support the adjustment by technical factors (up to 3) and corresponding 2-way interaction terms with the BM variable, if needed.

Feature Adjustment: The features themselves can be adjusted in the following way:

$$Y\text{-}\hat{Y}\text{-}X\{\text{circumflex over }(\beta)\}$$

where {circumflex over (β)} are the estimated coefficients from the terms in the feature selection linear model equation which involve technical factors. In some instances, the model matrix will contain only the variables containing the technical factor and will not contain the column of 1's (the intercept term).

In unsupervised correction, the technical factor (TF) covariate can be used to shift the means between samples of one type (e.g., banked FNA) and those of another (e.g., prospective FNA). A boxplot of all the probe intensities for each sample will show whether such a "shift in means" exists due to known factors of technical variation.

In some embodiments, only if the technical source of variability is simply a global "shift in means" or linear and is not confounded by disease subtype then the regression method in an unsupervised setting will be applied. This would be an unsupervised correction, i.e., no disease labels will be used in the correction step.

In some embodiments, if evidence of technical variability is present in the data, but biological signal overwhelms it, no correction is applied to the data sets. A list of co-variables that can be examined by the subject algorithm is shown in Table 7.

TABLE 7

Technical factors or variables considered in the algorithm

| Variable | Values |
| --- | --- |
| Collection source | OR vs. Clinic |
| Collection method | Banked FNA vs. Prospective FNA |
| Collection media | Trizol vs. RNAProtect |
| RNA RIN | Continuous |
| WTA yield | Continuous |
| ST yield | Continuous |
| Hybridization site | Laboratory 1 vs. Laboratory 2 |
| Hybridization quality (AUC) | Continuous |
| General pathology | Benign vs. Malignant |
| Subtype pathology | LCT, NHP, FA, HA, FC, FVPTC, PTC, MTC |
| Experiment batch | FNA TRIzol 1-4 vs. FNA RNAprotect 1-4 or FNA TRIzol vs. FNA RNAprotect |
| Lab contamination | Dominant peak, band seen, both |

Classification accuracy, sensitivity, specificity, ROC curves, error vs number of markers curves, positive predictive value (PPV) and negative predictive value (NPV) can be reported using these approaches. The methods of the present invention have sensitivity required to detect rare transcripts, which are expressed at a few copies per cell, and to reproducibly detect at least approximately two-fold differences in the expression levels. In some embodiments, the subject methods provide a high sensitivity of detecting gene expression and therefore detecting a genetic disorder or cancer that is greater than 60%, 65%, 70%, 75%, 80%, 85%, 90%, 91%, 92%, 93%, 94%, 95%, 95.5%, 96%, 96.5%, 97%, 97.5%, 98%, 98.5%, 99%, 99.5% or more. Therefore, the sensitivity of detecting and classifying a genetic disorder or cancer is increased. The classification accuracy of the subject methods in classifying genetic disorders or cancers can be greater than 70%, 75%, 80%, 85%, 90%, 91%, 92%, 93%, 94%, 95%, 95.5%, 96%, 96.5%, 97%, 97.5%, 98%, 98.5%, 99%, 99.5% or more. In some embodiments, the subject methods provide a high specificity of detecting and classifying gene expression that is greater than, for example, 80%, 85%, 90%, 91%, 92%, 93%, 94%, 95%, 95.5%, 96%, 96.5%, 97%, 97.5%, 98%, 98.5%, 99%, 99.5% or more. In some embodiments, the nominal specificity is greater than or equal to 70%. The nominal negative predictive value (NPV) is greater than or equal to 95%. In some embodiments, the NPV is about 95%, 95.5%, 96%, 96.5%, 97%, 97.5%, 98%, 98.5%, 99%, 99.5% or more.

In some embodiments, feature selection (gene selection) can also be combined with technical factor removal. Often a variable, such as the sample collection media, provides a distinct shift at the intensity level. If the variable is associated with the disease subtype (Benign vs Malignant) then feature selection can account for this variable (a confounder) in the regression model (LIMMA). The details of accounting for technical factor effects on the intensities in feature selection are described in Section 3 above. Repeatable feature selection can be carried out together with correction/removal of relevant technical factors present in the data set for each regression model applied to the genes.

In cross-validation mode at least two methods can be used, either one at a time, or in succession. The cross-validation methods are K-fold cross-validation and leave-one-out cross-validation (LOOCV). In one embodiment, feature selection (with or without technical factor removal) is incorporated within each loop of cross-validation. This enables the user to obtain unbiased estimates of error rates. Further, feature selection can also be performed within certain classifiers (e.g., random forest) in a multivariate setting. The classifier takes the features selected and the previously built training-set model and makes a classification call (Benign or not Benign) on the test set. This procedure of repeatedly splitting the data into training and test sets and providing a single averaged error rate at the end gives an unbiased error rate in the cross-validation mode.

Training and validation data sets can be normalized and processed together (APT, RMA with quantile normalization) including removal of technical factors when necessary. The data can be split into training and validation sets based on specific criteria (e.g., balancing each set by relevant covariate levels).

In several embodiments, algorithm training can be conducted on a sample of surgical tissue, FNA's collected in TRIzol, and/or FNAs collected in RNAProtect. In testing of algorithm performance results, results were obtained where approximately 90% non-benign percent agreement (aka sensitivity) and 93% benign agreement (aka specificity) on a select set of samples that pass certain pre- and post-chip metrics.

Training of the algorithm can include feature (ie. Gene) selection. Each round of training can result in a de novo set of markers, for example, 5, 10, 25, 50, 100, 200, 300 or 500 markers. In one example, comparison of marker lists across the three key discovery training sets (surgical tissue, FNA's collected in TRIzol, and FNAs collected in RNAProtect) revealed a total of 338 non-redundant markers; of these 158 markers are in all three marker lists.

In some embodiments, the exon array platform used in the present invention measures mRNA levels of all known human genes (24,000) and all known transcripts (>200,000). This array is used on every sample run in feasibility (i.e. gene discovery), therefore the algorithm is trained on the full complement of genes at every step. Throughout algorithm training, feature (i.e. gene) selection occurs de novo for every experimental set. Thus, features may be selected from multiple experiments and later combined.

Marker panels can be chosen to accommodate adequate separation of benign from non-benign expression profiles. Training of this multi-dimensional classifier, i.e., algorithm, was performed on over 500 thyroid samples, including >300 thyroid FNAs. Many training/test sets were used to develop the preliminary algorithm. First the overall algorithm error rate is shown as a function of gene number for benign vs non-benign samples. All results are obtained using a support vector machine model which is trained and tested in a cross-validated mode (30-fold) on the samples.

In some embodiments, the difference in gene expression level is at least 10%, 15%, 20%, 25%, 30%, 35%, 40%, 45% or 50% or more. In some embodiments, the difference in gene expression level is at least 2, 3, 4, 5, 6, 7, 8, 9, 10 fold or more. In some embodiments, the biological sample is identified as cancerous with an accuracy of greater than 75%, 80%, 85%, 90%, 95%, 99% or more. In some embodiments, the biological sample is identified as cancerous with a sensitivity of greater than 95%. In some embodiments, the biological sample is identified as cancerous with a specificity of greater than 95%. In some embodiments, the biological sample is identified as cancerous with a sensitivity of greater than 95% and a specificity of greater than 95%. In some embodiments, the accuracy is calculated using a trained algorithm.

In some embodiments of the present invention, results are classified using a trained algorithm. Trained algorithms of the present invention include algorithms that have been developed using a reference set of known malignant, benign, and normal samples. The classification scheme using the algorithms of the present invention is shown in FIG. 23. Algorithms suitable for categorization of samples include but are not limited to k-nearest neighbor algorithms, concept vector algorithms, naive bayesian algorithms, neural network algorithms, hidden markov model algorithms, genetic algorithms, and mutual information feature selection algorithms or any combination thereof. In some cases, trained algorithms of the present invention may incorporate data other than gene expression or alternative splicing data such as but not limited to scoring or diagnosis by cytologists or pathologists of the present invention, information provided by the pre-classifier algorithm of the present invention, or information about the medical history of the subject of the present invention.

Classification Methods

The methods may also involve comparing a set of expression levels (referred to as an expression pattern or profile) of informative-genes in a biological sample obtained from a subject with a plurality of sets of reference levels (referred to as reference patterns), each reference pattern being associated with a known lung cancer status, identifying the reference pattern that most closely resembles the expression pattern, and associating the known lung cancer status of the reference pattern with the expression pattern, thereby classifying (characterizing) the lung cancer status of the subject.

The methods may also involve building or constructing a prediction model, which may also be referred to as a classifier or predictor, that can be used to classify the disease status of a subject. As used herein, a "lung cancer-classifier" is a prediction model that characterizes the lung cancer status of a subject based on expression levels determined in a biological sample obtained from the subject. Typically the model is built using samples for which the classification (lung cancer status) has already been ascertained. Once the model (classifier) is built, it may then be applied to expression levels obtained from a biological sample of a subject whose lung cancer status is unknown in order to predict the lung cancer status of the subject. Thus, the methods may involve applying a lung cancer-classifier to the expression levels, such that the lung cancer-classifier characterizes the lung cancer status of a subject based on the expression levels. The subject may be further treated or evaluated, e.g., by a health care provider, based on the predicted lung cancer status.

The classification methods may involve transforming the expression levels into a lung cancer risk-score that is indicative of the likelihood that the subject has lung cancer. In some embodiments, such as, for example, when a linear discriminant classifier is used, the lung cancer risk-score may be obtained as the combination (e.g., sum, product, or other combination) of weighted expression levels, in which the expression levels are weighted by their relative contribution to predicting increased likelihood of having lung cancer.

It should be appreciated that a variety of prediction models known in the art may be used as a lung cancer-classifier. For example, a lung cancer-classifier may comprises an algorithm selected from logistic regression, partial least squares, linear discriminant analysis, quadratic discriminant analysis, neural network, naïve Bayes, C4.5 decision tree, k-nearest neighbor, random forest, support vector machine, or other appropriate method.

The lung cancer-classifier may be trained on a data set comprising expression levels of the plurality of informative-genes in biological samples obtained from a plurality of subjects identified as having lung cancer. For example, the lung cancer-classifier may be trained on a data set comprising expression levels of a plurality of informative-genes in biological samples obtained from a plurality of subjects identified as having lung cancer based histological findings. The training set will typically also comprise control subjects identified as not having lung cancer. As will be appreciated by the skilled artisan, the population of subjects of the training data set may have a variety of characteristics by design, e.g., the characteristics of the population may depend on the characteristics of the subjects for whom diagnostic methods that use the classifier may be useful. For example, the population may consist of all males, all females or may consist of both males and females. The population may consist of subjects with history of cancer, subjects without a history of cancer, or subjects from both categories. The population may include subjects who are smokers, former smokers, and/or non-smokers.

A class prediction strength can also be measured to determine the degree of confidence with which the model classifies a biological sample. This degree of confidence may serve as an estimate of the likelihood that the subject is of a particular class predicted by the model.

Accordingly, the prediction strength conveys the degree of confidence of the classification of the sample and evaluates when a sample cannot be classified. There may be instances in which a sample is tested, but does not belong, or cannot be reliably assigned to, a particular class. This may be accomplished, for example, by utilizing a threshold, or range, wherein a sample which scores above or below the determined threshold, or within the particular range, is not a sample that can be classified (e.g., a "no call").

Once a model is built, the validity of the model can be tested using methods known in the art. One way to test the validity of the model is by cross-validation of the dataset. To perform cross-validation, one, or a subset, of the samples is eliminated and the model is built, as described above, without the eliminated sample, forming a "cross-validation model." The eliminated sample is then classified according to the model, as described herein. This process is done with all the samples, or subsets, of the initial dataset and an error rate is determined. The accuracy the model is then assessed. This model classifies samples to be tested with high accuracy for classes that are known, or classes have been previously ascertained. Another way to validate the model is to apply the model to an independent data set, such as a new biological sample having an unknown lung cancer status.

As will be appreciated by the skilled artisan, the strength of the model may be assessed by a variety of parameters including, but not limited to, the accuracy, sensitivity and specificity. Methods for computing accuracy, sensitivity and specificity are known in the art and described herein (See, e.g., the Examples). The lung cancer-classifier may have an accuracy of at least 60%, at least 65%, at least 70%, at least 75%, at least 80%, at least 85%, at least 90%, at least 95%, at least 99%, or more. The lung cancer-classifier may have an accuracy in a range of about 60% to 70%, 70% to 80%, 80% to 90%, or 90% to 100%. The lung cancer-classifier may have a sensitivity of at least 60%, at least 65%, at least 70%, at least 75%, at least 80%, at least 85%, at least 90%, at least 95%, at least 99%, or more. The lung cancer-classifier may have a sensitivity in a range of about 60% to 70%, 70% to 80%, 80% to 90%, or 90% to 100%. The lung cancer-classifier may have a specificity of at least 60%, at least 65%, at least 70%, at least 75%, at least 80%, at least 85%, at least 90%, at least 95%, at least 99%, or more. The lung cancer-classifier may have a specificity in a range of about 60% to 70%, 70% to 80%, 80% to 90%, or 90% to 100%.

The Negative Predictive Value (NPV) may be greater than 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% for ruling out lung cancer in an intended use population.

The intended use population may have a prevalence of cancer at or about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Clinical Treatment/Management

In certain aspects, methods are provided for determining a treatment course for a subject. The methods typically involve determining the expression levels in a biological sample obtained from the subject of one or more informative-genes, and determining a treatment course for the subject based on the expression levels. Often the treatment course is determined based on a lung cancer risk-score derived from the expression levels. The subject may be identified as a candidate for a lung cancer therapy based on a lung cancer risk-score that indicates the subject has a relatively high likelihood of having lung cancer. The subject may be identified as a candidate for an invasive lung procedure (e.g., transthoracic needle aspiration, mediastinoscopy, or thoracotomy) based on a lung cancer risk-score that indicates the subject has a relatively high likelihood of having lung cancer (e.g., greater than 60%, greater than 70%, greater than 80%, greater than 90%). The subject may be identified as not being a candidate for a lung cancer therapy or an invasive lung procedure based on a lung cancer risk-score that indicates the subject has a relatively low likelihood (e.g., less than 50%, less than 40%, less than 30%, less than 20%) of having lung cancer. In some cases, an intermediate risk-score is obtained and the subject is not indicated as being in the high risk or the low risk categories. In some embodiments, a health care provider may engage in "watchful waiting" and repeat the analysis on biological samples taken at one or more later points in time, or undertake further diagnostics procedures to rule out lung cancer, or make a determination that cancer is present, soon after the risk determination was made. In a particular example, a subject is identified as intermediate risk due to a non-diagnostic bronchoscopy and is reassigned to non-invasive monitoring (such as CT surveillance) following a determination, using the methods herein, that the patient is at low-risk of cancer. In another particular example, the samples assayed as described herein may be used The methods may also involve creating a report that summarizes the results of the gene expression analysis. Typically the report would also include an indication of the lung cancer risk-score.

Computer Implemented Methods

Methods disclosed herein may be implemented in any of numerous ways. For example, certain embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, aspects of the disclosure may be embodied as a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above. As used herein, the term "non-transitory computer-readable storage medium" encompasses only a computer-readable medium that can be considered to be a manufacture (i.e., article of manufacture) or a machine.

The terms "program" or "software" are used herein in a generic sense to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

As used herein, the term "database" generally refers to a collection of data arranged for ease and speed of search and retrieval. Further, a database typically comprises logical and physical data structures. Those skilled in the art will recognize the methods described herein may be used with any type of database including a relational database, an object-relational database and an XML-based database, where XML stands for "eXtensible-Markup¬Language". For example, the gene expression information may be stored in and retrieved from a database. The gene expression information may be stored in or indexed in a manner that relates the gene expression information with a variety of other relevant information (e.g., information relevant for creating a report or document that aids a physician in establishing treatment protocols and/or making diagnostic determinations, or information that aids in tracking patient samples). Such relevant information may include, for example, patient identification information, ordering physician identification information, information regarding an ordering physician's office (e.g., address, telephone number), information regarding the origin of a biological sample (e.g., tissue type, date of sampling), biological sample processing information, sample quality control information, biological sample storage information, gene annotation information, lung-cancer risk classifier information, lung cancer risk factor information, payment information, order date information, etc.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

In some aspects of the disclosure, computer implemented methods for processing genomic information are provided. The methods generally involve obtaining data representing expression levels in a biological sample of one or more informative-genes and determining the likelihood that the subject has lung cancer based at least in part on the expression levels. Any of the statistical or classification methods disclosed herein may be incorporated into the computer implemented methods. In some embodiments, the methods involve calculating a risk-score indicative of the likelihood that the subject has lung cancer. Computing the risk-score may involve a determination of the combination (e.g., sum, product or other combination) of weighted expression levels, in which the expression levels are weighted by their relative contribution to predicting increased likelihood of having lung cancer. The computer implemented methods may also involve generating a report that summarizes the results of the gene expression analysis, such as by specifying the risk-score. Such methods may also involve transmitting the report to a health care provider of the subject.

Affymetrix Array

In some aspects, the Affymetrix Human Gene 1.0 ST array (Affymetrix Cat. #901087) is used to identify the mRNA or cDNA in a biological sample. The Affymetrix Human Gene 1.0 ST array utilizes numerous probes that are disclosed at the world wide web address: affymetrix.com/site/include/byproduct.affx?product=hugene-1_0-st-v1. Multiple probes are present that correspond to segments of specific genes, which is to say that that is not a 1:1 ratio of one probe per gene, rather multiple probes are present that correspond to multiple segments of a single gene. In one example, the LYPD2 gene is represented by three probe sets in the Human Gene 1.0 ST array (Release 32), probeset IDs 8153343, 8153344, and 8153345 as disclosed in the Affymetrix Human Gene 1.0 ST array (HuGene-1_0-st-v1 Probeset Annotations. Exemplary suitable builds of the array include release 32 (Sep. 30, 2011), release 33 (Mar. 27, 2013), release 34 Apr. 7, 2014), release 35 on (Apr. 15, 2015), and release 36. Additional releases, including future releases may also be used. Information correlating probe-sets and nucleic acid sequences can be found at Affymetrix.com, including at the world wide web address: affymetrix.com/site/include/byproduct.affx?product=hugene-1_0-st-v1. Furthermore, data sets are available on the NCBI Gene Expression Omnibus website under Platform GPL6244 detailing the probes and genes that may be utilized in practicing the methods of the present disclosure at the world wide web address: ncbi.nlm.nih.gov/geo/query/acc.cgi?acc=GPL6244. These documents, including those correlating the probesets and gene symbols are incorporated herein by reference.

Compositions and Kits

In some aspects, compositions and related methods are provided that are useful for determining expression levels of informative-genes. For example, compositions are provided that consist essentially of nucleic acid probes that specifically hybridize with informative-genes or with nucleic acids having sequences complementary to informative-genes. These compositions may also include probes that specifically hybridize with control genes or nucleic acids complementary thereto. These compositions may also include appropriate buffers, salts or detection reagents. The nucleic acid probes may be fixed directly or indirectly to a solid support (e.g., a glass, plastic or silicon chip) or a bead (e.g., a magnetic bead). The nucleic acid probes may be customized for used in a bead-based nucleic acid detection assay.

In some embodiments, compositions are provided that comprise up to 5, up to 10, up to 25, up to 50, up to 100, or up to 200 nucleic acid probes. In some cases, each of the nucleic acid probes specifically hybridizes with an mRNA selected from Table 11 or with a nucleic acid having a sequence complementary to the mRNA. In some embodiments, probes that detect informative-mRNAs are also included. In some cases, each of at least 2, at least 3, at least 4, at least 5, at least 6, at least 7, at least 8, at least 9, at least 10, or at least 20 of the nucleic acid probes specifically hybridizes with an mRNA selected from Table 11or with a nucleic acid having a sequence complementary to the mRNA. In some embodiments, the compositions are prepared for detecting different genes in biochemically separate reactions, or for detecting multiple genes in the same biochemical reactions. In some embodiments, the compositions are prepared for performing a multiplex reaction.

Also provided herein are oligonucleotide (nucleic acid) arrays that are useful in the methods for determining levels of multiple informative-genes simultaneously. Such arrays may be obtained or produced from commercial sources. Methods for producing nucleic acid arrays are also well known in the art. For example, nucleic acid arrays may be constructed by immobilizing to a solid support large numbers of oligonucleotides, polynucleotides, or cDNAs capable of hybridizing to nucleic acids corresponding to genes, or portions thereof. The skilled artisan is referred to Chapter 22 "Nucleic Acid Arrays" of Current Protocols In Molecular Biology (Eds. Ausubel et al. John Wiley and #38; Sons NY, 2000) or Liu C G, et al., An oligonucleotide microchip for genome-wide microRNA profiling in human and mouse tissues. Proc Nall Acad Sci USA. 2004 Jun. 29; 101(26):9740-4, which provide non-limiting examples of methods relating to nucleic acid array construction and use in detection of nucleic acids of interest. In some embodiments, the arrays comprise, or consist essentially of, binding probes for at least 2, at least 5, at least 10, at least 20, at least 50, at least 60, at least 70 or more informative-genes. In some embodiments, the arrays comprise, or consist essentially of, binding probes for up to 2, up to 5, up to 10, up to 20, up to 50, up to 60, up to 70 or more informative-genes. In some embodiments, an array comprises or consists of 1, 2, 3, 4, 5, 6, 7, 8, 9, or 10 of the mRNAs selected from Table 11. In some embodiments, an array comprises or consists of 4, 5, or 6 of the mRNAs selected from Table 11. Kits comprising the oligonucleotide arrays are also provided. Kits may include nucleic acid labeling reagents and instructions for determining expression levels using the arrays.

The compositions described herein can be provided as a kit for determining and evaluating expression levels of informative-genes. The compositions may be assembled into diagnostic or research kits to facilitate their use in diagnostic or research applications. A kit may include one or more containers housing the components of the disclosure and instructions for use. Specifically, such kits may include one or more compositions described herein, along with instructions describing the intended application and the proper use of these compositions. Kits may contain the components in appropriate concentrations or quantities for running various experiments.

The kit may be designed to facilitate use of the methods described herein by researchers, health care providers, diagnostic laboratories, or other entities and can take many forms. Each of the compositions of the kit, where applicable, may be provided in liquid form (e.g., in solution), or in solid form, (e.g., a dry powder). In certain cases, some of the compositions may be constitutable or otherwise processable, for example, by the addition of a suitable solvent or other substance, which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of diagnostic or biological products, which instructions can also reflect approval by the agency.

A kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The components may be in the form of a liquid, gel or solid (e.g., powder). The components may be prepared sterilely and shipped refrigerated. Alternatively they may be housed in a vial or other container for storage. A second container may have other components prepared sterilely.

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

All references described herein are incorporated by reference for the purposes described herein.

Exemplary embodiments of the disclosure will be described in more detail by the following examples. These embodiments are exemplary of the disclosure, which one skilled in the art will recognize is not limited to the exemplary embodiments.

EXAMPLES

Example 1: Development of a Microarray Based Prediction Model

Introduction

This example describes a method for developing a prediction algorithm. A final optimized model is described, including the combination of genes used in the model. The method uses Clinical Factor Genomic Correlates (CFGC) to aid in the selection of a cancer-specific signature.

The objectives were to develop and characterize a new cancer prediction model that effectively predicts lung cancer status after accounting gene expression signal attributed more specifically to clinical factors by deriving genomic correlates. Genomic correlates are defined herein as gene expression algorithms to predict the specific clinical characteristics, such as subject gender, smoking status, and smoking history.

An objective was to develop a prediction algorithm that meets the following specific performance criteria:
Negative Predictive Value (NPV) of greater than 90% for ruling out lung cancer in an intended use population, and
NPV of greater than 85% for subjects diagnosed with COPD.

Materials and Methods
Sample Processing and Analysis

Clinical specimens were collected from patients scheduled to undergo bronchoscopy for the suspicion of lung cancer. Bronchial epithelial cells (BECs) were collected from the mainstem bronchus of subjects using standard bronchial brushes during a scheduled bronchoscopy procedure.

Samples were analyzed on gene-expression microarrays using Gene 1.0 ST microarrays (Affymetrix). A pairwise correlation analysis of the array data was conducted to identify outliers (described herein). A total of 597 samples were retained as the final data set. The data set were then split into equivalently sized Training and Validation sets in a randomized manner.

Microarray CEL files were used for the development of a prediction algorithm. Subjects were first designated to independent Training and Validation sets, and gene selection and optimization of the prediction model was conducted within the Training set. The model was optimized and locked prior to predicting the cancer status of validation set samples.

Normalization/Batch Adjustment

RMA was used to compute gene expression values from Gene 1.0 ST (Affymetrix) CEL files. ComBat batch adjustment was used to correct for batch effects. All samples were analyzed within 5 separate microarray experiments (i.e., batches). Training and test samples were combined in RMA and ComBat pre-processing. Subsequent development was restricted to the Training set as previously described. CEL files corresponding to samples with a RIN score less than 4 were excluded, as were samples with average pairwise correlation less than 0.955 (see FIG. 1).

Genomic Correlates

Genomic correlates were established as a gene expression signature that accurately predict the corresponding clinical characteristic. The genomic correlates, in combination with separate genes to predict cancer status, are combined in a prediction algorithm. Correlates for the following clinical characteristics were developed and evaluated:
Gender
Smoking status (current versus former)
Smoking history (pack-year; PY)
Age The genomic correlates were developed by selecting top-ranked genes differentiating the clinical characteristic of interest and fitting those genes to a model using logistic regression. Scoring of clinical characteristics was based on the gene expression of those selected genes.

Two models were developed in parallel to be tested simultaneously in a Validation set. A first model (Score 1) was based on the methods described herein and factoring the reported Age into the prediction algorithm as well as the genomic signal. A second model (Score 2) was developed using a genomic correlate for age, which was then incorporated into the prediction algorithm.

Initial Gene Selection

A clinical factor model was developed, using logistic regression of cancer status (0/1) on age, gender, smoking status, and pack years. The residuals from the clinical factor model were used to select genes using an empirical Bayes linear model to test association of each gene with the residuals. The top 232 genes were selected based on the p-value and fold change from this model. The top 232 genes are listed in Table 11.

Clustering/Final Gene Selection

Gene selection and model fitting were conducted in an automated cross-validation approach in order to minimize bias during the selection process and to provide a robust final selection. The gene selection consisted of the following steps. Hierarchical clustering was used to divide the genes into 11 clusters. The cluster membership of each gene is identified in column 2 of the Table 11. For each of the clusters, cluster means were computed using all of the genes within each cluster. A combination of LASSO and backwards selection were used in repeated random subsets of the data to identify six clusters that were consistently selected to have independent predictive association with cancer status. Cross validation was then used to determine the approximate number of genes within each cluster that would retain the predictive strength of the cluster means.

A gene titration analysis was done to determine the sensitivity of the models to increased numbers of genes from the selected clusters within the final model. This was included as part of the optimization to determine if complementary genes could add additional clinical sensitivity to the model.

Software

R (Version 3.01) was used for the analysis, including the packages rms, limma, verification, and sva.

Results

Derivation of Genomic Correlates

Genes were selected to represent clinical characteristics using the whole Training set. These "genomic correlate genes" were based on a minimal set of genes to represent the clinical factor as accurately as possible. Genomic Gender (GG) was defined with 100% accuracy using a single gene. The values are set forth as follows: GG=1 (male) if RPS4Y1<threshold, and GG=0 (female) otherwise.

For genomic smoking status, genes were screened based on an empirical Bayes t-test. The top genes by p-value were included in a logistic regression model where smoking status was the dependent variable. The resulting predicted genomic smoking (GS) value was derived from this model (using gene symbols to represent the relative expression intensity), where, $$x = \beta\frac{GS}{0} + \beta\frac{GS}{1} * SLC7A11 + \beta\frac{GS}{2} * CLND10 + \beta\frac{GS}{3} * TKT,$$

in which $$\beta\frac{GS}{n}$$

are regression weights for the genomic regression model, and GS=exp(x)/(1+exp(x)).

For genomic pack years, genes were screened based on an empirical Bayes t-test. The top genes by p-value were included in a logistic regression model where pack years <10 was the dependent variable. The resulting predicted genomic pack years (GPY) value was derived from this model, where $$x = \beta\frac{GPY}{0} + \beta\frac{GPY}{1} * RUNX1T1 + \beta\frac{GPY}{2} * AKR1C2,$$

in which $$\beta\frac{GPY}{n}$$

are regression weights for the genomic pack years regression model, and GPY=exp(x)/(1+exp(x)).

For genomic age, genes were screened based on an empirical Bayes linear model. The top genes by p-value were included in a penalized linear regression model (LASSO) where age (in years) was the dependent variable. The resulting predicted genomic age (GA) value was derived from this model, where, $$(GA)) = \beta\frac{GA}{0} + \beta\frac{GA}{1} * CD52 + \beta\frac{GA}{2} * SYT8 +$$
$$\beta\frac{GA}{3} * TNNT3 + \beta\frac{GA}{4} * ALX1 + \beta\frac{GA}{5} * KLRK1 +$$
$$\beta\frac{GA}{6} * RASA3 + \beta\frac{GA}{7} * CERS3 + \beta\frac{GA}{8} * ASPA + \beta\frac{GA}{9} * GRP +$$
$$\beta\frac{GA}{10} * APOC1 + \beta\frac{GA}{11} * EPHX3 + \beta\frac{GA}{12} * REEP1 +$$
$$\beta\frac{GA}{13} * FAM198B + \beta\frac{GA}{14} * PCDHB4 + \beta\frac{GA}{15} * PCDHB16 +$$
$$\beta\frac{GA}{16} * FOXD1 + \beta\frac{GA}{17} * SPARC\beta\frac{GA}{18} * NKAPL + \beta\frac{GA}{19} * GPR110,$$

in which $$\beta\frac{GA}{n}$$

are regression weights for the genomic age regression model.

Derivation of the Cancer Genes

The top 232 gene were selected initially, followed by a down-selection of genes using the clustering analysis described in the methods section.

Cross validation was then used to determine the approximate number of genes within each cluster that would retain the predictive strength of the cluster means. This number was found to be between 2 and 4 genes per cluster. Final gene selection within each cluster was based on p-value, fold change, and strength of evidence for cancer association from the literature. Cluster means were recomputed using the reduced gene sets within each cluster, as follows:

C1A=mean of (BST1, CD177.1, CD177.2)
C1B=mean of (ATP 12A, TSPAN2)
C2=mean of (GABBRI, MCAM, NOVA1, SDC2)
C3=mean of (CDR1, CGREF1, CLND22, NKX3-1)
C4A=mean of (EPHX3, LYPD2)
C4B=mean of (MIA, RNF150).

Description of the Finalized Model

To estimate the final model coefficients, a penalized logistic regression model was used, with Age (in years), genomic gender (GG), genomic smoking status (GS), genomic pack years (GPY), and the six reduced gene cluster means (labeled C1A, C1B, C2, C3, C4A, C4B) as the independent predictors and cancer status (0/1) as the dependent variable. The penalization factor (lambda) was 0 for the clinical/genomic correlates and 10 for each of the gene expression clusters. The second model was built using the same approach, but replacing Age with genomic age (GA) as defined above. The model coefficients were then re-estimated.

The final classification algorithm was of the form, $$x_{score1} = W_0 + W_1 \times GG + W_2 \times GS + W_3 \times GPY + W_4 \times \text{Reported Age} + W_5 \times C1A + W_6 \times C1B + W_7 \times C2 + W_8 \times C3 + W_9 \times C4A + W_{10} \times C4B$$

$$X^{score2} = W_0 + W_1 \times GG + W_2 \times GS + W_3 \times GPY + W_4 \times GA + W_5 \times C1A + W_6 \times C1B + W_7 \times C2 + W_8 \times C3 + W_9 \times C4A + W_{10} \times C4B.$$

The logistic regression score is then converted to a prediction score, ranging from 0 to 1, using the equation $$\text{Prediction Score} = \frac{e^{x^{Score1 \text{ or } Score 2}}}{\left(1 + e^{x^{Score 1 \text{ or } Score 2}}\right)}$$

Evaluation of Prediction Models

A cross-validation approach was used in which the Training set samples were randomly split (90:10) into training and testing groups, respectively. The clinical accuracy was recorded and the process was repeated 100-fold. Scores for the training set were reported as the average of the total iterations for each sample. Results were reported as ROC curves, AUC, and sensitivity and specificity after defining the score threshold to yield 50% specificity and to maximize the clinical sensitivity.

Figure 2:
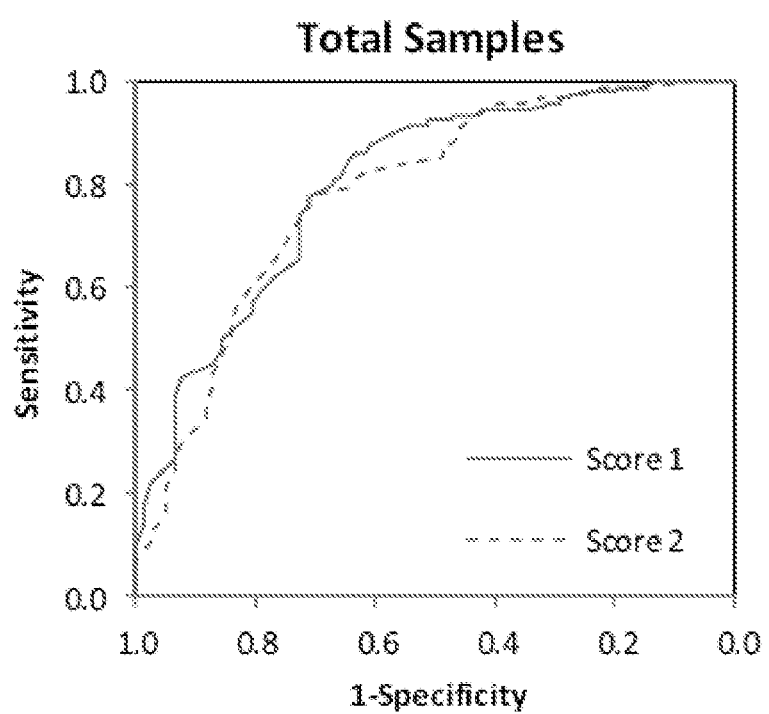
FIG. 2 is a non-limiting example of ROC curves for prediction models based on a set of training samples.
Figure 3:
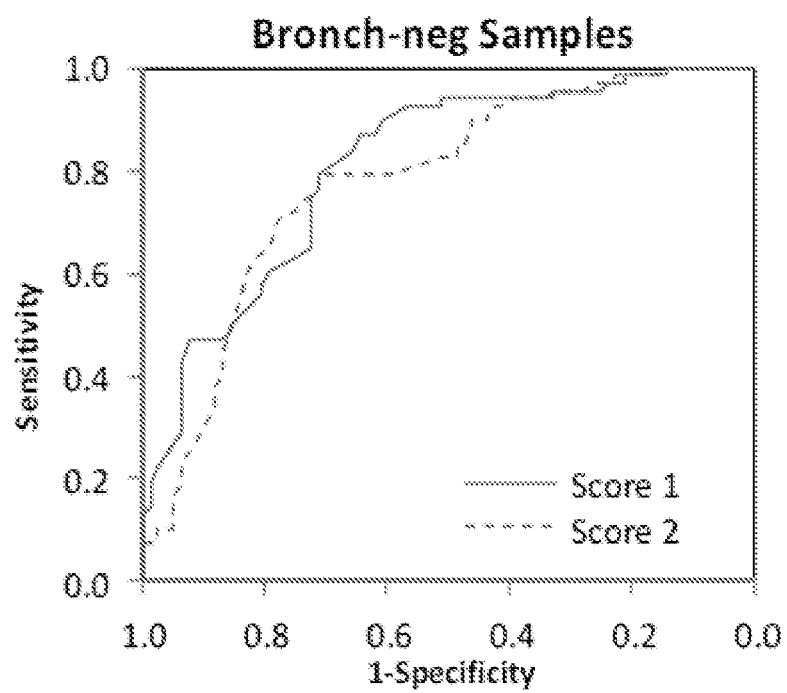
FIG. 3 is a non-limiting example of ROC curves for prediction models based on a set of bronchoscopy negative training samples.

The scores for all training set samples were generated and compared to recorded clinical status. ROC curves for Score 1 and Score 2 are shown in for all samples in FIG. 2, and for bronchoscopy-negative samples only in FIG. 3. The AUC's were calculated as, Score 1=0.803, and Score 2=0.785, for all samples, and Score 1=0.808, and Score 2=0.778 for the bronch-negative set. Table 1 provides a list of informative genes used in the prediction score models. Table 1.1 provides a non-limiting list of probe sequences for detecting expression of such genes.

TABLE 1

Gene list and function

| Gene Symbol | Function | Gene Symbol | Function |
|---|---|---|---|
| RPS4Y1 | GG | TSPAN2 | CA |
| SLC7A11 | GS | MCAM | CA |
| CLDN10 | GS | ATP12A | CA |
| TKT | GS | NOVA1 | CA |
| RUNX1T1 | GPY | MIA | CA |
| AKR1C2 | GPY | CD177.1 | CA |
| CD52 | GA | EPHX3 | CA |
| SYT8 | GA | CD177.2 | CA |
| TNNT3 | GA | CGREF1 | CA |
| ALX1 | GA | BST1 | CA |
| KLRK1 | GA | RNF150 | CA |
| RASA3 | GA | CLND22 | CA |
| CERS3 | GA | GABBR1 | CA |
| ASPA | GA | SDC2 | CA |
| GRP | GA | NKX3-1 | CA |
| APOC1 | GA | LYPD2 | CA |
| EPHX3 | GA, CA | CDR1 | CA |
| REEP1 | GA | | |

TABLE 1-continued

Gene list and function

| Gene Symbol | Function | Gene Symbol | Function |
|---|---|---|---|
| FAM198B | GA | | |
| PCDHB4 | GA | | |
| PCDHB 16 | GA | | |
| FOXD1 | GA | | |
| SPARC | GA | | |
| NKAPL | GA | | |
| GPR110 | GA | | |

TABLE 1.1

Non-limiting examples of probe sequences for detecting informative-genes.

| | Probe Sequence | SEQ ID NO: |
|---|---|---|
| Gene: Cancer | | |
| TSPAN2 | TCAACATTAAGAAGTCTTAATTCAG | 1 |
| MCAM | GCTTTAATCCCCATGAAGGACAGTG | 2 |
| ATP12A | GCGGTGGAGATACCGGCGGCGGCGC | 3 |
| NOVA1 | GACGAAATTCAGACATGGAGCATCA | 4 |
| MIA | ATGACACCAAGGCACACCAGGGACC | 5 |
| CD177.1 | GACCCGTCTGTGGCTGGTAATCTCT | 6 |
| EPHX3 | GCTCCACTGGAAGAGAGGTATACCC | 7 |
| CD177.2 | TTCCTGTGTCCCATTGAGCAGGTTG | 8 |
| CGREF1 | TAGGGTACAGCACTTAACGCAATCT | 9 |
| BST1 | TGTTTGCCGTTTCCCGTTCCAGACA | 10 |
| RNF150 | TGGTTAATCCAAGCCGCAGCCTGGT | 11 |
| CLDN22 | GGTGTTTCTCGTCTCCAGTTCTTGA | 12 |
| GABBR1 | TACGGAGCCATTACCTGGGCAGTGC | 13 |
| SDC2 | TGAGCCTGCTTCTCCGGGCTCCCCT | 14 |
| NKX3-1 | TTTGTGCTGGCTAGTACTCCGGTCG | 15 |
| LYPD2 | TTCTTCAAGGCATTCGGGGCTGGGC | 16 |
| CDR1 | AACAACTCCGGGTCTTCCAGCGACT | 17 |
| Gene: Gender | | |
| RP S4Y1 | TAAACCGCAGGAAGTCAGATGAGTG | 18 |
| Gene: Smoking | | |
| SLC7A11 | GGTTGAAGCAACTAGAAGCGTGACA | 19 |
| CLDN10 | GACAGCGTTTCATGCTCGGATGGCC | 20 |
| TKT | GGTTTATTCTCTCCAGACGGTCAGG | 21 |
| Gene: PY | | |
| RUNX1T1 | TAACAGGGAGGAGGTCAAATCTATC | 22 |
| AKR1 C2 | TAGCTGTAGCTTACTGAAGTCGCCA | 23 |

Table 2 below provides a summary of performance characteristics for the two models for bronchoscopy-negative subjects in the training set. The number of bronch-negative subjects (N) corresponds to CA+subjects for sensitivity and CA-subjects for specificity.

TABLE 2

| | N | Score 1 | Score 2 |
|---|---|---|---|
| Sensitivity | 68 | 91.2% | 82.4% |
| Specificity | 76 | 56.6% | 48.7% |
| AUC | | 80.8% | 77.8% |
| NPV* | | 95.5% | 90.0% |

*NPV is calculated assuming a 50% prevalence of cancer combined with the observed sensitivity and specificity of bronchoscopy and prediction model.

Model Performance

Calculation of the sensitivity and specificity of the prediction models (based on scores 1 and 2) was done using a specific score threshold, to differentiate prediction of CA+ and CA-samples. The same threshold that was selected for both models in the Training Set (Model Score=0.65) was used in the Validation Set. Prediction accuracy was first determined in the bronchoscopy-negative samples (the intended-use cases) for both models and is summarized in The sensitivity of the prediction model was also calculated for several subgroup categories within the Validation Set. Results are shown in Tables 3-9 for both models. Sub¬categories contain different numbers of samples which affect confidence intervals.

TABLE 3

Sensitivity of prediction model as a function of the mass size of the observed lesion-Score 1

| Mass Size | N | Sens Sens. | Sens, | PM + BR Sens. |
|---|---|---|---|---|
| <1 | 13 | 100.00% | 83.30% | 100.00% |
| 1 to 2 | 35 | 87.50% | 50.00% | 100.00% |
| 2 to 3 | 41 | 90.60% | 53.10% | 96.90% |
| >3 | 155 | 85.10% | 79.40% | 95.00% |
| Infiltrate | 32 | 100.00% | 100.00% | 100.00% |
| Unknown | 21 | 100.00% | 80.00% | 100.00% |

PM = Prediction Model;
BR = Bronchoscopy

TABLE 4

Sensitivity of prediction model as a function of the mass size of the observed lesion-Score 2

| Mass Size | N | PMs. | Senens. | |
|---|---|---|---|---|
| BR Sens. | PM + BR S | | | |
| <1 | 13 | 66.70% | 83.30% | 100.00% |
| 1 to 2 | 35 | 87.50% | 50.00% | 93.80% |
| 2 to 3 | 41 | 81.30% | 53.10% | 93.80% |
| >3 | 155 | 83.00% | 79.40% | 95.70% |
| Infiltrate | 32 | 90.00% | 100.00% | 100.00% |
| Unknown | 21 | 100.00% | 80.00% | 100.00% |

TABLE 5

Sensitivity of prediction model as a function of the location of the observed lesion in the lung (Score 1)

| Mass Size | N | PM Sens | BR Sens | PM + BR Sens |
|---|---|---|---|---|
| Central | 97 | 84.40% | 79.20% | 93.50% |
| Peripheral | 86 | 90.70% | 61.10% | 96.30% |
| Both | 90 | 90.50% | 78.40% | 100.00% |
| Unknown | 25 | 86.70% | 80.00% | 93.30% |

TABLE 6

Sensitivity of prediction model as a function of the location of the observed lesion in the lung (Score 2)

| Mass Size | N | PM Sens. | BR Sens. | PM + BR Sens. |
|---|---|---|---|---|
| Central | 97 | 79.20% | 79.20% | 93.50% |
| Peripheral | 86 | 81.50% | 61.10% | 96.30% |
| Both | 90 | 89.20% | 78,40% | 98.60% |
| Unknown | 25 | 93.30% | 80.00% | 93.30% |

TABLE 7

Sensitivity of prediction model as a function of the cancer sub-type as determined in pathology (Score 1)

| Cancer Type | N | P M Sens. | BR Sens. | PM + BR Sens. |
|---|---|---|---|---|
| AC | 67 | 83.60% | 70.10% | 94.00% |
| SCC | 72 | 94.40% | 75.00% | 95.80% |
| LC | 7 | 71.40% | 85.70% | 100.00% |
| NSCLC | 26 | 92.30% | 73.10% | 76.90% |
| SCLC | 37 | 89.20% | 86.50% | 97.30% |
| NSCLC/SCLC | 2 | 50.00% | 100.00% | 100.00% |
| Unknown | 86 | 75.00% | 37.50% | 100.00% |

TABLE 8

Sensitivity of prediction model as a function of the cancer sub-type as determined in pathology (Score 2)

| Cancer Type | N | PM Sens. | BR Sens. | P M + BR Sens. |
|---|---|---|---|---|
| AC | 67 | 80.60% | 70.10% | 94.00% |
| SCC | 72 | 87.50% | 75.00% | 97.20% |
| LC | 7 | 85.70% | 85.70% | 100.00% |
| NSCLC | 26 | 69.20% | 73.10% | 80.80% |
| SCLC | 37 | 89.20% | 86.50% | 97.30% |
| NSCLC/SCLC | 2 | 0.00% | 100.00% | 100.00% |
| Unknown | 86 | 62.50% | 37.50% | 87.50% |

PM = Prediction Model;
BR = Bronchoscopy

TABLE 9

Sensitivity of prediction model as a function of cancer stage

| Stage | N | PM Sens. | BR Sens. | PM + BR |
|---|---|---|---|---|
| Score 1 | | | | |
| I | 13 | 92.3% | 38.5% | 100.0% |
| IIa | 2 | 100.0% | 0.0% | 100.0% |
| IIb | 13 | 92.3% | 76.9% | 100.0% |
| Early | 28 | 92.9% | 53.6% | 100.0% |
| Ina | 27 | 92.6% | 74.1% | 96.3% |
| IIIb | 19 | 89.5% | 89.5% | 100.0% |
| IV | 47 | 87.2% | 89.4% | 100.0% |
| Extensive | 15 | 73.3% | 73.3% | 93.3% |
| Score 2 | | | | |
| I | 13 | 84.6% | 38.5% | 92.3% |
| IIa | 2 | 100.0% | 0.0% | 100.0% |
| Jib | 13 | 92.3% | 76.9% | 100.0% |
| Early | 28 | 89.3% | 53.6% | 96.4% |
| Ina | 27 | 92.6% | 74.1% | 100.0% |
| IIIb | 19 | 78.9% | 89.5% | 94.7% |
| IV | 47 | 80.9% | 89.4% | 100.0% |
| Extensive | 15 | 80.0% | 73.3% | 93.3% |

Comparison of Performance in Training and Validation Sets

The overall prediction accuracy of the prediction models in the Training and Validation Sets was compared in order to evaluate the reproducibility of the models in independent cohorts. Results are provided in Table 10.

TABLE 10

Comparison of sensitivity, specificity and AUC for two models in Training and Validation sets

|  | Score 1 | | | | Score 2 | | | |
| --- | --- | --- | --- | --- | --- | --- | --- | --- |
|  | Training | | Validation | | Training | | Validation | |
|  | All samples | BR-neg samples | All samples | BR-neg samples | All samples | BR-neg samples | All samples | BR-neg samples |
| Sensitivity | 90.6% | 91.2% | 88.2% | 85.7% | 85.7% | 82.4% | 84.1% | 83.9% |
| Specificity | 56.6% | 56.6% | 47.4% | 47.4% | 48.7% | 48.7% | 47.4% | 47.4% |
| AUC | 0.803 | 0.808 | 0.793 | 0.764 | 0.785 | 0.778 | 0.751 | 0.739 |

Significant difference (p>0.05) in sensitivity or specificity were not observed between the Training and Validation Sets for either model. Likewise the small differences in AUC for each model between the two cohorts was not statistically significant (based on p>0.05). The sensitivity and specificity is also similar for the bronch-negative samples compared to all samples (bronch-neg and bronch-pos combined). The was a relatively small drop in overall performance between Score 1 and Score 2, with the latter showing a 2-4% point drop in AUC compared to score 1.

TABLE 11

232 differentially expressed genes and cluster membership

| Symbol | Cluster | Tstat | p.value |
| --- | --- | --- | --- |
| TMEM51 | 1 | −3.73334 | 0.000227 |
| CR1L | 1 | −2.84036 | 0.00482 |
| PDZK1IP 1 | 1 | −3.65419 | 0.000305 |
| MICAL2 | 1 | −3.08175 | 0.002252 |
| VWA5A | 1 | −3.01006 | 0.002838 |
| ACAD8 | 1 | −3.25793 | 0.001253 |
| SAA4 | 1 | −2.84375 | 0.00477 |
| GLYATL2 | 1 | −3.02638 | 0.002693 |
| ETV6 | 1 | −4.46414 | 1.15E−05 |
| CD177 | 1 | −3.68455 | 0.000273 |
| CEACAM7 | 1 | −5.40343 | 1.35E−07 |
| CD177 | 1 | −3.85704 | 0.000141 |
| QPCT | 1 | −3.16572 | 0.001709 |
| CASP10 | 1 | −3.07674 | 0.002289 |
| PI3 | 1 | −5.27363 | 2.59E−07 |
| BST1 | 1 | −4.29031 | 2.42E−05 |
| MTNR1A | 1 | −4.47628 | 1.09E−05 |
| STARD4 | 1 | −2.94146 | 0.003525 |
| CFB | 1 | −2.87447 | 0.004341 |
| SLC26A8 | 1 | −3.09768 | 0.002138 |
| VNN2 | 1 | −2.88831 | 0.00416 |
| HDAC9 | 1 | −3.27926 | 0.001165 |
| SLC26A4 | 1 | −3.93362 | 0.000104 |
| LCN2 | 1 | −3.64257 | 0.000319 |
| CFB | 1 | −2.86774 | 0.004432 |
| CCDC18 | 2 | −2.89401 | 0.004087 |
| FAM72D | 2 | −3.41712 | 0.000722 |
| NUF2 | 2 | −3.35293 | 0.000904 |
| FAM72D | 2 | −3.65638 | 0.000303 |
| FBXO28 | 2 | −2.93189 | 0.003633 |
| GPR137B | 2 | −3.29637 | 0.001099 |
| STIL | 2 | −3.05607 | 0.002448 |
| DEPDC1 | 2 | −3.10412 | 0.002094 |
| TSPAN2 | 2 | −3.92967 | 0.000106 |
| FAM72D | 2 | −3.18098 | 0.001624 |
| ASPM | 2 | −3.21677 | 0.001441 |
| KIF14 | 2 | −3.09106 | 0.002185 |
| KIF20B | 2 | −2.95904 | 0.003336 |
| RAD51AP1 | 2 | −3.38028 | 0.000822 |
| GAS2L3 | 2 | −3.22465 | 0.001403 |
| SPIC | 2 | −3.00214 | 0.00291 |
| SMAGP | 2 | −3.38429 | 0.00081 |
| ATP12A | 2 | −3.49107 | 0.000555 |
| BRCA2 | 2 | −2.9535 | 0.003395 |
| BORA | 2 | −2.81443 | 0.005215 |
| SKA3 | 2 | −2.94422 | 0.003495 |
| DLGAP5 | 2 | −2.8962 | 0.00406 |
| CASC5 | 2 | −2.98473 | 0.003076 |
| LRRC28 | 2 | −3.78219 | 0.000188 |
| PYCARD | 2 | −3.0296 | 0.002666 |
| TXNL4B | 2 | −3.75986 | 0.000205 |
| EFCAB5 | 2 | −4.15228 | 4.31E−05 |
| SPAG5 | 2 | −3.28148 | 0.001157 |
| FAM72D | 2 | −3.66614 | 0.000292 |
| ABCA12 | 2 | −3.25495 | 0.001266 |
| AURKA | 2 | −3.06413 | 0.002385 |
| SGOL1 | 2 | −2.87447 | 0.004341 |
| BANK1 | 2 | −3.22839 | 0.001385 |
| CENPE | 2 | −2.90302 | 0.003975 |
| CASP6 | 2 | −2.96202 | 0.003305 |
| MAD2L1 | 2 | −3.2685 | 0.001209 |
| CCNA2 | 2 | −3.12554 | 0.001952 |
| CCNB1 | 2 | −3.43884 | 0.000668 |
| KIF20A | 2 | −3.16017 | 0.001741 |
| CENPK | 2 | −3.38809 | 0.000799 |
| ERAP1 | 2 | −3.0003 | 0.002927 |
| FAM54A | 2 | −3.5307 | 0.000481 |
| PHTF2 | 2 | −2.82226 | 0.005093 |
| CLDN12 | 2 | −3.10361 | 0.002097 |
| BPGM | 2 | −2.89166 | 0.004117 |
| PCMTD1 | 2 | −2.92723 | 0.003686 |
| MELK | 2 | −2.90007 | 0.004011 |
| MST4 | 2 | −3.46215 | 0.000615 |
| CR1 | 3 | −3.1375 | 0.001876 |
| GOS2 | 3 | −3.08943 | 0.002197 |
| CSF3R | 3 | −3.326 | 0.000992 |
| S100A12 | 3 | −2.93619 | 0.003584 |
| SELL | 3 | −2.81834 | 0.005154 |
| NCF2 | 3 | −2.8535 | 0.00463 |
| LIPN | 3 | −3.16551 | 0.00171 |
| ZNF438 | 3 | −3.31249 | 0.00104 |
| NAMPT | 3 | −2.85014 | 0.004678 |
| CBL | 3 | −3.77272 | 0.000195 |
| CASP5 | 3 | −2.96813 | 0.003242 |
| CARD16 | 3 | −3.32829 | 0.000985 |
| CARD17 | 3 | −2.96301 | 0.003295 |
| CLEC4A | 3 | −2.9666 | 0.003257 |
| LRRK2 | 3 | −3.38419 | 0.00081 |
| HMGN2P46 | 3 | −3.56798 | 0.00042 |
| AQP9 | 3 | −3.18953 | 0.001578 |
| BCL2A1 | 3 | −2.88499 | 0.004203 |
| ITGAX | 3 | −2.92718 | 0.003687 |
| GPR97 | 3 | −3.39828 | 0.000771 |
| CCL4 | 3 | −2.86648 | 0.004449 |
| PSTPIP2 | 3 | −2.88175 | 0.004245 |
| IFI30 | 3 | −2.81741 | 0.005168 |
| FFAR2 | 3 | −3.20036 | 0.001522 |
| EMR3 | 3 | −3.09579 | 0.002151 |
| FPR1 | 3 | −3.03905 | 0.002586 |

TABLE 11-continued 232 differentially expressed genes and cluster membership

| Symbol | Cluster | Tstat | p.value |
|---|---|---|---|
| LILRA5 | 3 | −2.87193 | 0.004375 |
| PLEK | 3 | −3.08569 | 0.002223 |
| MXD1 | 3 | −2.9859 | 0.003064 |
| TNFAIP6 | 3 | −3.05049 | 0.002492 |
| CXCR2 | 3 | −3.51316 | 0.000512 |
| IL1B | 3 | −3.27702 | 0.001174 |
| CXCR1 | 3 | −3.38462 | 0.000809 |
| SIRPB1 | 3 | −3.65291 | 0.000307 |
| NCF4 | 3 | −3.14344 | 0.00184 |
| IRAK2 | 3 | −3.27512 | 0.001182 |
| PROK2 | 3 | −3.43542 | 0.000677 |
| TLR2 | 3 | −2.82581 | 0.005038 |
| TREM1 | 3 | −2.96731 | 0.00325 |
| SOD2 | 3 | −3.16918 | 0.001689 |
| CREB 5 | 3 | −3.32746 | 0.000987 |
| NAMPT | 3 | −2.80465 | 0.005372 |
| TNFRSF10C | 3 | −2.80794 | 0.005318 |
| CSGALNACT1 | 3 | −3.54557 | 0.000455 |
| ASAP1 | 3 | −2.80888 | 0.005303 |
| PLA2G2A | 4 | 3.087887 | 0.002208 |
| NFYC | 4 | 3.20083 | 0.00152 |
| RASSF10 | 4 | 3.105541 | 0.002084 |
| GLB1L3 | 4 | 2.800517 | 0.005439 |
| TRIM3 | 4 | 3.207674 | 0.001485 |
| MCAM | 4 | 2.70666 | 0.007192 |
| MSRB3 | 4 | 3.432075 | 0.000685 |
| SLITRK5 | 4 | 3.963535 | 9.27E−05 |
| GAS6 | 4 | 2.820157 | 0.005125 |
| NOVA1 | 4 | 2.729315 | 0.006728 |
| GABRG3 | 4 | 2.904108 | 0.003961 |
| ABCA3 | 4 | 3.321624 | 0.001008 |
| LPO | 4 | 3.513723 | 0.000511 |
| FSCN2 | 4 | 2.781525 | 0.005759 |
| RASD1 | 4 | 3.198556 | 0.001531 |
| HILS1 | 4 | 3.002738 | 0.002905 |
| SDK2 | 4 | 3.45176 | 0.000638 |
| NTN5 | 4 | 3.159291 | 0.001746 |
| KCNA7 | 4 | 3.631462 | 0.000332 |
| ATOH8 | 4 | 3.062376 | 0.002398 |
| KCNIP3 | 4 | 2.994468 | 0.002982 |
| INHBB | 4 | 3.056753 | 0.002442 |
| VSTM2L | 4 | 3.520433 | 0.000499 |
| ZNRF3 | 4 | 3.592073 | 0.000384 |
| PLEKHG4B | 4 | 2.830968 | 0.00496 |
| GNMT | 4 | 3.274623 | 0.001184 |
| GABBR1 | 4 | 2.881256 | 0.004252 |
| ARHGEF10 | 4 | 3.270419 | 0.001201 |
| SDC2 | 4 | 2.847433 | 0.004717 |
| CRB2 | 4 | 3.452184 | 0.000637 |
| GAS1 | 4 | 3.470173 | 0.000598 |
| PNPLA7 | 4 | 2.715581 | 0.007006 |
| RAI2 | 4 | 3.25911 | 0.001248 |
| PLA2G2A | 4 | 2.899771 | 0.004015 |
| ID3 | 5 | 3.213565 | 0.001456 |
| PGLYRP4 | 5 | −3.64634 | 0.000314 |
| SFTPA1 | 5 | 3.189676 | 0.001578 |
| SFTPA1 | 5 | 3.189676 | 0.001578 |
| LIPK | 5 | −2.99802 | 0.002949 |
| SFTPA2 | 5 | 3.858853 | 0.00014 |
| SFTPA2 | 5 | 3.858853 | 0.00014 |
| ASCL3 | 5 | 2.764568 | 0.006059 |
| RPPH1 | 5 | 2.832278 | 0.00494 |
| CD209 | 5 | 3.331793 | 0.000973 |
| GPR32 | 5 | −2.98245 | 0.003098 |
| UGT2A3 | 5 | −2.84993 | 0.004681 |
| CD58 | 6 | −3.35673 | 0.000892 |
| LBR | 6 | −3.62457 | 0.000341 |
| ARHGDIB | 6 | −3.22018 | 0.001424 |
| SLC12A6 | 6 | −4.12377 | 4.85E−05 |
| LPCAT2 | 6 | −3.5142 | 0.00051 |
| PLEKHB2 | 6 | −3.02046 | 0.002745 |
| KYNU | 6 | −4.13269 | 4.68E−05 |
| ANKRD36B | 6 | −3.84654 | 0.000147 |
| ANKRD36B | 6 | −3.49272 | 0.000551 |
| ANKRD36B | 6 | −3.55319 | 0.000443 |
| SRD5A3 | 6 | −4.25485 | 2.81E−05 |
| NEIL3 | 6 | −3.23716 | 0.001345 |
| TLR1 | 6 | −2.90118 | 0.003997 |
| BCAP29 | 6 | −3.44601 | 0.000652 |
| MGAM | 6 | −3.11565 | 0.002016 |
| TPK1 | 6 | −3.21156 | 0.001466 |
| ATP6V1B2 | 6 | −3.57198 | 0.000414 |
| LYN | 6 | −3.1938 | 0.001556 |
| SDCBP | 6 | −2.80868 | 0.005307 |
| GK | 6 | −2.91501 | 0.003829 |
| GLA | 6 | −3.30241 | 0.001077 |
| ADRA2A | 7 | 3.550905 | 0.000447 |
| PRKCDBP | 7 | 2.741146 | 0.006496 |
| PRR4 | 7 | 3.898998 | 0.00012 |
| PRB4 | 7 | 2.988547 | 0.003039 |
| PRB3 | 7 | 3.690625 | 0.000266 |
| PRB1 | 7 | 2.976402 | 0.003158 |
| PRB2 | 7 | 3.201779 | 0.001515 |
| BMP4 | 7 | 2.886357 | 0.004185 |
| PRKCA | 7 | 3.80528 | 0.000172 |
| CYP1B1-AS1 | 7 | 2.720927 | 0.006897 |
| CGREF1 | 7 | 3.275505 | 0.00118 |
| RPRM | 7 | 2.944897 | 0.003488 |
| SDPR | 7 | 2.84669 | 0.004728 |
| BPIFB2 | 7 | 3.949534 | 9.80E−05 |
| BPIFB 6 | 7 | 2.98498 | 0.003073 |
| SNCA | 7 | 2.777053 | 0.005837 |
| CLDN22 | 7 | 3.502336 | 0.000533 |
| COBL | 7 | 3.1512 | 0.001793 |
| NKX3-1 | 7 | 2.92659 | 0.003693 |
| CDR1 | 7 | 4.307308 | 2.25E−05 |
| CH25H | 8 | 3.168911 | 0.001691 |
| FXC1 | 8 | 3.17821 | 0.001639 |
| DLG2 | 8 | 2.948964 | 0.003443 |
| NRXN3 | 8 | 2.863338 | 0.004493 |
| CES1P1 | 8 | 3.630652 | 0.000333 |
| CES1 | 8 | 3.122943 | 0.001968 |
| KCNJ16 | 8 | 3.53821 | 0.000468 |
| APCDD1 | 8 | 3.103106 | 0.002101 |
| TMEM178 | 8 | 2.7868 | 0.005668 |
| MYRIP | 8 | 2.958247 | 0.003344 |
| FLNB | 8 | 2.911823 | 0.003867 |
| ENPP5 | 8 | 2.788207 | 0.005644 |
| SEMA3E | 8 | 2.940987 | 0.003531 |
| SLC7A2 | 8 | 3.321666 | 0.001007 |
| ARHGAP6 | 8 | 3.220932 | 0.001421 |
| ANO3 | 9 | −2.98289 | 0.003094 |
| SLC22A10 | 9 | −3.04806 | 0.002512 |
| UFM1 | 9 | −3.15354 | 0.001779 |
| EPHX3 | 9 | −3.73504 | 0.000225 |
| KLF7 | 9 | −2.84977 | 0.004683 |
| LGSN | 9 | −3.5566 | 0.000438 |
| LYPD2 | 9 | −2.93177 | 0.003634 |
| CES3 | 10 | −3.3613 | 0.000878 |
| MIA | 10 | −3.23844 | 0.001339 |
| RNF150 | 10 | −4.32839 | 2.06E−05 |
| SLC9A3 | 10 | −2.88577 | 0.004193 |
| MYOT | 11 | −3.40228 | 0.000761 |

Example 2: Validation of Bronchial Genomic Classifier for Lung Cancer Patients Undergoing Diagnostic Chronchoscopy Introduction Bronchoscopy is frequently non-diagnostic in patients with pulmonary lesions suspicious for lung cancer. This often results in additional invasive testing, although many lesions are benign. We sought to validate a bronchial gene expression classifier that could improve the diagnostic performance of bronchoscopy.

Lesions suspicious for lung cancer are frequently identified on chest imaging. The decision of whether to pursue surveillance imaging or an invasive evaluation requiring tissue sampling is complex and requires assessment of the likelihood of malignancy, ability to biopsy, surgical risk, and patient preferences [1]. When a biopsy is required, the approach can include bronchoscopy, transthoracic needle biopsy (TTNB), or surgical lung biopsy (SLB). The choice between these modalities is usually determined by considerations such as lesion size and location, presence of adenopathy, risk of procedure and local expertise. Bronchoscopy is a safe procedure, with less than 1% complicated by pneumothorax [2]. There are approximately 500,000 bronchoscopies performed per year in the U.S. [3], of which roughly half are for the diagnostic workup of lung cancer. However, bronchoscopy is limited by its sensitivity, ranging between 34-88% depending on the location and size of the lesion [4]. Even with newer bronchoscopic guidance techniques, the sensitivity is only ~70% for peripheral lesions [5].

Patients with a non-diagnostic bronchoscopy often undergo further invasive testing to establish a definitive diagnosis. SLB is not the initial preferred approach given the inherent risks, with a complication rate of approximately of 5% and 30-day mortality of ~1% [6]. Importantly, 20-25% of SLBs are performed in patients ultimately diagnosed with benign lesions [7,8]. Furthermore, TTNB is associated with significant morbidity including a 15% pneumothorax rate [9], of which 6% require chest tube drainage [10,11]. Given the pitfalls of invasive procedures, alternative approaches are needed to identify patients with lower likelihood of malignancy who are appropriate for imaging surveillance.

Classification of biological disease states, including cancer, using gene expression measurements of clinical specimens is well established [12]. In the setting of lung cancer, there are distinct cancer-associated gene expression patterns in cytologically-normal epithelium collected from the proximal airways of smokers [13]. Recently, we developed a gene expression classifier in bronchial epithelial cells (BECs) collected from the mainstem bronchus via bronchoscopy that distinguishes patients with and without lung cancer amongst current and former smokers (manuscript submitted). We undertook the present studies to validate this classifier in two prospective multicenter trials of patients undergoing bronchoscopy for suspected lung cancer and to assess how this classifier alters the diagnostic performance of bronchoscopy.

Materials and Methods
Study Design, Population, and Protocol

Current and former smokers undergoing bronchoscopy for suspicion of lung cancer were enrolled in AEGIS 1 and AEGIS 2, two independent, prospective, multicenter, observational studies (NCT01309087 and NCT00746759). Patients were enrolled at 28 sites in the U.S, Canada, and Ireland. Cytology brushes were used to collect normal appearing BECs from the mainstem bronchus and submerged in an RNA preservative. Results of the classifier were not reported to physicians or patients. Patients were screened prior to bronchoscopy to determine if they met the requirements of the study protocol. Exclusion criteria included subjects <21 year old, never smokers (defined as smoking <100 cigarettes in lifetime), and patients with a concurrent cancer or a history of lung cancer. Patients who had been on a mechanical ventilator for >24 hours immediately prior to bronchoscopy, or could not consent or comply with the study, were excluded. Patients were followed until a final diagnosis was established or until 12 months post bronchoscopy. A diagnosis of lung cancer was established at the time of index bronchoscopy or by subsequent biopsy using TTNB, SLB, a second bronchoscopy, or other invasive procedures. The specific bronchoscopic methods used and subsequent surveillance imaging or procedures performed after non-diagnostic bronchoscopy was at the discretion of the treating physician. Patients diagnosed as cancer-free had a specific benign diagnosis or radiographic stability/resolution at 12 months of follow-up. Patients without a definitive diagnosis of cancer, a specific benign diagnosis or stability/resolution at 12 months of follow-up were excluded from further analysis. The treating physician assessed each patient's pre-test probability of malignancy (POM) prior to bronchoscopy using a five level scale (<10%, 10-39%, 40-60%, 61-85%, and >85%). The study protocol was approved by the institutional review board at each participating center, and all patients provided written informed consent before enrollment.

A total of 855 patients in AEGIS 1 and 502 in AEGIS 2 qualified and were enrolled between January 2009 and August 2012 (FIG. 4) at twenty-eight medical centers in the United States, Canada, and Ireland (Table 12). The sites were a mix of tertiary/academic medical centers (n=20), community based hospitals (n=6), and Veteran's Administration hospitals (n=2).

Figure 4:
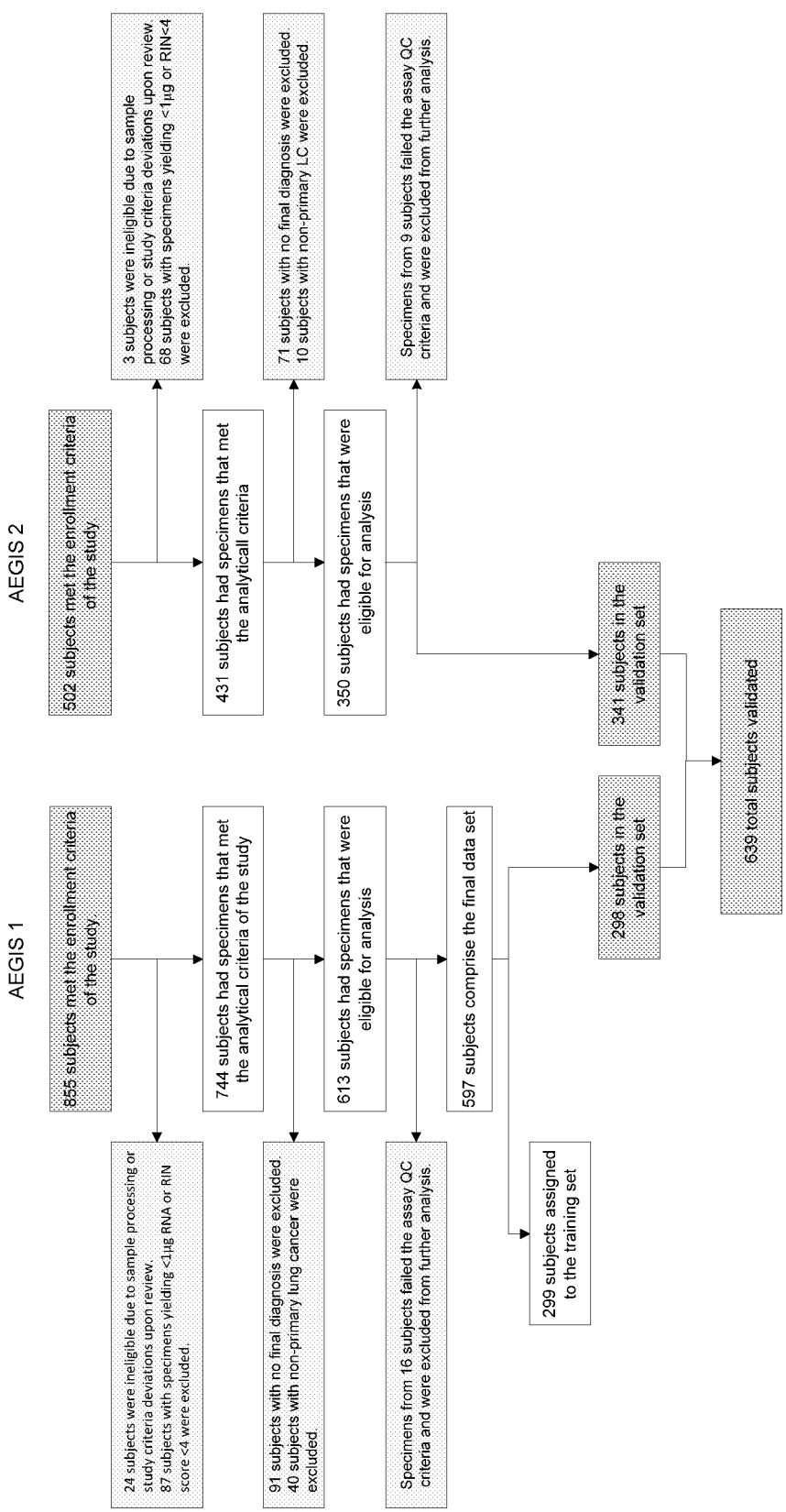
FIG. 4 depicts the following color-coding: patients that met inclusion criteria of the study (blue); patients who were excluded (yellow); patients who were included in the final analysis (green).

Additional patients were excluded from the study after enrollment based on the following criteria (see FIG. 4). First, a total of 111 patients in AEGIS 1 and 71 patients in AEGIS 2 were ineligible due to the following protocol deviations: In AEGIS 1, 24 patients either did not meet the study enrollment criteria upon review, had specimens collected that did not meet the acceptance criteria in accessioning, or were enrolled but did not have a specimen collected. An additional 87 samples did not meet minimum QC criteria after RNA isolation, either due to a RIN score <4, or RNA yield <1 µg. In AEGIS 2, there were 3 ineligible patients due to having specimens collected that did not meet the acceptance criteria in accessioning, and 68 samples that did not meet the minimum QC criteria for RNA. Second, patients diagnosed with a non-primary lung cancer, including 40 patients in AEGIS 1 and 10 patients in AEGIS 2 were excluded. Additionally, upon review at 12 months, patients without a final diagnosis were also excluded from the study, including 91 subjects in AEGIS 1 and 71 patients in AEGIS 2. Approximately two thirds of these 162 patients (n=106) from AEGIS 1 and 2 were lost to follow-up after their initial bronchoscopy, while the remaining third (n=56) did not have a definitive diagnosis at 12 months post-bronchoscopy. Finally, we excluded 16 patients in AEGIS 1 and 9 patients in AEGIS 2 with gene expression data that failed the assay QC criteria (described below under Microarray Processing methods).

The AEGIS 1 cohort had previously been divided into equal training and test sets in a randomized manner. The training set (n=299 patients) was used to derive the gene expression classifier composed of 23 genes plus age and has been described elsewhere (manuscript submitted). In the training set, the classifier was found to have an AUC of 0.78 (95% CI, 0.71-0.85) in patients whose bronchoscopy did not lead to a diagnosis of lung cancer (n=134), with a sensitivity of 93% and specificity of 57%. The current study is focused on validation of the locked classifier in two independent validation sets.

The baseline demographics and clinical characteristics of the final AEGIS 1 and AEGIS 2 validation sets are compared in Table 1. A separate comparison of patients diagnosed with cancer and benign disease within each cohort is provided in Table 12.

TABLE 12

Characteristics of patients in the AEGIS 1 and AEGIS 2 test sets.

|  | AEGIS 1 Test Set | | | AEGIS 2 Test Set | | |
|---|---|---|---|---|---|---|
|  | Ca+ | Ca− | P | Ca+ | Ca− | P |
| N | 220 | 78 |  | 267 | 74 |  |
| Sex |  |  | 0.506 |  |  | 0.091 |
| Female | 95 | 30 |  | 77 | 29 |  |
| Male | 125 | 48 |  | 190 | 45 |  |
| Age (IQR) [a] | 64 (15) | 57 (14) | <0.001 | 65 (13) | 60 (18) | <0.001 |
| Race [b] |  |  | 0.878 |  |  | 0.426 |
| White | 166 | 60 |  | 206 | 61 |  |
| Black | 42 | 13 |  | 55 | 11 |  |
| Other/unknown | 12 | 5 |  | 6 | 2 |  |
| Smoking Status |  |  | 0.065 |  |  | 0.026 |
| Current | 115 | 31 |  | 141 | 28 |  |
| Former | 105 | 47 |  | 126 | 46 |  |
| Smoking History (PY) (IQR) [a] | 45 (30) | 30 (36) | <0.001 | 50 (35) | 20 (30) | <0.001 |

[a] Reported as the median value (and interquartile range; IQR). P-values calculated using the Mann-Whitney test.
[b] P-value calculated for white vs. non-white.

Clinical and demographic data was collected for each patient and recorded on a study clinical report form (CRF). Additional pathology and radiology reports were maintained in the medical records of each patient and were available for review. All source documents were monitored and entered into databases maintained by the study sponsor. Size and location of the pulmonary lesions were obtained from the CT scan report. Subjects were followed up to twelve months post bronchoscopy to collect data for a clinical diagnosis. A diagnosis of lung cancer was based on results from pathology and copies of pathology reports were collected from the medical centers. The specimen leading to a clinical diagnosis of cancer was either obtained during bronchoscopy or from a subsequent invasive when bronchoscopy was non-diagnostic. Data on all clinical procedures performed after a non-diagnostic bronchoscopy was collected during the study. The subsequent evaluation of patients with non-diagnostic bronchoscopies was at the discretion of the treating physician at each study center. In some cases, more than one procedure after bronchoscopy was required to successfully render a diagnosis, but in all cases the procedure that led to the diagnosis of lung cancer was collected. Invasive follow-up procedures were defined as either a second bronchoscopy, TTNB, or surgical lung biopsy (SLB), which could include a mediastinoscopy, thoracoscopy, thoracotomy, or video-assisted thoracoscopic surgery (VATS).

The records of patients who were not diagnosed with cancer underwent an adjudication process in order to declare subjects as cancer-free. The process consisted of a review of the available medical records for each patient by a panel of five pulmonologists. Two pulmonologists from this panel independently reviewed each case and the patient was determined to be cancer-free if he/she met one of the following criteria: patient was diagnosed with an alternative diagnosis that explained the initial suspicious abnormality, the abnormality was determined to be stable, or the abnormality resolved. Patients whom did not meet these criteria at the completion of the 12-month follow-up period had no final diagnosis and were excluded from further analysis in the study.

Histology (Table 13) and cancer stage (Table 14) data was analyzed for patients diagnosed with primary lung cancer. Data was extracted from the study CRFs and were confirmed by review of complete medical records. Of the total cancers, 80% (175/220; 95% CI, 74-84%) in AEGIS 1 and 83% (222/267; 95% CI, 78-87%) in AEGIS 2 were NSCLC. There were 17% (38/220; 95% CI, 13-23%) and 16% (42/267 95% CI, 12-21%) SCLC cancers, respectively. Of the patients with NSCLC with known cancer stage data, early stage (stage I or 2) was present in 40% (53/139 95% CI, 32-48%) in AEGIS 1 and 37% (67/199; 95% CI, 30-44%) in AEGIS 2.

TABLE 13

Summary demographics and clinical characteristics of study participants: A comparison of AEGIS 1 vs. AEGIS 2 patients was performed across all clinical characteristics. Significant differences are indicated by *p < .05, **p < .001. The p-value for race was calculated for white versus non-white, and for lung cancer histology using NSCLC versus SCLC.

|  | AEGIS 1 | AEGIS 2 |
|---|---|---|
| N | 298 | 341 |
| Sex* |  |  |
| Female | 125 | 106 |
| Male | 173 | 235 |
| Age*, median(IQR) | 62 (16) | 64 (15) |
| Race |  |  |
| White | 226 | 267 |
| Black | 55 | 66 |
| Other | 15 | 4 |
| Unknown | 2 | 4 |
| Smoking Status |  |  |
| Current | 146 | 169 |
| Former | 152 | 172 |
| Tobacco Pack-years, median, (IQR) | 40 (36) | 45 (38) |
| Lesion Size** |  |  |
| <2 cm | 48 | 83 |
| 2 to 3 cm | 41 | 39 |
| >3 cm | 155 | 188 |
| Infiltrate | 32 | 28 |
| Unknown | 22 | 3 |
| Lesion Location** |  |  |
| Central | 98 | 127 |
| Peripheral | 86 | 108 |
| Central & Peripheral | 90 | 102 |
| Unknown | 24 | 4 |
| Lung Cancer Histology | 220 | 267 |
| Small cell lung cancer | 38 | 42 |
| Nonsmall cell lung cancer | 175 | 222 |
| Adenocarcinoma | 69 | 100 |
| Squamous | 72 | 81 |
| Large cell | 8 | 8 |
| NSCLC, not otherwise specified | 26 | 33 |
| Unknown | 7 | 3 |
| Benign Diagnoses | 78 | 74 |
| Infection | 18 | 14 |
| Sarcoidosis | 16 | 15 |
| Resolution or Stability | 27 | 24 |
| Other | 17 | 21 |

TABLE 14

Stage data of patients diagnosed with primary lung cancer.

| Histology | Stage | AEGIS 1 | AEGIS 2 |
|---|---|---|---|
| SCLC |  | 38 | 42 |
|  | Limited | 16 | 14 |
|  | Extensive | 19 | 23 |
|  | Unknown | 3 | 5 |

TABLE 14-continued

Stage data of patients diagnosed with primary lung cancer.

| Histology | Stage | AEGIS 1 | AEGIS 2 |
|---|---|---|---|
| NSCLC | | 175 | 222 |
| | 1 | 37 | 49 |
| | 2 | 16 | 18 |
| | 3 | 44 | 65 |
| | 4 | 42 | 67 |
| | Unknown | 36 | 23 |
| Unknown | | 7 | 3 |
| Total | | 220 | 267 |

Data about each of the benign diagnoses was extracted from medical records and summarized in Table 15. In both studies approximately two-thirds of cancer-free subjects had alternative diagnoses, with the specific alternative diagnoses enumerated in Table S4 for each study. Diagnosis of patients with abnormalities that were determined to have resolved or were stable was based on review of medical records, including follow-up imaging, at 12 months post-bronchoscopy, and approximately one-third of cancer-free patients were in this category in both studies.

TABLE 15

Alternative diagnoses of patients with benign disease

| Category | AEGIS 1 | AEGIS 2 |
|---|---|---|
| Resolution or Stability* | 27 | 24 |
| Alternative Diagnosis | 51 | 50 |
| Sarcoidosis | 16 | 15 |
| Inflammation | 4 | 4 |
| Benign growth | 5 | 6 |
| Fibrosis | 4 | 5 |
| Other | 4 | 6 |
| Infection | 18 | 14 |
| Fungal | 8 | 3 |
| Mycobacteria | 5 | 4 |
| Bacterial | 5 | 7 |
| Total | 78 | 74 |

During the clinically indicated bronchoscopy, study participants underwent collection of mucosal brushings of the right or left main-stem bronchus using a standard, disposable cytology brush rubbed against the bronchial wall. Two brushings were obtained from each subject; physicians were trained to obtain brushings of normal appearing epithelial tissue and to avoid sampling tumor tissue or dysplastic cells. All samples were stored in an RNA preservative (RNAprotect; Qiagen) and were shipped to a central CLIA-certified laboratory for accessioning and processing. Centers were requested to store samples at 4° C. for up to 14 days, and to ship at sub-ambient temperatures (4-20° C.) using 2-day shipping and insulated shipping containers (NanoCool) provided by the sponsor.

Laboratory Methods

All BEC specimens were processed to isolate and analyze RNA for quality and yield prior to gene expression analysis; Only specimens with an RNA yield of at least 1 μg and RIN score of >4 were run on Gene-ST 1.0 microarrays. All microarray data has been deposited in GEO as GSE66499.

The samples were lysed and RNA was isolated using a column-based method (miRNeasy Kit; Qiagen) and the manufacturer's recommended protocol. The large RNA fraction was analyzed on a spectrophotometer (Nanodrop; ThermoFisher) to determine the concentration, purity, and yield. Samples were also analyzed for RNA integrity (Bioanalyzer), reported as the MN score. Samples with a yield of <1 μg and MN score <4 were excluded from the study. Approximately 10% of specimens in AEGIS 1 and 13% in AEGIS 2 were excluded due to insufficient RNA quality or quantity. The RNA was then stored frozen (−80° C.) until further processing.

200 ng of total RNA was converted to sense strand cDNA using Ambion WT Expression kit (Life technologies Cat. #4440536), and subsequently labeled with Affymetrix GeneChip WT terminal labeling kit (Affymetrix Cat. #900671). For hybridization, a hybridization cocktail was prepared and added to the labeled cDNA target using the Hybridization, Wash and Stain kit (Affymetrix Cat. #900720), applied to Human Gene 1.0 ST arrays (Affymetrix Cat. #901087), and incubated at 45° C. for 16 hours. Following hybridization, arrays were washed and stained using standard Affymetrix procedures before they were scanned on the Affymetrix GeneChip Scanner. Data was extracted using Expression Console software (Affymetrix).

The Affymetrix Human Gene 1.0 ST array (Affymetrix Cat. #901087) utilizes numerous probes that are disclosed at the world wide web address: affymetrix.com/site/include/byproduct.affx?product=hugene-1_0-st-v1. Multiple probes are present that correspond to segments of specific genes, which is to say that that is not a 1:1 ratio of one probe per gene, rather multiple probes are present that correspond to multiple segments of a single gene. In one example, the LYPD2 gene is represented by three probe sets in the Human Gene 1.0 ST array (Release 32), probeset IDs 8153343, 8153344, and 8153345 as disclosed in the Affymetrix Human Gene 1.0 ST array (HuGene-1_0-st-v1 Probeset Annotations, release 32 on Sep. 30, 2011, release 33 on Mar. 27, 2013, and release 34 on Apr. 7, 2014). Information correlating probe-sets and nucleic acid sequences can be found at Affymetrix.com, including at the world wide web address: affymetrix.com/site/include/byproduct.affx?product=hugene-1_0-st-v1. Furthermore, data sets are available on the NCBI Gene Expression Omnibus website under Platform GPL6244 detailing the probes and genes that may be utilized in practicing the methods of the present disclosure at the world wide web address: ncbi.nlm.nih.gov/geo/query/acc.cgi?acc=GPL6244. These documents, including those correlating the probesets and gene symbols are incorporated herein by reference.

Microarray data (CEL files) corresponding to the samples in the final data set of each cohort were normalized using RMA [22]. The AEGIS 1 samples were run in a total of 5 batches and ComBat [23] was used to correct for batch effects. The AEGIS 2 samples were all run in a single microarray batch. After normalization, outliers were identified as having a genome-wide pairwise correlation of less than 0.955 in global gene expression. All microarray data has been deposited in GEO under accession #GSE66499.

Normalization and preprocessing of the microarray data are described in the Supplementary Appendix. Subjects enrolled in AEGIS 1 had previously been randomly assigned into independent training and validation sets (FIG. 4) and the classifier algorithm was derived strictly within the AEGIS 1 training set and locked, as described previously. Scores for each sample in the AEGIS 1 validation set and for all AEGIS 2 samples were generated using this pre-specified classifier that was based on the expression of 23 genes and patient age. These scores were dichotomized as test-positive and test-negative using a pre-specified threshold value.

Performance of the classifier was evaluated using receiver operator characteristic (ROC) curves, calculation of area under the curve (AUC) [14], and estimates of sensitivity, specificity, negative predictive value (NPV), positive predictive value (PPV) and the negative likelihood ratio (NLR) which was defined as (1-sensitivity)/specificity. A Mann-Whitney non-parametric test was used for analysis of continuous variables and Fisher's exact test was used for categorical variables. All confidence intervals are reported as the two-sided binomial 95% confidence intervals (95% CI). Statistical analysis was performed using R software (Version 3.01).

Physicians were asked to assess the pre-test POM for all subjects enrolled based on expert opinion and available medical records prior to bronchoscopy, using one of the following categories: <10%, 10-39%, 40-60%, 61-85%, and >85%. The results were collapsed into categories of <10%, 10-60%, and >60%. We then calculated the actual prevalence of cancer in each of the POM categories in order to compare the actual prevalence of cancer in the stratified POM levels (Table 16). Additionally, we found that the prevalence of lung cancer post-non diagnostic bronchoscopy was 3%, 29% and 80% in the <10, 10-60% and >60% POM groups respectively.

TABLE 16

Correlation of physician assessed POM and the prevalence of cancer.

| Pre-test POM [a] | CA+ patients | Total patients | Prevalence [b] |
|---|---|---|---|
| <10% | 3 | 62 | 5% |
| 10-60% | 41 | 101 | 41% |
| >60% | 404 | 425 | 95% |
| Unknown | 39 | 51 | 77% |

[a] POM = probability of malignancy; assessed by treating physicians prior to bronchoscopy.
[b] Prevalence was calculated as the fraction diagnosed with lung cancer within each of the POM categories.

The prediction accuracy of the bronchial genomic classifier stratified by lesion size is summarized in Table 2, and by pre-test POM in Table 3. The sensitivity of the classifier is also reported for patients diagnosed with lung cancer stratified by stage and histology, in Tables S5 and S6. The classifier in combination with bronchoscopy leads to a sensitivity >90% for all categories.

| Size (mm) | $N_{total}$ | $N_{cancer}$ | Bronchoscopy (95% CI) | Classifier (95% CI) | Classifier & bronchoscopy combined (95% CI) |
|---|---|---|---|---|---|
| All patients | 639 | 487 | 75% (71-79) | 89% (82-94) | 97% (95-98) |
| Size (mm) | | | | | |
| <2 cm | 131 | 73 | 55% (43-66) | 91% (76-98) | 96% (88-99) |
| 2-3 cm | 80 | 60 | 58% (46-70) | 92% (74-99) | 97% (88-100) |
| >3 cm | 343 | 313 | 82% (78-86) | 85% (74-93) | 97% (95-99) |
| Infiltrate | 60 | 25 | 84% (65-94) | 100% (45-100) | 100% (84-100) |
| Unknown | 25 | 16 | 80% (54-94) | 100% (38-100) | 100% (76-100) |
| Location | | | | | |
| Central | 225 | 174 | 84% (78-89) | 81% (63-92) | 97% (93-99) |
| Peripheral | 194 | 133 | 55% (46-63) | 90% (80-96) | 95% (90-98) |
| Both | 192 | 164 | 82% (75-87) | 97% (82-100) | 99% (96-100) |
| Unknown | 28 | 16 | 81% (56-94) | 67% (20-94) | 94% (70-100) |

Results
Characteristics of the Study Participants 298 patients from AEGIS 1 served as a first validation set and all 341 patients from AEGIS 2 meeting study criteria were used as a second validation set (FIG. 4 & Table 13). The prevalence of lung cancer was 74% and 78% for the AEGIS 1 and AEGIS 2 cohorts, respectively. Patients with lung cancer were older (p<0.001), had higher cumulative tobacco exposure compared to patients without cancer (p<0.001) and were more likely to be current smokers (p=0.07 in AEGIS 1 and p=0.03 in AEGIS 2; Table 12). A summary of cancer stage and categories of benign diagnoses are shown in Tables 15 and 16, respectively.

Performance of Bronchoscopy

A total of 639 patients underwent bronchoscopy for suspected lung cancer. Of those, 272 (43%; 95% CI, 39 to 46) were non-diagnostic, including 120 of 487 patients (25%; 95% CI, 21 to 29) ultimately diagnosed with lung cancer. The sensitivity of bronchoscopy for lung cancer was 74% (95% CI, 68 to 79) and 76% (95% CI, 71 to 81) in AEGIS 1 and AEGIS 2, respectively. Follow-up procedure data was available for 98% (267 of 272) of the patients with a non-diagnostic bronchoscopy. Invasive procedures following non-diagnostic bronchoscopy were performed in 170 of 267 patients (64%; 95% CI, 58 to 69), including 52 of 147 (35%; 95% CI, 24 to 38) with benign lesions and 118 of 120 (98%; 95% CI, 94 to 99) with cancer. SLB was performed in 76 patients, of which 27 (36%; 95% CI, 26 to 47) had benign lesions.

Performance of Gene Expression Classifier

Figure 5:
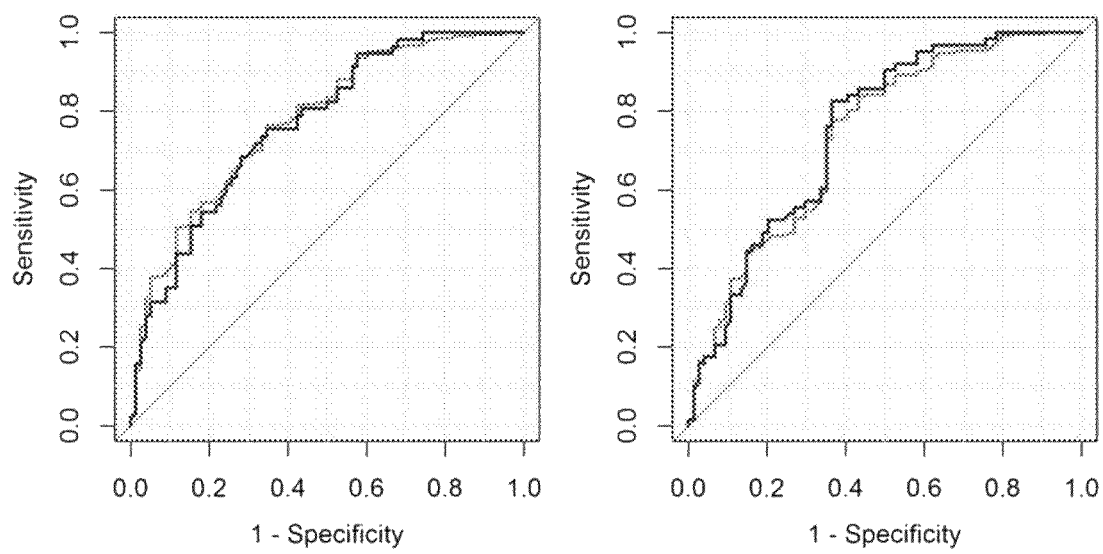
FIG. 5 depicts ROC curves for total patients (light gray) and the subset of patients with a non-diagnostic bronchoscopy (black) in the AEGIS 1 (left) and AEGIS 2 (right) cohorts is shown. In AEGIS 1 the AUC=0.78 (95% CI, 0.73 to 0.83) and AUC=0.76 (95% CI, 0.68 to 0.83) for the two groups, respectively (p=0.31). In AEGIS 2 the AUC=0.74 (95% CI, 0.68 to 0.80) and AUC=0.75 (95% CI, 0.68 to 0.82) in the two groups (p=0.85). The AUC was also not significantly different for patients with a non-diagnostic bronchoscopy comparing AEGIS 1 and AEGIS 2 (p=0.61).

The classifier alone had an AUC=0.78 (95% CI, 0.73 to 0.83) and accurately identified 194 of 220 patients with cancer (88% sensitivity; 95% CI, 83 to 92), and 37 of 78 patients without cancer (47% specificity; 95% CI, 37 to 58) in AEGIS 1 (FIG. 5). In AEGIS 2, the classifier had an AUC=0.74 (95% CI, 0.68 to 0.80) and correctly identified 237 of 267 patients with cancer (89% sensitivity; 95% CI, 84 to 92), and 35 of 74 without cancer (47% specificity; 95%, 36 to 59). The combination of the classifier with bronchoscopy increased the sensitivity to 96% (95% CI, 93 to 98) and 98% (95% CI, 96 to 99) in AEGIS 1 and 2, respectively compared to 74% and 76%, respectively, for bronchoscopy alone (p<0.001).

In patients with a non-diagnostic bronchoscopy, the classifier accurately identified cancer in 49 of 57 patients in AEGIS 1 (86% sensitivity; 95% CI, 74 to 94) and in 62 of 67 patients in AEGIS 2 (92% sensitivity; 95% CI, 82 to 97). As there was no significant difference between patients in the two cohorts with regard to the classifier AUC either across all patients (p=0.32) or for patients with a non-diagnostic bronchoscopy (p=0.61) (FIG. 5), we combined the two cohorts for subsequent analyses of sub-groups. The sensitivity of bronchoscopy alone was lower in lesions that were <3 cm (p<0.001) or peripherally located (p<0.001) (Table 17). In contrast, the sensitivity of the classifier alone and the classifier combined with bronchoscopy were consistently high and not significantly associated with size or location of the lesion (Table 17), cancer stage (Table 18) or histological subtype (Table 19).

TABLE 18

Sensitivity of the classifier and bronchoscopy according to cancer stage.

| Histology | Stage | N | Bronchoscopy | Classifier | Combined |
|---|---|---|---|---|---|
| NSCLC | 1 | 86 | 41% | 88% | 93% |
|  | 2 | 34 | 68% | 82% | 94% |
|  | 3 | 109 | 83% | 94% | 99% |
|  | 4 | 109 | 86% | 93% | 99% |
|  | Unknown | 59 | 80% | 92% | 98% |
| Total NSCLC |  | 397 | 73% | 89% | 97% |
| SCLC | Limited | 30 | 80% | 83% | 97% |
|  | Extensive | 42 | 93% | 100% | 100% |
|  | Unknown | 8 | 88% | n/a | 88% |
| Total SCLC |  | 80 | 88% | 80% | 98% |
| Unknown |  | 10 | 70% | 100% | 100% |
| Total Cancers |  | 487 | 74% | 86% | 97% |

TABLE 19

Sensitivity of the classifier and bronchoscopy according to histology.

| Histology | N | Bronchoscopy | Classifier | Combined |
|---|---|---|---|---|
| Adenocarcinoma | 169 | 65% | 86% | 95% |
| Squamous | 153 | 80% | 90% | 98% |
| Large Cell | 16 | 75% | 100% | 100% |
| NSCLC-NOS | 59 | 78% | 100% | 100% |
| SCLC | 80 | 88% | 80% | 98% |
| Unknown | 10 | 70% | 100% | 100% |

Accuracy of the Classifier in Patients with Intermediate Probability of Cancer

We combined the physician-assessed probability of malignancy (POM) into categories of low (<10%), intermediate (10-60%), and high (>60%) POM (Table 3), to align with guideline recommendations for assessing lung cancer risk [1]. Bronchoscopy was non-diagnostic for cancer in 83% of patients with an intermediate pre-test POM (n=101), despite a 41% cancer prevalence rate. In this group of patients, the classifier achieved a NPV of 91% (95% CI, 75 to 98) among those with a non-diagnostic bronchoscopy and a PPV of 40% (95% CI, 28 to 54) (Table 20).

TABLE 20

Performance of bronchoscopy and the classifier stratified pre-test POM.

|  |  | Pre-test POM Category | | | |
|---|---|---|---|---|---|
|  | N | <10% | 10-60% | >60% | Unknown |
|  |  | Patient population | | | |
| Total Patients [a] | 639 | 62 | 101 | 425 | 51 |
| Lung Cancer | 487 | 3 (5%) | 41 (41%) | 404 (95%) | 39 (76%) |
| Benign | 152 | 59 (95%) | 60 (59%) | 21 (5%) | 12 (24%) |
|  |  | Bronchoscopy performance | | | |
| Bronchoscopy sensitivity (95% CI) |  | 33% (6-80) | 41% (28-57) | 79% (74-82) | 79% (64-89) |
| Patients with non-diagnostic bronchoscopy [b] | 272 | 61 (98%) | 84 (83%) | 107 (25%) | 20 (39%) |
|  |  | Classifier performance | | | |
| Classifier sensitivity (95% CI) [c] |  | 100% (29-100) | 88% (68-96) | 90% (82-95) | 88% (51-100) |
| Classifier specificity (95% CI) [d] |  | 56% (43-68) | 48% (36-61) | 29% (14-50) | 33% (14-61) |
| Classifier NPV (95% CI) [e] |  | 100% (88-100) | 91% (75-98) | 40% (20-64) | 80% (36-98) |
| Classifier PPV (95% CI) [f] |  | 7% (1-24) | 40% (28-54) | 84% (75-90) | 47% (25-70) |
| Combined classifier & bronchoscopy sensitivity |  | 100% (38-100) | 93% (80-98) | 98% (96-99) | 97% (86-100) |

[a] There were 639 total patients across the POM categories shown.

[b] Bronchoscopy was non-diagnostic for 272 of 639 patients (43%; 95% CI, 39 to 46), including 120 of 487 patients (25%; 95% CI, 21 to 29) diagnosed with lung cancer.

[c] The classifier accurately predicted 107 of 120 total patients overall (89%; 95% CI, 82 to 94) with cancer. Sensitivity is reported in each POM category for patients with non-diagnostic bronchoscopy procedures.

[d] The classifier accurately predicted 72 of 152 patients overall (47%; 95% CI, 40 to 55) without cancer. Specificity is reported in each POM category for patients with non-diagnostic bronchoscopy procedures.

[e] NPV, and [f] PPV is reported for patients with non-diagnostic bronchoscopy procedures.

Although the classifier had a high NPV in patients with a non-diagnostic bronchoscopy, there were 13 patients with a non-diagnostic bronchoscopy who had lung cancer and a negative classifier score (i.e. false negatives). The majority (10 of 13) had a high (>60%) POM with only three patients in the 10-60% pre-test POM group.

Figure 6A:
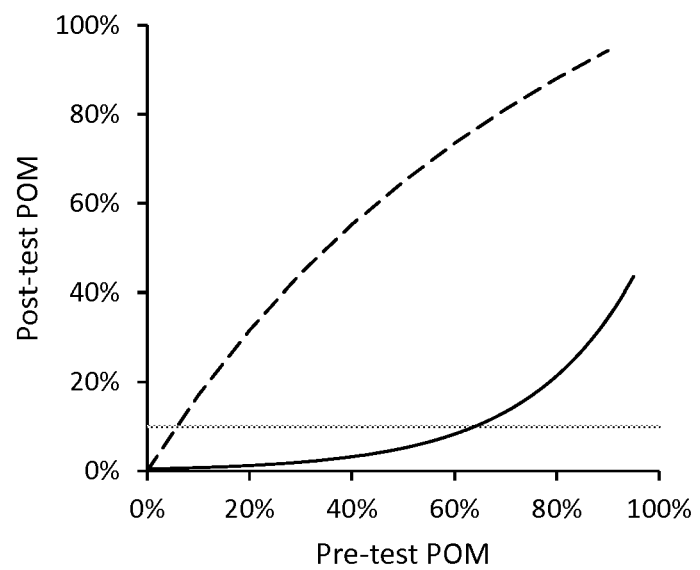
FIG. 6A and FIG. 6B.
Figure 6B:
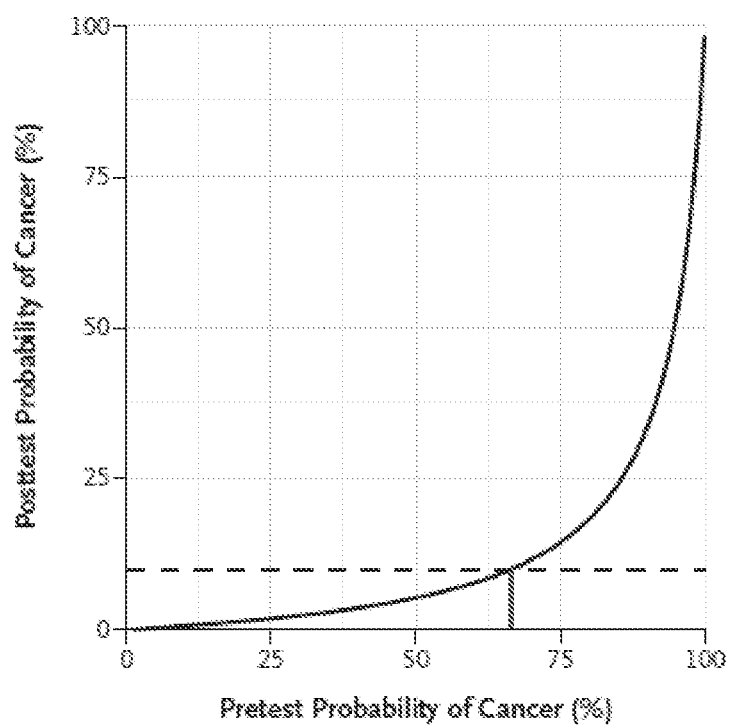

The NLR of the classifier in combination with bronchoscopy was calculated to determine the range of pre-test POM in which the post-test probability would be <10%. The NLR of bronchoscopy (0.244; 95% CI, 0.21 to 0.29) improves when combined with the classifier to 0.056 (95% CI, 0.03 to 0.10). As a result, when both bronchoscopy and the classifier are negative, the post-test POM is reduced to <10% for patients with a pre-test POM up to 66% (FIG. 6).

Evaluation of Results

This study describes the validation of a bronchial genomic classifier that identifies patients without lung cancer among those undergoing bronchoscopy in two independent prospective cohorts. We find that the gene-expression classifier has high sensitivity across different sizes, locations, stages, and cell types of lung cancer in the combined cohorts. The combination of the classifier and bronchoscopy has a sensitivity of 96% and 98% in the AEGIS-1 and AEGIS-2 validation cohorts respectively. We also report several additional findings that support the clinical need for this type of classifier. First, our studies confirm the previously reported observations that non-diagnostic bronchoscopy is common (particularly in patients of intermediate pre-test POM) and leads to further invasive testing including SLB, often in patients ultimately found to not have lung cancer. Second, in contrast to the high sensitivity of the classifier, we find that bronchoscopy performed poorly in small, peripheral or early stage cancers. Third, the classifier has a high NPV in patients with intermediate POM and a non-diagnostic bronchoscopy. These findings suggest that this classifier has the potential to assist clinical decision making in patients with intermediate POM in whom the prevalence of lung cancer is 41% but the sensitivity of bronchoscopy is only 41%. Due to the high NPV, a negative classifier score in patients with a non-diagnostic bronchoscopy and intermediate POM warrants a more conservative diagnostic strategy with active surveillance via imaging.

Although the high NPV of the classifier would help avoid unnecessary invasive procedures in patients with an intermediate POM that are classifier negative, there were a small number of patients in this group who have lung cancer; the negative gene-expression classifier result may delay further invasive testing in these patients. However, this group of patients would undergo active surveillance via imaging, which is the standard practice when an immediate invasive strategy is not employed [1,15]. This would allow for identification of lesion growth, triggering additional invasive testing to establish a definitive diagnosis. In contrast to the high NPV observed in patients with an intermediate POM, the classifier has a modest PPV of 40% in this setting. Thus, a positive result with the classifier does not warrant alteration in the diagnostic strategy; further testing would need to be based on traditional factors used to choose between an invasive versus an imaging surveillance strategy.

This gene expression classifier is measured in proximal BECs and not from cells within the pulmonary lesion. The ability of gene-expression alterations in cytologically-normal proximal airway to detect the presence of lung cancer within the lung parenchyma stems directly from the "field of injury" paradigm [13]. Spira, et al. has previously shown that there is a distinct pattern of gene-expression alterations in cytologically-normal bronchial epithelial cells among current and previous smokers with lung cancer [13,16]. Additionally oncogenic signaling pathways are activated in the proximal airway epithelium of smokers with lung cancer and smokers with premalignant airway lesions [17]. More recently, Kadara, et al. [18] demonstrated that genes whose expression is altered in non-small cell lung cancer itself and the adjacent small airway epithelium are enriched among those genes that are altered in the proximal airway epithelium, suggesting that the gene-expression changes within the proximal airway reflect, in part, the altered transcriptome observed in lung tumors.

A bronchoscopy was considered as "diagnostic" only when the procedure yielded a lung cancer diagnosis. There were a relatively small number of bronchoscopies that were potentially diagnostic of a specific benign etiology, but most of these patients received further invasive testing including patients ultimately diagnosed with lung cancer, suggesting that the concern for lung cancer remained elevated despite the initial benign finding on bronchoscopy. Finally, we did not assess the accuracy of a model incorporating the classifier in combination with clinical variables. Although clinical risk prediction models have been developed for solitary pulmonary nodules [1,20,21], there are no validated models for patients selected to undergo diagnostic bronchoscopy, which includes patients with a broad range of findings, including larger lesions (i.e. >3 cm), infiltrates or other features such as lymphadenopathy. Thus, most patients are selected for bronchoscopy based on the physician's qualitative assessment of lung cancer probability. Importantly, we demonstrate that our classifier performs well in patients with intermediate POM by physician assessment, a process that incorporates available clinical risk factors.

The potential impact of this work is bolstered by a number of key strengths in its study design. First, these were two independent prospective validation studies in which the classifier was measured in the setting in which the test would be used clinically (i.e. prior to diagnosis). This is a critical step in moving molecular biomarkers from discovery studies to their ultimate clinical application. Second, the large multicenter design enabled inclusion of patients undergoing bronchoscopy from different practice settings and geographic locations. Third, our data demonstrates the high prevalence of lung cancer among patients with a non-diagnostic bronchoscopy and intermediate pre-test POM, and show that the classifier has an NPV of 91% in this setting where there is the greatest uncertainty about cancer status. In this setting, the opportunity to use a classifier with high sensitivity for lung cancer allows for the confident identification of patients without lung cancer that might be followed by active surveillance, thereby avoiding potentially harmful invasive follow up testing.

Example 3: Derivation of Bronchial Genomic Classifier for Lung Cancer Patients in Patients Undergoing Diagnostic Chronchoscopy Introduction Lung cancer remains the leading cause of cancer mortality in the United States, with an estimated 224,000 new diagnoses, and 160,000 deaths in 2014, 90% of which are due to smoking [24]. Recently, the National Lung Cancer Screening Trial showed that low dose Computed Tomography (CT) screening results in a 20% relative mortality reduction in high risk individuals [25]. The mortality reduction, however, was accompanied by a high rate (~96%) of false-positive CT findings, which in turn has generated concern for the over-utilization of invasive diagnostic procedures [26].

Patients with suspected lung cancer are often referred for bronchoscopy where the primary aim is to sample a suspicious pulmonary lesion for pathological analysis. It is estimated that 500,000 bronchoscopies are performed per year in the U.S. [27], of which roughly half are for the diagnosis of lung cancer. Bronchoscopy is considered to be safer than other invasive sampling methods, such as transthoracic needle biopsy (TTNB), or surgical techniques. However the diagnostic sensitivity of bronchoscopy is sub-optimal, ranging from 34% (for <2 cm peripheral nodules) to 88% (for larger, centrally located lesions) [28]. Adoption of guidance techniques has expanded the applicability of bronchoscopy to more challenging suspicious lesions (i.e., solitary pulmonary nodules which are often peripheral in the lung), but the overall clinical sensitivity of bronchoscopy for lung cancer has not improved substantially [29,30]. When bronchoscopy is non-diagnostic, physicians are often left with the ambiguity of whether to pursue further invasive diagnostic procedures, with associated complications [31,32], or choose imaging surveillance. In current practice when these invasive procedures are performed, approximately a third of patients are determined to have benign disease [33], suggesting that these procedures are avoidable. Methods that reduce this ambiguity by substantially improving the diagnostic yield of bronchoscopy could improve patient care.

It has previously been demonstrated that cigarette smoke creates a molecular field of injury in airway epithelial cells that line the entire respiratory tract [34]. The reversible and irreversible impact of cigarette smoke on the bronchial airway transcriptome has been characterized and a set of gene-expression alterations in the bronchial epithelium have been identified in current and former smokers with lung cancer [35]. These cancer-associated gene expression profiles have previously been shown to yield a sensitive classifier for detecting lung cancer when bronchoscopy is non-diagnostic. The high sensitivity of this classifier, measured in a biospecimen readily accessible during bronchoscopy, results in a very low probability of lung cancer when the test result is negative, and suggests that physicians might be enabled to confidently pursue active surveillance and reduce risky invasive procedures in subjects without lung cancer.

Materials and Methods

Training Set Patient Population

Patients were enrolled in the AEGIS trials (Airway Epithelium Gene Expression In the DiagnosiS of Lung Cancer), designed as prospective, observational, cohort studies (registered as NCT01309087 and NCT00746759) of current and former cigarette smokers with a suspicion of lung cancer undergoing bronchoscopy as part of their diagnostic workup. A set of patients from one of the cohorts ("AEGIS 1") was selected for the exclusive purpose of training a gene expression classifier. The study was approved by IRB at each of the participating medical centers, and all patients signed an informed consent prior to enrollment. All enrolled patients were followed post-bronchoscopy until a final diagnosis was made, or for 12 months. Patients were diagnosed as having primary lung cancer based on cytopathology obtained at bronchoscopy or upon subsequent lung biopsy (such as TTNB or surgical lung biopsy (SLB) when bronchoscopy did not lead to a diagnosis of lung cancer). Patients were diagnosed as having benign disease based on a review of medical records and follow-up procedures at 12 months post-bronchoscopy (described in more detail in Additional File 1). Bronchoscopy was considered "diagnostic" when clinical samples collected at the time of the bronchoscopy procedure yielded a confirmed lung cancer diagnosis via cytology or pathology.

Patients enrolled in the NIH-registered AEGIS studies (NCT01309087 and NCT00746759) were patients undergoing clinically indicated bronchoscopy for suspicion of lung cancer who were at least 21 years of age and had smoked at least 100 cigarettes in their lifetime. Study exclusions included patients who had previously been diagnosed with primary lung cancer, who had been on a mechanical ventilator for >24 consecutive hours immediately prior to bronchoscopy, or who could not consent or comply with the study. Additional patients were excluded prior to training the classifier to exclude patients with a malignancy other than primary lung cancer. This included the exclusion of patients with a history of any malignancy, confirmed metastatic cancer to the lung, or found to have an active non-lung primary cancer after enrollment. Also, patients without a final definitive diagnosis were excluded. Finally, after specimen processing, those with insufficient yield (<1 µg) or quality (RIN<4) of RNA were excluded from further analysis.

Patients were followed for up to twelve months post bronchoscopy and records were reviewed to confirm or determine a final clinical diagnosis. A diagnosis of cancer was based on cytopathology of cells/tissue collected either during bronchoscopy, or in follow-up procedures when bronchoscopy was non-diagnostic. Follow-up procedures leading to diagnosis consisted of a second bronchoscopy, transthoracic needle aspiration (TTNA), surgical lung biopsy (SLB), or a combination of procedures. Records of patients who were not diagnosed with cancer, and who had been followed for 12 months, underwent an adjudication process by a panel of five pulmonologists. The process consisted of a review of the available medical records and patients were only declared to be cancer-free if the patient met one of the following criteria: diagnosed with an alternative diagnosis that explained the initial suspicious abnormality, the abnormality was determined to be stable, or the abnormality resolved. Patients who did not meet these criteria at the completion of the 12-month follow-up period were labeled as "indeterminate" and were excluded from training, due to lack of diagnostic "truth".

Sample Collection

Physicians at each of 25 participating medical centers were instructed to collect normal appearing bronchial epithelial cells (BEC) from the right mainstem bronchus (or the left side if any abnormalities were observed on the right) during bronchoscopy using standard bronchoscopic cytology brushes. Following collection, the cytology brushes were cut and placed in an RNA preservative (Qiagen RNA-Protect, Cat. 76526) immediately after collection and stored at 4° C. Specimens were then shipped at 4-20° C. to a central laboratory for further processing.

A shipping container was provided to all sites enabling the transport of specimens at 4-20° C. within a 48 hour period. Sites were asked to send specimens using 2-day shipping services. Upon receipt in the central laboratory, specimens were inspected and accessioned into a laboratory information system. Accepted specimens were stored at 4° C. prior to RNA isolation, which was typically conducted within 7 days of receipt. Records of all storage, and shipping times were retained, and the cumulative time between specimen collection and RNA isolation was less than 30 days (consistent with manufacturer's recommendations for the RNA preservative).

RNA Isolation

BECs were separated from cytology brushes using a vortex mixer and were then pelleted and processed using QIAzol lysis reagent (Qiagen). RNA was isolated by phenol/chloroform extractions and purified on a silica membrane spin-column (Qiagen miRNeasy kit, Cat. #217004) according to manufacturer's recommendations. RNA was analyzed on a NanoDrop ND-1000 spectrophotometer (Thermo Scientific) to determine concentration and purity, and RNA integrity (RIN) was measured on a 2100 Bioanalyzer (Agilent Technologies). Each sample was then stored at −80° C. until processing further on microarrays.

cDNA Preparation

Total RNA was converted to sense strand cDNA, amplified using the Ambion WT Expression kit (Life Technologies Cat. #4440536) designed for use with Affymetrix microarrays. Starting with 200 ng of total RNA, single stranded cDNA was prepared through reverse transcription using T7 promoter primers protocol. Single-strand cDNA was converted to double stranded cDNA using DNA polymerase.

Microarray Processing cDNA obtained from the total RNA was labeled with Affymetrix GeneChip WT terminal labeling kit (Affymetrix Cat. #900671). The labeled cDNA was hybridized to Gene 1.0 ST microarrays (Affymetrix Cat. #901085) and analyzed on an Affymetrix GeneChip Scanner. Individual CEL files for each of the patient samples were normalized using the standard Affymetrix Gene 1.0 ST CDF and RMA [38].

Total RNA was converted to sense-strand cDNA using a commercial kit (Ambion WT; Life Technologies, Cat. #4440536) designed for use with Affymetrix microarrays. Starting with 200 ng of total RNA, single stranded cDNA was prepared through reverse transcription using T7 promoter primers protocol. Single-strand cDNA was converted to double stranded cDNA using DNA polymerase. Double stranded cDNA acts as a template for in vitro transcription of cRNA which was then purified to remove enzymes, salts, inorganic phosphates and unincorporated nucleotides. The yield of cRNA was measured using UV-adsorption and labeled sense-stranded cDNA was then generated using 10 μg of the purified cRNA by reverse transcription with random primers and a mix of dUTP/dNTPs, fragmented, and labeled using the GeneChip WT Terminal labeling kit (Affymetrix, Cat. #900671). The labeled cDNA was hybridized to Gene 1.0 ST microarrays (Affymetrix Cat. #901085) using the Hybridization, Wash and Stain kit (Affymetrix Cat. #900720), and incubated at 45° C. for 16 hours. Following hybridization, arrays were washed and stained using standard Affymetrix procedures before being scanned on the Affymetrix GeneChip Scanner, and data was extracted using Expression Console software (Affymetrix). Thus, microarrays described herein are not measuring the expression of natural molecules, rather the microarrays measure the expression of non-naturally occuring cDNA molecules.

Classifier Development

A gene expression classifier was derived in a multi-step process. Initial modeling consisted of using the training data to select genes ("gene expression correlates") which were associated with three clinical covariates (gender, tobacco use, and smoking history) to identify gene expression correlates of these clinical variables. Lung cancer-associated genes were then selected, and finally a classifier for predicting the likelihood of lung cancer based on the combination of the cancer genes, the gene expression correlates, and patient age was determined. All aspects of this classifier development procedure were determined using cross validation and using only data from the training set samples.

Clinical Factor Gene Expression Correlates (CFGC)

Covariates of lung cancer in this study population, including sex (male/female), smoking status (current/former), and pack years (<10/>10), were modeled to identify gene expression correlates for the clinical factors. Empirical Bayes t-tests were used to identify genes whose expression was significantly associated with each of the clinical factors. Next, genes were selected in a sparse manner [36] that could be used to predict the value of each clinical factor. Finally, the predicted values from the gene expression correlates for gender (GG), smoking status (GS), and pack-years (GPY) were computed for each patient and used in selecting genes with lung-cancer associated gene expression and in the lung cancer classifier described below.

Selection of Lung Cancer Genes

A logistic regression model with lung cancer status (1=cancer-positive and 0=cancer-negative) as the dependent variable was fit using the training data, CFGC's, and patient age as predictors. Next an empirical Bayes linear model was fit using gene expression values as the independent variable and the logistic regression model residuals as the dependent variable. This was used to select genes most directly correlated with disease status and independent of clinical covariates. The top lung cancer-associated genes from this analysis were grouped using hierarchical clustering. Genes were selected in an iterative manner to maximize AUC using cross-validation to estimate prediction accuracy. The aim was to select clusters that cumulatively provide the best classifier performance, and specific genes that best represent each of the clusters. A gene titration analysis was also performed to determine the number of genes per cluster providing optimal performance. For the clusters selected, the top genes were averaged, yielding cluster mean estimates for each patient/cluster combination. Functional analysis of genes within each of the cancer clusters was performed using DAVID [37] to identify biological terms describing the cancer-associated genes in the classifier.

Lung Cancer Classifier

A lung cancer classifier was developed using lung cancer status as the outcome variable and the cancer gene expression estimates, patient age, and CFGC's for gender (GG), smoking status (GS), pack years (GPY) as predictors. The model was fit using a penalized logistic regression model; the penalization factor (lambda) was 0 for the clinical/gene expression correlates and 10 for each of the gene expression cluster estimates. The resulting score is on a 0 to 1 scale. A score threshold for predicting lung cancer status was established to achieve a sensitivity of approximately 90% for patients with a non-diagnostic bronchoscopy. An evaluation of the benefit of the gene expression classifier to predict lung cancer compared to clinical factors alone was performed by generating a "clinical model" that included age, gender, smoking status, and pack-years (determined clinically) in a logistic regression model to predict lung cancer status. The difference in performance between the complete gene expression classifier and the clinical factors classifier to predict lung cancer status was assessed by comparing the AUC's of each model in the training set.

Analysis of an Independent Test Set

Data from a prior study [35] were used as an independent test set to assess the performance of the locked classifier derived in this study. In that study BECs were collected at bronchoscopy from patients undergoing bronchoscopy for suspicion of lung cancer, and RNA was analyzed on microarrays (Affymetrix HG-U133A). CEL files from that study (n=163) were re-normalized to produce gene-level expression values using Robust Multiarray Average (RMA) [38] in the Bioconductor R package (version 1.28.1). This processing used the Entrez Gene-specific probeset chip definition file (CDF) [39] in place of the standard U133A CDF provided by Affymetrix in order to facilitate cross-platform analyses. Analyses were performed using the R environment for statistical computing (version 2.9.2).

The classifier was applied to patients in the test set with two modifications to account for the difference in microarray platforms. First, the HG-U133A RMA expression values were adjusted by a gene-wise constant which shifted the mean of each gene's expression levels in the test set to the mean observed in the training set. Second, for the classifier genes where a corresponding HG-U133A probeset was not available (LYPD2 and RNF150), the gene's mean expression value in the training set was used for all of the test set samples.

Statistical Methods

Classifier accuracy was assessed using standard measures of prediction accuracy: the area under the curve (AUC), sensitivity, specificity, NPV and PPV. Cross-validation, using a 10% sample hold-out set, was used in the training set to estimate the performance of the prediction classifiers generated using these approaches [40]. These performance estimates were used to guide the development of the classifier discovery procedure. A final model was set prior to performing a one-time analysis of the test set. Fisher's exact test was used to calculate statistical significance of all categorical variables and a t-test was used for continuous variables.

Results

Study Populations

A set of 299 patients from AEGIS 1 consisting of 223 patients diagnosed with lung cancer and 76 patients diagnosed with benign disease (Table 1) were used to derive our gene expression classifier. Characteristics of the independent test set have been previously described and are summarized here. Although the study design was similar to the one described here, there were some differences in the study populations. The patients were older on average in the training set compared to the test set (p<0.001) (although there was no significant difference in age (p=0.959) for patients diagnosed with lung cancer). The training set also consisted of fewer current smokers (p=0.050); and a lower proportion of patients with <3 cm lesions (p<0.001). In addition, the prevalence of lung cancer was higher in the training set (75% versus 48%; p<0.001).

TABLE 21

Clinical and demographic characteristics of the patients used to train the classifier.

| Category | Sub-category | Lung cancer | Benign disease | p |
|---|---|---|---|---|
| N |  | 223 | 76 |  |
| Sex | Female | 97 | 26 | 0.178 |
|  | Male | 126 | 50 |  |
| Age (median years) |  | 65 | 56 | <0.0001 |
| Race | Caucasian | 168 | 59 | 0.757 |
|  | African-American | 47 | 13 |  |
|  | Other | 5 | 3 |  |
|  | Unknown | 3 | 1 |  |
| Smoking Status | Current | 101 | 26 | 0.107 |
|  | Former | 122 | 50 |  |
| Smoking History (median PY) |  | 43 | 30 | <0.0001 |
| Mass size | <2 cm | 46 | 23 |  |
|  | >2 to <3 cm | 30 | 12 |  |
|  | ≥3 cm | 122 | 19 |  |
|  | ill-defined infiltrate | 10 | 13 |  |
|  | Unknown | 15 | 9 |  |
| Mass Location | Central | 86 | 16 |  |
|  | Peripheral | 60 | 30 |  |
|  | Central & peripheral | 60 | 18 |  |
|  | Unknown | 17 | 12 |  |
| Histology | Sub-type |  |  |  |
| SCLC |  | 40 |  |  |
| NSCLC |  | 180 |  |  |
|  | Adenocarcinoma | 83 |  |  |
|  | Squamous | 73 |  |  |
|  | Large cell | 6 |  |  |
|  | Mixed/undefined | 18 |  |  |
| Unknown |  | 3 |  |  |
| Histology | Stage |  |  |  |
| SCLC | Limited | 16 |  |  |
|  | Extensive | 18 |  |  |
|  | Unknown | 6 |  |  |
| NSCLC | 1 | 28 |  |  |
|  | 2 | 16 |  |  |
|  | 3 | 42 |  |  |
|  | 4 | 62 |  |  |
|  | Unknown | 32 |  |  |
| Benign disease | Sub-category |  |  |  |
| Alternative Diagnosis |  |  | 54 |  |
|  | Infection |  | 23 |  |
|  | Sarcoid |  | 14 |  |
|  | Inflammation |  | 7 |  |
|  | Fibrosis |  | 4 |  |
|  | Other |  | 4 |  |
|  | Benign growths |  | 2 |  |
| Resolution/Stability |  |  | 22 |  |

Derivation of the Classifier and Evaluation of Performance

Gene expression was associated with current smoking status for a large fraction of the genes on the array (6477 genes with p<0.001; top 10 genes reported in Table 22). Three of the top ranked genes (SLC7A11, TKT, and CLND10) were selected to serve as a logistic regression-based smoking status classifier based on cross-validation. This smoking status classifier had an AUC of 0.93 within the training set. An additional CFGC was derived for smoking history, independent of smoking status, and was based on cumulative smoke exposure, measured in pack-years. Smoking history (<10 PY vs >10 PY) was significantly associated with the expression of 531 genes (p<0.001; top 10 genes reported in Table 23). Two of the top genes were selected to serve as a logistic regression-based smoking history classifier (RUNX1T1, AKR1C2) which had an AUC of 0.78 within the training set. Sex was significantly associated with 339 genes (p<0.001; top 10 genes reported in Table 24). The top ranked gene (RPS4Y1) was a perfect classifier (AUC=1) of sex within the training set.

TABLE 22

Top differentially expressed genes associated with smoking status

| ID | Symbol | logFC | AveExpr | T | P.Value | GS term |
|---|---|---|---|---|---|---|
| 8102800 | SLC7A11 | −2.31513 | 7.80246 | −19.0302 | 1.44E−53 | YES |
| 8088106 | TKT | −0.70341 | 9.137779 | −18.3095 | 7.46E−51 | YES |
| 8084630 | NA | −1.39188 | 6.897858 | −18.2898 | 8.86E−51 | |
| 8136336 | AKR1B10 | −2.27454 | 6.839364 | −18.2346 | 1.43E−50 | |
| 7969640 | CLDN10 | −0.94118 | 9.579322 | −18.1835 | 2.23E−50 | YES |
| 8171435 | PIR | −0.80298 | 8.924225 | −18.0114 | 9.97E−50 | |
| 7937465 | TALDO1 | −0.62614 | 10.07378 | −17.8271 | 4.95E−49 | |
| 8051583 | CYP1B1 | −2.8955 | 8.179293 | −17.7765 | 7.69E−49 | |
| 8020653 | CABYR | −1.19744 | 8.009791 | −17.6885 | 1.65E−48 | |
| 7979658 | GPX2 | −1.10719 | 10.62466 | −17.524 | 6.93E−48 | |

TABLE 23

Top differentially expressed genes associated with smoking history

| ID | Symbol | logFC | AveExpr | T | P.Value | GPY term |
|---|---|---|---|---|---|---|
| 8151768 | RUNX1T1 | 0.435653 | 5.905711 | 8.547091 | 6.44E−16 | Yes |
| 8077989 | TPRXL | −0.36913 | 8.733733 | −6.22283 | 1.63E−09 | |
| 7994058 | SCNN1G | 0.685624 | 8.450023 | 5.90033 | 9.75E−09 | |
| 8069764 | NA | −0.32511 | 7.23309 | −5.82162 | 1.49E−08 | |
| 8145470 | DPYSL2 | 0.260084 | 7.62917 | 5.749689 | 2.19E−08 | |
| 7931832 | AKR1C2 | −0.81612 | 10.93402 | −5.72526 | 2.50E−08 | Yes |
| 8039674 | ZNF154 | 0.372911 | 7.366637 | 5.724589 | 2.51E−08 | |
| 8150978 | CA8 | 0.415392 | 6.182963 | 5.638727 | 3.95E−08 | |
| 8129497 | EPB41L2 | 0.4248 | 6.895569 | 5.589681 | 5.10E−08 | |
| 8039672 | NA | 0.437196 | 4.729487 | 5.515997 | 7.48E−08 | |

TABLE 24

Top differentially expressed genes associated with gender

| ID | Symbol | logFC | AveExpr | T | P.Value | GS term |
|---|---|---|---|---|---|---|
| 8176375 | RPS4Y1 | −3.16276 | 7.851579 | −84.6047 | 6.46E−212 | YES |
| 8176624 | DDX3Y | −4.05255 | 7.702569 | −84.0882 | 3.79E−211 | |
| 8177232 | KDM5D | −2.23316 | 7.443775 | −80.4804 | 1.17E−205 | |
| 8176578 | USP9Y | −3.35997 | 7.485794 | −79.3437 | 7.01E−204 | |
| 8177137 | UTY | −3.38728 | 7.655898 | −78.9665 | 2.76E−203 | |
| 8176698 | TXLNG2P | −2.82024 | 6.904035 | −70.7168 | 1.36E−189 | |
| 8176709 | CYorf15B | −2.63878 | 7.07696 | −68.9368 | 1.87E−186 | |
| 8176719 | EIF1AY | −3.02926 | 7.079489 | −66.6741 | 2.34E−182 | |
| 8176384 | ZFY | −1.6795 | 6.679083 | −59.2385 | 5.47E−168 | |
| 8176460 | PRKY | −1.33643 | 7.761388 | −52.0418 | 1.48E−152 | |

Figure 7:
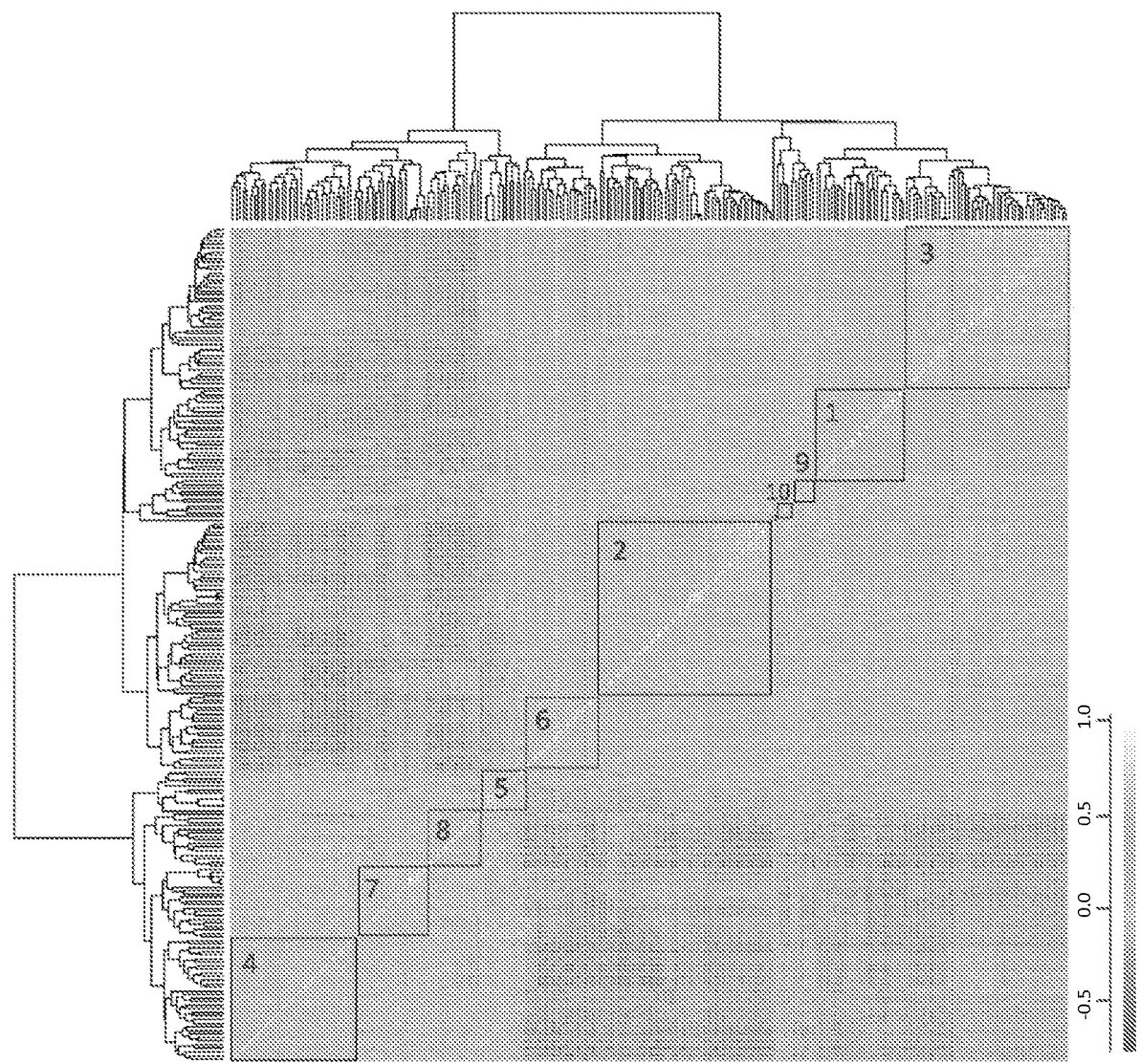
FIG. 7 depicts a pairwise correlation of genes with cancer-associated gene expression. The correlation between all possible pairs of genes with cancer-associated gene expression (n=232) were assessed to identify groups of genes that share a similar pattern of gene expression. Unsupervised hierarchical clustering was used to group correlated genes into 11 clusters, with the dendrogram threshold level to establish clusters indicated on the y-axis (green line). Genes were selected from the clusters in a parsimonious manner to predict lung cancer status using linear regression. The classifier genes came from specific clusters (outlined in blue), using 2-4 genes from each cluster. Clusters 4 and 7 contain genes which were up-regulated in lung cancer, and clusters 1, 2, 9, and 10 were down-regulated in lung cancer.

As described in the methods, we identified genes whose expression is significantly associated with the residuals from the CFGC model for lung cancer. A total of 232 cancer associated genes (Table 25) met the significance criteria (T score>2.7). A pairwise correlation of the 232 genes followed by hierarchical clustering was examined to identify genes with similar expression patterns and partitioned the genes into 11 clusters (FIG. 7). Since genes were correlated within each cluster, we hypothesized that the mean of a small set of genes within each cluster could be used to represent the cluster in a sparse manner. We optimized the classifier, using cross validation to estimate the AUC. We selected genes to represent the gene clusters whose expression was most strongly associated with lung cancer and determined that inclusion of clusters 1, 2, 4, 7, 9 and 10 gave the best AUC. We also determined that beyond 2-4 genes per cluster the performance of the test did not improve. In cross-validation, AUC=0.80 (95% CI 0.75-0.84) for all patients in the training set (n=299); for the subset of patients with non-diagnostic bronchoscopy (n=134) the performance was similar (AUC=0.81; 95% CI 0.74-0.87).

TABLE 25

Genes associated with cancer which are included in the classifier

| ID | Symbol | T | p.value | FC | Cluster | Final Model |
|---|---|---|---|---|---|---|
| 8094228 | BST1 | −4.29031 | 2.41E−05 | 0.89208 | 1 | Yes |
| 8037298 | CD177 | −3.85704 | 0.00014 | 0.715357 | 1 | Yes |
| 8029280 | CD177 | −3.68455 | 0.000272 | 0.840725 | 1 | Yes |
| 7918857 | TSPAN2 | −3.92967 | 0.000106 | 0.845904 | 2 | Yes |
| 7968062 | ATP12A | −3.49107 | 0.000553 | 0.794623 | 2 | Yes |
| 8124654 | GABBR1 | 2.881256 | 0.004247 | 1.071879 | 4 | Yes |
| 8147461 | SDC2 | 2.847433 | 0.004712 | 1.089453 | 4 | Yes |
| 7978391 | NOVA1 | 2.729315 | 0.006721 | 1.094912 | 4 | Yes |
| 7952205 | MCAM | 2.70666 | 0.007186 | 1.06072 | 4 | Yes |
| 8175531 | CDR1 | 4.307308 | 2.24E−05 | 1.468199 | 7 | Yes |
| 8103877 | CLDN22 | 3.502336 | 0.000531 | 1.329189 | 7 | Yes |
| 8051001 | CGREF1 | 3.275505 | 0.001178 | 1.056672 | 7 | Yes |
| 8149811 | NKX3-1 | 2.92659 | 0.003689 | 1.175825 | 7 | Yes |
| 8034974 | EPHX3 | −3.73504 | 0.000225 | 0.898923 | 9 | Yes |
| 8153342 | LYPD2 | −2.93177 | 0.00363 | 0.887468 | 9 | Yes |
| 8102938 | RNF150 | −4.32839 | 2.05E−05 | 0.880745 | 10 | Yes |
| 8028924 | MIA | −3.23844 | 0.001337 | 0.906368 | 10 | Yes |

Figure 9:
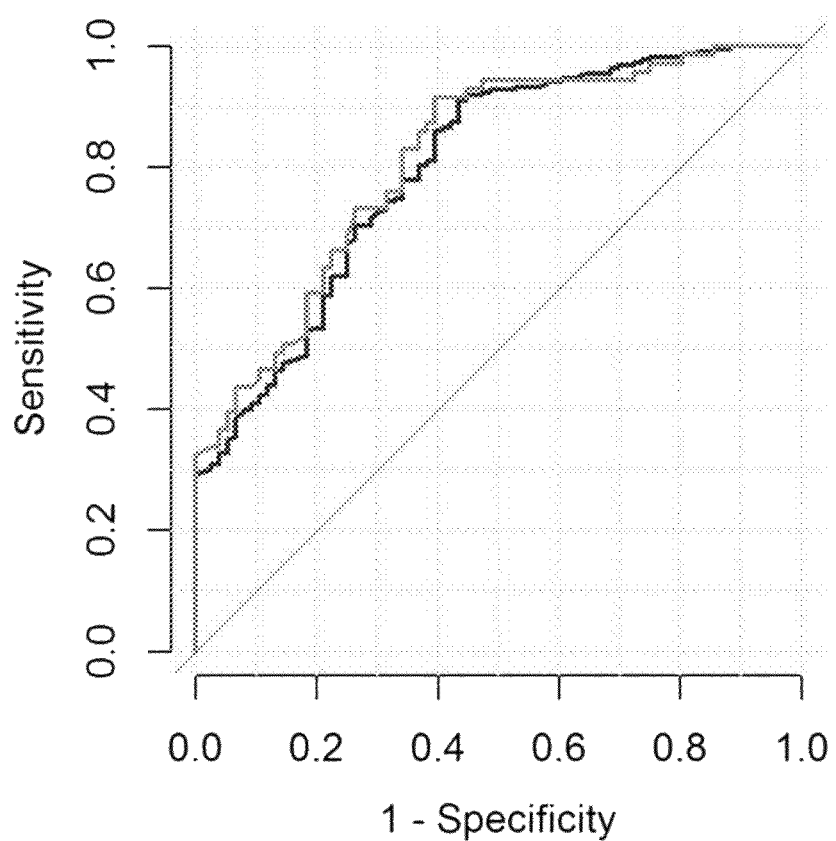
FIG. 9 depicts gene expression data corresponding to all patients in the training set (black line), and the subset of patients with a non-diagnostic bronchoscopy (grey line) were analyzed using the locked classifier. The AUC was calculated as 0.78 (95% CI, 0.73-0.82) and 0.78 (95% CI, 0.71-0.85), for the two groups respectively.

The final lung cancer classifier was then determined using the finalized classifier discovery procedure on the entire training set. The classifier consisted of a combination of the six cancer gene clusters (represented by 17 genes in total), patient age, and the gene expression correlates (GG, GS, GPY) (Table 26) as predictors. Dichotomous classification was performed using a score threshold of 0.65 (patients with scores $\geq$/=0.65 were predicted as cancer-positive and <0.65, cancer-negative). The classifier had a sensitivity of 93% and specificity of 57% in the training set and there was no difference in the AUC of the classifier for the entire training set (0.78; 95% CI, 0.73-0.82), compared with the subset of patients whose bronchoscopy was non-diagnostic for lung cancer (AUC=0.78; 95% 0.71-0.85), (see, FIG. 9).

TABLE 26

Description of the gene expression classifier [a]

| Feature [b], ($x_i$) | Coefficient, ($b_i$) | Informative Genes within features | | |
|---|---|---|---|---|
| Age | 0.0623 | | | |
| GG | 0.5450 | RPS4Y1 | | |
| GS | 0.1661 | SLC7A11 | CLDN10 | TKT |
| GPY | 3.0205 | RUNX1T1 | AKR1C2 | |
| CA (1) | −0.4406 | BST1 | CD177.1 | CD177.2 |
| CA (2) | −0.3402 | ATP12A | TSPAN2 | |
| CA (4) | 0.1725 | GABBR1 | MCAM | NOVA1 | SDC2 |
| CA (7) | 0.5670 | CDR1 | CGREF1 | CLDN22 | NKX3-1 |
| CA (9) | −0.3160 | EPHX3 | LYPD2 | |
| CA (10) | −0.3791 | MIA | RNF150 | |
| Intercept ($b_0$) | 3.3173 | | | |

[a] Genomic gender was defined as GG = 1 (female) if RPS4Y1 < 7.5, 0 (male) otherwise. The predicted genomic smoking (GS) value was derived, where x = 40.8579-0.4462 * SLC7A11-2.1298 * CLND10-1.8256 * TKT, and genomic smoking GS = $e^x/(1 + e^x)$. The predicted genomic pack years (GPY) value was derived, where x = −5.1429 + 2.1891 * RUNX1T1-0.9506 * AKR1C2, and genomic pack years GPY = $\exp(x)/(1 + \exp(x))$. The generalized equation for the prediction classifier was: Score = $e^y/(1 + e^y)$, where, y = $b_0$ + $\Sigma(b_i * x_i)$, where $b_0$ is the intercept, $b_i$ is the coefficient, and $x_i$ is the feature (as shown).
[b] Features include patient age (as reported), GG, GS, GPY as described in the methods, and CA (i), the lung cancer gene clusters (shown in FIG. 7).

b) Features include patient age (as reported), GG, GS, GPY as described in the methods, and CA (i), the lung cancer gene clusters (shown in FIG. 7).

The gene expression classifier performed significantly better (AUC=0.78; 95% CI, 0.73-0.82) than a model using clinical factors alone (AUC=0.72; 95% CI, 0.67-0.77) in the training set (p<0.001). Functional analysis of the 17 cancer genes is summarized separately (Table 27). Nine of the genes are down-regulated and 8 are up-regulated in association with cancer.

TABLE 27

Biological characterization of classifier genes.

| Cluster | Direction in Cancer | Biomarker genes | Biological themes |
|---|---|---|---|
| 1 | Down | BST1, CD177.1, CD177.2 | Innate immune response |
| 2 | Down | ATP12A, TSPAN2 | Mitotic cell cycle |
| 4 | Up | GABBR1, MCAM, NOVA1, SDC2 | Response to retinoic acid, cell cycle |
| 7 | Up | CGREF1, CDR1, CLDN22, NKX3-1 | Submucosal gland markers |
| 9 | Down | EPHX3, LYPD2 | Xenobiotic detoxification |
| 10 | Down | MIA, RNF150 | Cartilaginous markers |

Validation in an Independent Test Set

Figure 8:
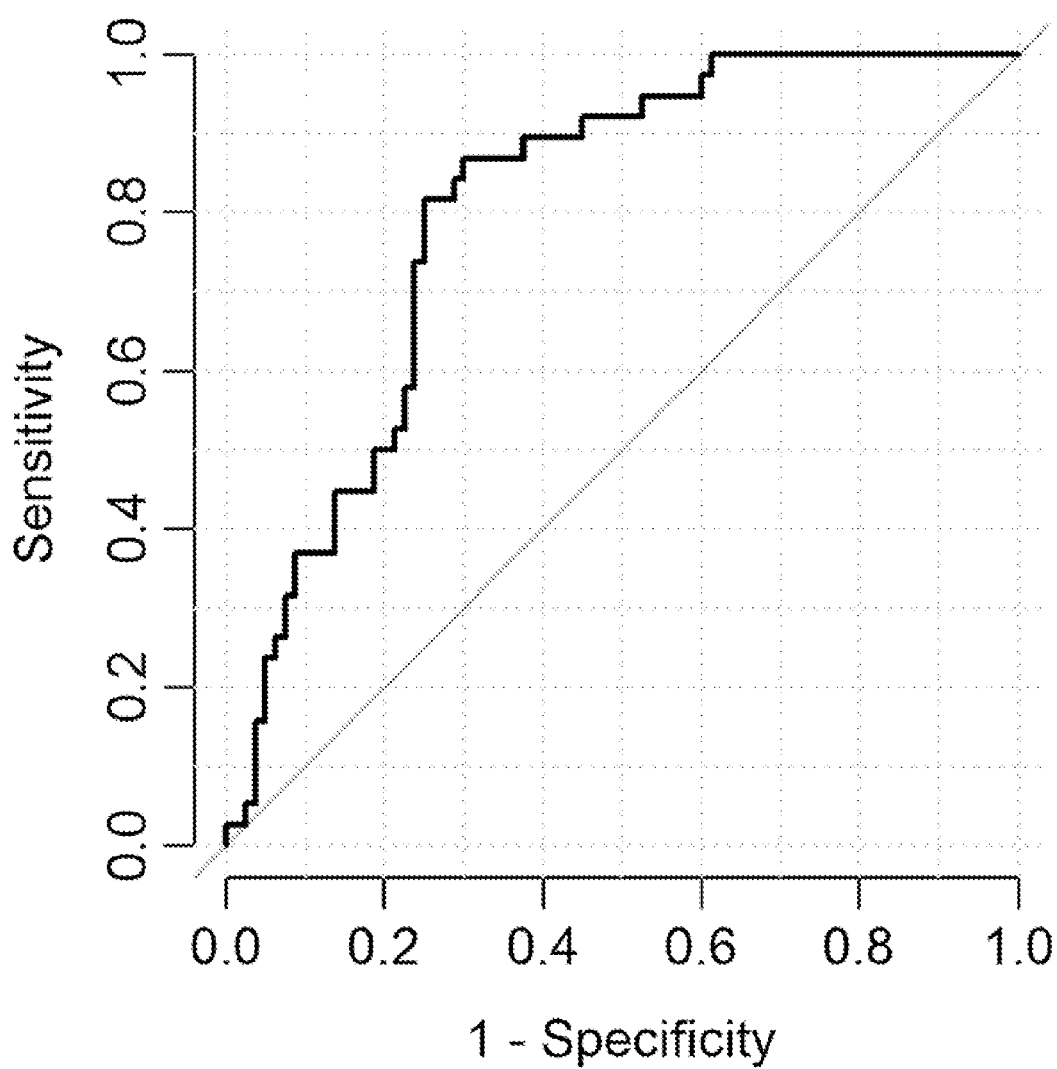
FIG. 8 depicts an ROC curve of patients with a non-diagnostic bronchoscopy in the test set. The AUC=0.81 for the 123 patients whose bronchoscopy did not result in a diagnosis of lung cancer (in which the prevalence of lung cancer=31%).

In the patients with non-diagnostic bronchoscopy (n=123) of the independent test set, the AUC of the classifier was 0.81 (95% CI, 0.73-0.88), (FIG. 8) which was similar to the performance in patients with non-diagnostic bronchoscopy in the training set (AUC=0.78; 95% 0.71-0.85; p=0.495). The sensitivity was 92% and with a specificity of 55%, the NPV was 94% (95% CI, 83-99%), (see Table 28). Interestingly we did not observe any effect of cancer histology or stage (Table 29, or lesion size (Table 30) on the classifier's sensitivity for cancer. Moreover, in the test set the classifier had an AUC of 0.79 in current smokers and 0.82 in former smokers, suggesting that smoking status does not have a dramatic effect on classifier performance (p=0.710). When compared with bronchoscopy alone, the combination of the gene expression classifier with bronchoscopy improved the sensitivity from 51% to 95% (p<0.001).

TABLE 28

Performance of bronchoscopy, classifier, and the combined procedures in the test set.

| Category [a] | Bronchoscopy | Classifier [b] | Classifier & bronchoscopy combined |
|---|---|---|---|
| N, total | 163 | 123 | 163 |
| N, Lung cancer | 78 | 38 | 78 |
| N, Benign disease | 85 | 85 | 85 |

TABLE 28-continued

Performance of bronchoscopy, classifier, and the combined procedures in the test set.

| Category [a] | Bronchoscopy | Classifier [b] | Classifier & bronchoscopy combined |
|---|---|---|---|
| Sensitivity (95% CI) | 51% (40-62%) | 92% (78-98%) | 96% (89-99%) |
| Specificity (95% CI) | 100% (95-100%) | 53% (42-63%) | 53% (42-63%) |
| NPV (95% CI) | 69% (60-77%) | 94% (83-98%) | 94% (83-98%) |
| PPV (95% CI) | 100% (90-100%) | 47% (36-58%) | 65% (56-73%) |

[a] Patients diagnosed with cancer = CA+ and benign disease = CA−

[b] The performance of the classifier was evaluated in patients in which bronchoscopy did not result in a finding of cancer (n = 123).

TABLE 29

Sensitivity of bronchoscopy, the classifier, and the combined procedures for patients with lung cancer in the test set.

| Histology | Sub-type | N | Bronchoscopy Sensitivity | Classifier Sensitivity | Combined Sensitivity |
|---|---|---|---|---|---|
| All Cancers | | 78 | 51% [a] | 92% [b] | 96% [c] |
| SCLC | | 14 | 64% | 100% | 100% |
| NSCLC | | 64 | 48% | 91% | 95% |
| | Adenocarcinoma | 18 | 33% | 83% | 89% |
| | Squamous | 27 | 56% | 92% | 96% |
| | Large Cell | 4 | 25% | 100% | 100% |
| | Undefined | 15 | 60% | 83% | 93% |
| Histology | Stage | | | | |
| SCLC | | | | | |
| | Limited | 9 | 78% | 100% | 100% |
| | Extensive | 5 | 40% | 100% | 100% |
| NSCLC | | | | | |
| | 1 | 14 | 36% | 100% | 100% |
| | 2 | 2 | 50% | 100% | 100% |
| | 3 | 25 | 52% | 92% | 96% |
| | 4 | 22 | 55% | 80% | 91% |
| | Unknown | 1 | 0% | 100% | 100% |

Of 163 patients who underwent a diagnostic bronchoscopy procedure for suspicion of lung cancer, 78 were diagnosed with cancer. A lung cancer diagnosis was made at bronchoscopy [a] in 40 patients (51%; 95% CI, 40-62%), and in the remaining lung cancer patients where no diagnosis was made at bronchoscopy, the classifier correctly predicted 34 [b] of them (89%; 95% CI, 75-96%). The classifier combined with bronchoscopy yielded a detection of 74 of 78 (95%; 95% CI, 87-98%) patients with lung cancer [c]. The sensitivities of bronchoscopy, the classifier, and the combined procedures are also shown for lung cancers according to sub-type and stage.

TABLE 30

Sensitivity of bronchoscopy, the classifier, and the combined procedures in the test set stratified by size of suspicious lesions.

| Mass size [a] | N | Bronchoscopy Sensitivity | Classifier Sensitivity | Combined Sensitivity |
|---|---|---|---|---|
| <3 cm | 99 | 44% | 87% | 93% |
| >3 cm | 48 | 58% | 94% | 98% |
| Ill-def Infiltrate | 16 | 38% | 100% | 100% |

Includes patients diagnosed with lung cancer and those with benign disease.

Table 26 recites multiple gene expression classifiers of interest. The following table, Table 31, provides a Gene ID, as available on NCBI, providing descriptive support for the gene expression classifiers. Gene classifier CD177 is depicted in Table 31 with two designations, CD177.1 and CD177.2. The 0.1 and 0.2 designations identify that two different probe sets are used in the arrays which detect differential expression of the genes represented by the gene classifiers. FIG. 10A discloses 19 probes utilized in hybridizing to CD177, accounting for CD177.1. FIG. 10B discloses 4 probes utilized in hybridizing to CD177, accounting for CD177.2.

TABLE 31

NCBI Gene ID Numbers corresponding to gene expression classifiers.

| Gene Classifier | Gene ID Number | Gene Classifier | Gene ID Number |
|---|---|---|---|
| RPS4Y1 | 6192 | MCAM | 4162 |
| SLC7A11 | 23657 | NOVA1 | 4857 |
| CLDN10 | 9071 | SDC1 | 6382 |
| TKT | 7086 | CDR1 | 1038 |
| AKR1C2 | 1646 | CGREF1 | 10669 |
| BST1 | 683 | CLDN22 | 53842 |
| CD177.1 | 57126 (See FIG. 10A) | NKX3-1 | 4824 |
| CD177.2 | 57126 (See FIG. 10B) | EPHX3 | 79852 |
| ATP12A | 479 | LYPD2 | 137797 |
| TSPAN2 | 10100 | MIA | 8190 |
| GABBR1 | 2550 | RNF150 | 57484 |
| RUNX1T1 | 862 | | |

Evaluation of Results

Work has demonstrated that there are persistent gene-expression alterations in normal epithelial cells from the bronchial airway that are associated with exposure to cigarette smoke and the presence of lung cancer in current and former smokers [32,41,42,43]. These cancer-associated differences can be used to derive classifiers capable of accurately detecting lung cancer in these relatively non-invasively collected biospecimens obtained during bronchoscopy [35]. In current practice it is challenging to rule out lung cancer when bronchoscopy does not lead to a finding of malignancy, and the false-negative rate can range from 20-70% [28]. Current guidelines suggest that patients with elevated risk of disease should be pursued with more invasive follow-up diagnostic procedures [28], which carry increased risk of complications [31]. However due to uncertainty these procedures often performed in patients found to have benign disease [33]. Therefore our goal was to derive a gene-expression classifier from the proximal airway during bronchoscopy to increase the overall sensitivity, minimize ambiguity when bronchoscopy is non-diagnostic, and reduce the need for unnecessary invasive procedures.

In this study, we leveraged a cohort of current and former smokers undergoing bronchoscopy for suspected lung cancer from a larger multicenter study to derive a gene-expression classifier for lung cancer. The classifier is a multivariate logistic regression model that has high sensitivity and high NPV. Importantly, we have validated the performance of the classifier in an independent cohort, using data from a previously published study of airway samples collected from smokers undergoing bronchoscopy for suspected lung cancer. The sensitivity is 92% in patients whose bronchoscopy is non-diagnostic in the test set with a specificity of 55%. The NPV is 94% in the test set compared to an NPV of 69% for bronchoscopy alone suggesting that the classifier could help physicians reliably identify patients unlikely to have lung cancer after a non-diagnostic bronchoscopy.

The functions of the differentially expressed genes in the normal appearing airway epithelium in current and former smokers with lung cancer provide insight into the biology underlying the field of injury. Among genes that are suppressed, there are a number involved in the immune response, including CD177 and BST1, suggesting an impaired immune response in the airway of smokers with lung cancer. The gene TSPAN2, whose expression is depressed by p53 knockdown and is associated with poor prognosis in lung adenocarcinomas [44] was also expressed at lower levels in patients with cancer. Also EPHX3, a gene involved in xenobiotic metabolism, processing of carcinogens in tobacco smoke, and carcinogenesis in other epithelial cancers is down-regulated [45]. Among the classifier genes that are up-regulated in lung cancer, NOVA1 and CDR1 are predominantly expressed in neurons, but are also expressed in tumors and are associated with para-neoplastic antibodies in several malignancies, including small-cell lung cancer [46,47,48,49,50]. Furthermore, MCAM which is up-regulated in lung cancer, is expressed in basal bronchial epithelial cells [51]. MCAM is also strongly and transiently up-regulated in tracheal epithelium during repair [52], is required for tracheal epithelial regeneration [53], and is up-regulated in the bronchial epithelium of patients with COPD [54] and asthma [55]. A number of classifier genes that regulate cell growth and proliferation are up-regulated in patients with lung cancer, including SDC2, and NKX3-1 as well as the cell-cycle-arrest mediator CGREF1. Finally the CFGC genes selected to predict smoking status (SLC7A11, CLDN10, TKT) and smoking history (RUNX1T1, AKR1C2) in our classifier have been previously reported as being altered by tobacco smoke exposure, confirming the robust effect of smoking on airway epithelium biology [11,18,33].

Our discovery approach extends earlier work on gene-expression based lung cancer diagnostics [35] primarily in the explicit modeling of clinical covariates as components of the predictive model prior to selection of features with lung cancer-associated expression. It is known that the response to environmental insults and other clinical factors can vary substantially between individuals. Therefore our approach was to use gene expression to capture the patient-level physiological response to an environmental insult (e.g., cumulative smoke exposure), as this response may be more reflective of disease risk than the actual reported values [57]. Another component of our approach was selecting genes whose expression is associated with cancer after accounting for the modeled clinical factors. We hypothesized that this approach would help ensure that the information about the likelihood of cancer captured by the genes with cancer-associated gene expression is independent from the information about cancer captured by the modeled clinical factors. An additional important aspect of our classifier discovery approach was our methodology to identify patterns of independent cancer-associated gene expression through clustering and then to model cancer as the additive effects of each of the cancer-associated gene expression modules. This is in contrast to selecting only genes that are globally top-ranked according to their association with cancer which could potentially result in selecting an entire panel of genes that reflect a single cancer-associated molecular process. Previous studies to derive a gene expression classifier to predict risk of lung cancer in normal appearing airway epithelial cells have described similar results with high sensitivity and NPV when bronchoscopy is non-diagnostic [35]. While there are no common genes in that classifier compared to the one described here, we believe that our new classifier represents similar mechanisms of action given the strong performance in the independent test set. However, the differences in the specific genes selected this may be due to differences in the feature selection process.

We have derived a gene expression classifier for lung cancer using cells from the proximal airway that can be used in conjunction with bronchoscopy for suspected lung cancer. We have validated the performance of this classifier in an independent test set. The classifier adds substantial sensitivity to the bronchoscopy procedure resulting in high NPV. This classifier can be used to aid in decision-making when bronchoscopy is non-diagnostic by identifying patients who are at low risk of having lung cancer.

Having thus described several aspects of at least one embodiment of this disclosure, it is to be appreciated that various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only and the disclosure is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

INCORPORATION BY REFERENCE

All references, articles, publications, patents, patent publications, and patent applications cited herein are incorporated by reference in their entireties for all purposes.

REFERENCES

1. Gould, M. K., Donington, J., Lynch, W. R., et al. Evaluation of individuals with pulmonary nodules: When is it lung cancer?: Diagnosis and management of lung cancer: American College of Chest Physicians evidence-based clinical practice guidelines. CHEST Journal 2013; 143 (5_suppl): e93S-e120S.
2. Tukey, M. H., & Wiener, R. S. Population-based estimates of transbronchial lung biopsy utilization and complications. Respiratory medicine 2012; 106(11): 1559-1565.
3. Ernst A, Silvestri G, Johnstone D. Interventional Pulmonary Procedures: Guidelines from the American College of Chest Physicians. Chest 2003; 123; 1693-1717
4. Rivera M P, Mehta A C, Wahidi M M. Establishing the Diagnosis of Lung Cancer: Diagnosis and Management of Lung Cancer, 3rd ed: American College of Chest Physicians Evidence-Based Clinical Practice Guidelines. Chest 2013; 143: e142S-65S.
5. Memoli, J. S. W., Nietert, P. J., & Silvestri, G. A. Meta-analysis of guided bronchoscopy for the evaluation of the pulmonary nodule. CHEST Journal 2012; 142(2): 385-393.
6. Ost, D., Fein, A. M., & Feinsilver, S. H. (2003). The solitary pulmonary nodule. New England Journal of Medicine, 348(25), 2535-2542.
7. Grogan, E. L., Weinstein, J. J., Deppen, S. A., et al. Thoracic operations for pulmonary nodules are frequently not futile in patients with benign disease. Journal of thoracic oncology: official publication of the International Association for the Study of Lung Cancer 2011, 6(10): 1720.
8. Detterbeck, F. C., Mazzone, P. J., Naidich, D. P., & Bach, P. B. Screening for lung cancer: diagnosis and management of lung cancer: American College of Chest Physicians evidence-based clinical practice guidelines. CHEST Journal 2013; 143(5_suppl): e78S-e92S.

9. Wiener, R. S., Wiener, D. C., & Gould, M. K. Risks of Transthoracic Needle Biopsy: How High? Clinical pulmonary medicine 2013; 20(1): 29.
10. Covey, A. M., Gandhi, R., Brody, L. A., Getrajdman, G., Thaler, H. T., & Brown, K. T. Factors associated with pneumothorax and pneumothorax requiring treatment after percutaneous lung biopsy in 443 consecutive patients. Journal of vascular and interventional radiology 2004; 15(5): 479-483.
11. Geraghty, P. R., Kee, S. T., McFarlane, G., Razavi, M. K., Sze, D. Y., & Dake, M. D. CT-guided Transthoracic Needle Aspiration Biopsy of Pulmonary Nodules: Needle Size and Pneumothorax Rate 1. Radiology 2003; 229(2): 475-481.
12. Golub, T. R., Slonim, D. K., Tamayo, P., et al. Molecular classification of cancer: class discovery and class prediction by gene expression monitoring. Science 1999; 286 (5439): 531-537.
13. Spira A, Beane J E, Shah V, et al. Airway epithelial gene expression in the diagnostic evaluation of smokers with suspect lung cancer. Nature medicine 2007; 13:361-6.
14. Hanley J A, McNeil B J. The meaning and use of the area under a receiver operating characteristic (ROC) curve. Radiology 1982; 143:29-36.
15. MacMahon, H., Austin, J. H., Gamsu, G., et al. Guidelines for management of small pulmonary nodules detected on CT scans: a statement from the Fleischner Society 1. Radiology 2005, 237(2): 395-400.
16. Beane, J., Sebastiani, P., Whitfield, T. H., et al. A prediction model for lung cancer diagnosis that integrates genomic and clinical features. Cancer Prevention Research 2008; 1(1): 56-64.
17. Gustafson, A. M., Soldi, R., Anderlind, C., et al. Airway PI3K pathway activation is an early and reversible event in lung cancer development. Science translational medicine 2010; 2(26): 26ra25-26ra25.
18. Kadara, H., Fujimoto, J., Yoo, S. Y., Maki, et al. Transcriptomic architecture of the adjacent airway field cancerization in non-small cell lung cancer. Journal of the National Cancer Institute 2014; 106(3): dju004.
19. Alexander, E. K., Kennedy, G. C., Baloch, et al. Preoperative diagnosis of benign thyroid nodules with indeterminate cytology. New England Journal of Medicine 2012, 367(8): 705-715.
20. McWilliams A, Tammemagi M C, Mayo J R, et al. Probability of cancer in pulmonary nodules detected on first screening CT. N Engl J Med 2013; 369:910-9.
21. Ost D E, Gould M K. Decision making in patients with pulmonary nodules. American journal of respiratory and critical care medicine 2012; 185:363-72.
22. Irizarry, R. A., Bolstad, B. M., Collin, F., Cope, L. M., Hobbs, B., & Speed, T. P. (2003). Summaries of Affymetrix GeneChip probe level data. Nucleic acids research, 31(4), e15-e15.
23. Johnson W E, Li C, Rabinovic A. Adjusting batch effects in microarray expression data using empirical Bayes methods. Biostatistics 2007; 8: 118-127.
24. Howlader N, Noone A M, Krapcho M, et al. SEER stat fact sheets: lung and bronchus. Available online at the world wide web address: seer.cancer.gov/statfacts/html/lungb.html.
25. The National Lung Screening Trial Research Team. Reduced Lung-Cancer Mortality with Low-Dose Computed Tomographic Screening. N Engl J Med 2011; 365:395-409
26. Tanoue L T, Tanner N T, Gould M K, Silvestri G A. Lung Cancer Screening. Am J Respir Crit Care Med. published online 4 Nov. 2014
27. Ernst A, Silvestri G, Johnstone D. Interventional Pulmonary Procedures: Guidelines from the American College of Chest Physicians. Chest 2003; 123; 1693-1717
28. Rivera, M. P., Mehta, A. C., & Wahidi, M. M. (2013). Establishing the Diagnosis of Lung Cancer Diagnosis and Management of Lung Cancer, 3rd ed: American College of Chest Physicians Evidence-Based Clinical Practice Guidelines. CHEST Supplement. Chest, 143, e1435.
29. Silvestri, G. A., Feller-Kopman, D., Chen, A., Wahidi, M., Yasufuku, K., & Ernst, A. (2012). Latest Advances in Advanced Diagnostic and Therapeutic Pulmonary Procedures Update on Pulmonary Procedures. CHEST Journal, 142(6), 1636-1644.
30. Gildea, T. R., Mazzone, P. J., Karnak, D., Meziane, M., & Mehta, A. C. (2006). Electromagnetic navigation diagnostic bronchoscopy: a prospective study. American journal of respiratory and critical care medicine, 174(9), 982-989.
31. Wiener, R. S., Schwartz, L. M., Woloshin, S., & Welch, H. G. (2011). Population-based risk for complications after transthoracic needle lung biopsy of a pulmonary nodule: an analysis of discharge records. Annals of internal medicine, 155(3), 137-144.
32. Fontaine-Delaruelle, C., Ferretti, G., Gamondes, D., Pradat, E., Souquet, P. J., & Couraud, S. (2014). Is transthoracic core needle biopsy under CT scan a good deal for benign diseases' diagnosis?, European Respiratory Journal, 44(Suppl 58), P679.
33. Smith M A, Battafarano R J, Meyers B F, Zoole J B, Cooper J D, Patterson G A. Prevalence of benign disease in patients undergoing resection for suspected lung cancer. The Annals of thoracic surgery 2006; 81:1824-1828; discussion 1828-1829
34. Beane, J., Sebastiani, P., Liu, G., Brody, J. S., Lenburg, M. E., & Spira, A. (2007). Reversible and permanent effects of tobacco smoke exposure on airway epithelial gene expression. Genome Biol, 8(9), R201.
35. Spira A, Beane J E, Shah V, Steiling K, Liu G, Schembri F, Gilman S, Dumas Y M, Calner P, Sebastiani P, Sridhar S, Beamis J, Lamb C, Anderson T, Gerry N, Keane J, Lenburg M E, Brody J. Airway epithelial gene expression in the diagnostic evaluation of smokers with suspect lung cancer. Nature Medicine 2007; 13(3):361-6
36. Tibshirani, R. (1996). Regression shrinkage and selection via the lasso. Journal of the Royal Statistical Society. Series B (Methodological), 267-288.
37. Da Wei Huang, B. T. S., & Lempicki, R. A. (2008). Systematic and integrative analysis of large gene lists using DAVID bioinformatics resources. Nature protocols, 4(1), 44-57.
38. Irizarry, R. A., Hobbs, B., Collin, F., Beazer-Barclay, Y. D., Antonellis, K. J., Scherf, U., & Speed, T. P. (2003). Exploration, normalization, and summaries of high density oligonucleotide array probe level data. Biostatistics, 4(2), 249-264.
39. Dai, M., Wang, P., Boyd, A. D., Kostov, G., Athey, B., Jones, E. G., et al., (2005). Evolving gene/transcript definitions significantly alter the interpretation of GeneChip data. Nucleic acids research, 33(20), e175-e175.
40. Golub, T. R., Slonim, D. K., Tamayo, P., Huard, C., Gaasenbeek, M., Mesirov, J. P., et al., (1999). Molecular 41. Kadara, H., Fujimoto, J., Yoo, S. Y., Maki, Y., Gower, A. C., Kabbout, M., et al., (2014). Transcriptomic Architecture of the Adjacent Airway Field Cancerization in Non-Small cell lung cancer. Journal of the National Cancer Institute, 106(3)
42. Steiling, K., Ryan, J., Brody, J. S., & Spira, A. (2008). The field of tissue injury in the lung and airway. Cancer prevention research, 1(6), 396-403.
43. Bosse, Y., Postma, D. S., Sin, D. D., Lamontagne, M., Couture, C., Gaudreault, N., et al., (2012). Molecular signature of smoking in human lung tissues. Cancer research, 72(15), 3753-3763.
44. Otsubo, C., Otomo, R., Miyazaki, M., Matsushima-Hibiya, Y., Kohno, T., Iwakawa, R., et al., (2014). TSPAN2 Is Involved in Cell Invasion and Motility during Lung Cancer Progression. Cell reports, 7(2), 527-538.
45. Oster, B., Thorsen, K., Lamy, P., Wojdacz, T. K., Hansen, L. L., Birkenkamp-Demtroder, K., et al., (2011). Identification and validation of highly frequent CpG island hypermethylation in colorectal adenomas and carcinomas. International journal of cancer, 129(12), 2855-2866.
46. Knudsen, A., Monstad, S. E., Dorum, A., Lonning, P. E., Salvesen, H. B., Drivsholm, L., et al., (2006). Ri antibodies in patients with breast, ovarian or small cell lung cancer determined by a sensitive immunoprecipitation technique. Cancer Immunology, Immunotherapy, 55(10), 1280-1284.
47. Buckanovich, R. J., Posner, J. B., & Darnell, R. B. (1993). Nova, the paraneoplastic Ri antigen, is homologous to an RNA-binding protein and is specifically expressed in the developing motor system. Neuron, 11(4), 657-672.
48. Salemi, M., Fraggetta, F., Galia, A., Pepe, P., Cimino, L., Condorelli, R. A., & Calogero, A. E. (2013). Cerebellar degeneration-related autoantigen 1 (CDR1) gene expression in prostate cancer cell lines. The International journal of biological markers, 30; 29(3):e288-90
49. Tanaka, M., Tanaka, K., Onodera, O., & Tsuji, S. (1995). Trial to establish an animal model of paraneoplastic cerebellar degeneration with anti-Yo antibody: 1. Mouse strains bearing different MHC molecules produce antibodies on immunization with recombinant Yo protein, but do not cause Purkinje cell loss. Clinical neurology and neurosurgery, 97(1), 95-100.
50. Furneaux, H. M., Rosenblum, M. K., Dalmau, J., Wong, E., Woodruff, P., Graus, F., & Posner, J. B. (1990). Selective expression of Purkinje-cell antigens in tumor tissue from patients with paraneoplastic cerebellar degeneration. New England Journal of Medicine, 322(26), 1844-1851.
51. Shih, I. M., Nesbit, M., Herlyn, M., & Kurman, R. J. (1998). A new Mel-CAM (CD146)-specific monoclonal antibody, MN-4, on paraffin-embedded tissue. Modern pathology: an official journal of the United States and Canadian Academy of Pathology, Inc, 11(11), 1098-1106.
52. Tsukamoto, Y., Taira, E., Miki, N., & Sasaki, F. (2001). The role of gicerin, a novel cell adhesion molecule, in development, regeneration and neoplasia. Histol Histopathol. 2001; 16(2):563-71.
53. Tsukamoto, Y., Taira, E., Kotani, T., Yamate, J., Wada, S., Takaha, N., et al., (1996). Involvement of gicerin, a cell adhesion molecule, in tracheal development and regeneration. Cell Growth Differ. 7(12), 1761-1767.
54. Schulz, C., Petrig, V., Wolf, K., Kratzel, K., Köhler, M., Becker, B., & Pfeifer, M. (2003). Upregulation of MCAM in primary bronchial epithelial cells from patients with COPD. Eur Respir J. 2003; 22(3):450-6.
55. Simon, G. C., Martin, R. J., Smith, S., Thaikoottathil, J., Bowler, R. P., Barenkamp, S. J., & Chu, H. W. (2011). Up-regulation of MUC18 in airway epithelial cells by IL-13: implications in bacterial adherence. Am J Resp Cell Mol Biol, 44(5), 606-613.
56. Penning, T. M., & Lerman, C. (2008). Genomics of smoking exposure and cessation: lessons for cancer prevention and treatment. Cancer Prevention Research, 1(2), 80-83.
57. Lampe, J. W., Stepaniants, S. B., Mao, M., Radich, J. P., Dai, H., Linsley, P. S., et al., (2004). Signatures of environmental exposures using peripheral leukocyte gene expression: tobacco smoke. Cancer Epidemiology Biomarkers & Prevention, 13(3), 445-453.

What is claimed is:

1. A method, comprising:
(a) performing an imaging analysis on a subject to detect a presence of a pulmonary nodule in said subject, wherein said imaging analysis comprises computer-aided tomography, magnetic resonance imaging, ultrasonography, or chest X-ray;
(b) determining, based at least in part on said imaging analysis, that said pulmonary nodule is indeterminate for indicating a presence of lung cancer in said subject or an absence of lung cancer in said subject;
(c) responsive to said determining that said pulmonary nodule is indeterminate, obtaining a nasal sample from a nose of said subject, wherein said subject is suspected of having lung cancer based at least in part on said imaging analysis of said subject;
(d) assaying messenger ribonucleic acid (mRNA) molecules from said nasal sample to determine a plurality of gene expression levels in said nasal sample,
wherein said plurality of gene expression levels comprises at least one gene expression level of a gene that correlates with self-reportable characteristics of said subject and at least one gene expression level of an informative gene that is differentially expressed in subjects with lung cancer as compared to subjects without lung cancer;
(e) processing said plurality of gene expression levels to determine that said pulmonary nodule is associated with or is likely to be associated with presence of said lung cancer in said subject,
wherein said processing comprises weighting said at least one gene expression level that correlates with said self-reportable characteristics of said subject by its relative contribution to said determining in (e),
wherein said self-reportable characteristics comprise two or more members selected from the group consisting of smoking status, age, and gender; and
(f) responsive to said determining in (e), administering a treatment to said subject thereby treating said subject for said lung cancer, wherein said treatment is selected from the group consisting of surgical resection, chemotherapy, chemoradiation, stereotactic body radiotherapy, and radiofrequency ablation.

2. The method of claim 1, wherein said lung cancer is adenocarcinoma, squamous cell carcinoma, small cell lung cancer, or non-small cell lung cancer.

3. The method of claim 1, wherein (e) further comprises determining a lung cancer risk of said subject by applying a model to said plurality of gene expression levels.

4. The method of claim 3, wherein said lung cancer risk is determined using a combination of weighted expression levels.

5. The method of claim 4, wherein said weighted expression levels are weighted by a relative contribution to predicting an increased likelihood of having said lung cancer.

6. The method of claim 3, wherein said model has a Negative Predictive Value (NPV) of greater than 90% for ruling out said lung cancer.

7. The method of claim 3, wherein said model has a Negative Predictive Value (NPV) of greater than 85% for ruling out said lung cancer in subjects diagnosed with chronic obstructive pulmonary disease (COPD).

8. The method of claim 1, further comprising, responsive to said determining in (e), performing an invasive lung procedure on said subject for detecting said lung cancer in said subject.

9. The method of claim 8, wherein said invasive lung procedure is selected from the group consisting of a bronchoscopy, a transthoracic needle aspiration, a transthoracic needle biopsy (TTNB), a surgical lung biopsy (SLB), a mediastinoscopy, a thoracoscopy, a thoracotomy, and a video-assisted thoracoscopic surgery (VATS).

10. The method of claim 9, wherein said invasive lung procedure is said bronchoscopy.

11. The method of claim 1, wherein said assaying comprises use of at least one nucleic acid probe that specifically hybridizes with a messenger ribonucleic acid molecule in said nasal sample.

12. The method of claim 11, wherein said at least one nucleic acid probe is immobilized on a solid support.

13. The method of claim 1, wherein said processing comprises comparing said plurality of gene expression levels to a reference level.

14. The method of claim 1, wherein said subject is suspected of having lung cancer based at least in part on said subject exhibiting one or more symptoms of said lung cancer.

15. The method of claim 14, wherein said one or more symptoms of said lung cancer comprise a persistent cough, worsening of an existing cough, blood in sputum of said subject, persistent bronchitis, chest pain, unexplained weight loss, shortness of breath, or wheezing.

16. The method of claim 1, wherein said assaying comprises performing hybridization on said nasal sample using at least one probe for said gene that relates to said one or more self-reportable characteristics of said subject.

17. The method of claim 1, further comprising repeating (c) to (e) within six months.

18. The method of claim 1, wherein said subject is asymptomatic for said lung cancer.

19. The method of claim 1, wherein said nasal sample comprises respiratory epithelium of said nose of said subject.

20. The method of claim 1, wherein said informative gene is selected from the group consisting of: TMEM51, CRIL, PDZK1IP 1, MICAL2, VWA5A, ACAD8, SAA4, GLYATL2, ETV6, CD177, CEACAM7, CD177, QPCT, CASP10, PI3, BST1, MTNRIA, STARD4, CFB, SLC26A8, VNN2, HDAC9, SLC26A4, LCN2, CFB, CCDC18, FAM72D, NUF2, FAM72D, FBXO28, GPR137B, STIL, DEPDCI, TSPAN2, FAM72D, ASPM, KIF14, KIF20B, RAD51AP1, GAS2L3, SPIC, SMAGP, ATP12A, BRCA2, BORA, SKA3, DLGAP5, CASC5, LRRC28, PYCARD, TXNL4B, EFCAB5, SPAG5, FAM72D, ABCA12, AURKA, SGOL1, BANKI, CENPE, CASP6, MAD2L1, CCNA2, CCNB1, KIF20A, CENPK, ERAP1, FAM54A, PHTF2, CLDN12, BPGM, PCMTD1, MELK, MST4, CR1, GOS2, CSF3R, S100A12, SELL, NCF2, LIPN, ZNF438, NAMPT, CBL, CASP5, CARD16, CARD17, CLEC4A, LRRK2, HMGN2P46, AQP9, BCL2A1, ITGAX, GPR97, CCL4, PSTPIP2, IFI30, FFAR2, EMR3, FPRI, LILRA5, PLEK, MXDI, TNFAIP6, CXCR2, IL1B, CXCR1, SIRPB1, NCF4, IRAK2, PROK2, TLR2, TREM1, SOD2, CREB 5, NAMPT, TNFRSF10C, CSGALNACT1, ASAP1, PLA2G2A, NFYC, RASSF10, GLB1L3, TRIM3, MCAM, MSRB3, SLITRK5, GAS6, NOVA1, GABRG3, ABCA3, LPO, FSCN2, RASD1, HILS1, SDK2, NTN5, KCNA7, ATOH8, KCNIP3, INHBB, VSTM2L, ZNRF3, PLEKHG4B, GNMT, GABBR1, ARHGEF10, SDC2, CRB2, GAS1, PNPLA7, RAI2, PLA2G2A, ID3, PGLYRP4, SFTPA1, SFTPA1, LIPK, SFTPA2, SFTPA2, ASCL3, RPPH1, CD209, GPR32, UGT2A3, CD58, LBR, ARHGDIB, SLC12A6, LPCAT2, PLEKHB2, KYNU, ANKRD36B, ANKRD36B, ANKRD36B, SRD5A3, NEIL3, TLR1, BCAP29, MGAM, TPK1, ATP6V1B2, LYN, SDCBP, GK, GLA, ADRA2A, PRKCDBP, PRR4, PRB4, PRB3, PRB1, PRB2, BMP4, PRKCA, CYP1B1-AS1, CGREF1, RPRM, SDPR, BPIFB2, BPIFB 6, SNCA, CLDN22, COBL, NKX3-1, CDR1, CH25H, FXCI, DLG2, NRXN3, CES1P1, CES1, KCNJ16, APCDD1, TMEM178, MYRIP, FLNB, ENPP5, SEMA3E, SLC7A2, ARHGAP6, ANO3, SLC22A10, UFM1, EPHX3, KLF7, LGSN, LYPD2, CES3, MIA, RNF150, SLC9A3, and MYOT.

21. The method of claim 1, wherein said treatment is said surgical resection.

22. The method of claim 1, wherein said treatment is said chemotherapy.

23. The method of claim 1, wherein said treatment is said chemoradiation.

24. The method of claim 1, wherein said treatment is said stereotactic body radiotherapy.

25. The method of claim 1, wherein said treatment is said radiofrequency ablation.

\* \* \* \* \*

SEQUENCE LISTING

```
<160> NUMBER OF SEQ ID NOS: 46

<210> SEQ ID NO 1
<211> LENGTH: 25
<212> TYPE: DNA
<213> ORGANISM: Artificial Sequence
<220> FEATURE:
<223> OTHER INFORMATION: TSPAN2 Probe Sequence

<400> SEQUENCE: 1
tcaacattaa gaagtcttaa ttcag                                      25

<210> SEQ ID NO 2
<211> LENGTH: 25
<212> TYPE: DNA
<213> ORGANISM: Artificial Sequence
<220> FEATURE:
<223> OTHER INFORMATION: MCAM Probe Sequence

<400> SEQUENCE: 2
gctttaatcc ccatgaagga cagtg                                      25
```

```
<210> SEQ ID NO 3
<211> LENGTH: 25
<212> TYPE: DNA
<213> ORGANISM: Artificial Sequence
<220> FEATURE:
<223> OTHER INFORMATION: ATP12A Probe Sequence

<400> SEQUENCE: 3
gcggtggaga taccggcggc ggcgc                                    25

<210> SEQ ID NO 4
<211> LENGTH: 25
<212> TYPE: DNA
<213> ORGANISM: Artificial Sequence
<220> FEATURE:
<223> OTHER INFORMATION: NOVA1 Probe Sequence

<400> SEQUENCE: 4
gacgaaattc agacatggag catca                                    25

<210> SEQ ID NO 5
<211> LENGTH: 25
<212> TYPE: DNA
<213> ORGANISM: Artificial Sequence
<220> FEATURE:
<223> OTHER INFORMATION: MIA Probe Sequence

<400> SEQUENCE: 5
atgacaccaa ggcacaccag ggacc                                    25

<210> SEQ ID NO 6
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 6
gacccgtctg tggctggtaa tctct                                    25

<210> SEQ ID NO 7
<211> LENGTH: 25
<212> TYPE: DNA
<213> ORGANISM: Artificial Sequence
<220> FEATURE:
<223> OTHER INFORMATION: EPHX3 Probe Sequence

<400> SEQUENCE: 7
gctccactgg aagagaggta taccc                                    25

<210> SEQ ID NO 8
<211> LENGTH: 25
<212> TYPE: DNA
<213> ORGANISM: Artificial Sequence
<220> FEATURE:
<223> OTHER INFORMATION: CD177.2 Probe Sequence

<400> SEQUENCE: 8
ttcctgtgtc ccattgagca ggttg                                    25

<210> SEQ ID NO 9
<211> LENGTH: 25
<212> TYPE: DNA
<213> ORGANISM: Artificial Sequence
<220> FEATURE:
<223> OTHER INFORMATION: CGREF1
```

```
<400> SEQUENCE: 9
tagggtacag cacttaacgc aatct                                              25

<210> SEQ ID NO 10
<211> LENGTH: 25
<212> TYPE: DNA
<213> ORGANISM: Artificial Sequence
<220> FEATURE:
<223> OTHER INFORMATION: BST1 Probe Sequence

<400> SEQUENCE: 10
tgtttgccgt ttcccgttcc agaca                                              25

<210> SEQ ID NO 11
<211> LENGTH: 25
<212> TYPE: DNA
<213> ORGANISM: Artificial Sequence
<220> FEATURE:
<223> OTHER INFORMATION: RNF150 Probe Sequence

<400> SEQUENCE: 11
tggttaatcc aagccgcagc ctggt                                              25

<210> SEQ ID NO 12
<211> LENGTH: 25
<212> TYPE: DNA
<213> ORGANISM: Artificial Sequence
<220> FEATURE:
<223> OTHER INFORMATION: CLDN22 Probe Sequence

<400> SEQUENCE: 12
ggtgtttctc gtctccagtt cttga                                              25

<210> SEQ ID NO 13
<211> LENGTH: 25
<212> TYPE: DNA
<213> ORGANISM: Artificial Sequence
<220> FEATURE:
<223> OTHER INFORMATION: GABBR1 Probe Sequence

<400> SEQUENCE: 13
tacggagcca ttacctgggc agtgc                                              25

<210> SEQ ID NO 14
<211> LENGTH: 25
<212> TYPE: DNA
<213> ORGANISM: Artificial Sequence
<220> FEATURE:
<223> OTHER INFORMATION: SDC2 Probe Sequence

<400> SEQUENCE: 14
tgagcctgct tctccgggct cccct                                              25

<210> SEQ ID NO 15
<211> LENGTH: 25
<212> TYPE: DNA
<213> ORGANISM: Artificial Sequence
<220> FEATURE:
<223> OTHER INFORMATION: NKX3-1 Probe Sequence

<400> SEQUENCE: 15
tttgtgctgg ctagtactcc ggtcg                                              25

<210> SEQ ID NO 16
```

```
<211> LENGTH: 25
<212> TYPE: DNA
<213> ORGANISM: Artificial Sequence
<220> FEATURE:
<223> OTHER INFORMATION: LYPD2 Probe Sequence

<400> SEQUENCE: 16
ttcttcaagg cattcggggc tgggc                                  25

<210> SEQ ID NO 17
<211> LENGTH: 25
<212> TYPE: DNA
<213> ORGANISM: Artificial Sequence
<220> FEATURE:
<223> OTHER INFORMATION: CDR1

<400> SEQUENCE: 17
aacaactccg ggtcttccag cgact                                  25

<210> SEQ ID NO 18
<211> LENGTH: 25
<212> TYPE: DNA
<213> ORGANISM: Artificial Sequence
<220> FEATURE:
<223> OTHER INFORMATION: RPS4Y1 Probe Sequence

<400> SEQUENCE: 18
taaaccgcag gaagtcagat gagtg                                  25

<210> SEQ ID NO 19
<211> LENGTH: 25
<212> TYPE: DNA
<213> ORGANISM: Artificial Sequence
<220> FEATURE:
<223> OTHER INFORMATION: SLC7A11

<400> SEQUENCE: 19
ggttgaagca actagaagcg tgaca                                  25

<210> SEQ ID NO 20
<211> LENGTH: 25
<212> TYPE: DNA
<213> ORGANISM: Artificial Sequence
<220> FEATURE:
<223> OTHER INFORMATION: CLDN10 Probe Sequence

<400> SEQUENCE: 20
gacagcgttt catgctcgga tggcc                                  25

<210> SEQ ID NO 21
<211> LENGTH: 25
<212> TYPE: DNA
<213> ORGANISM: Artificial Sequence
<220> FEATURE:
<223> OTHER INFORMATION: TKT Probe Sequence

<400> SEQUENCE: 21
ggtttattct ctccagacgg tcagg                                  25

<210> SEQ ID NO 22
<211> LENGTH: 25
<212> TYPE: DNA
<213> ORGANISM: Artificial Sequence
<220> FEATURE:
<223> OTHER INFORMATION: RUNX1T1 Probe Sequence

<400> SEQUENCE: 22
```
taacagggag gaggtcaaat ctatc       25

<210> SEQ ID NO 23
<211> LENGTH: 25
<212> TYPE: DNA
<213> ORGANISM: Artificial Sequence
<220> FEATURE:
<223> OTHER INFORMATION: AKR1C2 Probe Sequence

<400> SEQUENCE: 23
tagctgtagc ttactgaagt cgcca       25

<210> SEQ ID NO 24
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 24
gacgtgaacc agaccaatga agggc       25

<210> SEQ ID NO 25
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 25
tcccataggg caagtccgga tgctc       25

<210> SEQ ID NO 26
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 26
agcaggaagg gcaaaccact cccca       25

<210> SEQ ID NO 27
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 27
ccaagtgaga gactccaggc cctca       25

<210> SEQ ID NO 28
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 28
aggaggctgc acatcacgct tctca       25

<210> SEQ ID NO 29
<211> LENGTH: 25
<212> TYPE: DNA

```
<213> ORGANISM: Artificial Sequence
<220> FEATURE:
<223> OTHER INFORMATION: CD177.1 Probe Sequence

<400> SEQUENCE: 29
ggaggctgca catcacgctt ctcac                                              25

<210> SEQ ID NO 30
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 30
acaagaagct ggaaggttgg gccac                                              25

<210> SEQ ID NO 31
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 31
aatgctcatt ttggtggaca gccca                                              25

<210> SEQ ID NO 32
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 32
ctacatctag gagcagcagc gtctc                                              25

<210> SEQ ID NO 33
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 33
agcagcgtct cctgacacac ctgcc                                              25

<210> SEQ ID NO 34
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 34
tcttgagcca agtttccgtg tgtca                                              25

<210> SEQ ID NO 35
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 35
tccgtgtgtc ataatggtgg tcccc                                              25
```

<210> SEQ ID NO 36
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 36
gttaacgagg ttgttgcaga agtcc                                              25

<210> SEQ ID NO 37
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 37
ttggagagca ccaggctcac ttggg                                              25

<210> SEQ ID NO 38
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 38
tctcaatgag catcaacgtg tcctg                                              25

<210> SEQ ID NO 39
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 39
gcaggtcgga caccttccac acatg                                              25

<210> SEQ ID NO 40
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 40
agggccagca gtaataccgc gctca                                              25

<210> SEQ ID NO 41
<211> LENGTH: 25
<212> TYPE: DNA
<213> ORGANISM: Artificial Sequence
<220> FEATURE:
<223> OTHER INFORMATION: CD177.1 Probe Sequence

<400> SEQUENCE: 41
gggccagcag taataccgcg ctcat                                              25

<210> SEQ ID NO 42
<211> LENGTH: 25
<212> TYPE: DNA
<213> ORGANISM: Artificial Sequence
<220> FEATURE:

<223> OTHER INFORMATION: CD177.1 Probe Sequence

<400> SEQUENCE: 42
gacccgtctg tggctggtaa tctct                                              25

<210> SEQ ID NO 43
<211> LENGTH: 25
<212> TYPE: DNA
<213> ORGANISM: Artificial Sequence
<220> FEATURE:
<223> OTHER INFORMATION: CD177.2 Probe Sequence

<400> SEQUENCE: 43
ttcctgtgtc ccattgagca ggttg                                              25

<210> SEQ ID NO 44
<211> LENGTH: 25
<212> TYPE: DNA
<213> ORGANISM: Artificial Sequence
<220> FEATURE:
<223> OTHER INFORMATION: CD177.2 Probe Sequence

<400> SEQUENCE: 44
tcccattgag caggttgcaa actgg                                              25

<210> SEQ ID NO 45
<211> LENGTH: 25
<212> TYPE: DNA
<213> ORGANISM: Artificial Sequence
<220> FEATURE:
<223> OTHER INFORMATION: CD177.2 Probe Sequence

<400> SEQUENCE: 45
cctgaggagg ccatcataac agtgt                                              25

<210> SEQ ID NO 46
<211> LENGTH: 25
<212> TYPE: DNA
<213> ORGANISM: Artificial Sequence
<220> FEATURE:
<223> OTHER INFORMATION: CD177.2 Probe Sequence

<400> SEQUENCE: 46
aggccatcat aacagtgtgt ggtcc                                              25